US010022552B2

(12) United States Patent
Stahler et al.

(10) Patent No.: US 10,022,552 B2
(45) Date of Patent: Jul. 17, 2018

(54) SYSTEM AND METHOD FOR OPTOGENETIC THERAPY

(71) Applicants: Circuit Therapeutics, Inc., Menlo Park, CA (US); Kathryn J. Stahler, Belmont, CA (US)

(72) Inventors: Greg Stahler, Belmont, CA (US); Ananya Mitra, Menlo Park, CA (US); Joyce Huang, Redwood City, CA (US); Dan Andersen, Menlo Park, CA (US); Alexander K. Arrow, Lake Forest, CA (US); David Moore, San Carlos, CA (US)

(73) Assignee: Circuit Therapeutics, Inc., Menlo Park, CA (US)

( * ) Notice: Subject to any disclaimer, the term of this patent is extended or adjusted under 35 U.S.C. 154(b) by 119 days.

(21) Appl. No.: 14/449,087

(22) Filed: Jul. 31, 2014

(65) Prior Publication Data
US 2016/0051838 A1 Feb. 25, 2016

Related U.S. Application Data

(63) Continuation of application No. PCT/US2013/000262, filed on Nov. 21, 2013.
(Continued)

(51) Int. Cl.
*A61N 5/06* (2006.01)
*A61K 48/00* (2006.01)
(Continued)

(52) U.S. Cl.
CPC ...... *A61N 5/0601* (2013.01); *A61B 17/00234* (2013.01); *A61B 17/3403* (2013.01);
(Continued)

(58) Field of Classification Search
None
See application file for complete search history.

(56) References Cited

U.S. PATENT DOCUMENTS

| 3,964,482 A | 6/1976 | Gerstel et al. |
| 5,334,207 A | 8/1994 | Gay, Jr. |

(Continued)

FOREIGN PATENT DOCUMENTS

| JP | 2011-524183 A | 9/2011 |
| JP | 2011-525130 A | 9/2011 |

(Continued)

OTHER PUBLICATIONS

International Search Report and Written Opinion dated Apr. 18, 2014, International Patent Application No. PCT/US2013/000262, International Filing Date of Nov. 21, 2013, (20 Pages).

(Continued)

*Primary Examiner* — Brian T Gedeon
(74) *Attorney, Agent, or Firm* — David C. Lundmark

(57) ABSTRACT

Configurations are described for utilizing light-activated proteins within cell membranes and subcellular regions to assist with medical treatment paradigms, such as hypertension treatment via anatomically specific and temporally precise modulation of renal plexus activity. The invention provides for proteins, nucleic acids, vectors and methods for genetically targeted expression of light-sensitive proteins to specific cells or defined cell populations. In particular the invention provides systems, devices, and methods for millisecond-timescale temporal control of certain cell activities using moderate light intensities, such as the generation or inhibition of electrical spikes in nerve cells and other excitable cells.

31 Claims, 102 Drawing Sheets

Related U.S. Application Data

(60) Provisional application No. 61/729,283, filed on Nov. 21, 2012.

(51) Int. Cl.

| | | |
|---|---|---|
| *A61K 41/00* | (2006.01) | |
| *A61K 38/17* | (2006.01) | |
| *A61N 1/05* | (2006.01) | |
| *A61N 1/36* | (2006.01) | |
| *A61K 38/16* | (2006.01) | |
| *A61M 25/01* | (2006.01) | |
| *A61M 37/00* | (2006.01) | |
| *A61B 17/00* | (2006.01) | |
| *A61B 17/34* | (2006.01) | |
| *A61M 5/142* | (2006.01) | |
| *A61M 5/20* | (2006.01) | |
| *A61N 5/067* | (2006.01) | |

(52) U.S. Cl.
CPC .......... *A61K 38/16* (2013.01); *A61K 38/164* (2013.01); *A61K 38/168* (2013.01); *A61K 38/177* (2013.01); *A61K 41/00* (2013.01); *A61K 41/0057* (2013.01); *A61K 48/00* (2013.01); *A61K 48/0075* (2013.01); *A61M 5/142* (2013.01); *A61M 5/20* (2013.01); *A61M 25/0105* (2013.01); *A61M 25/0147* (2013.01); *A61M 37/0015* (2013.01); *A61N 1/0551* (2013.01); *A61N 1/3605* (2013.01); *A61N 1/36053* (2013.01); *A61N 5/062* (2013.01); *A61N 5/0622* (2013.01); *A61B 2017/3413* (2013.01); *A61M 2037/0023* (2013.01); *A61M 2037/0061* (2013.01); *A61M 2205/3576* (2013.01); *A61M 2205/50* (2013.01); *A61N 2005/063* (2013.01); *A61N 2005/067* (2013.01); *A61N 2005/0612* (2013.01); *A61N 2005/0626* (2013.01); *A61N 2005/0627* (2013.01); *A61N 2005/0631* (2013.01); *A61N 2005/0643* (2013.01); *A61N 2005/0651* (2013.01); *A61N 2005/0653* (2013.01); *A61N 2005/0665* (2013.01)

(56) References Cited

U.S. PATENT DOCUMENTS

| | | |
|---|---|---|
| 5,354,279 A | 10/1994 | Hofling |
| 5,383,923 A | 1/1995 | Webster, Jr. |
| 5,411,537 A | 5/1995 | Munshi et al. |
| 5,766,234 A | 6/1998 | Chen et al. |
| 5,908,446 A | 6/1999 | Imran |
| 5,928,222 A | 7/1999 | Kleinerman |
| 5,941,845 A | 8/1999 | Tu et al. |
| 6,442,435 B2 * | 8/2002 | King .................... 607/116 |
| 6,689,103 B1 | 2/2004 | Palasis |
| 7,650,192 B2 * | 1/2010 | Wahlstrand ....... A61M 5/14276 607/61 |
| 8,267,889 B2 | 9/2012 | Cantor et al. |
| 9,649,503 B2 | 5/2017 | Delp et al. |
| 9,662,508 B2 | 5/2017 | Delp et al. |
| 2002/0128689 A1 | 9/2002 | Connelly et al. |
| 2004/0073278 A1 | 4/2004 | Pachys |
| 2007/0129775 A1 | 6/2007 | Mordaunt et al. |
| 2007/0249999 A1 | 10/2007 | Sklar et al. |
| 2008/0269734 A1 | 10/2008 | Echague et al. |
| 2009/0054954 A1 | 2/2009 | Foley et al. |
| 2009/0234426 A1 | 9/2009 | Pellinen et al. |
| 2010/0190229 A1 | 7/2010 | Zhang et al. |
| 2010/0198316 A1 | 8/2010 | Toselli et al. |
| 2011/0040357 A1 | 2/2011 | Arai et al. |
| 2011/0125077 A1 | 5/2011 | Denison et al. |
| 2011/0125078 A1 | 5/2011 | Denison et al. |
| 2011/0184337 A1 | 7/2011 | Evans et al. |
| 2011/0230747 A1 | 9/2011 | Rogers et al. |
| 2011/0307034 A1 | 12/2011 | Hastings et al. |
| 2012/0016308 A1 | 1/2012 | Schott |
| 2012/0065493 A1 | 3/2012 | Gertner |
| 2012/0191079 A1 | 7/2012 | Moll et al. |
| 2012/0197374 A1 | 8/2012 | Vogt et al. |
| 2012/0253261 A1 | 10/2012 | Poletto et al. |
| 2015/0246242 A1 | 9/2015 | Delp et al. |
| 2016/0038755 A1 | 2/2016 | Lundmark et al. |
| 2016/0045764 A1 | 2/2016 | Delp et al. |
| 2016/0051836 A1 | 2/2016 | Lundmark et al. |
| 2016/0096034 A1 | 4/2016 | Lundmark et al. |
| 2017/0304003 A1 | 10/2017 | McMillan et al. |

FOREIGN PATENT DOCUMENTS

| | | |
|---|---|---|
| WO | 2007/024391 A2 | 3/2007 |
| WO | 2009/155369 A1 | 12/2009 |
| WO | 2009/155371 A1 | 12/2009 |
| WO | 2011/094367 | 8/2011 |
| WO | 2012/061684 A1 | 5/2012 |

OTHER PUBLICATIONS

European Patent Application No. 13856423.2, Extended European Search Report dated Jun. 9, 2016, (6 pages).
Final Office Action dated Feb. 6, 2017, U.S. Appl. No. 14/499,090, filed Jul. 31, 2014, (16 pages).
Communication Pursuant to Article 94(3) EPC dated May 15, 2017, European Patent Application No. 13 856 423.3, (4 pages).
Examination Report No. 1 dated Jul. 24, 2017, Australian Patent Application No. 2013348395, (4 pages).
First Office Action dated Dec. 14, 2016, Chinese Patent Application for Invention No. 201380071014.6, (15 pages).
First Office Action dated Oct. 19, 2017, Japanese Patent Application No. 2016-225548 with English Translation, (14 pages).
Non Final Office Action dated Jun. 7, 2017, U.S. Appl. No. 14/444,844, filed Jul. 28, 2014, (24 pages).
Non Final Office Action dated Jun. 9, 2017, U.S. Appl. No. 14/444,767, filed Jul. 28, 2014, (20 pages).
Non Final Office Action dated Sep. 5, 2017, U.S. Appl. No. 14/449,096, filed Jul. 31, 2014, (23 pages).
Notice of Allowance dated Jul. 19, 2017, U.S. Appl. No. 14/444,841, filed Jul. 28, 2014, (6 pages).
Office Action—Notice of Reasons for Rejection—dated Sep. 26, 2017 with English Translation, Japanese Patent Application No. 2015-544050, (22 pages).
Second Chinese Office Action dated Sep. 13, 2017, Chinese Patent Application for Invention No. 201380071014.6, (12 pages).
Non Final Office Action dated Dec. 5, 2017, U.S. Appl. No. 14/449,077, (15 pages).
Non Final Office Action dated Nov. 14, 2017, U.S. Appl. No. 14/449,097, (24 pages).

* cited by examiner

| Wavelength (nm) | Color Name | Fwd Voltage (Vf@20ma) | Imtensity 5mm LEDs | Viewing Angle | LED dye Material |
|---|---|---|---|---|---|
| 940 | Infrared | 1.5 | 16mW @50mA | 15° | GaAIAs/GaAs—Gallium Aluminum Arsenide/Gallium Arsenide |
| 880 | Infrared | 1.7 | 18mW @50mA | 15° | GaAIAs/GaAs—Gallium Aluminum Arsenide/Gallium Arsenide |
| 850 | Infrared | 1.7 | 26mW @50mA | 15° | GaAIAs/GaAs—Gallium Aluminum Arsenide/Gallium Arsenide |
| 660 | Ultra Red | 1.8 | 2000mcd @50mA | 15° | GaAIAs/GaAs—Gallium Aluminum Arsenide/Gallium Arsenide |
| 635 | High Eff. Red | 2.0 | 200mcd @20mA | 15° | GaAsP/GaP—Gallium Arsenide Phosphide/Gallium Phosphide |
| 633 | Super Red | 2.2 | 3500mcd @20mA | 15° | InGaAIP—Indium Gallium Aluminum Phosphide |
| 620 | Super Orange | 2.2 | 4500mcd @20mA | 15° | InGaAIP—Indium Gallium Aluminum Phosphide |
| 612 | Super Orange | 2.2 | 6500mcd @20mA | 15° | InGaAIP—Indium Gallium Aluminum Phosphide |
| 605 | Orange | 2.1 | 160mcd @20mA | 15° | GaAsP/GaP—Gallium Arsenic Phosphide/Gallium Phosphide |
| 595 | Super Yellow | 2.2 | 5500mcd @20mA | 15° | InGaAIP—Indium Gallium Aluminum Phosphide |
| 592 | Super Pure Yellow | 2.1 | 7000mcd @20mA | 15° | InGaAIP—Indium Gallium Aluminum Phosphide |

FIG. 4C-1

| | | | | | |
|---|---|---|---|---|---|
| 585 | Yellow | 2.1 | 100mcd @20mA | 15° | GaAsP/GaP—Gallium Arsenic Phosphide/ Gallium Phosphide |
| 4500K | "Incan- descent" White | 3.6 | 2000mcd @20mA | 20° | SiC/GaN—Silicon Carbide/Gallium Nitride |
| 6500K | Pale White | 3.6 | 4000mcd @20mA | 20° | SiC/GaN—Silicon Carbide/Gallium Nitride |
| 8000K | Cool White | 3.6 | 6000mcd @20mA | 20° | SiC/GaN—Silicon Carbide/Gallium Nitride |
| 574 | Super Lime Yellow | 2.4 | 1000mcd @20mA | 15° | InGaAIP—Indium Gallium Aluminum Phosphide |
| 570 | Super Lime Green | 2.0 | 1000mcd @20mA | 15° | InGaAIP—Indium Gallium Aluminum Phosphide |
| 565 | High Efficiency Green | 2.1 | 200mcd @20mA | 15° | GaP/GaP—Gallium Phosphide/Gallium Phosphide |
| 560 | Super Pure Green | 2.1 | 350mcd @20mA | 15° | InGaAIP—Indium Gallium Aluminum Phosphide |
| 555 | Pure Green | 2.1 | 80mcd @20mA | 15° | GaP/GaP—Gallium Phosphide/Gallium Phosphide |
| 525 | Aqua Green | 3.5 | 10000mcd @20mA | 15° | SiC/GaN—Silicon Carbide/Gallium Nitride |
| 505 | Blue Green | 3.5 | 2000mcd @20mA | 45° | SiC/GaN—Silicon Carbide/Gallium Nitride |
| 470 | Super Blue | 3.6 | 3000mcd @20mA | 15° | SiC/GaN—Silicon Carbide/Gallium Nitride |
| 430 | Ultra Blue | 3.8 | 100mcd @20mA | 15° | SiC/GaN—Silicon Carbide/Gallium Nitride |

SECTION AA

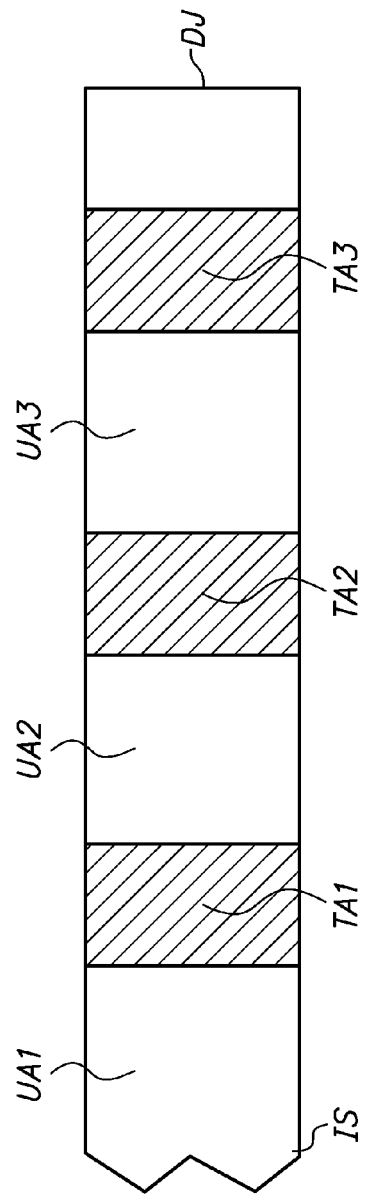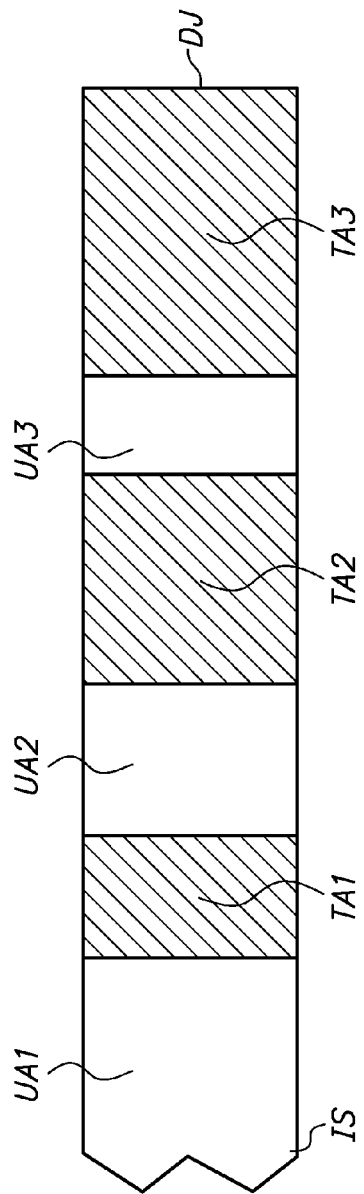

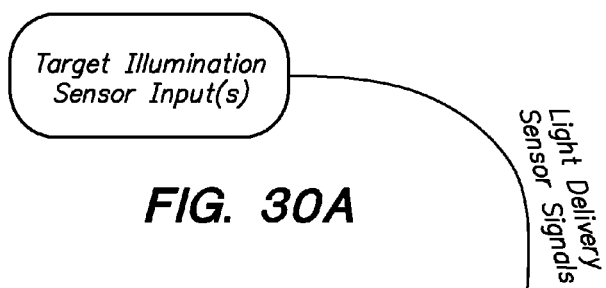
FIG. 30A
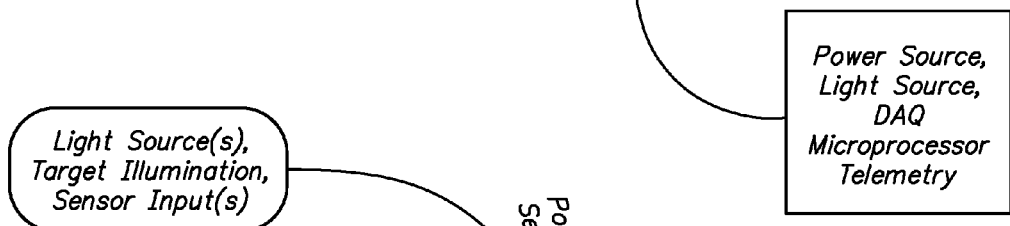
FIG. 30B
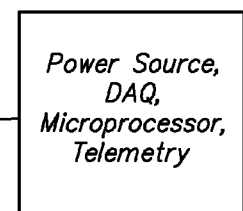

ChR2 [gi|134153990|gb|AB064386.1] [SEQ ID NO: 1]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTCP
VILIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51A

ChR2 (C128A) [SFO] [SEQ ID NO: 2]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTAP
VILIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51B

ChR2 (C128S) [SFO] [SEQ ID NO: 3]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTSP
VILIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51C

ChR2 (C128T) [SFO] [SEQ ID NO: 4]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTTP
VLIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51D

ChR2 (D156A) [SFO] [SEQ ID NO: 5]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTCP
VLIHLSNLTG
LSNDYSRRTMGLLVSAIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51E

ChR2 (D156A/C128S) (SSFO) [SEQ ID NO: 6]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTSP
VLIHLSNLTG
LSNDYSRRTMGLLVSAIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

FIG. 51F

ChR2 (T159C) [SEQ ID NO: 7]
MDYGGALSAVGRELLFVTNPVVVNGSVLVPEDQCYCAGWIESRGTNGAQTASNVLQWLAAGFSILLLMFY
AYQTWKSTCGWEEIYVCAIEMVKVILEFFFEFKNPSMLYLATGHRVQWLRYAEWLLTCPVILIHLSNLTG
LSNDYSRRTMGLLVSDIGCIVWGATSAMATGYVKVIFFCLGLCYGANTFFHAAKAYIEGYHTVPKGRCRQ
VVTGMAWLFFVSWGMFPILFILGPEGFGVLSVYGSTVGHTIIDLMSKNCWGLLGHYLRVLIHEHILIHGD
IRKTTKLNIGGTEIEVETLVEDEAEAGAVP

FIG. 51G

ChR2(L132C) (CatCH) [SEQ ID NO: 8]
MDYGGALSAVGRELLFVTNPVVVNGSVLVPEDQCYCAGWIESRGTNGAQTASNVLQWLAAGFSILLLMFY
AYQTWKSTCGWEEIYVCAIEMVKVILEFFFEFKNPSMLYLATGHRVQWLRYAEWLLTCPVICIHLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSVYGSTVGHTIIDLMSKNCWGLLGHYLRVLIHEHILIHGD
IRKTTKLNIGGTEIEVETLVEDEAEAGAVP

FIG. 51H

ChR2 (E123T/T159C) [SEQ ID NO: 9]
MDYGGALSAVGRELLFVTNPVVVNGSVLVPEDQCYCAGWIESRGTNGAQTASNVLQWLAAGFSILLLMFY
AYQTWKSTCGWEEIYVCAIEMVKVILEFFFEFKNPSMLYLATGHRVQWLRYATWLLTCPVILIHLSNLTG
LSNDYSRRTMGLLVSDIGCIVWGATSAMATGYVKVIFFCLGLCYGANTFFHAAKAYIEGYHTVPKGRCRQ
VVTGMAWLFFVSWGMFPILFILGPEGFGVLSVYGSTVGHTIIDLMSKNCWGLLGHYLRVLIHEHILIHGD
IRKTTKLNIGGTEIEVETLVEDEAEAGAVP

FIG. 51I

ChR2 (H134R) [SEQ ID NO: 10]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAEWLLTCP
VILIRLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

*FIG. 51J*

ChR2 ChETA (E123A) [SEQ ID NO: 11]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYAAWLLTCP
VILIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

*FIG. 51K*

ChR2 ChETA (E123T) [SEQ ID NO: 12]
MDYGGALSAVGRELLFVTNPVVVNGSVLVPEDQCYCAGWIESRGTNGAQTASNVLQWLA
AGFSILLLMFY
AYQTWKSTCGWEEIYVCAIEMVKVILEFFFEFKNPSMLYLATGHRVQWLRYATWLLTCP
VILIHLSNLTG
LSNDYSRRTMGLLVSDIGTIVWGATSAMATGYVKVIFFCLGLCYGANTFFHAAKAYIEG
YHTVPKGRCRQ
VVTGMAWLFFVSWGMFPILFILGPEGFGVLSVYGSTVGHTIIDLMSKNCWGLLGHYLRV
LIHEHILIHGD
IRKTTKLNIGGTEIEVETLVEDEAEAGAVP

*FIG. 51L*

C1V1 (splice variant 2) [gi|342356711|gb|AEL28924.1] [SEQ ID NO: 13]
MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVLLIHLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
PYGSAIGHSILDLIAKNMWGVLGNYLRVKIHEHILLYGDIRKKQKITIAGQEMEVETLVAEEED

FIG. 52A

C1V1 (splice variant 2) ChETA (E122T) [SEQ ID NO: 14]
MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWETIYVATIEMIKFIIEYFHE
FDEPAVIYSSNGNKTVWLRYAEWLLTCPVLLIHLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
PYGSAIGHSILDLIAKNMWGVLGNYLRVKIHEHILLYGDIRKKQKITIAGQEMEVETLVAEEED

FIG. 52B

C1V1 (splice variant 2) ChETA (E162T) [SEQ ID NO: 15]
MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYATWLLTCPVLLIHLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
PYGSAIGHSILDLIAKNMWGVLGNYLRVKIHEHILLYGDIRKKQKITIAGQEMEVETLVAEEED

FIG. 52C

C1V1 (splice variant 2) ChETA (E122T/E162T) [SEQ ID NO: 16]
MSRRPWLLALALAVALAAGSAGASTGSDATVPVATQDGPDYVFHRAHERMLFQTSYTLE
NNGSVICIPNN
GQCFCLAWLKSNGTNAEKLAANILQWITFALSALCLMFYGYQTWKSTCGWETIYVATIE
MIKFIIEYFHE
FDEPAVIYSSNGNKTVWLRYATWLLTCPVLLIHLSNLTGLKDDYSKRTMGLLVSDVGCI
VWGATSAMCTG
WTKILFFLISLSYGMYTYFHAAKVYIEAFHTVPKGICRELVRVMAWTFFVAWGMFPVLF
LLGTEGFGHIS
PYGSAIGHSILDLIAKNMWGVLGNYLRVKIHEHILLYGDIRKKQKITIAGQEMEVETLV
AEEED

FIG. 52D

C1V1 (splice variant 1) ChETA (E162T)
[gi|342356709|gb|AEL28923.1] [SEQ ID NO: 17]
MSRRPWLLALALAVALAAGSAGASTGSDATVPVATQDGPDY17VFHRAHERMLFQTSYT
LENNGSVICIPNN
GQCFCLAWLKSNGTNAEKLAANILQWITFALSALCLMFYGYQTWKSTCGWEEIYVATIE
MIKFIIEYFHE
FDEPATLWLSSGNGVVWMRYGTWLLTCPVLLIHLSNLTGLKDDYSKRTMGLLVSDIACI
VWGATSAMCTG
WTKILFFLISLSYGMYTYFHAAKVYIEAFHTVPKGICRELVRVMAWTFFVAWGMFPVLF
LLGTEGFGHIS
PYGSAIGHSILDLIAKNMWGVLGNYLRVKIHEHILLYGDIRKKQKITIAGQEMEVETLV
AEEEDDTVKQS
TAKYASR

FIG. 52E

C1V1 (splice variant 1) ChETA (E122T) [SEQ ID NO: 18]
MSRRPWLLALALAVALAAGSAGASTGSDATVPVATQDGPDYVFHRAHERMLFQTSYTLE
NNGSVICIPNN
GQCFCLAWLKSNGTNAEKLAANILQWITFALSALCLMFYGYQTWKSTCGWETIYVATIE
MIKFIIEYFHE
FDEPATLWLSSGNGVVWMRYGEWLLTCPVLLIHLSNLTGLKDDYSKRTMGLLVSDIACI
VWGATSAMCTG
WTKILFFLISLSYGMYTYFHAAKVYIEAFHTVPKGICRELVRVMAWTFFVAWGMFPVLF
LLGTEGFGHIS
PYGSAIGHSILDLIAKNMWGVLGNYLRVKIHEHILLYGDIRKKQKITIAGQEMEVETLV
AEEEDDTVKQSnphr
TAKYASR

FIG. 52F

C1V1 splice variant 1 ChETA (E122T/E162T) [SEQ ID NO: 19]
MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWETIYVATIEMIKFIIEYFHE
FDEPATLWLSSGNGVVWMRYGTWLLTCPVLLIHLSNLTGLKDDYSKRTMGLLVSDIACIVWGATSAMCTG
WTKILFFLISLSYGMYTYFHAAKVYIEAFHTVPKGICRELVRVMAWTFFVAWGMFPVLFLLGTEGFGHIS
PYGSAIGHSILDLIAKNMWGVLGNYLRVKIHEHILLYGDIRKKQKITIAGQEMEVETLVAEEEDDTVKQS
TAKYASR

FIG. 52G

C1V1 splice variant 1 [SEQ ID NO: 49]
MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPATLWLSSGNGVVWMRYGEWLLTCPVLLIHLSNLTGLKDDYSKRTMGLLVSDIACIVWGATSAMCTG
WTKILFFLISLSYGMYTYFHAAKVYIEAFHTVPKGICRELVRVMAWTFFVAWGMFPVLFLLGTEGFGHIS
PYGSAIGHSILDLIAKNMWGVLGNYLRVKIHEHILLYGDIRKKQKITIAGQEMEVETLVAEEEDDTVKQS
TAKYASR

FIG. 52H

VChR1 [gi|189015852|gb|ACD70142.1] [SEQ ID NO: 20]
MDYPVARSLIVRYPTDLGNGTVCMPRGQCYCEGWLRSRGTSIEKTIAITLQWVVFALSVACLGWYAYQAW
RATCGWEEVYVALIEMMKSIIEAFHEFDSPATLWLSSGNGVVWMRYGEWLLTCPVLLIHLSNLTGLKDDY
SKRTMGLLVSDVGCIVWGATSAMCTGWTKILFFLISLSYGMYTYFHAAKVYIEAFHTVPKGICRELVRVM
AWTFFVAWGMFPVLFLLGTEGFGHISPYGSAIGHSILDLIAKNMWGVLGNYLRVKIHEHILLYGDIRKKQ
KITIAGQEMEVETLVAEEED

FIG. 53A

VChR1 (C123S) [VSFO] [SEQ ID NO: 21]
MDYPVARSLIVRYPTDLGNGTVCMPRGQCYCEGWLRSRGTSIEKTIAITLQWVVFALSV
ACLGWYAYQAW
RATCGWEEVYVALIEMMKSIIEAFHEFDSPATLWLSSGNGVVWMRYGEWLLTSPVLLIH
LSNLTGLKDDY
SKRTMGLLVSDVGCIVWGATSAMCTGWTKILFFLISLSYGMYTYFHAAKVYIEAFHTVP
KGICRELVRVM
AWTFFVAWGMFPVLFLLGTEGFGHISPYGSAIGHSILDLIAKNMWGVLGNYLRVKIHEH
ILLYGDIRKKQ
KITIAGQEMEVETLVAEEED

*FIG. 53B*

VChR1 (C123S/D151A) (VSSFO) [SEQ ID NO: 22]
MDYPVARSLIVRYPTDLGNGTVCMPRGQCYCEGWLRSRGTSIEKTIAITLQWVVFALSV
ACLGWYAYQAW
RATCGWEEVYVALIEMMKSIIEAFHEFDSPATLWLSSGNGVVWMRYGEWLLTSPVLLIH
LSNLTGLKDDY
SKRTMGLLVSAVGCIVWGATSAMCTGWTKILFFLISLSYGMYTYFHAAKVYIEAFHTVP
KGICRELVRVM
AWTFFVAWGMFPVLFLLGTEGFGHISPYGSAIGHSILDLIAKNMWGVLGNYLRVKIHEH
ILLYGDIRKKQ
KITIAGQEMEVETLVAEEED

*FIG. 53C*

ReaChR [gi|530752655|gb|AGT48260.1] [SEQ ID NO: 23]
MVSRRPWLLALALAVALAAGSAGASTGSDATVPVATQDGPDYVFHRAHERMLFQTSYTL
ENNGSVICIPN
NGQCFCLAWLKSNGTNAEKLAANILQWVVFALSVACLGWYAYQAWRATCGWEEVYVALI
EMMKSIIEAFH
EFDSPATLWLSSGNGVVWMRYGEWLLTCPVILIHLSNLTGLKDDYSKRTMGLLVSDVGC
IVWGATSAMCT
GWTKILFFLISLSYGMYTYFHAAKVYIEAFHTVPKGLCRQLVRAMAWLFFVSWGMFPVL
FLLGPEGFGHI
SPYGSAIGHSILDLIAKNMWGVLGNYLRVKIHEHILLYGDIRKKQKITIAGQEMEVETL
VAEEEDKYESS

*FIG. 54A*

VCOMET [gi|530752657|gb|AGT48261.1] [SEQ ID NO: 24]
MVSRRPWLLALALAVALAAGSAGASTGSDATVPVATQDGPDYVFHRAHERMLFQTSYTL
ENNGSVICIPN
NGQCFCLAWLKSNGTNAEKLAANILQWVVFALSVACLGWYAYQAWRATCGWEEVYVALI
EMMKSIIEAFH
EFDSPATLWLSSGNGVVWMRYGEWLLTCPVLLIHLSNLTGLKDDYSKRTMGLLVSDVGC
IVWGATSAMCT
GWTKILFFLISLSYGMYTYFHAAKVYIEAFHTVPKGLCRQLVRAMAWLFFVSWGMFPVL
FLLGPEGFGHI
SPYGSAIGHSILDLIAKNMWGVLGNYLRVKIHEHILLYGDIRKKQKITIAGQEMEVETL
VAEEEDKYESS

*FIG. 54B*

Arch [gi|282892261|gb|ADB03110.1 [SEQ ID NO: 25]
MDPIALQAGYDLLGDGRPETLWLGIGTLLMLIGTFYFLVRGWGVTDKDAREYYAVTILV
PGIASAAYLSM
FFGIGLTEVTVGGEMLDIYYARYADWLFTTPLLLLDLALLAKVDRVTIGTLVGVDALMI
VTGLIGALSHT
AIARYSWWLFSTICMIVVLYFLATSLRSAAKERGPEVASTFNTLTALVLVLWTAYPILW
IIGTEGAGVVG
LGIETLLFMVLDVTAKVGFGFILLRSRAILGDTEAPEPSAGADVSAAD

*FIG. 55A*

ArchT [gi 328672376|gb|AEB26832.1] [SEQ ID NO: 26]
MDPIALQAGYDLLGDGRPETLWLGIGTLLMLIGTFYFIVKGWGVTDKEAREYYSITILV
PGIASAAYLSM
FFGIGLTEVTVAGEVLDIYYARYADWLFTTPLLLLDLALLAKVDRVSIGTLVGVDALMI
VTGLIGALSHT
PLARYSWWLFSTICMIVVLYFLATSLRAAAKERGPEVASTFNTLTALVLVLWTAYPILW
IIGTEGAGVVG
LGIETLLFMVLDVTAKVGFGFILLRSRAILGDTEAPEP

*FIG. 55B* eArch3.0-EYFP [SEQ ID NO:24 from published PCT application from Published PCT application WO/2013/126521] [SEQ ID NO: 27]
MDPIALQAGYDLLGDGRPETLWLGIGTLLMLIGTFYFLVRGWGVTDKDAREYYAVTILV
PGIASA
AYLSMFFGIGLTEVTVGGEMLDIYYARYADWLFTTPLLLLDLALLAKVDRVTIGTLVGV
DALMIV
TGLIGALSHTAIARYSWWLFSTICMIVVLYFLATSLRSAAKERGPEVASTFNTLTALVL
VLWTAYP
ILWIIGTEGAGVVGLGIETLLFMVLDVTAKVGFGFILLRSRAILGDTEAPEPSAGADVS
AADRPVV
AVSKAAAKSRITSEGEYIPLDQIDINVVSKGEELFTGVVPILVELDGDVNGHKFSVSGE
GEGDATY
GKLTLKFICTTGKLPVPWPTLVTTFGYGLQCFARYPDHMKQHDFFKSAMPEGYVQERTI
FFKDDG
NYKTRAEVKFEGDTLVNRIELKGIDFKEDGNILGHKLEYNYNSHNVYIMADKQKNGIKV
NFKIRH
NIEDGSVQLADHYQQNTPIGDGPVLLPDNHYLSYQSALSKDPNEKRDHMVLLEFVTAAG
ITLGM DELYKFCYENEV

FIG. 55C

Mac [gi|282892265|gb|ADB03112.1] [SEQ ID NO: 28]
MIVDQFEEVLMKTSQLFPLPTATQSAQPTHVAPVPTVLPDTPIYETVGDSGSKTLWVVF
VLMLIASAAFT
ALSWKIPVNRRLYHVITTIITLTAALSYFAMATGHGVALNKIVIRTQHDHVPDTYETVY
RQVYYARYIDW
AITTPLLLLDLGLLAGMSGAHIFMAIVADLIMVLTGLFAAFGSEGTPQKWGWYTIACIA
YIFVVWHLVLN
GGANARVKGEKLRSFFVAIGAYTLILWTAYPIVWGLADGARKIGVDGEIIAYAVLDVLA
KGVFGAWLLVT
HANLRESDVELNGFWANGLNREGAIRIGEDDGA

FIG. 56

BR [Published US patent application 20130019325] [SEQ ID NO: 29]
MLELLPTAVEGVSQAQITGRPEWIWLALGTALMGLGTLYFLVKGMGVSDPDAKKFYAIT
TLVPAIAFTMYLSMLLGYGLT
MVPFGGEQNPIYWARYADWLFTTPLLLLDLALLVDADQGTILALVGADGIMIGTGLVGA
LTKVYSYRFVWWAISTAAMLY
ILYVLFFGFTSKAESMRPEVASTFKVLRNVTVVLWSAYPVVWLIGSEGAGIVPLNIETL
LFMVLDVSAKVGFGLILLRSR
AIFGEAEAPEPSAGDGAAATSD

FIG. 57

DChR1 [gi|373427779|gb|AEY68833.1] [SEQ ID NO: 30]
MRRRESQLAYLCLFVLIAGWAPRLTESAPDLAERRPPSERNTPYANIKKVPNITEPNAN
VQLDGWALYQD
FYYLAGSDKEWVVGPSDQCYCRAWSKSHGTDREGEAAVVWAYIVFAICIVQLVYFMFAA
WKATVGWEEVY
VNIIELVHIALVIWVEFDKPAMLYLNDGQMVPWLRYSAWLLSCPVILIHLSNLTGLKGD
YSKRTMGLLVS
DIGTIVFGTSAALAPPNHVKVILFTIGLLYGLFTFFTAAKVYIEAYHTVPKGQCRNLVR
AMAWTYFVSWA
MFPILFILGREGFGHITYFGSSIGHFILEIFSKNLWSLLGHGLRYRIRQHIIIHGNLTK
KNKINIAGDNV
EVEEYVDSNDKDSDV

FIG. 58A

GtR3 [gi|373427781|gb|AEY68834.1] [SEQ ID NO: 31]
MDYGGALSAVGRELLFVTNPVVVNGSVLVPEDQCYCAGWIESRGTNGASSFGKALLEFV
FIVFACITLLL
GINAAKSKAASRVLFPATFVTGIASIAYFSMASGGGWVIAPDCRQLFVARYLDWLITTP
LLLIDLGLVAG
VSRWDIMALCLSDVLMIATGAFGSLTVGNVKWVWWFFGMCWFLHIIFALGKSWAEAAKA
KGGDSASVYSK
IAGITVITWFCYPVVWVFAEGFGNFSVTFEVLIYGVLDVISKAVFGLILMSGAATGYES
I

FIG. 58B

NpHR [gi|134153992|gb|AB064387.1] [SEQ ID NO: 32]
MTETLPPVTESAVALQAEVTQRELFEFVLNDPLLASSLYINIALAGLSILLFVFMTRGL
DDPRAKLIAVS
TILVPVVSIASYTGLASGLTISVLEMPAGHFAEGSSVMLGGEEVDGVVTMWGRYLTWAL
STPMILLALGL
LAGSNATKLFTAITFDIAMCVTGLAAALTTSSHLMRWFWYAISCACFLVVLYILLVEWA
QDAKAAGTADM
FNTLKLLTVVMWLGYPIVWALGVEGIAVLPVGVTSWGYSFLDIVAKYIFAFLLLNYLTS
NESVVSGSILD
VPSASGTPADD

FIG. 59A eYFP-NpHR3.0 [SEQ ID NO:2 from Published PCT application
WO/2013/126521] [SEQ ID NO: 33]
MTETLPPVTESAVALQAEVTQRELFEFVLNDPLLASSLYINIALAGLSILLFVFMTRGL
DDPRAKLIAV
STILVPVVSIASYTGLASGLTISVLEMPAGHFAEGSSVMLGGEEVDGVVTMWGRYLTWA
LSTPMILL
ALGLLAGSNATKLFTAITFDIAMCVTGLAAALTTSSHLMRWFWYAISCACFLVVLYILL
VEWAQDA
KAAGTADMFNTLKLLTVVMWLGYPIVWALGVEGIAVLPVGVTSWGYSFLDIVAKYIFAF
LLLNYLT
SNESVVSGSILDVPSASGTPADDAAAKSRITSEGEYIPLDQIDINVVSKGEELFTGVVP
ILVELDGDVN
GHKFSVSGEGEGDATYGKLTLKFICTTGKLPVPWPTLVTTFGYGLQCFARYPDHMKQHD
FFKSAMP
EGYVQERTIFFKDDGNYKTRAEVKFEGDTLVNRIELKGIDFKEDGNILGHKLEYNYNSH
NVYIMAD
KQKNGIKVNFKIRHNIEDGSVQLADHYQQNTPIGDGPVLLPDNHYLSYQSALSKDPNEK
RDHMVLL EFVTAAGITLGMDELYKFCYENEV

FIG. 59B eYFP-NpHR3.1 [SEQ ID NO:3 from Published PCT application WO/2013/126521] [SEQ ID NO: 34]
MVTQRELFEFVLNDPLLASSLYINIALAGLSILLFVFMTRGLDDPRAKLIAVSTILVPVVSIASYTGLA
SGLTISVLEMPAGHFAEGSSVMLGGEEVDGVVTMWGRYLTWALSTPMILLALGLLAGSNATKLFT
AITFDIAMCVTGLAAALTTSSHLMRWFWYAISCACFLVVLYILLVEWAQDAKAAGTADMFNTLKL
LTVVMWLGYPIVWALGVEGIAVLPVGVTSWGYSFLDIVAKYIFAFLLLNYLTSNESVVSGSILDVPS
ASGTPADDAAAKSRITSEGEYIPLDQIDINVVSKGEELFTGVVPILVELDGDVNGHKFSVSGEGEGDA
TYGKLTLKFICTTGKLPVPWPTLVTTFGYGLQCFARYPDHMKQHDFFKSAMPEGYVQERTIFFKDD
GNYKTRAEVKFEGDTLVNRIELKGIDFKEDGNILGHKLEYNYNSHNVYIMADKQKNGIKVNFKIRH
NIEDGSVQLADHYQQNTPIGDGPVLLPDNHYLSYQSALSKDPNEKRDHMVLLEFVTAAGITLGMDE LYKFCYENEV

*FIG. 59C*

Optoβ2AR [Published US patent application 20110112179] [SEQ ID NO: 35]
MNGTEGPNFYVPFSNKTGVVRSPFEAPQYYLAEPWQFSMLAAYMFLLIMLGFPINFLTLYVIAKFERLQTVLNYILLNLA
VADLFMVFGGFTTTLYTSLHGYFVFGPTGCNLEGFFATLGGEIALWSLVVLAIERYVVVTSPFKYQSLLTKNKAIMGVAF
TWVMALACAAPPLVGWSRYIPEGMQCSCGIDYYTPHEETNNESFVIYMFVVHFIIPLIVIFFCYGRVFQVAKRQLQKIDK
SEGRFHSPNLGQVEQDGRSGHGLRRSSKFCLKEHKALRMVIIMVIAFLICWLPYAGVAFYIFTHQGSDFGPIFMTIPAFF
AKTSAVYNPVIYIMMNKQFRIAFQELLCLRRSSSKAYGNGYSSNSNGKTDYMGEASGCQLGQEKESERLCEDPPGTESFV
NCQGTVPSLSLDSQGRNCSTNDSPLTETSQVAPA

*FIG. 60A*

Optoα1AR [Published US patent application 20110112179] [SEQ ID NO: 36]
MNGTEGPNFYVPFSNKTGVVRSPFEAPQYYLAEPWQFSMLAAYMFLLIMLGFPINFLTLYVVACHRHLHSVLNYILLNLA
VADLFMVFGGFTTTLYTSLHGYFVFGPTGCNLEGFFATLGGEIALWSLVVLAIERYVVVSYPLRYPTIVTQRRAIMGVAF
TWVMALACAAPPLVGWSRYIPEGMQCSCGIDYYTPHEETNNESFVIYMFVVHFIIPLIVIFFCYGRVYVVAKRESRGLKS
GLKTDKSDSEQVTLRIHRKNAPAGGSGMASAKTKTHFSVRLLKFSREKKAARMVIIMVIAFLICWLPYAGVAFYIFTHQG
SDFGPIFMTIPAFFAKTSAVYNPVIYIMMNKQFRKAFQNVLRIQCLCRKQSSKHALGYTLHPPSQAVEGQHKDMVRIPVG
SRETFYRISKTDGVCEWKFFSSMPRGSARITVSKDQSSCTTARVRSKSFLQVCCCVGPSTPSLDKNHQVPTIKVHTISLS
ENGEEVTETSQVAPA

FIG. 60B

Trafficking sequence of human inward rectifier potassium channel Kir2.1 [SEQ ID NO: 12 from Published PCT application WO/2013/126521] [SEQ ID NO: 37]
KSRITSEGEYIPLDQIDINV

FIG. 61A

Signal peptide of hChR2 [SEQ ID NO: 13 from Published PCT application WO/2013/126521] [SEQ ID NO: 38]
MDYGGALSAVGRELLFVTNPVVVNGS

FIG. 61B

β2 subunit signal peptide of the neuronal nicotinic acetylcholine receptor [SEQ ID NO: 14 from Published PCT application WO/2013/126521] [SEQ ID NO: 39]
MAGHSNSMALFSFSLLWLCSGVLGTEF

FIG. 61C

Nicotinic acetylcholine receptor signal sequence [SEQ ID NO: 15 from Published PCT application WO/2013/126521] [SEQ ID NO: 40]
MGLRALMLWLLAAAGLVRESLQG

*FIG. 61D*

Nicotinic acetylcholine receptor signal sequence [SEQ ID NO: 16 from Published PCT application WO/2013/126521] [SEQ ID NO: 41]
MRGTPLLLVVSLFSLLQD

*FIG. 61E*

Endoplasmic reticulum (ER) export sequence [Published PCT application WO/2013/126521] [SEQ ID NO: 42]
VXXSL (where X is any amino acid)

*FIG. 61F*

Endoplasmic reticulum (ER) export sequence [SEQ ID NO: 17 from Published PCT application WO/2013/126521] [SEQ ID NO: 43]
VKESL

*FIG. 61G*

Endoplasmic reticulum (ER) export sequence [SEQ ID NO: 18 from Published PCT application WO/2013/126521] [SEQ ID NO: 44]
VLGSL

*FIG. 61H*

Endoplasmic reticulum (ER) export sequence [SEQ ID NO: 19 from Published PCT application WO/2013/126521] [SEQ ID NO: 45]
NANSFCYENEVALTSK

FIG. 61I

Endoplasmic reticulum (ER) export sequences [SEQ ID NO: 20 from Published PCT application WO/2013/126521] [SEQ ID NO: 46]
FXYENE (where X is any amino acid)

FIG. 61J

Endoplasmic reticulum (ER) export sequence [SEQ ID NO: 21 from Published PCT application WO/2013/126521] [SEQ ID NO: 47]
FCYENEV

FIG. 61K

Signal peptide [SEQ ID NO: 22 from Published PCT application WO/2013/126521] [SEQ ID NO: 48]
MTETLPPVTESAVALQAE

FIG. 61L

Polynucleotide encoding Champ [SEQ ID NO: 50]
cctgcaggcagctgcgcgctcgctcgctcactgaggccgcccgggcaaagcccgggcgt
cgggcgacctttggtcgcccg
gcctcagtgagcgagcgagcgcgcagagagggagtggccaactccatcactaggggttc
ctgcggccgcacgcgtgtgtc
tagactgcagagggccctgcgtatgagtgcaagtgggttttaggaccaggatgaggcgg
ggtgggggtgcctacctgacg
accgaccccgacccactggacaagcacccaaccccccattccccaaattgcgcatcccct
atcagagaggggagggggaaa
caggatgcggcgaggcgcgtgcgcactgccagcttcagcaccgcggacagtgccttcgc
ccccgcctggcggcgcgcgcc
accgccgcctcagcactgaaggcgcgctgacgtcactcgccggtcccccgcaaactccc
cttcccggccaccttggtcgc
gtccgcgccgccgccggcccagccggaccgcaccacgcgaggcgcgagataggggggca
cgggcgcgaccatctgcgctg
cggcgccggcgactcagcgctgcctcagtctgcggtgggcagcggaggagtcgtgtcgt
gcctgagagcgcagtcgagaa
ggtaccggatccgccaccatggaccccatcgctctgcaggctggttacgacctgctggg
tgacggcagacctgaaactct
gtggctgggcatcggcactctgctgatgctgattggaaccttctactttctggtccgcg
gatggggagtcaccgataagg
atgcccgggaatattacgctgtgactatcctggtgcccggaatcgcatccgccgcatat
ctgtctatgttctttggtatc
gggcttactgaggtgaccgtcggggggcgaaatgttggatatctattatgccaggtacgc
cgactggctgtttaccacccc
acttctgctgctggatctggcccttctcgctaaggtggatcgggtgaccatcggcaccc
tggtgggtgtggacgccctga
tgatcgtcactggcctcatcggagccttgagccacacggccatagccagatacagttgg
tggttgttctctacaatttgc
atgatagtggtgctctatttctggctacatccctgcgatctgctgcaaaggagcgggg
ccccgaggtggcatctaccTT

```
taacaccctgacagctctggtcttggtgctgtggaccgcttaccctatcctgtggatca
taggcactgagggcgctggcg
tggtgggcctgggcatcgaaactctgctgtttatggtgttggacgtgactgccaaggtc
ggctttggctttatcctgttg
agatcccgggctattctgggcgacaccgaggcaccagaacccagtgccggtgccgatgt
cagtgccgccgacaagagcag
gatcaccagcgagggcgagtacatcccctggaccagatcgacatcaacgtgggcgcgc
ccggctccggagccacgaact
tctctctgttaaagcaagcaggagacgtggaagaaaaccccggtcccatggacctgaag
gagtcaccaagcgagggatca
ctgcagccatcaagcattcagattttcgctaatacaagcacactgcacggcatccggca
tatcttcgtgtacggcccact
gaccattcggagagtcctgtgggcagtggcctttgtcggaagcctgggactgctgctgg
tggagagctccgaaagagtca
gttactatttctcatatcagcacgtgactaaggtggacgaggtggtcgctcagtccctg
gtgtttccgcagtcaccctg
tgcaacctgaatgggttcaggttttctcgcctgaccacaaacgacctgtaccacgccgg
agagctgctggctctgctgga
tgtgaatctgcagatcccagacccccatctggccgatccaaccgtgctggaagcactga
ggcagaaggccaacttcaaac
actacaagcccaaacagttcagcatgctggagtttctgcaccgcgtgggacatgacctg
aaagatatgatgctgtattgc
aagttcaaaggccaggagtgtgggcatcaggacttcactaccgtgtttacaaagtacgg
caaatgttacatgttcaactc
cggggaagatggaaaacctctgctgacaactgtgaagggcgggacagggaatggactgg
agatcatgctggacattcagc
aggatgagtacctgccaatctggggagaaactgaggaaaccacattcgaggccggcgtg
aaggtccagatccactcacag
agcgagccccctttcattcaggaactgggatttggagtggcaccaggattccagacatt
tgtcgctactcaggagcagcg
cctgacctatctgccaccccttggggcgagtgccgatctagtgaaatggggctggact
tctttcctgtgtactctatca
```

FIG. 61M-2 ccgcctgccgaattgattgtgagacacggtatatcgtggaaaactgcaattgtaggatg
gtccacatgcctggcgacgcc
ccattctgcactcccgaacagcataaagagtgtgctgaacctgcactggggctgctggc
tgagaaggatagtaactactg
cctgtgtagaacaccctgtaacctgactaggtataataaggaactgagcatggtgaaga
tcccttccaaaacatctgcaa
agtacctggagaagaagttcaacaagtctgagaagtacatcagtgaaaacattctggtg
ctggacatcttctttgaagct
ctgaattacgagaccattgaacagaagaaagcatatgaggtggccgctctgctggggga
tattggaggccagatgggact
gttcatcggcgccagcctgctgacaattctggagctgtttgactacatctatgagctga
ttaaggaaaaactgctggatc
tgctggggaaggaggaagaggaaggatcacacgacgaaaacatgagcacttgcgatacc
atgcctaatcacagcgagacc
atctcccatacagtgaatgtcccactgcagactgcactgggcaccctggaggaaattgc
ctgtgcggccgccaagagcag
gatcaccagcgagggcgagtacatcccctggaccagatcgacatcaacgtggtgagca
agggcgaggagctgttcaccg
gggtggtgcccatcctggtcgagctggacggcgacgtaaacggccacaagttcagcgtg
tccggcgagggcgagggcgat
gccacctacggcaagctgaccctgaagttcatctgcaccaccggcaagctgcccgtgcc
ctggcccaccctcgtgaccac
cttcggctacggcctgcagtgcttcgcccgctaccccgaccacatgaagcagcacgact
tcttcaagtccgccatgcccg
aaggctacgtccaggagcgcaccatcttcttcaaggacgacggcaactacaagacccgc
gccgaggtgaagttcgagggc
gacaccctggtgaaccgcatcgagctgaagggcatcgacttcaaggaggacggcaacat
cctggggcacaagctggagta
caactacaacagccacaacgtctatatcatggccgacaagcagaagaacggcatcaagg
tgaacttcaagatccgccaca
acatcgaggacggcagcgtgcagctcgccgaccactaccagcagaacacccccatcggc
gacggccccgtgctgctgccc

```
gacaaccactacctgagctaccagtccgccctgagcaaagaccccaacgagaagcgcga
tcacatggtcctgctggagtt
cgtgaccgccgccgggatcactctcggcatggacgagctgtacaagttctgctacgaga
acgaggtgtaatgagaattcg
atatcaagcttatcgataatcaacctctggattacaaatttgtgaaagattgactggt
attcttaactatgttgctcct
tttacgctatgtggatacgctgctttaatgcctttgtatcatgctattgcttcccgtat
ggctttcattttctcctcctt
gtataaatcctggttgctgtctctttatgaggagttgtggcccgttgtcaggcaacgtg
gcgtggtgtgcactgtgtttg
ctgacgcaaccccactggttggggcattgccaccacctgtcagctcctttccgggact
tcgctttccccctccctatt
gccacggcggaactcatcgccgcctgccttgcccgctgctggacaggggctcggctgtt
gggcactgacaattccgtggt
gttgtcggggaaatcatcgtcctttccttggctgctcgcctgtgttgccacctggattc
tgcgcgggacgtccttctgct
acgtcccttcggccctcaatccagcggaccttccttcccgcggcctgctgccggctctg
cggcctcttccgcgtcttcgc
cttcgccctcagacgagtcggatctccctttgggccgcctccccgcatcgataccgagc
gctgctcgagagatctacggg
tggcatccctgtgaccccctccccagtgcctctcctggccctggaagttgccactccagt
gcccaccagccttgtcctaat
aaaattaagttgcatcattttgtctgactaggtgtccttctataatattatggggtgga
ggggggtggtatggagcaagg
ggcaagttgggaagacaacctgtagggcctgcggggtctattgggaaccaagctggagt
gcagtggcacaatcttggctc
actgcaatctccgcctcctgggttcaagcgattctcctgcctcagcctcccgagttgtt
gggattccaggcatgcatgac
caggctcagctaattttgtttttttggtagagacggggtttcaccatattggccaggc
tggtctccaactcctaatctc
aggtgatctacccaccttggcctcccaaattgctgggattacaggcgtgaaccactgct
cccttccctgtccttctgatt
```

*FIG. 61M-4*

```
ttgtaggtaaccacgtgcggaccgagcggccgcaggaaccccctagtgatggagttggcc
actccctctctgcgcgctcgc
tcgctcactgaggccgggcgaccaaaggtcgcccgacgcccgggctttgcccgggcggc
ctcagtgagcgagcgagcgcg
cagctgcctgcaggggcgcctgatgcggtattttctccttacgcatctgtgcggtattt
cacaccgcatacgtcaaagca
accatagtacgcgccctgtagcggcgcattaagcgcggcgggtgtggtggttacgcgca
gcgtgaccgctacacttgcca
gcgccctagcgcccgctccttcgctttcttcccttcctttctcgccacgttcgccggc
tttccccgtcaagctctaaat
cgggggctcccttttagggttccgatttagtgctttacggcacctcgaccccaaaaaact
tgatttgggtgatggttcacg
tagtgggccatcgccctgatagacggttttttcgccctttgacgttggagtccacgttct
ttaatagtggactcttgttcc
aaactggaacaacactcaaccctatctcgggctattcttttgatttataagggattttg
ccgatttcggcctattggtta
aaaaatgagctgatttaacaaaaatttaacgcgaattttaacaaaatattaacgtttac
aattttatggtgcactctcag
tacaatctgctctgatgccgcatagttaagccagccccgacacccgccaacacccgctg
acgcgccctgacgggcttgtc
tgctcccggcatccgcttacagacaagctgtgaccgtctccggggagctgcatgtgtcag
aggttttcaccgtcatcaccg
aaacgcgcgagacgaaagggcctcgtgatacgcctatttttataggttaatgtcatgat
aataatggtttcttagacgtc
aggtggcacttttcggggaaatgtgcgcggaacccctatttgtttattttttctaaatac
attcaaatatgtatccgctca
tgagacaataaccctgataaatgcttcaataatattgaaaaaggaagagtatgagtatt
caacatttccgtgtcgccctt
attccctttttgcggcattttgccttcctgttttttgctcacccagaaacgctggtgaa
agtaaaagatgctgaagatca
gttgggtgcacgagtgggttacatcgaactggatctcaacagcggtaagatccttgaga
gttttcgccccgaagaacgtt
```

FIG. 61M-5 ttccaatgatgagcacttttaaagttctgctatgtggcgcggtattatcccgtattgac
gccgggcaagagcaactcggt
cgccgcatacactattctcagaatgacttggttgagtactcaccagtcacagaaaagca
tcttacggatggcatgacagt
aagagaattatgcagtgctgccataaccatgagtgataacactgcggccaacttacttc
tgacaacgatcggaggaccga
aggagctaaccgcttttttgcacaacatgggggatcatgtaactcgccttgatcgttgg
gaaccggagctgaatgaagcc
ataccaaacgacgagcgtgacaccacgatgcctgtagcaatggcaacaacgttgcgcaa
actattaactggcgaactact
tactctagcttcccggcaacaattaatagactggatggaggcggataaagttgcaggac
cacttctgcgctcggcccttc
cggctggctggtttattgctgataaatctggagccggtgagcgtgggtctcgcggtatc
attgcagcactggggccagat
ggtaagccctcccgtatcgtagttatctacacgacggggagtcaggcaactatggatga
acgaaatagacagatcgctga
gataggtgcctcactgattaagcattggtaactgtcagaccaagtttactcatatatac
tttagattgatttaaaacttc
attttaatttaaaaggatctaggtgaagatccttttttgataatctcatgaccaaaatc
ccttaacgtgagttttcgttc
cactgagcgtcagaccccgtagaaaagatcaaaggatcttcttgagatcctttttttct
gcgcgtaatctgctgcttgca
aacaaaaaaaccaccgctaccagcggtggtttgtttgccggatcaagagctaccaactc
tttttccgaaggtaactggct
tcagcagagcgcagataccaaatactgtccttctagtgtagccgtagttaggccaccac
ttcaagaactctgtagcaccg
cctacatacctcgctctgctaatcctgttaccagtggctgctgccagtggcgataagtc
gtgtcttaccgggttggactc
aagacgatagttaccggataaggcgcagcggtcgggctgaacggggggttcgtgcacac
agcccagcttggagcgaacga
cctacaccgaactgagatacctacagcgtgagctatgagaaagcgccacgcttcccgaa
gggagaaaggcggacaggtat

FIG. 61M-6 ccggtaagcggcagggtcggaacaggagagcgcacgagggagcttccaggggggaaacgc
ctggtatctttatagtcctgt
cgggtttcgccacctctgacttgagcgtcgattttgtgatgctcgtcaggggggcgga
gcctatggaaaaacgccagca
acgcggccttttacggttcctggccttttgctggccttttgctcacatgt

| $\tau_{off}$ | Excite | Inhibit | Biochemical Modulation |
|---|---|---|---|
| Fast (~1–100 millisecond $\tau_{off}$) | by depolarization:<br>ChR2<br>ChR2 (H134R)<br><br>ChETAs:<br>ChR2 (E123A)<br>ChR2 (E123T)<br><br>ChIEF<br><br>ChRFR (FR, channelrhodopsin-fast receiver)<br><br>ChRGR (GR, channelrhodopsin-green receiver)<br><br>ChRWR (channelrhodopsin-wide receiver)<br><br>VChR1<br>C1V1<br>C1V1 ChETA (E162T)<br>C1V1 ChETA (E122T/E162T)<br><br>ChR2 (T159C)<br>ChR2 (L132C) (CatCH)<br><br>ChR2 (E123T/T159C)<br><br>ReaChR<br>VCOMET<br><br>DChR1 | by hyperpolarization<br>NpHR<br>Arch<br>ArchT<br>eBR<br>GtR3 (Guillardia theta Rhodopsin 3)<br>Mac<br><br>by depolarization block:<br>ChR2<br>ChR2 (H134R)<br><br>ChETAs:<br>ChR2 (E123A)<br>ChR2 (E123T)<br><br>ChIEF<br><br>ChRFR (FR, channelrhodopsin-fast receiver)<br><br>ChRGR (GR, channelrhodopsin-green receiver)<br><br>ChRWR (channelrhodopsin-wide receiver)<br><br>VChR1<br>C1V1<br>C1V1 ChETA (E162T)<br>C1V1 ChETA (E122T/E162T)<br><br>ChR2 (T159C)<br>ChR2 (L132C)(CatCH)<br><br>ChR2 (E123T/T159C)<br>ReaChR<br>VCOMET<br>DChR1<br>Champ | |
| Slow (~1–100 second $\tau_{off}$) | by depolarization:<br>ChR2-step function opsins<br>ChR2 (C128A)<br>ChR2 (C128S)<br>ChR2 (D156A)<br>ChR2 (C128T)<br><br>VCHR1-step function | by depolarization block:<br>ChR2-step function opsins<br>ChR2 (C128A)<br>ChR2 (C128S)<br>ChR2 (D156A)<br>ChR2 (C128T)<br><br>VChR1-step function opsins<br>VChR1 (C123S) | Opto-β2AR<br>Opto-α1AR<br>Rh-CT(5-HT1A)<br>bPAC<br>BlaC |

| | opsins<br>VChR1 (C123S) | | |
|---|---|---|---|
| Very Slow<br>(~minutes<br>$\tau_{off}$) | by depolarization:<br>ChR2 (D156A/C128S)<br>(SSFO)<br><br>VChR1 (C123S/D151A)<br>(VSSFO) | by depolarization block:<br>ChR2 (D156A/C128S)(SSFO)<br><br>VChR1 (C123S/D151A)(VSSFO) | |

FIG. 62J-2

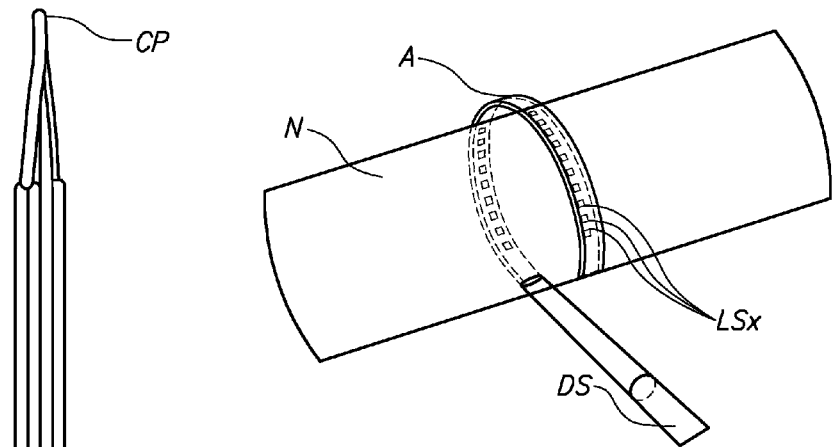
FIG. 79
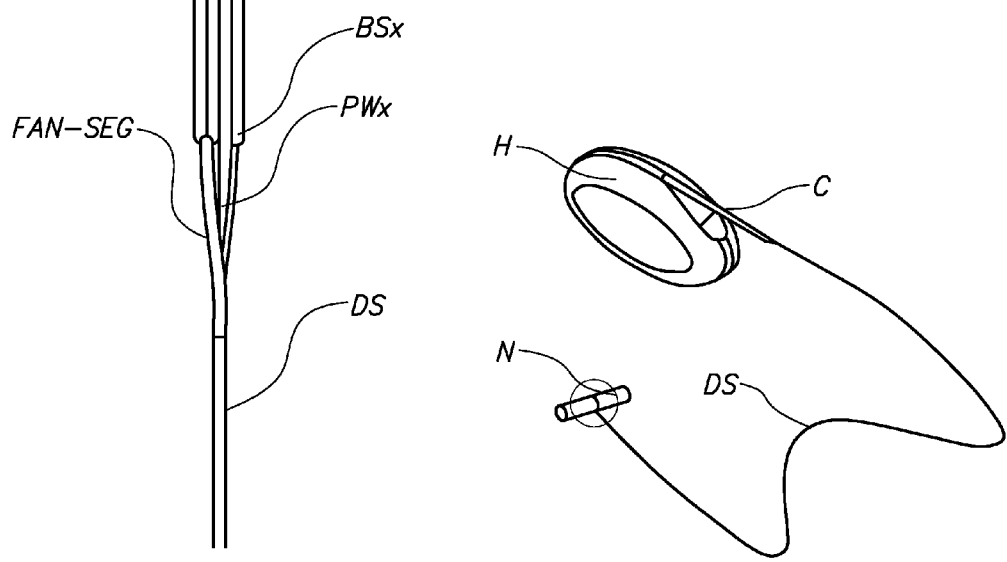
FIG. 78
FIG. 80

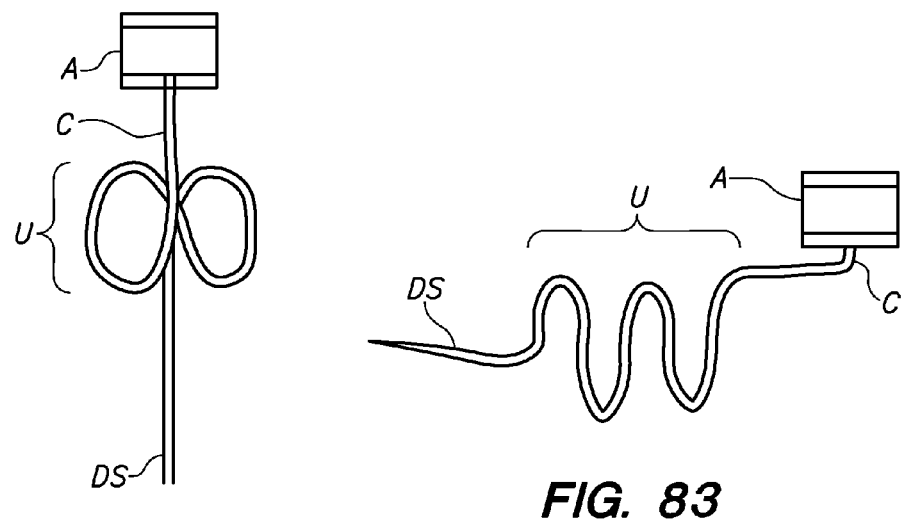
FIG. 82D
FIG. 83
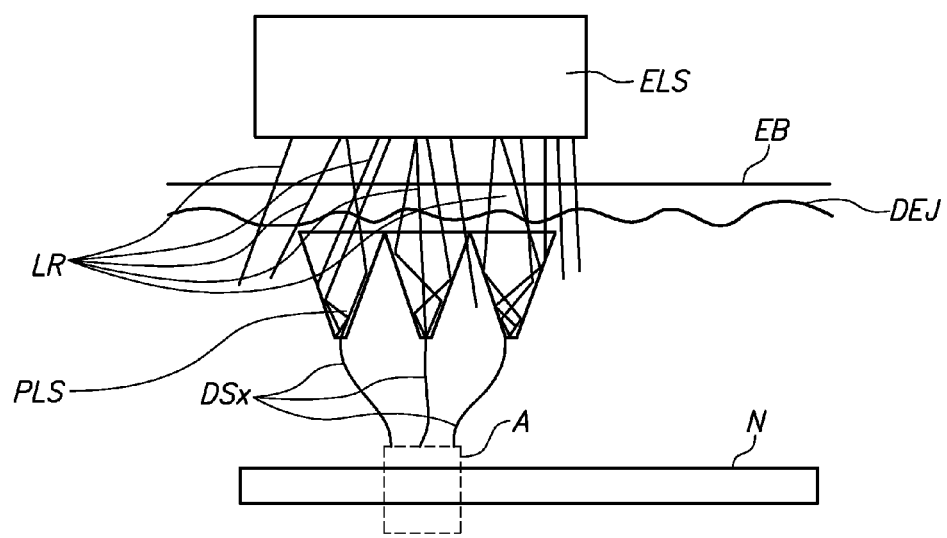
FIG. 84

SEQUENCE LISTING

```
<160> NUMBER OF SEQ ID NOS: 50

<210> SEQ ID NO 1
<211> LENGTH: 310
<212> TYPE: PRT
<213> ORGANISM: Chlamydomonas rheinhardtii

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175
```

```
Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 2
<211> LENGTH: 310
<212> TYPE: PRT
<213> ORGANISM: Chlamydomonas rheinhardtii

<400> SEQUENCE: 2

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ala
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240
```

```
Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 3
<211> LENGTH: 310
<212> TYPE: PRT
<213> ORGANISM: Chlamydomonas rheinhardtii

<400> SEQUENCE: 3

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
```

290                 295                 300
Glu Ala Gly Ala Val Pro
305                 310

<210> SEQ ID NO 4
<211> LENGTH: 310
<212> TYPE: PRT
<213> ORGANISM: Chlamydomonas rheinhardtii

<400> SEQUENCE: 4

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Thr
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 5
<211> LENGTH: 310
<212> TYPE: PRT
<213> ORGANISM: Chlamydomonas rheinhardtii

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Pro
305             310

<210> SEQ ID NO 6
<211> LENGTH: 310
<212> TYPE: PRT
<213> ORGANISM: Chlamydomonas rheinhardtii

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

```
Gln Thr Ala Ser Asn Val Leu Gln Trp Leu Ala Ala Gly Phe Ser Ile
     50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 7
<211> LENGTH: 310
<212> TYPE: PRT
<213> ORGANISM: Chlamydomonas rheinhardtii

<400> SEQUENCE: 7

Met Asp Tyr Gly Gly Ala Leu Ser Ala Val Gly Arg Glu Leu Leu Phe
 1                   5                  10                  15

Val Thr Asn Pro Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
     50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110
```

```
Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Cys Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro
305                 310

<210> SEQ ID NO 8
<211> LENGTH: 310
<212> TYPE: PRT
<213> ORGANISM: Chlamydomonas rheinhardtii

<400> SEQUENCE: 8

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
            50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
                115                 120                 125

Pro Val Ile Cys Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
```

```
                    165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
            195                 200                 205
Arg Gln Val Val Thr Gly Met Ala Trp Leu Phe Phe Val Ser Trp Gly
            210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
            245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
            290                 295                 300
Glu Ala Gly Ala Val Pro
305                 310

<210> SEQ ID NO 9
<211> LENGTH: 310
<212> TYPE: PRT
<213> ORGANISM: Chlamydomonas rheinhardtii

<400> SEQUENCE: 9

Met Asp Tyr Gly Gly Ala Leu Ser Ala Val Gly Arg Glu Leu Leu Phe
1               5                   10                  15
Val Thr Asn Pro Val Val Val Asn Gly Ser Val Leu Val Pro Glu Asp
            20                  25                  30
Gln Cys Tyr Cys Ala Gly Trp Ile Glu Ser Arg Gly Thr Asn Gly Ala
            35                  40                  45
Gln Thr Ala Ser Asn Val Leu Gln Trp Leu Ala Ala Gly Phe Ser Ile
50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Thr Trp Leu Leu Thr Cys
            115                 120                 125
Pro Val Ile Leu Ile His Leu Ser Asn Leu Thr Gly Leu Ser Asn Asp
            130                 135                 140
Tyr Ser Arg Arg Thr Met Gly Leu Leu Val Ser Asp Ile Gly Cys Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
            195                 200                 205
Arg Gln Val Val Thr Gly Met Ala Trp Leu Phe Phe Val Ser Trp Gly
            210                 215                 220
```

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
    275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 10
<211> LENGTH: 310
<212> TYPE: PRT
<213> ORGANISM: Chlamydomonas rheinhardtii

<400> SEQUENCE: 10

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
    275                 280                 285
```

```
Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 11
<211> LENGTH: 310
<212> TYPE: PRT
<213> ORGANISM: Chlamydomonas rheinhardtii

<400> SEQUENCE: 11

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Ala Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 12
<211> LENGTH: 310
<212> TYPE: PRT
```

<213> ORGANISM: Chlamydomonas rheinhardtii

<400> SEQUENCE: 12

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Thr Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 13
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 13

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 14
<211> LENGTH: 285
<212> TYPE: PRT
<213> ORGANISM: Artificial sequence
<220> FEATURE:
<223> OTHER INFORMATION: Synthetic polypeptide

<400> SEQUENCE: 14

Asn Asn Gly Ser Val Ile Cys Ile Pro Asn Asn Gly Gln Cys Phe Cys
 1               5                   10                  15

Leu Ala Trp Leu Lys Ser Asn Gly Thr Asn Ala Glu Lys Leu Ala Ala
             20                  25                  30

Asn Ile Leu Gln Trp Ile Thr Phe Ala Leu Ser Ala Leu Cys Leu Met
         35                  40                  45

```
Phe Tyr Gly Tyr Gln Thr Trp Lys Ser Thr Cys Gly Trp Glu Thr Ile
     50                  55                  60

Tyr Val Ala Thr Ile Glu Met Ile Lys Phe Ile Glu Tyr Phe His
65                  70                  75                  80

Glu Phe Asp Glu Pro Ala Val Ile Tyr Ser Ser Asn Gly Asn Lys Thr
                 85                  90                  95

Val Trp Leu Arg Tyr Ala Glu Trp Leu Leu Thr Cys Pro Val Leu Leu
                100                 105                 110

Ile His Leu Ser Asn Leu Thr Gly Leu Lys Asp Asp Tyr Ser Lys Arg
            115                 120                 125

Thr Met Gly Leu Leu Val Ser Asp Val Gly Cys Ile Val Trp Gly Ala
        130                 135                 140

Thr Ser Ala Met Cys Thr Gly Trp Thr Lys Ile Leu Phe Phe Leu Ile
145                 150                 155                 160

Ser Leu Ser Tyr Gly Met Tyr Thr Tyr Phe His Ala Ala Lys Val Tyr
                165                 170                 175

Ile Glu Ala Phe His Thr Val Pro Lys Gly Ile Cys Arg Glu Leu Val
                180                 185                 190

Arg Val Met Ala Trp Thr Phe Phe Val Ala Trp Gly Met Phe Pro Val
            195                 200                 205

Leu Phe Leu Leu Gly Thr Glu Gly Phe Gly His Ile Ser Pro Tyr Gly
        210                 215                 220

Ser Ala Ile Gly His Ser Ile Leu Asp Leu Ile Ala Lys Asn Met Trp
225                 230                 235                 240

Gly Val Leu Gly Asn Tyr Leu Arg Val Lys Ile His Glu His Ile Leu
                245                 250                 255

Leu Tyr Gly Asp Ile Arg Lys Lys Gln Lys Ile Thr Ile Ala Gly Gln
                260                 265                 270

Glu Met Glu Val Glu Thr Leu Val Ala Glu Glu Asp
            275                 280                 285

<210> SEQ ID NO 15
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 15

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125
```

```
Glu Met Ile Lys Phe Ile Ile Glu Tyr Phe His Glu Phe Asp Glu Pro
        130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 16
<211> LENGTH: 344
<212> TYPE: PRT
<213> ORGANISM: Artificial sequence
<220> FEATURE:
<223> OTHER INFORMATION: Synthetic polypeptide

<400> SEQUENCE: 16

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140
```

-continued

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Ile His Leu Ser Asn
            165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 17
<211> LENGTH: 357
<212> TYPE: PRT
<213> ORGANISM: Artificial sequence
<220> FEATURE:
<223> OTHER INFORMATION: Synthetic polypeptide

<400> SEQUENCE: 17

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
    130                 135                 140

Ala Thr Leu Trp Leu Ser Ser Gly Asn Gly Val Val Trp Met Arg Tyr
145                 150                 155                 160

```
Gly Thr Trp Leu Leu Thr Cys Pro Val Leu Ile His Leu Ser Asn
                165                 170                 175
Leu Thr Gly Leu Lys Asp Asp Tyr Ser Lys Arg Thr Met Gly Leu Leu
        180                 185                 190
Val Ser Asp Ile Ala Cys Ile Val Trp Gly Ala Thr Ser Ala Met Cys
            195                 200                 205
Thr Gly Trp Thr Lys Ile Leu Phe Phe Leu Ile Ser Leu Ser Tyr Gly
        210                 215                 220
Met Tyr Thr Tyr Phe His Ala Ala Lys Val Tyr Ile Glu Ala Phe His
225                 230                 235                 240
Thr Val Pro Lys Gly Ile Cys Arg Glu Leu Val Arg Val Met Ala Trp
                245                 250                 255
Thr Phe Phe Val Ala Trp Gly Met Phe Pro Val Leu Phe Leu Leu Gly
            260                 265                 270
Thr Glu Gly Phe Gly His Ile Ser Pro Tyr Gly Ser Ala Ile Gly His
        275                 280                 285
Ser Ile Leu Asp Leu Ile Ala Lys Asn Met Trp Gly Val Leu Gly Asn
    290                 295                 300
Tyr Leu Arg Val Lys Ile His Glu His Ile Leu Leu Tyr Gly Asp Ile
305                 310                 315                 320
Arg Lys Lys Gln Lys Ile Thr Ile Ala Gly Gln Glu Met Glu Val Glu
                325                 330                 335
Thr Leu Val Ala Glu Glu Glu Asp Asp Thr Val Lys Gln Ser Thr Ala
            340                 345                 350
Lys Tyr Ala Ser Arg
        355

<210> SEQ ID NO 18
<211> LENGTH: 361
<212> TYPE: PRT
<213> ORGANISM: Artificial sequence
<220> FEATURE:
<223> OTHER INFORMATION: Synthetic polypeptide

<400> SEQUENCE: 18

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
            20                  25                  30
Val Ala Thr Gln Asp Gly Pro Asp Tyr Val Phe His Arg Ala His Glu
        35                  40                  45
Arg Met Leu Phe Gln Thr Ser Tyr Thr Leu Glu Asn Asn Gly Ser Val
    50                  55                  60
Ile Cys Ile Pro Asn Asn Gly Gln Cys Phe Cys Leu Ala Trp Leu Lys
65                  70                  75                  80
Ser Asn Gly Thr Asn Ala Glu Lys Leu Ala Ala Asn Ile Leu Gln Trp
                85                  90                  95
Ile Thr Phe Ala Leu Ser Ala Leu Cys Leu Met Phe Tyr Gly Tyr Gln
            100                 105                 110
Thr Trp Lys Ser Thr Cys Gly Trp Glu Thr Ile Tyr Val Ala Thr Ile
        115                 120                 125
Glu Met Ile Lys Phe Ile Ile Glu Tyr Phe His Glu Phe Asp Glu Pro
    130                 135                 140
Ala Thr Leu Trp Leu Ser Ser Gly Asn Gly Val Val Trp Met Arg Tyr
145                 150                 155                 160
```

```
Gly Glu Trp Leu Leu Thr Cys Pro Val Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Ile Ala Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp Asp Thr Val Lys Gln Ser Asn Pro
            340                 345                 350

His Arg Thr Ala Lys Tyr Ala Ser Arg
        355                 360

<210> SEQ ID NO 19
<211> LENGTH: 357
<212> TYPE: PRT
<213> ORGANISM: Artificial sequence
<220> FEATURE:
<223> OTHER INFORMATION: Synthetic polypeptide

<400> SEQUENCE: 19

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Thr Leu Trp Leu Ser Ser Gly Asn Gly Val Val Trp Met Arg Tyr
145                 150                 155                 160
```

```
Gly Thr Trp Leu Leu Thr Cys Pro Val Leu Ile His Leu Ser Asn
                165                 170                 175
Leu Thr Gly Leu Lys Asp Asp Tyr Ser Lys Arg Thr Met Gly Leu Leu
        180                 185                 190
Val Ser Asp Ile Ala Cys Ile Val Trp Gly Ala Thr Ser Ala Met Cys
            195                 200                 205
Thr Gly Trp Thr Lys Ile Leu Phe Phe Leu Ile Ser Leu Ser Tyr Gly
        210                 215                 220
Met Tyr Thr Tyr Phe His Ala Ala Lys Val Tyr Ile Glu Ala Phe His
225                 230                 235                 240
Thr Val Pro Lys Gly Ile Cys Arg Glu Leu Val Arg Val Met Ala Trp
                245                 250                 255
Thr Phe Phe Val Ala Trp Gly Met Phe Pro Val Leu Phe Leu Leu Gly
            260                 265                 270
Thr Glu Gly Phe Gly His Ile Ser Pro Tyr Gly Ser Ala Ile Gly His
        275                 280                 285
Ser Ile Leu Asp Leu Ile Ala Lys Asn Met Trp Gly Val Leu Gly Asn
    290                 295                 300
Tyr Leu Arg Val Lys Ile His Glu His Ile Leu Leu Tyr Gly Asp Ile
305                 310                 315                 320
Arg Lys Lys Gln Lys Ile Thr Ile Ala Gly Gln Glu Met Glu Val Glu
                325                 330                 335
Thr Leu Val Ala Glu Glu Glu Asp Asp Thr Val Lys Gln Ser Thr Ala
            340                 345                 350
Lys Tyr Ala Ser Arg
        355

<210> SEQ ID NO 20
<211> LENGTH: 300
<212> TYPE: PRT
<213> ORGANISM: Volvox carteri

<400> SEQUENCE: 20

Met Asp Tyr Pro Val Ala Arg Ser Leu Ile Val Arg Tyr Pro Thr Asp
1               5                   10                  15
Leu Gly Asn Gly Thr Val Cys Met Pro Arg Gly Gln Cys Tyr Cys Glu
            20                  25                  30
Gly Trp Leu Arg Ser Arg Gly Thr Ser Ile Glu Lys Thr Ile Ala Ile
        35                  40                  45
Thr Leu Gln Trp Val Val Phe Ala Leu Ser Val Ala Cys Leu Gly Trp
    50                  55                  60
Tyr Ala Tyr Gln Ala Trp Arg Ala Thr Cys Gly Trp Glu Glu Val Tyr
65              70                  75                  80
Val Ala Leu Ile Glu Met Met Lys Ser Ile Ile Glu Ala Phe His Glu
                85                  90                  95
Phe Asp Ser Pro Ala Thr Leu Trp Leu Ser Ser Gly Asn Gly Val Val
            100                 105                 110
Trp Met Arg Tyr Gly Glu Trp Leu Leu Thr Cys Pro Val Leu Leu Ile
        115                 120                 125
His Leu Ser Asn Leu Thr Gly Leu Lys Asp Asp Tyr Ser Lys Arg Thr
    130                 135                 140
Met Gly Leu Leu Val Ser Asp Val Gly Cys Ile Val Trp Gly Ala Thr
145                 150                 155                 160
Ser Ala Met Cys Thr Gly Trp Thr Lys Ile Leu Phe Phe Leu Ile Ser
```

```
                      165                 170                 175
Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
        210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 21
<211> LENGTH: 300
<212> TYPE: PRT
<213> ORGANISM: Volvox carteri

<400> SEQUENCE: 21

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Ser Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240
```

```
Ala Ile Gly His Ser Ile Leu Asp Leu Ile Ala Lys Asn Met Trp Gly
            245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 22
<211> LENGTH: 300
<212> TYPE: PRT
<213> ORGANISM: Volvox carteri

<400> SEQUENCE: 22

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Ser Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Ala Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 23
```

```
<211> LENGTH: 350
<212> TYPE: PRT
<213> ORGANISM: Chlamydomonas rheinhardtii

<400> SEQUENCE: 23
```

| | | | | | | | | | | | | | | |
|---|---|---|---|---|---|---|---|---|---|---|---|---|---|---|
| Met | Val | Ser | Arg | Arg | Pro | Trp | Leu | Leu | Ala | Leu | Ala | Leu | Ala | Val | Ala |
| 1 | | | | 5 | | | | | 10 | | | | | 15 | |
| Leu | Ala | Ala | Gly | Ser | Ala | Gly | Ala | Ser | Thr | Gly | Ser | Asp | Ala | Thr | Val |
| | | | 20 | | | | | 25 | | | | | 30 | | |
| Pro | Val | Ala | Thr | Gln | Asp | Gly | Pro | Asp | Tyr | Val | Phe | His | Arg | Ala | His |
| | | | 35 | | | | | 40 | | | | | 45 | | |
| Glu | Arg | Met | Leu | Phe | Gln | Thr | Ser | Tyr | Thr | Leu | Glu | Asn | Asn | Gly | Ser |
| | 50 | | | | | 55 | | | | | 60 | | | | |
| Val | Ile | Cys | Ile | Pro | Asn | Asn | Gly | Gln | Cys | Phe | Cys | Leu | Ala | Trp | Leu |
| 65 | | | | | 70 | | | | | 75 | | | | | 80 |
| Lys | Ser | Asn | Gly | Thr | Asn | Ala | Glu | Lys | Leu | Ala | Ala | Asn | Ile | Leu | Gln |
| | | | | 85 | | | | | 90 | | | | | 95 | |
| Trp | Val | Val | Phe | Ala | Leu | Ser | Val | Ala | Cys | Leu | Gly | Trp | Tyr | Ala | Tyr |
| | | | 100 | | | | | 105 | | | | | 110 | | |
| Gln | Ala | Trp | Arg | Ala | Thr | Cys | Gly | Trp | Glu | Glu | Val | Tyr | Val | Ala | Leu |
| | | | 115 | | | | | 120 | | | | | 125 | | |
| Ile | Glu | Met | Met | Lys | Ser | Ile | Ile | Glu | Ala | Phe | His | Glu | Phe | Asp | Ser |
| | 130 | | | | | 135 | | | | | 140 | | | | |
| Pro | Ala | Thr | Leu | Trp | Leu | Ser | Ser | Gly | Asn | Gly | Val | Val | Trp | Met | Arg |
| 145 | | | | | 150 | | | | | 155 | | | | | 160 |
| Tyr | Gly | Glu | Trp | Leu | Leu | Thr | Cys | Pro | Val | Ile | Leu | Ile | His | Leu | Ser |
| | | | | 165 | | | | | 170 | | | | | 175 | |
| Asn | Leu | Thr | Gly | Leu | Lys | Asp | Asp | Tyr | Ser | Lys | Arg | Thr | Met | Gly | Leu |
| | | | 180 | | | | | 185 | | | | | 190 | | |
| Leu | Val | Ser | Asp | Val | Gly | Cys | Ile | Val | Trp | Gly | Ala | Thr | Ser | Ala | Met |
| | | | 195 | | | | | 200 | | | | | 205 | | |
| Cys | Thr | Gly | Trp | Thr | Lys | Ile | Leu | Phe | Phe | Leu | Ile | Ser | Leu | Ser | Tyr |
| | 210 | | | | | 215 | | | | | 220 | | | | |
| Gly | Met | Tyr | Thr | Tyr | Phe | His | Ala | Ala | Lys | Val | Tyr | Ile | Glu | Ala | Phe |
| 225 | | | | | 230 | | | | | 235 | | | | | 240 |
| His | Thr | Val | Pro | Lys | Gly | Leu | Cys | Arg | Gln | Leu | Val | Arg | Ala | Met | Ala |
| | | | | 245 | | | | | 250 | | | | | 255 | |
| Trp | Leu | Phe | Phe | Val | Ser | Trp | Gly | Met | Phe | Pro | Val | Leu | Phe | Leu | Leu |
| | | | 260 | | | | | 265 | | | | | 270 | | |
| Gly | Pro | Glu | Gly | Phe | Gly | His | Ile | Ser | Pro | Tyr | Gly | Ser | Ala | Ile | Gly |
| | | | 275 | | | | | 280 | | | | | 285 | | |
| His | Ser | Ile | Leu | Asp | Leu | Ile | Ala | Lys | Asn | Met | Trp | Gly | Val | Leu | Gly |
| | 290 | | | | | 295 | | | | | 300 | | | | |
| Asn | Tyr | Leu | Arg | Val | Lys | Ile | His | Glu | His | Ile | Leu | Leu | Tyr | Gly | Asp |
| 305 | | | | | 310 | | | | | 315 | | | | | 320 |
| Ile | Arg | Lys | Lys | Gln | Lys | Ile | Thr | Ile | Ala | Gly | Gln | Glu | Met | Glu | Val |
| | | | | 325 | | | | | 330 | | | | | 335 | |
| Glu | Thr | Leu | Val | Ala | Glu | Glu | Glu | Asp | Lys | Tyr | Glu | Ser | Ser | | |
| | | | 340 | | | | | 345 | | | | | 350 | | |

```
<210> SEQ ID NO 24
<211> LENGTH: 350
<212> TYPE: PRT
<213> ORGANISM: Artificial sequence
<220> FEATURE:
<223> OTHER INFORMATION: Synthetic polypeptide
```

<400> SEQUENCE: 24

| | | | | | | | | | | | | | | | |
|---|---|---|---|---|---|---|---|---|---|---|---|---|---|---|---|
| Met | Val | Ser | Arg | Arg | Pro | Trp | Leu | Leu | Ala | Leu | Ala | Leu | Ala | Val | Ala |
| 1 | | | | 5 | | | | | 10 | | | | | 15 | |
| Leu | Ala | Ala | Gly | Ser | Ala | Gly | Ala | Ser | Thr | Gly | Ser | Asp | Ala | Thr | Val |
| | | | 20 | | | | | 25 | | | | | 30 | | |
| Pro | Val | Ala | Thr | Gln | Asp | Gly | Pro | Asp | Tyr | Val | Phe | His | Arg | Ala | His |
| | | | 35 | | | | | 40 | | | | | 45 | | |
| Glu | Arg | Met | Leu | Phe | Gln | Thr | Ser | Tyr | Thr | Leu | Glu | Asn | Asn | Gly | Ser |
| | 50 | | | | | 55 | | | | | 60 | | | | |
| Val | Ile | Cys | Ile | Pro | Asn | Asn | Gly | Gln | Cys | Phe | Cys | Leu | Ala | Trp | Leu |
| 65 | | | | | 70 | | | | | 75 | | | | | 80 |
| Lys | Ser | Asn | Gly | Thr | Asn | Ala | Glu | Lys | Leu | Ala | Ala | Asn | Ile | Leu | Gln |
| | | | | 85 | | | | | 90 | | | | | 95 | |
| Trp | Val | Val | Phe | Ala | Leu | Ser | Val | Ala | Cys | Leu | Gly | Trp | Tyr | Ala | Tyr |
| | | | 100 | | | | | 105 | | | | | 110 | | |
| Gln | Ala | Trp | Arg | Ala | Thr | Cys | Gly | Trp | Glu | Glu | Val | Tyr | Val | Ala | Leu |
| | | | 115 | | | | | 120 | | | | | 125 | | |
| Ile | Glu | Met | Met | Lys | Ser | Ile | Ile | Glu | Ala | Phe | His | Glu | Phe | Asp | Ser |
| | 130 | | | | | 135 | | | | | 140 | | | | |
| Pro | Ala | Thr | Leu | Trp | Leu | Ser | Ser | Gly | Asn | Gly | Val | Val | Trp | Met | Arg |
| 145 | | | | | 150 | | | | | 155 | | | | | 160 |
| Tyr | Gly | Glu | Trp | Leu | Leu | Thr | Cys | Pro | Val | Leu | Leu | Ile | His | Leu | Ser |
| | | | | 165 | | | | | 170 | | | | | 175 | |
| Asn | Leu | Thr | Gly | Leu | Lys | Asp | Asp | Tyr | Ser | Lys | Arg | Thr | Met | Gly | Leu |
| | | | 180 | | | | | 185 | | | | | 190 | | |
| Leu | Val | Ser | Asp | Val | Gly | Cys | Ile | Val | Trp | Gly | Ala | Thr | Ser | Ala | Met |
| | | | 195 | | | | | 200 | | | | | 205 | | |
| Cys | Thr | Gly | Trp | Thr | Lys | Ile | Leu | Phe | Phe | Leu | Ile | Ser | Leu | Ser | Tyr |
| | 210 | | | | | 215 | | | | | 220 | | | | |
| Gly | Met | Tyr | Thr | Tyr | Phe | His | Ala | Ala | Lys | Val | Tyr | Ile | Glu | Ala | Phe |
| 225 | | | | | 230 | | | | | 235 | | | | | 240 |
| His | Thr | Val | Pro | Lys | Gly | Leu | Cys | Arg | Gln | Leu | Val | Arg | Ala | Met | Ala |
| | | | | 245 | | | | | 250 | | | | | 255 | |
| Trp | Leu | Phe | Phe | Val | Ser | Trp | Gly | Met | Phe | Pro | Val | Leu | Phe | Leu | Leu |
| | | | | 260 | | | | | 265 | | | | | 270 | |
| Gly | Pro | Glu | Gly | Phe | Gly | His | Ile | Ser | Pro | Tyr | Gly | Ser | Ala | Ile | Gly |
| | | | | 275 | | | | | 280 | | | | | 285 | |
| His | Ser | Ile | Leu | Asp | Leu | Ile | Ala | Lys | Asn | Met | Trp | Gly | Val | Leu | Gly |
| | 290 | | | | | 295 | | | | | 300 | | | | |
| Asn | Tyr | Leu | Arg | Val | Lys | Ile | His | Glu | His | Ile | Leu | Leu | Tyr | Gly | Asp |
| 305 | | | | | 310 | | | | | 315 | | | | | 320 |
| Ile | Arg | Lys | Lys | Gln | Lys | Ile | Thr | Ile | Ala | Gly | Gln | Glu | Met | Glu | Val |
| | | | | 325 | | | | | 330 | | | | | 335 | |
| Glu | Thr | Leu | Val | Ala | Glu | Glu | Asp | Lys | Tyr | Glu | Ser | Ser | | | |
| | | | 340 | | | | | 345 | | | | | 350 | | |

<210> SEQ ID NO 25
<211> LENGTH: 258
<212> TYPE: PRT
<213> ORGANISM: Halorubrum sodomense

<400> SEQUENCE: 25

| | | | | | | | | | | | | | | | |
|---|---|---|---|---|---|---|---|---|---|---|---|---|---|---|---|
| Met | Asp | Pro | Ile | Ala | Leu | Gln | Ala | Gly | Tyr | Asp | Leu | Leu | Gly | Asp | Gly |
| 1 | | | | 5 | | | | | 10 | | | | | 15 | |

Arg Pro Glu Thr Leu Trp Leu Gly Ile Gly Thr Leu Met Leu Ile
            20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
 50                      55                  60

Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
                 85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 26
<211> LENGTH: 248
<212> TYPE: PRT
<213> ORGANISM: Artificial sequence
<220> FEATURE:
<223> OTHER INFORMATION: Synthetic polypeptide

<400> SEQUENCE: 26

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Met Leu Ile
            20                  25                  30

Gly Thr Phe Tyr Phe Ile Val Lys Gly Trp Gly Val Thr Asp Lys Glu
            35                  40                  45

Ala Arg Glu Tyr Tyr Ser Ile Thr Ile Leu Val Pro Gly Ile Ala Ser
 50                      55                  60

Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
                 85                  90                  95

Leu Phe Thr Thr Pro Leu Leu Leu Asp Leu Ala Leu Leu Ala Lys
            100                 105                 110

```
Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245
```

<210> SEQ ID NO 27
<211> LENGTH: 534
<212> TYPE: PRT
<213> ORGANISM: Artificial sequence
<220> FEATURE:
<223> OTHER INFORMATION: Synthetic polypeptide

<400> SEQUENCE: 27

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220
```

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
            245                 250                 255

Ala Asp Arg Pro Val Val Ala Val Ser Lys Ala Ala Lys Ser Arg
        260                 265                 270

Ile Thr Ser Glu Gly Glu Tyr Ile Pro Leu Asp Gln Ile Asp Ile Asn
    275                 280                 285

Val Val Ser Lys Gly Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Phe Ile
            325                 330                 335

Cys Thr Thr Gly Lys Leu Pro Val Pro Trp Pro Thr Leu Val Thr Thr
            340                 345                 350

Phe Gly Tyr Gly Leu Gln Cys Phe Ala Arg Tyr Pro Asp His Met Lys
        355                 360                 365

Gln His Asp Phe Phe Lys Ser Ala Met Pro Glu Gly Tyr Val Gln Glu
    370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
            405                 410                 415

Ile Asp Phe Lys Glu Asp Gly Asn Ile Leu Gly His Lys Leu Glu Tyr
        420                 425                 430

Asn Tyr Asn Ser His Asn Val Tyr Ile Met Ala Asp Lys Gln Lys Asn
    435                 440                 445

Gly Ile Lys Val Asn Phe Lys Ile Arg His Asn Ile Glu Asp Gly Ser
450                 455                 460

Val Gln Leu Ala Asp His Tyr Gln Gln Asn Thr Pro Ile Gly Asp Gly
465                 470                 475                 480

Pro Val Leu Leu Pro Asp Asn His Tyr Leu Ser Tyr Gln Ser Ala Leu
            485                 490                 495

Ser Lys Asp Pro Asn Glu Lys Arg Asp His Met Val Leu Leu Glu Phe
        500                 505                 510

Val Thr Ala Ala Gly Ile Thr Leu Gly Met Asp Glu Leu Tyr Lys Phe
    515                 520                 525

Cys Tyr Glu Asn Glu Val
    530

<210> SEQ ID NO 28
<211> LENGTH: 313
<212> TYPE: PRT
<213> ORGANISM: Leptosphaeria maculans

<400> SEQUENCE: 28

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

```
Ala Ser Ala Ala Phe Thr Ala Leu Ser Trp Lys Ile Pro Val Asn Arg
 65                  70                  75                  80

Arg Leu Tyr His Val Ile Thr Thr Ile Ile Thr Leu Thr Ala Ala Leu
                 85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 29
<211> LENGTH: 262
<212> TYPE: PRT
<213> ORGANISM: Halobacterium salinarum

<400> SEQUENCE: 29

Met Leu Glu Leu Leu Pro Thr Ala Val Glu Gly Val Ser Gln Ala Gln
 1               5                  10                  15

Ile Thr Gly Arg Pro Glu Trp Ile Trp Leu Ala Leu Gly Thr Ala Leu
                20                  25                  30

Met Gly Leu Gly Thr Leu Tyr Phe Leu Val Lys Gly Met Gly Val Ser
             35                  40                  45

Asp Pro Asp Ala Lys Lys Phe Tyr Ala Ile Thr Thr Leu Val Pro Ala
         50                  55                  60

Ile Ala Phe Thr Met Tyr Leu Ser Met Leu Leu Gly Tyr Gly Leu Thr
 65                  70                  75                  80

Met Val Pro Phe Gly Gly Glu Gln Asn Pro Ile Tyr Trp Ala Arg Tyr
                 85                  90                  95

Ala Asp Trp Leu Phe Thr Thr Pro Leu Leu Leu Leu Asp Leu Ala Leu
            100                 105                 110

Leu Val Asp Ala Asp Gln Gly Thr Ile Leu Ala Leu Val Gly Ala Asp
```

```
            115                 120                 125
Gly Ile Met Ile Gly Thr Gly Leu Val Gly Ala Leu Thr Lys Val Tyr
        130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                    165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
        195                 200                 205

Ala Gly Ile Val Pro Leu Asn Ile Glu Thr Leu Leu Phe Met Val Leu
    210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                    245                 250                 255

Ala Ala Ala Thr Ser Asp
            260

<210> SEQ ID NO 30
<211> LENGTH: 365
<212> TYPE: PRT
<213> ORGANISM: Dunaliella salina

<400> SEQUENCE: 30

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
    130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220
```

```
Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
            245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
            275                 280                 285

Gly Arg Glu Gly Phe Gly His Ile Thr Tyr Phe Gly Ser Ser Ile Gly
            290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
            355                 360                 365

<210> SEQ ID NO 31
<211> LENGTH: 270
<212> TYPE: PRT
<213> ORGANISM: Guillardia theta

<400> SEQUENCE: 31

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Ser Ser Phe Gly Lys Ala Leu Leu Glu Phe Val Phe Ile Val Phe Ala
        50                  55                  60

Cys Ile Thr Leu Leu Leu Gly Ile Asn Ala Ala Lys Ser Lys Ala Ala
65                  70                  75                  80

Ser Arg Val Leu Phe Pro Ala Thr Phe Val Thr Gly Ile Ala Ser Ile
                85                  90                  95

Ala Tyr Phe Ser Met Ala Ser Gly Gly Gly Trp Val Ile Ala Pro Asp
            100                 105                 110

Cys Arg Gln Leu Phe Val Ala Arg Tyr Leu Asp Trp Leu Ile Thr Thr
            115                 120                 125

Pro Leu Leu Leu Ile Asp Leu Gly Leu Val Ala Gly Val Ser Arg Trp
130                 135                 140

Asp Ile Met Ala Leu Cys Leu Ser Asp Val Leu Met Ile Ala Thr Gly
145                 150                 155                 160

Ala Phe Gly Ser Leu Thr Val Gly Asn Val Lys Trp Val Trp Trp Phe
                165                 170                 175

Phe Gly Met Cys Trp Phe Leu His Ile Ile Phe Ala Leu Gly Lys Ser
            180                 185                 190

Trp Ala Glu Ala Ala Lys Ala Lys Gly Gly Asp Ser Ala Ser Val Tyr
            195                 200                 205

Ser Lys Ile Ala Gly Ile Thr Val Ile Thr Trp Phe Cys Tyr Pro Val
        210                 215                 220

Val Trp Val Phe Ala Glu Gly Phe Gly Asn Phe Ser Val Thr Phe Glu
225                 230                 235                 240
```

```
Val Leu Ile Tyr Gly Val Leu Asp Val Ile Ser Lys Ala Val Phe Gly
                245                 250                 255

Leu Ile Leu Met Ser Gly Ala Ala Thr Gly Tyr Glu Ser Ile
            260                 265                 270

<210> SEQ ID NO 32
<211> LENGTH: 291
<212> TYPE: PRT
<213> ORGANISM: Natromonas pharaonis

<400> SEQUENCE: 32

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290

<210> SEQ ID NO 33
<211> LENGTH: 559
<212> TYPE: PRT
<213> ORGANISM: Artificial sequence
<220> FEATURE:
<223> OTHER INFORMATION: Synthetic polypeptide
```

<400> SEQUENCE: 33

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
                115                 120                 125

Leu Ser Thr Pro Met Ile Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
                195                 200                 205

Asp Met Phe Asn Thr Leu Lys Leu Leu Thr Val Val Met Trp Leu Gly
                210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
                275                 280                 285

Ala Asp Asp Ala Ala Lys Ser Arg Ile Thr Ser Glu Gly Glu Tyr
                290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
                340                 345                 350

Tyr Gly Lys Leu Thr Leu Lys Phe Ile Cys Thr Thr Gly Lys Leu Pro
                355                 360                 365

Val Pro Trp Pro Thr Leu Val Thr Thr Phe Gly Tyr Gly Leu Gln Cys
                370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
```

```
                        405                 410                 415
Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
            450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
                485                 490                 495

Gln Gln Asn Thr Pro Ile Gly Asp Gly Pro Val Leu Leu Pro Asp Asn
            500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
530                 535                 540

Leu Gly Met Asp Glu Leu Tyr Lys Phe Cys Tyr Glu Asn Glu Val
545                 550                 555
```

<210> SEQ ID NO 34
<211> LENGTH: 542
<212> TYPE: PRT
<213> ORGANISM: Artificial sequence
<220> FEATURE:
<223> OTHER INFORMATION: Synthetic polypeptide

<400> SEQUENCE: 34

```
Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Ser Ile Ala Ser
50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
            85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
            115                 120                 125

Ala Thr Lys Leu Phe Thr Ala Ile Thr Phe Asp Ile Ala Met Cys Val
            130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
            195                 200                 205

Pro Ile Val Trp Ala Leu Gly Val Glu Gly Ile Ala Val Leu Pro Val
```

```
                    210                 215                 220
Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
                260                 265                 270

Asp Asp Ala Ala Ala Lys Ser Arg Ile Thr Ser Glu Gly Glu Tyr Ile
                275                 280                 285

Pro Leu Asp Gln Ile Asp Ile Asn Val Val Ser Lys Gly Glu Leu
290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
                340                 345                 350

Pro Trp Pro Thr Leu Val Thr Thr Phe Gly Tyr Gly Leu Gln Cys Phe
                355                 360                 365

Ala Arg Tyr Pro Asp His Met Lys Gln His Asp Phe Phe Lys Ser Ala
370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
                420                 425                 430

Ile Leu Gly His Lys Leu Glu Tyr Asn Tyr Asn Ser His Asn Val Tyr
                435                 440                 445

Ile Met Ala Asp Lys Gln Lys Asn Gly Ile Lys Val Asn Phe Lys Ile
                450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
                485                 490                 495

Tyr Leu Ser Tyr Gln Ser Ala Leu Ser Lys Asp Pro Asn Glu Lys Arg
                500                 505                 510

Asp His Met Val Leu Leu Glu Phe Val Thr Ala Ala Gly Ile Thr Leu
                515                 520                 525

Gly Met Asp Glu Leu Tyr Lys Phe Cys Tyr Glu Asn Glu Val
530                 535                 540

<210> SEQ ID NO 35
<211> LENGTH: 434
<212> TYPE: PRT
<213> ORGANISM: Artificial sequence
<220> FEATURE:
<223> OTHER INFORMATION: Synthetic polypeptide

<400> SEQUENCE: 35

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
                20                  25                  30

Glu Pro Trp Gln Phe Ser Met Leu Ala Ala Tyr Met Phe Leu Leu Ile
```

```
                    35                  40                  45
Met Leu Gly Phe Pro Ile Asn Phe Leu Thr Leu Tyr Val Ile Ala Lys
         50                  55                  60

Phe Glu Arg Leu Gln Thr Val Leu Asn Tyr Ile Leu Leu Asn Leu Ala
 65                  70                  75                  80

Val Ala Asp Leu Phe Met Val Phe Gly Gly Phe Thr Thr Thr Leu Tyr
                 85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
            115                 120                 125

Val Val Leu Ala Ile Glu Arg Tyr Val Val Thr Ser Pro Phe Lys
            130                 135                 140

Tyr Gln Ser Leu Leu Thr Lys Asn Lys Ala Ile Met Gly Val Ala Phe
145                 150                 155                 160

Thr Trp Val Met Ala Leu Ala Cys Ala Ala Pro Pro Leu Val Gly Trp
                165                 170                 175

Ser Arg Tyr Ile Pro Glu Gly Met Gln Cys Ser Cys Gly Ile Asp Tyr
            180                 185                 190

Tyr Thr Pro His Glu Glu Thr Asn Asn Glu Ser Phe Val Ile Tyr Met
            195                 200                 205

Phe Val Val His Phe Ile Ile Pro Leu Ile Val Ile Phe Phe Cys Tyr
210                 215                 220

Gly Arg Val Phe Gln Val Ala Lys Arg Gln Leu Gln Lys Ile Asp Lys
225                 230                 235                 240

Ser Glu Gly Arg Phe His Ser Pro Asn Leu Gly Gln Val Glu Gln Asp
                245                 250                 255

Gly Arg Ser Gly His Gly Leu Arg Arg Ser Ser Lys Phe Cys Leu Lys
            260                 265                 270

Glu His Lys Ala Leu Arg Met Val Ile Met Val Ile Ala Phe Leu
            275                 280                 285

Ile Cys Trp Leu Pro Tyr Ala Gly Val Ala Phe Tyr Ile Phe Thr His
290                 295                 300

Gln Gly Ser Asp Phe Gly Pro Ile Phe Met Thr Ile Pro Ala Phe Phe
305                 310                 315                 320

Ala Lys Thr Ser Ala Val Tyr Asn Pro Val Ile Tyr Ile Met Met Asn
                325                 330                 335

Lys Gln Phe Arg Ile Ala Phe Gln Glu Leu Leu Cys Leu Arg Arg Ser
            340                 345                 350

Ser Ser Lys Ala Tyr Gly Asn Gly Tyr Ser Ser Asn Ser Asn Gly Lys
            355                 360                 365

Thr Asp Tyr Met Gly Glu Ala Ser Gly Cys Gln Leu Gly Gln Glu Lys
            370                 375                 380

Glu Ser Glu Arg Leu Cys Glu Asp Pro Pro Gly Thr Glu Ser Phe Val
385                 390                 395                 400

Asn Cys Gln Gly Thr Val Pro Ser Leu Ser Leu Asp Ser Gln Gly Arg
                405                 410                 415

Asn Cys Ser Thr Asn Asp Ser Pro Leu Thr Glu Thr Ser Gln Val Ala
            420                 425                 430

Pro Ala

<210> SEQ ID NO 36
<211> LENGTH: 495
```

```
<212> TYPE: PRT
<213> ORGANISM: Artificial sequence
<220> FEATURE:
<223> OTHER INFORMATION: Synthetic polypeptide

<400> SEQUENCE: 36

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Val Ala Cys
50                  55                  60

His Arg His Leu His Ser Val Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Ser Tyr Pro Leu Arg
130                 135                 140

Tyr Pro Thr Ile Val Thr Gln Arg Arg Ala Ile Met Gly Val Ala Phe
145                 150                 155                 160

Thr Trp Val Met Ala Leu Ala Cys Ala Ala Pro Pro Leu Val Gly Trp
                165                 170                 175

Ser Arg Tyr Ile Pro Glu Gly Met Gln Cys Ser Cys Gly Ile Asp Tyr
            180                 185                 190

Tyr Thr Pro His Glu Glu Thr Asn Asn Glu Ser Phe Val Ile Tyr Met
        195                 200                 205

Phe Val Val His Phe Ile Ile Pro Leu Ile Val Ile Phe Phe Cys Tyr
210                 215                 220

Gly Arg Val Tyr Val Ala Lys Arg Glu Ser Arg Gly Leu Lys Ser
225                 230                 235                 240

Gly Leu Lys Thr Asp Lys Ser Asp Ser Glu Gln Val Thr Leu Arg Ile
                245                 250                 255

His Arg Lys Asn Ala Pro Ala Gly Gly Ser Gly Met Ala Ser Ala Lys
            260                 265                 270

Thr Lys Thr His Phe Ser Val Arg Leu Leu Lys Phe Ser Arg Glu Lys
        275                 280                 285

Lys Ala Ala Arg Met Val Ile Ile Met Val Ile Ala Phe Leu Ile Cys
290                 295                 300

Trp Leu Pro Tyr Ala Gly Val Ala Phe Tyr Ile Phe Thr His Gln Gly
305                 310                 315                 320

Ser Asp Phe Gly Pro Ile Phe Met Thr Ile Pro Ala Phe Phe Ala Lys
                325                 330                 335

Thr Ser Ala Val Tyr Asn Pro Val Ile Tyr Ile Met Met Asn Lys Gln
            340                 345                 350

Phe Arg Lys Ala Phe Gln Asn Val Leu Arg Ile Gln Cys Leu Cys Arg
        355                 360                 365

Lys Gln Ser Ser Lys His Ala Leu Gly Tyr Thr Leu His Pro Pro Ser
370                 375                 380
```

-continued

```
Gln Ala Val Glu Gly Gln His Lys Asp Met Val Arg Ile Pro Val Gly
385                 390                 395                 400

Ser Arg Glu Thr Phe Tyr Arg Ile Ser Lys Thr Asp Gly Val Cys Glu
            405                 410                 415

Trp Lys Phe Phe Ser Ser Met Pro Arg Gly Ser Ala Arg Ile Thr Val
        420                 425                 430

Ser Lys Asp Gln Ser Ser Cys Thr Thr Ala Arg Val Arg Ser Lys Ser
    435                 440                 445

Phe Leu Gln Val Cys Cys Cys Val Gly Pro Ser Thr Pro Ser Leu Asp
    450                 455                 460

Lys Asn His Gln Val Pro Thr Ile Lys Val His Thr Ile Ser Leu Ser
465                 470                 475                 480

Glu Asn Gly Glu Glu Val Thr Glu Thr Ser Gln Val Ala Pro Ala
            485                 490                 495

<210> SEQ ID NO 37
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 37

Lys Ser Arg Ile Thr Ser Glu Gly Glu Tyr Ile Pro Leu Asp Gln Ile
1               5                   10                  15

Asp Ile Asn Val
            20

<210> SEQ ID NO 38
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 38

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 39
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 39

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 40
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 40
```

```
Met Gly Leu Arg Ala Leu Met Leu Trp Leu Leu Ala Ala Ala Gly Leu
1               5                   10                  15

Val Arg Glu Ser Leu Gln Gly
            20
```

<210> SEQ ID NO 41
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 41

```
Met Arg Gly Thr Pro Leu Leu Leu Val Val Ser Leu Phe Ser Leu Leu
1               5                   10                  15

Gln Asp
```

<210> SEQ ID NO 42
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 42

```
Val Xaa Xaa Ser Leu
1               5
```

<210> SEQ ID NO 43
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 43

```
Val Lys Glu Ser Leu
1               5
```

<210> SEQ ID NO 44
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 44

```
Val Leu Gly Ser Leu
1               5
```

<210> SEQ ID NO 45
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 45

```
Asn Ala Asn Ser Phe Cys Tyr Glu Asn Glu Val Ala Leu Thr Ser Lys
1               5                   10                  15
```

<210> SEQ ID NO 46

<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 46

Phe Xaa Tyr Glu Asn Glu
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 47

Phe Cys Tyr Glu Asn Glu Val
1               5

<210> SEQ ID NO 48
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 48

Met Thr Glu Thr Leu Pro Pro Val Thr Glu Ser Ala Val Ala Leu Gln
1               5                   10                  15

Ala Glu

<210> SEQ ID NO 49
<211> LENGTH: 357
<212> TYPE: PRT
<213> ORGANISM: Artificial Sequence
<220> FEATURE:
<223> OTHER INFORMATION: Synthetic polypeptide

<400> SEQUENCE: 49

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
        130                 135                 140

Ala Thr Leu Trp Leu Ser Ser Gly Asn Gly Val Val Trp Met Arg Tyr
145                 150                 155                 160

Gly Glu Trp Leu Leu Thr Cys Pro Val Leu Ile His Leu Ser Asn
            165                 170                 175

Leu Thr Gly Leu Lys Asp Asp Tyr Ser Lys Arg Thr Met Gly Leu Leu
        180                 185                 190

Val Ser Asp Ile Ala Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Asp Asp Thr Val Lys Gln Ser Thr Ala
        340                 345                 350

Lys Tyr Ala Ser Arg
        355

<210> SEQ ID NO 50
<211> LENGTH: 7811
<212> TYPE: DNA
<213> ORGANISM: Artificial Sequence
<220> FEATURE:
<223> OTHER INFORMATION: Synthetic oligonucleotide

<400> SEQUENCE: 50
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgtgtc tagactgcag agggccctgc     180
gtatgagtgc aagtgggttt taggaccagg atgaggcggg gtgggggtgc ctacctgacg     240
accgaccccg acccactgga caagcaccca accccattc cccaaattgc gcatccccta     300
tcagagaggg ggaggggaaa caggatgcgg cgaggcgcgt gcgcactgcc agcttcagca     360
ccgcggacag tgccttcgcc cccgcctggc ggcgcgcgcc accgccgcct cagcactgaa     420
ggcgcgctga cgtcactcgc cggtcccccg caaactcccc ttccggccca ccttggtcgc     480
gtccgcgccg ccgccggccc agccggaccg caccacgcga ggcgcgagat agggggggcac    540 gggcgcgacc atctgcgctg cggcgccggc gactcagcgc tgcctcagtc tgcggtgggc    600
agcggaggag tcgtgtcgtg cctgagagcg cagtcgagaa ggtaccggat ccgccaccat    660 ggacccatc gctctgcagg ctggttacga cctgctgggt gacggcagac ctgaaactct    720
gtggctgggc atcggcactc tgctgatgct gattggaacc ttctactttc tggtccgcgg    780

```
atggggagtc accgataagg atgcccggga atattacgct gtgactatcc tggtgcccgg    840
aatcgcatcc gccgcatatc tgtctatgtt ctttggtatc gggcttactg aggtgaccgt    900
cgggggcgaa atgttggata tctattatgc caggtacgcc gactggctgt ttaccacccc    960
acttctgctg ctggatctgg cccttctcgc taaggtggat cgggtgacca tcggcaccct   1020
ggtgggtgtg gacgccctga tgatcgtcac tggcctcatc ggagccttga gccacacggc   1080
catagccaga tacagttggt ggttgttctc tacaatttgc atgatagtgg tgctctattt   1140
tctggctaca tccctgcgat ctgctgcaaa ggagcggggc cccgaggtgg catctacctt   1200
taacaccctg acagctctgg tcttggtgct gtggaccgct tacctatcc tgtggatcat   1260
aggcactgag ggcgctggcg tggtgggcct gggcatcgaa actctgctgt ttatggtgtt   1320
ggacgtgact gccaaggtcg gctttggctt tatcctgttg agatcccggg ctattctggg   1380
cgacaccgag gcaccagaac ccagtgccgg tgccgatgtc agtgccgccg acaagagcag   1440
gatcaccagc gagggcgagt acatcccccct ggaccagatc gacatcaacg tgggcgcgcc   1500
cggctccgga gccacgaact tctctctgtt aaagcaagca ggagacgtgg aagaaaaccc   1560
cggtcccatg gacctgaagg agtcaccaag cgagggatca ctgcagccat caagcattca   1620
gattttcgct aatacaagca cactgcacgg catccggcat atcttcgtgt acggcccact   1680
gaccattcgg agagtcctgt gggcagtggc ctttgtcgga agcctgggac tgctgctggt   1740
ggagagctcc gaaagagtca gttactattt ctcatatcag cacgtgacta aggtggacga   1800
ggtggtcgct cagtccctgg tgtttcccgc agtcaccctg tgcaacctga tgggttcag   1860
gttttctcgc ctgaccacaa acgacctgta ccacgccgga gagctgctgg ctctgctgga   1920
tgtgaatctg cagatcccag acccccatct ggccgatcca accgtgctgg aagcactgag   1980
gcagaaggcc aacttcaaac actacaagcc caaacagttc agcatgctgg agtttctgca   2040
ccgcgtggga catgacctga agatatgat gctgtattgc aagttcaaag ccaggagtg   2100
tgggcatcag gacttcacta ccgtgtttac aaagtacggc aaatgttaca tgttcaactc   2160
cggggaagat ggaaaacctc tgctgacaac tgtgaagggc gggacaggga atggactgga   2220
gatcatgctg acattcagc aggatgagta cctgccaatc tggggagaaa ctgaggaaac   2280
cacattcgag gccggcgtga aggtccagat ccactcacag agcgagcccc ctttcattca   2340
ggaactggga tttggagtgg caccaggatt ccagacattt gtcgctactc aggagcagcg   2400
cctgacctat ctgccacccc cttggggcga gtgccgatct agtgaaatgg ggctggactt   2460
ctttcctgtg tactctatca ccgcctgccg aattgattgt gagacacggt atatcgtgga   2520
aaactgcaat tgtaggatgg tccacatgcc tggcgacgcc ccattctgca ctcccgaaca   2580
gcataaagag tgtgctgaac ctgcactggg gctgctggct gagaaggata gtaactactg   2640
cctgtgtaga acaccctgta acctgactag gtataataag gaactgagca tggtgaagat   2700
cccttccaaa acatctgcaa agtacctgga gaagaagtt c aacaagtctg agaagtacat   2760
cagtgaaaac attctggtgc tggacatctt ctttgaagct ctgaattacg agaccattga   2820
acagaagaaa gcatatgagg tggccgctct gctgggggat attggaggcc agatgggact   2880
gttcatcggc gccagcctgc tgacaattct ggagctgttt gactacatct atgagctgat   2940
taaggaaaaa ctgctggatc tgctggggaa ggaggaagag gaaggatcac acgacgaaaa   3000
catgagcact tgcgatacca tgcctaatca cagcgagacc atctcccata cagtgaatgt   3060
cccactgcag actgcactgg gcaccctgga ggaaattgcc tgtgcggccg ccaagagcag   3120
gatcaccagc gagggcgagt acatcccccct ggaccagatc gacatcaacg tggtgagcaa   3180
```

```
gggcgaggag ctgttcaccg gggtggtgcc catcctggtc gagctggacg gcgacgtaaa    3240
cggccacaag ttcagcgtgt ccggcgaggg cgagggcgat gccacctacg gcaagctgac    3300
cctgaagttc atctgcacca ccggcaagct gcccgtgccc tggcccaccc tcgtgaccac    3360
cttcggctac ggcctgcagt gcttcgcccg ctacccgac cacatgaagc agcacgactt    3420
cttcaagtcc gccatgcccg aaggctacgt ccaggagcgc accatcttct tcaaggacga    3480
cggcaactac aagacccgcg ccgaggtgaa gttcgagggc gacaccctgg tgaaccgcat    3540
cgagctgaag ggcatcgact tcaaggagga cggcaacatc ctggggcaca agctggagta    3600
caactacaac agccacaacg tctatatcat ggccgacaag cagaagaacg gcatcaaggt    3660
gaacttcaag atccgccaca acatcgagga cggcagcgtg cagctcgccg accactacca    3720
gcagaacacc cccatcggcg acggccccgt gctgctgccc gacaaccact acctgagcta    3780
ccagtccgcc ctgagcaaag accccaacga gaagcgcgat cacatggtcc tgctggagtt    3840
cgtgaccgcc gccgggatca ctctcggcat ggacgagctg tacaagttct gctacgagaa    3900
cgaggtgtaa tgagaattcg atatcaagct tatcgataat caacctctgg attacaaaat    3960
ttgtgaaaga ttgactggta ttcttaacta tgttgctcct tttacgctat gtggatacgc    4020
tgctttaatg ccttttgtatc atgctattgc ttcccgtatg gctttcattt tctcctcctt    4080
gtataaatcc tggttgctgt ctctttatga ggagttgtgg cccgttgtca ggcaacgtgg    4140
cgtggtgtgc actgtgtttg ctgacgcaac ccccactggt tggggcattg ccaccacctg    4200
tcagctcctt tccgggactt tcgctttccc cctccctatt gccacggcgg aactcatcgc    4260
cgcctgcctt gcccgctgct ggacaggggc tcggctgttg ggcactgaca attccgtggt    4320
gttgtcgggg aaatcatcgt cctttccttg gctgctcgcc tgtgttgcca cctggattct    4380
gcgcgggacg tccttctgct acgtcccttc ggccctcaat ccagcggacc ttccttcccg    4440
cggcctgctg ccggctctgc ggcctcttcc gcgtcttcgc cttcgccctc agacgagtcg    4500
gatctccctt tgggccgcct ccccgcatcg ataccgagcg ctgctcgaga gatctacggg    4560
tggcatccct gtgacccctc cccagtgcct ctcctggccc tggaagttgc cactccagtg    4620
cccaccagcc ttgtcctaat aaaattaagt tgcatcattt tgtctgacta ggtgtccttc    4680
tataatatta tggggtggag ggggtggta tggagcaagg ggcaagttgg gaagacaacc    4740
tgtagggcct gcggggtcta ttgggaacca agctggagtg cagtggcaca atcttggctc    4800
actgcaatct ccgcctcctg ggttcaagcg attctcctgc ctcagcctcc cgagttgttg    4860
ggattccagg catgcatgac caggctcagc taatttttgt tttttggta gagacggggt    4920 ttcaccatat tggccaggct ggtctccaac tcctaatctc aggtgatcta cccaccttgg    4980
cctcccaaat tgctgggatt acaggcgtga accactgctc ccttccctgt ccttctgatt    5040
ttgtaggtaa ccacgtgcgg accgagcggc cgcaggaacc cctagtgatg gagttggcca    5100
ctccctctct gcgcgctcgc tcgctcactg aggccgggcg accaaaggtc gcccgacgcc    5160
cgggctttgc ccgggcggcc tcagtgagcg agcgagcgcg cagctgcctg caggggcgcc    5220
tgatgcggta ttttctcctt acgcatctgt gcggtatttc acaccgcata cgtcaaagca    5280
accatagtac gcgccctgta gcggcgcatt aagcgcggcg ggtgtggtgg ttacgcgcag    5340
cgtgaccgct acacttgcca gcgccctagc gcccgctcct ttcgctttct tcccttcctt    5400
tctcgccacg ttcgccggct ttccccgtca agctctaaat cggggggctcc ctttagggtt    5460 ccgatttagt gctttacggc acctcgaccc caaaaaactt gatttgggtg atggttcacg    5520
```

```
tagtgggcca tcgccctgat agacggtttt tcgcccttttg acgttggagt ccacgttctt    5580
taatagtgga ctcttgttcc aaactggaac aacactcaac cctatctcgg gctattcttt    5640
tgatttataa gggattttgc cgatttcggc ctattggtta aaaatgagc tgatttaaca     5700
aaaatttaac gcgaatttta acaaaatatt aacgtttaca attttatggt gcactctcag   5760
tacaatctgc tctgatgccg catagttaag ccagccccga cacccgccaa cacccgctga    5820
cgcgccctga cgggcttgtc tgctcccggc atccgcttac agacaagctg tgaccgtctc    5880
cgggagctgc atgtgtcaga ggttttcacc gtcatcaccg aaacgcgcga cgaaaggg     5940
cctcgtgata cgcctatttt tataggttaa tgtcatgata ataatggttt cttagacgtc    6000
aggtggcact tttcggggaa atgtgcgcgg aaccccctatt tgtttatttt tctaaataca   6060
ttcaaatatg tatccgctca tgagacaata accctgataa atgcttcaat aatattgaaa    6120
aaggaagagt atgagtattc aacatttccg tgtcgccctt attccctttt ttgcggcatt    6180
ttgccttcct gtttttgctc acccagaaac gctggtgaaa gtaaaagatg ctgaagatca    6240
gttgggtgca cgagtgggtt acatcgaact ggatctcaac agcggtaaga tccttgagag    6300
ttttcgcccc gaagaacgtt ttccaatgat gagcactttt aaagttctgc tatgtggcgc    6360
ggtattatcc cgtattgacg ccgggcaaga gcaactcggt cgccgcatac actattctca    6420
gaatgacttg gttgagtact caccagtcac agaaaagcat cttacggatg gcatgacagt    6480
aagagaatta tgcagtgctg ccataaccat gagtgataac actgcggcca acttacttct    6540
gacaacgatc ggaggaccga aggagctaac cgcttttttg cacaacatgg ggatcatgt     6600
aactcgcctt gatcgttggg aaccggagct gaatgaagcc ataccaaacg acgagcgtga    6660
caccacgatg cctgtagcaa tggcaacaac gttgcgcaaa ctattaactg gcgaactact    6720
tactctagct tcccggcaac aattaataga ctggatggag gcggataaag ttgcaggacc    6780
acttctgcgc tcggcccttc cggctggctg gtttattgct gataaatctg gagccggtga    6840
gcgtgggtct cgcggtatca ttgcagcact ggggccagat ggtaagccct cccgtatcgt    6900
agttatctac acgacgggga gtcaggcaac tatggatgaa cgaaatagac agatcgctga    6960
gataggtgcc tcactgatta agcattggta actgtcagac caagtttact catatatact    7020
ttagattgat ttaaaacttc atttttaatt taaaaggatc taggtgaaga tcctttttga    7080
taatctcatg accaaaatcc cttaacgtga gttttcgttc cactgagcgt cagacccgt     7140
agaaaagatc aaaggatctt cttgagatcc ttttttttctg cgcgtaatct gctgcttgca    7200
aacaaaaaaa ccaccgctac cagcggtggt ttgtttgccg gatcaagagc taccaactct    7260
ttttccgaag gtaactggct tcagcagagc gcagatacca aatactgtcc ttctagtgta    7320
gccgtagtta ggccaccact tcaagaactc tgtagcaccg cctacatacc tcgctctgct    7380
aatcctgtta ccagtggctg ctgccagtgg cgataagtcg tgtcttaccg ggttggactc    7440
aagacgatag ttaccggata aggcgcagcg gtcgggctga acggggggtt cgtgcacaca    7500
gcccagcttg gagcgaacga cctacaccga actgagatac ctacagcgtg agctatgaga    7560
aagcgccacg cttcccgaag ggagaaaggc ggacaggtat ccggtaagcg gcagggtcgg    7620
aacaggagag cgcacgaggg agcttccagg gggaaacgcc tggtatcttt atagtcctgt    7680
cgggtttcgc cacctctgac ttgagcgtcg attttttgtga tgctcgtcag gggggcggag   7740
cctatggaaa aacgccagca acgcggcctt tttacggttc ctggccttttt gctggccttt   7800
tgctcacatg t                                                         7811
```

SYSTEM AND METHOD FOR OPTOGENETIC THERAPY

RELATED APPLICATION DATA

This is a continuation application of International Application No. PCT/US2013/000262, filed on Nov. 21, 2013, which claims priority to U.S. Provisional Application Ser. No. 61/729,283, filed on Nov. 21, 2012. The foregoing applications are hereby incorporated by reference into the present application in their entirety. Priority to the aforementioned applications is hereby expressly claimed in accordance with 35 U.S.C. §§ 119, 120, and 365 and any other applicable statutes.

INCORPORATION-BY-REFERENCE OF MATERIAL SUBMITTED ELECTRONICALLY

Incorporated by reference in its entirety is a computer-readable nucleotide/amino acid sequence listing submitted concurrently herewith, and identified as follows: One 122 KiloByte ASCII (Text) file named "14_449_087_SeqList_ST25.txt" created on Mar. 13, 2015.

FIELD OF THE INVENTION

The present invention relates generally to systems, devices, and processes for facilitating various levels of control over cells and tissues in vivo, and more particularly to systems and methods for physiologic intervention wherein light may be utilized as an input to tissues which have been modified to become light sensitive.

BACKGROUND

Pharmacological and direct electrical neuromodulation techniques have been employed in various interventional settings to address challenges such as prolonged orthopaedic pain, epilepsy, and hypertension. Pharmacological manipulations of the neural system may be targeted to certain specific cell types, and may have relatively significant physiologic impacts, but they typically act on a time scale of minutes, whereas neurons physiologically act on a time scale of milliseconds. Electrical stimulation techniques, on the other hand, may be more precise from an interventional time scale perspective, but they generally are not cell type specific and may therefore involve significant clinical downsides. A new neurointerventional field termed "Optogenetics" is being developed which involves the use of light-sensitive proteins, configurations for delivering related genes in a very specific way to targeted cells, and targeted illumination techniques to produce interventional tools with both low latency from a time scale perspective, and also high specificity from a cell type perspective.

For example, optogenetic technologies and techniques recently have been utilized in laboratory settings to change the membrane voltage potentials of excitable cells, such as neurons, and to study the behavior of such neurons before and after exposure to light of various wavelengths. In neurons, membrane depolarization leads to the activation of transient electrical signals (also called action potentials or "spikes"), which are the basis of neuronal communication. Conversely, membrane hyperpolarization leads to the inhibition of such signals. By exogenously expressing light-activated proteins that change the membrane potential in neurons, light can be utilized as a triggering means to induce inhibition or excitation.

One approach is to utilize naturally-occurring genes that encode light-sensitive proteins, such as the so-called "opsins". These light-sensitive transmembrane proteins may be covalently bonded to chromophore retinal, which upon absorption of light, isomerizes to activate the protein. Notably, retinal compounds are found in most vertebrate cells in sufficient quantities, thus eliminating the need to administer exogenous molecules for this purpose. The first genetically encoded system for optical control in mammalian neurons using light-sensitive signaling proteins was established in *Drosophila melanogaster*, a fruit fly species, and neurons expressing such proteins were shown to respond to light exposure with waves of depolarization and spiking. More recently it has been discovered that opsins from microorganisms which combine the light-sensitive domain with an ion pump or ion channel in the same protein may also modulate neuronal signaling to facilitate faster control in a single, easily-expressed, protein. In 2002, it was discovered that a protein that causes green algae (*Chlamydomonas reinhardtii*) to move toward areas of light exposure is a light-sensitive channel; exposure to light of a particular wavelength (maximum results at blue light spectrum i.e., about 480 nm) for the opsin ChR2, also known as "channelrhodopsin") causes the membrane channel to open, allowing positive ions, such as sodium ions, to flood into the cell, much like the influx of ions that cause nerve cells to fire. Various other excitatory opsins, such as Volvox Channelrhodopsin ("VChR1"), Step Function Opsins (or "SFO"; ChR2 variants which can produce prolonged, stable, excitable states with blue-wavelength light exposure, and be reversed with exposure to green-wavelength light, i.e., about 590 nm), or red-shifted optical excitation variants, such as "C1V1", have been described by Karl Deisseroth and others, such as at the opsin sequence information site hosted at the URL: http://www.stanford.edu/group/dlab/optogenetics/sequence_info.ht ml, the content of which is incorporated by reference herein in its entirety. Examples of opsins are described in U.S. patent application Ser. Nos. 11/459,638, 12/988,567, 12/522,520, and 13/577,565, and in Yizhar et al. 2011, Neuron 71:9-34 and Zhang et al. 2011, Cell 147:1446-1457, all of which are incorporated by reference herein in their entirety.

While excitation is desirable in some clinical scenarios, such as to provide a perception of a sensory nerve stimulation equivalent, relatively high-levels of excitation may also be utilized to provide the functional equivalent of inhibition in an "overdrive" or "hyperstimulation" configuration. For example, a hyperstimulation configuration has been utilized with capsaicin, the active component of chili peppers, to essentially overdrive associated pain receptors in a manner that prevents pain receptors from otherwise delivering pain signals to the brain (i.e., in an analgesic indication). An example of clinical use of hyperstimulation is the Brindley anterior sacral nerve root stimulator for electrical stimulation of bladder emptying (Brindley et al. Paraplegia 1982 20:365-381; Brindley et al. Journal of Neurology, Neurosurgery, and Psychiatry 1986 49:1104-1114; Brindley Paraplegia 1994 32:795-805; van der Aa et al. Archives of Physiology and Biochemistry 1999 107:248-256; Nosseir et al. Neurourology and Urodynamics 2007 26:228-233; Martens et al. Neurourology and Urodynamics 2011 30:551-555). In a parallel manner, hyperstimulation or overdriving of excitation with an excitatory opsin configuration may provide inhibitory functionality. It may also be referred to as a hyperstimulation block when used to produce a depolarization block.

Other opsin configurations have been found to directly inhibit signal transmission without hyperstimulation or overdriving. For example, light stimulation of halorhodopsin ("NpHR"), a chloride ion pump, hyperpolarizes neurons and directly inhibits spikes in response to yellow-wavelength (~589 nm) light irradiation. Other more recent variants (such as those termed "eNpHR2.0" and "eNpHR3.0") exhibit improved membrane targeting and photocurrents in mammalian cells. Light driven proton pumps such as archaerhodopsin-3 ("Arch") and "eARCH", and ArchT, *Leptosphaeria maculans* fungal opsins ("Mac"), enhanced bacteriorhodopsin ("eBR"), and Guillardia theta rhodopsin-3 ("GtR3") may also be utilized to hyperpolarize neurons and block signaling. Direct hyperpolarization is a specific and physiological intervention that mimics normal neuronal inhibition. Suitable inhibitory opsins are also described in the aforementioned incorporated by reference resources.

Further, a ChR2 variant known as a Stabilized Step Function Opsin (or "SSFO") provides light-activated ion channel functionality that can inhibit neural activity by depolarization block at the level of the axon. This occurs when the depolarization results in a depolarized membrane potential such that sodium channels are inactivated and no action potential of spikes can be generated.

C1V1-T refers to C1V1 (E122T) or C1V1 (E162T). C1V1-TT refers to C1V1 (E122T/E162T).

The term light-sensitive protein, as used herein, refers to all the aforementioned types of ion channels and ion transporters/pumps in the context of modulating a membrane potential.

With a variety of opsins available for optogenetic experimentation in the laboratory, there is a need to bring such technologies to the stage of medical intervention, which requires not only a suitable selection of opsin-based tools for excitation and/or inhibition, but also a means for delivering the genetic material to the subject patient and a means for controllably illuminating the subject tissue within the patient to utilize the light-driven capabilities. There is a need for practical configurations and techniques for utilizing optogenetic technologies in the clinical setting to address various clinical challenges of modern medicine with specificity and temporal control precision.

SUMMARY OF THE INVENTION

One embodiment is directed to a method for illuminating, from within the intrathecal space of the spine of a patient, a nerve root pair that has been genetically modified to comprise light sensitive protein, which may comprise surgically delivering an implantable optical applicator in a compressed state through a small surgical access created between calcified structures of the spine to the intrathecal space, and the implantable optical applicator inside of the intrathecal space to an expanded state, wherein the implantable optical applicator comprises a first lighting segment and a second lighting segment, the first lighting segment configured to illuminate a first nerve root of a selected nerve root pair while the second lighting segment is configured to illuminate a second nerve root from the selected nerve root pair. The method may further comprise providing a first implantable light source immediately coupled to the first lighting segment of the implantable optical applicator, and a second implantable light source immediately coupled to the second lighting segment, wherein each of the light sources is operatively coupled to a power supply and a controller, such that the controller activates the first and second implantable light sources by controlling current thereto from the power supply. The method may further comprise operatively coupling the first and second light sources to the power supply and controller with a delivery segment configured to carry electrical current. The power supply may be implantable. The controller may be implantable. The method may further comprise coupling the power supply to one or more implantable inductive coils configured to receive magnetic flux from a transcutaneous magnetic flux source configured to recharge the implantable power supply. The method may further comprise configuring a transcutaneous magnetic flux source to be positioned in a charging position near the skin adjacent the one or more implantable inductive coils. The method may further comprise coupling the transcutaneous magnetic flux source to a mounting device configured to retain the transcutaneous magnetic flux source in the charging position for a period of time while the patient is active. The mounting device may be selected from the group consisting of: a vest, a sling, a strap, a shirt, and a pant. The method may further comprise housing the power supply and controller within a common implantable housing. The light source may comprise a light emitting diode. The light source may comprise a laser. The method may further comprise genetically modifying the tissue structure comprising the light sensitive protein to encode an opsin protein. The opsin protein may be an inhibitory opsin protein. The inhibitory opsin protein may be selected from the group consisting of: NpHR, eNpHR 1.0, eNpHR 2.0, eNpHR 3.0, Mac, Mac 3.0, Arch, and ArchT. The opsin protein may be a stimulatory opsin protein. The stimulatory opsin protein may be selected from the group consisting of: ChR2, C1V1-T, C1V1-TT, CatCh, VChR1-SFO, and ChR2-SFO. The method may further comprise operatively coupling each of the first and second lighting segments to an implantable light source. The method may further comprise intercoupling a delivery segment between the implantable light source and the implantable optical applicator, the delivery segment configured to propagate light from the implantable light source to the implantable optical applicator where it may be distributed to the nerve root pair through the first and second lighting segments. The delivery segment may comprise a waveguide configured to propagate substantially all light that is passed through it via total internal reflection. The method may further comprise operatively coupling the implantable light source to a power supply and controller, such that the controller activates the light source by controlling current thereto from the power supply. The method may further comprise housing the implantable light source, power supply, and controller within a common implantable housing. The implantable light source may comprise a light emitting diode. The method may further comprise coupling the power supply to one or more implantable inductive coils configured to receive magnetic flux from a transcutaneous magnetic flux source configured to recharge the implantable power supply. The method may further comprise providing a transcutaneous magnetic flux source configured to be positioned in a charging position near the skin adjacent the one or more implantable inductive coils. The method may further comprise coupling the transcutaneous magnetic flux source to a mounting device configured to retain the transcutaneous magnetic flux source in the charging position for a period of time while the patient is active. The mounting device may be selected from the group consisting of: a vest, a sling, a strap, a shirt, and a pant. The tissue structure may comprise the light sensitive protein has been genetically modified to encode an opsin protein. The opsin protein may be an inhibitory opsin protein. the inhibitory opsin protein may be selected from the group consisting of: NpHR, eNpHR 1.0, eNpHR 2.0, eNpHR 3.0, Mac, Mac 3.0, Arch, and ArchT. The opsin protein may be a stimulatory opsin protein. The stimulatory opsin protein may be selected from the group consisting of: ChR2, C1V1-T, C1V1-TT, CatCh, VChR1-SFO, and ChR2-SFO. The method may further comprise aligning, in the expanded state, the first lighting segment to be immediately adjacent the first nerve root of the selected nerve root pair, and aligning, in the expanded state, the second lighting segment to be immediately adjacent the second nerve root of the selected nerve root pair, to form a deployment geometric configuration. The method may further comprise providing a biasing segment operatively coupled to the implantable optical applicator and configured to retain the deployment geometric configuration when activated. The method may further comprise operatively coupling a pullwire to the biasing segment, the pullwire configured to adjust the geometry of the implantable optical applicator to facilitate reaching the deployment geometric configuration. The nerve root pair may be a dorsal root pair. The nerve root pair may be a ventral root pair.

BRIEF DESCRIPTION OF THE DRAWINGS

FIGS. 4C1 and 4C2 depict an LED specification table for various LEDs that may be utilized in embodiments of the present invention.

FIGS. 30A-39C depict various aspects of embodiments of light delivery configurations and related issues and data, which may be utilized for optogenetic treatment of a human in accordance with the present invention.

FIGS. 51A-61M-7 depict various amino acid sequences of exemplary opsins, signal peptides, signal sequences, ER export sequences, and a trafficking sequence, as well as a polynucleotide sequence encoding Champ.

FIGS. 62A-62J-2 depict tables and charts containing descriptions of at least some of the opsins described herein.

FIGS. 76A-78 depict various aspects of embodiments of configurations which may be utilized for optogenetic treatment of the spine in accordance with the present invention.

FIGS. 79-81 depict various aspects of embodiments of light delivery configurations and related issues and data, which may be utilized for optogenetic treatment of a human in accordance with the present invention.

FIGS. 82A-83 depict various aspects of embodiments of light delivery strain relief configurations and related issues and data, which may be utilized for optogenetic treatment of a human in accordance with the present invention.

FIGS. 84-86 depict various aspects of embodiments of in-vivo light collection configurations and related issues and data, which may be utilized for optogenetic treatment of a human in accordance with the present invention.

DETAILED DESCRIPTION

Figure 1:
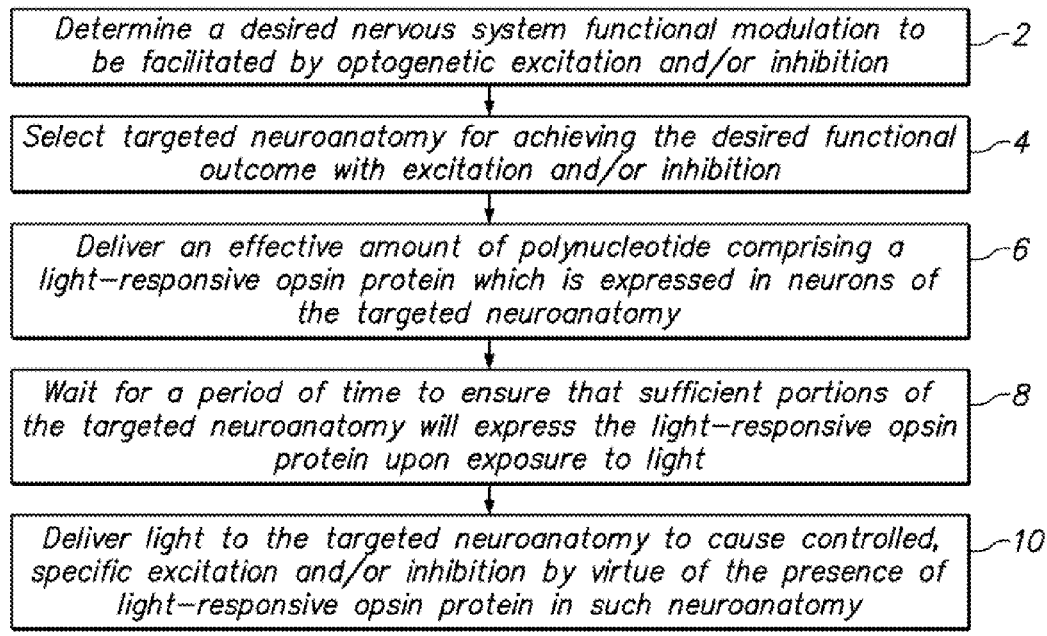
FIG. 1 depicts an embodiment of a technique for optogenetic treatment of a human in accordance with the present invention.

Referring to FIG. 1, from a high-level perspective, an optogenetics-based neuromodulation intervention involves determination of a desired nervous system functional modulation which can be facilitated by optogenetic excitation and/or inhibition (2), followed by a selection of neuroanatomic resource within the patient to provide such outcome (4), delivery of an effective amount of polynucleotide comprising a light-responsive opsin protein which is expressed in neurons of the targeted neuroanatomy (6), waiting for a period of time to ensure that sufficient portions of the targeted neuroanatomy will indeed express the light responsive opsin protein upon exposure to light (8), and delivering light to the targeted neuroanatomy to cause controlled, specific excitation and/or inhibition of such neuroanatomy by virtue of the presence of the light-responsive opsin protein therein (10).

While the development and use of transgenic animals has been utilized to address some of the aforementioned challenges, such techniques are not suitable in human medicine. Means to deliver the light-responsive opsin to cells in vivo are required; there are a number of potential methodologies that can be used to achieve this goal. These include viral mediated gene delivery, electroporation, ultrasound, hydrodynamic delivery, or the introduction of naked DNA either by direct injection or complemented by additional facilitators such as cationic lipids or polymers. Minicircle DNA technology may also be used. Minicircles are episomal DNA vectors that may be produced as circular expression cassettes devoid of any bacterial plasmid DNA backbone. Their smaller molecular size may enable more efficient transfections and offer sustained expression.

Viral expression techniques, generally comprising delivery of DNA encoding a desired opsin and promoter/catalyst sequence packaged within a recombinant viral vector have been utilized with success in mammals to effectively transfect targeted neuroanatomy and deliver genetic material to the nuclei of targeted neurons, thereby inducing such neurons to produce light-sensitive proteins which are migrated throughout the neuron cell membranes where they are made functionally available to illumination components of the interventional system. Typically a viral vector will package what may be referred to as an "opsin expression cassette", which will contain the opsin (e.g., ChR2, NpHR, etc.) and a promoter that will be selected to drive expression of the particular opsin. In the case of Adeno-associated virus (or AAV), the gene of interest (opsin) can be in a single stranded configuration with only one opsin expression cassette or in a self-complementary structure with two copies of opsin expression cassette complimentary in sequence with one another and connected by hairpin loops. The self-complementary AAVs are thought to be more stable and show higher expression levels. The promoter may confer specificity to a targeted tissue, such as in the case of the human synapsin promoter ("hSyn") or the human Thy1 promoter ("hThy1") which allow protein expression of the gene under its control in neurons. Another example is the calcium/calmodulin-dependent kinase II promoter ("CAMKII"), which allows protein expression of the gene under its control only in excitatory neurons, a subset of the neuron population. Alternatively, a ubiquitous promoter may be utilized, such as the human cytomegalovirus ("CMV") promoter, or the chicken beta-actin ("CBA") promoter, each of which is not particularly neural specific, and each of which has been utilized safely in gene therapy trials for neurodegenerative disease. Alternatively, a combination of chicken beta-actin promoter and cytomegalovirus immediate-early enhancer, known as CAG promoter, may be utilized.

Alternatively, a promoter domain derived from transcription factor Hb9, "survival of motor neuron" (SMN1), and methyl-CpG-binding protein-2 (MeCP2) may be utilized. Alternatively, MCK (muscle creatine kinase) promoter, MCK/SV40 promoter, Troponin promoter, and promoters of the transcription factors Pax6, Nkx6.1, Olig2, and Mnr2 may be utilized. Alternatively, a promoter such as latency-associated promoter 2 (LAP2) or neuron-specific enolase (NSE) may be utilized. Alternatively, a human elongation factor-1 alpha EF1α promoter may be utilized, including for example those from isoforms $EF1α_1$ and $EF1α_2$. $EF1α_1$ promoter may confer expression in brain, placenta, lung, liver, kidney, and pancreas. $EF1α_2$ promoter may confer expression in terminally differentiated cells of the brain, heart, and skeletal muscle. In another embodiment, β-cell-specific rat insulin promoter (RIP) may be utilized. In another embodiment, a macrophage-specific transcription promoter (such as CD68, or a truncated version thereof) may be utilized. Alternatively, a promoter such as hGFAP (for example, to direct expression to astrocytes), TPH-2 (for example, to direct expression to Raphe serotonergic neurons), fugu SST promoter (fSST) (for example to direct expression to inhibitory neurons), MBP (for example to direct expression to oligodendrocytes), or mouse SST (to direct expression to pre-Bötzinger C somatostatin neurons), may be utilized. Viral constructs carrying opsins are optimized for specific neuronal populations and are not limited to such illustrative examples.

Viral expression systems have the dual advantages of fast and versatile implementation combined with high infective/copy number for robust expression levels in targeted neuroanatomy. Cellular specificity may be obtained with viruses by virtue of promoter selection if the promoters are small, specific, and strong enough, by localized targeting of virus injection, as discussed in further detail below, and by restriction of opsin activation (i.e., via targeted illumination) of particular cells or projections of cells, also as described in further detail below. In an embodiment, an opsin is targeted by methods described in Yizhar et al. 2011, Neuron 71:9-34. In addition, different serotypes of the virus (conferred by the viral capsid or coat proteins) will show different tissue trophism. Lenti- and adeno-associated ("AAV") viral vectors have been utilized successfully to introduce opsins into the mouse, rate and primate brain. Additionally, these have been well tolerated and highly expressed over relatively long periods of time with no reported adverse effects, providing the opportunity for long-term treatment paradigms. Lentivirus, for example, is easily produced using standard tissue culture and ultracentrifuge techniques, while AAV may be reliably produced either by individual laboratories or through core viral facilities. Viruses have been utilized to target many tissue structures and systems, including but not limited to hypocretin neurons in the hypothalamus, excitatory pyramidal neurons, basal ganglia dopaminergic neurons, striatal GABAergic neurons, amygdala glutamatergic neurons, prefrontal cortical excitatory neurons and others, as well as astroglia. For example, it has been shown that the use of AAV-delivered ChR2 to control astroglial activity in the brainstem of mice and create a mechanism by which astroglia can transfer systemic information from the blood to neurons underlying homeostasis, in this case directly modulating neurons that manipulate the rate of respiration. AAV is a preferred vector due to its safety profile, and AAV serotypes 1 and 6 have been shown to infect motor neurons following intramuscular injection in primates. Other vectors include but are not limited to equine infectious anemia virus pseudotyped with a retrograde transport protein (e.g., Rabies G protein), and herpes simplex virus ("HSV").

Referring back to FIG. 1, delivery of the polynucleotide comprising the light-responsive opsin protein to be expressed in neurons of the targeted neuroanatomy may involve injection with a syringe or other device, in one or more configurations, including but not limited to intramuscular injection (i.e., straight into the muscle belly associated with a targeted portion of neuroanatomy), intraparenchymal injection (i.e., injection into the parenchyma of an organ such as the kidney which may be associated with a targeted portion of neuroanatomy), tissue structure injection (i.e., injection into the wall of the stomach in the vicinity of a targeted portion of neuroanatomy such as stretch receptors of the gastric nerve), intrafascicular injection (i.e., injection directly into a targeted nerve or bundle thereof, such as into the vagus nerve), nerve ganglion injection (i.e., injection directly into the ganglion, which comprises nerve cell bodies), vascular wall injection (i.e., injection of a vascular structure such as a renal artery wall in the vicinity of a targeted portion of neuroanatomy such as the renal nerve plexus), and internal topical injection or application (i.e., injection upon a surface of a tissue structure associated with a targeted portion of neuroanatomy, or upon the neuroanatomy itself, generally after surgical access, such as via laparoscopic techniques). Each of these injection configurations is explored in further detail below.

Intramuscular delivery is a common technique for delivering genes to peripheral neurons. The muscle may be palpitated by the surgeon or operator to identify location and shape of the muscle. This information may then used to discern the likely site of the nerve endings (using anatomical knowledge). A hypodermic needle (e.g., 23G to 27G) may be inserted transcutaneously into the muscle tissue of the pertinent muscle in the vicinity of the nerve endings, and the vector solution may be injected through the needle where it may diffuse throughout the muscle tissue and be taken up by the nerve terminals (i.e. motor or sensory neurons). The vector solution may be injected as a single bolus dose, or slowly through an infusion pump (e.g., at a rate of between about 0.01 and 1.00 mL/min). An ultrasound guidance system may be used for deeper muscle targets. Once taken up by the neural terminals, the vector preferably is retrogradely transported to the pertinent neural cell bodies across the length of the axon. The number of injections and dose of virus injected to each muscle is dependent upon the muscle volume and topology. In the non-human primate study described in Towne et al Gene Ther. 2010 Jan.; 17(1):141-6, a single injection of 1 mL saline solution containing $1.3 \times 10^{12}$ viral genomes (vg) of AAV6 was injected into the triceps surae muscle (approximately 30 cm$^3$) to achieve efficient transduction of the entire motor neuron pool.

In one example of an intramuscular injection therapy step for targeting motor neurons for addressing spasticity problems, the flexor carpi ulnaris muscle (having a volume of approximately 40 cubic centimeters) of the hand may be injected intramuscularly. This muscle may be targeted with one to two injections containing a total of about 1 mL saline solution containing $10^{12}$ to $10^{13}$ vg. Larger muscles, such as the biceps brachii which has an approximate volume of 150 cubic centimeters, may require two to five injections with a higher total dose of vector $5 \times 10^{12}$ to $10^{14}$ vg in 1 to 5 mL. These ranges are illustrative, and doses are tested for each virus-promoter-opsin construct pairing them with the targeted neurons.

In another example of an intramuscular injection therapy step for targeting motor neurons for addressing urinary system problems, the external urethral sphincter ("EUS") may be injected intramuscularly with multiple injections around the circumference of the tissue structure (which has a volume between 1 and about 5 cubic centimeters in the adult human). For example, in one embodiment, this tissue structure may be injected using 4 or 5 injections with a total dose of vector $10^{12}$ to $10^{13}$ vg in 0.1 to 15 mL in rodents at the rate of 1 ml/min. For larger animals and humans, larger volumes and titers may be used that would be empirically determined.

Vector delivery into the parenchyma of a tissue has been shown to facilitate the targeting of neurons innervating that structure. A needle may be inserted into the parenchyma of a pertinent organ (e.g., a kidney) in the vicinity of the neural nerve endings (e.g., the renal nerve plexus). The vector solution may be injected through the needle where it may diffuse throughout the tissue and be taken up by the neural terminals (i.e., sympathetic or parasympathetic nerve endings). Once taken up by the neural terminals, the vector may be retrogradely transported to the neural cell body along the length of the axon. In one embodiment, intraparenchymal injections are performed through laparoscopic surgical access and instrumentation. A small incision may be made through the skin and other pertinent tissue structures (such as the abdominal wall) to allow insertion of the surgical apparatus (camera, needle, tools, etc.). The needle may be guided into the parenchyma of the organ (as visualized through the camera) at the desired depth to target the nerve endings, and the vector solution then may be injected as a single bolus dose, or slowly through an infusion pump (0.01 to 1 mL/min). More specifically in an exemplary configuration wherein a renal nerve plexus is targeted to address hypertension via intraparenchymal injection into one or more of the kidneys, the number of injections and dose of virus injected to the kidneys may be approximated from the primate viral retrograde transport study performed by Towne et al (Gene Ther. 2010 Jan.; 17(1):141-6), incorporated by reference in its entirety herein. Such protocols have been shown to achieve efficient retrograde transport following injection of 1 mL saline solution containing $1.3 \times 10^{12}$ viral genomes of AAV6 into a tissue of approximately 30 cm$^3$ volume. Considering that the total kidney parenchyma has a volume of approximately 150 cm$^3$, it is possible to achieve efficient retrograde transport using 5 mL saline solution containing approximately $6.5 \times 10^{12}$ viral genomes of the desired vector. This 5 mL may be injected over multiple sites to evenly disperse the vector throughout the volume of the kidney parenchyma. For example, in one embodiment, about 20 injections of 0.25 mL containing $3.25 \times 10^{10}$ vg of vector may be made at approximately equidistant sites throughout the parenchyma of the kidney for successful transfection. These ranges are illustrative, and doses are tested for each virus-promoter-opsin construct pairing them with the targeted neurons.

Tissue structures such as the wall of the stomach may also be directly targeted for viral injection. For example, in one embodiment it may be desirable to inject the stomach wall to target the stretch receptors to address obesity-related clinical challenges. In such an embodiment, after creating an access pathway, such as a small laparoscopic incision to allow laparoscopic tools (camera, needle, tools, etc.) to approach the stomach wall, a needle may be inserted into the stomach wall in the vicinity of the nerve endings for the stretch receptors. The needle may be guided into the pertinent anatomy using the available laparoscopic imaging tools, such as one or more cameras, ultrasound, fluoroscopy, or the like. The pertinent vector solution may injected through the needle where it may diffuse throughout the tissue and be taken up by the neural terminals (i.e. stretch and chemical afferent fiber nerve endings). The vector solution may be injected as a single bolus dose, or slowly through an infusion pump (0.01 to 1 mL/min). Once taken up by such neural terminals, the vector may be retrogradely transported to the pertinent neural cell body or bodies along the length of the pertinent axons. The number of injections and dose of virus injected to the stomach wall may be approximated from the primate viral retrograde transport study performed by Towne et al (Gene Ther. 2010 Jan.; 17(1):141-6), incorporated by reference herein in its entirety. This study demonstrated efficient retrograde transport following injection of 1 mL saline solution containing $1.3 \times 10^{12}$ viral genomes of AAV6 into a muscle of approximately 30 cm$^3$ volume. Considering that the stomach wall has an average thickness of approximately 4 mm and a surface area of approximately 150 cm$^2$ (total targeted tissue structure volume of about 60 cm$^3$), efficient retrograde transport may be achieved using 2 mL saline solution containing approximately $3 \times 10^{12}$ viral genomes of the desired vector. This 2 mL may be injected over multiple sites to evenly disperse the vector over the surface area of stomach wall. For example, about 20 injections of 0.1 mL containing $1.3\times10^{11}$ vg of vector may be conducted for each 7.5 $cm^2$ area of stomach wall. These titers and injection volumes are illustrative examples and are specifically determined for each viral construct-target neuron pairing.

In other embodiments, nerve fibers may be targeted by direct injection (i.e., injection into the nerve itself). This approach, which may be termed "intrafascicular" or "intraneural" injection, involves placing a needle into the fascicle of a nerve bundle. Intrafascicular injections are an attractive approach because they allow specific targeting those neurons which may innervate a relatively large target (e.g., fibers across entire kidney, fibers across entire dermatome of skin, fibers across entire stomach wall) with one injection (e.g., before the fibers enter the tissue and anatomically bifurcate). The pertinent vector solution may be injected through the needle where it may diffuse throughout the entire nerve bundle (10 to 1000's of axon fibers). The vector may then enter the individual axon fibers through active (receptor-mediated) or passive (diffusion across intact membranes or transiently disrupted membranes) means. Once it has entered the axon, the vector may be delivered to the cell body via retrograde transport mechanisms, as described above. The number of injections and dose of virus injected to the nerve are dependent upon the size of the nerve, and can be extrapolated from successful transduction studies. For example, injection of the sciatic nerve of mice (approximately 0.3 mm diameter) with 0.002 mL saline containing $1\times10^9$ vg of AAV has been shown to result in efficient transgene delivery to sensory neurons involved in pain sensing. Likewise, injection of the sciatic nerve of rats (1 mm diameter) with 0.010 mL saline containing $1\text{-}2\times10^{10}$ vg of AAV has also achieved desirable transfection results. The trigeminal nerve in humans is 2 mm in diameter, and through extrapolation of the data from these pertinent studies, the trigeminal nerve may be transfected to efficiently deliver a transgene to these pertinent pain neurons using a direct injection of 0.05 mL saline containing $4\times10^{10}\text{-}1\times10^{14}$ vg of AAV into the trigeminal bundle. These titers and injection volumes are illustrative examples and are specifically determined for each viral construct-target neuron pairing.

The protocol for nerve injections will vary depending upon the target. Superficial nerves may be targeted by making an incision through the skin, and then exposing the nerve through separation of muscles, fascia and tendons. Deeper nerves (i.e., outside of the abdominal and thoracic cavity—such as the pudendal nerve) may be targeted through ultrasound-guided surgical intervention. Nerves in the abdominal cavity may be targeted through laparoscopic surgical approaches wherein one or more small incisions may be made through the skin and other structures (such as the abdominal wall) to allow insertion of the surgical apparatus (camera, needle, tools, etc.) to a position adjacent the anatomy of interest. The needle may be guided into the nerve (as visualized through the camera and other available imaging systems, such as ultrasound, fluoroscopy, radiography, etc.). In all cases, the vector solution may be injected as a single bolus dose, or slowly through an infusion pump (0.001 to 0.1 mL/min).

In one particular example, the gastric and hepatic branches of the vagus nerve may be directly injected to control satiety. In such an embodiment, laparoscopic surgery may be performed to target the gastric and hepatic branches of the vagus nerve that lie adjacent to the esophagus and innervate the stomach with the clinical goal being to infect the fibers of the afferent stretch receptors in the stomach wall via direct injection of vector material into these vagus nerve branches, preferably as facilitated by one or more imaging technologies as described above.

In another particular example of intraneural injection, nociceptive fibers of the trigeminal nerve may be directly injected to address neuropathic pain symptoms, as briefly described above. In one embodiment, the trigeminal nerve may be directly injected with an AAV vector solution either through exposure of the nerve or through the skin via ultrasound guidance. Once in the nerve fascicle, the vector is configured to preferentially enter the non-myelinated or poorly-myelinated fibers that correspond to those cells mediating pain.

In another particular example of intraneural injection, the sciatic nerve may be injected with an AAV vector solution either through exposure of the nerve or through the skin via ultrasound guidance. The vector may be configured such that once it accesses the nerve fascicle, it preferentially enters the sensory neurons or motor neurons responsible for the symptoms of spasticity.

In another particular example of intraneural injection, the cervical vagus nerve may be injected with an AAV vector solution through exposure of the nerve in the neck. Once in the nerve fascicle, the vector may be configured to preferentially enter the relevant nerve fibers that are the mediators of the therapeutic effect of electrical vagus nerve stimulation for epilepsy.

In another particular example of intraneural injection, the cervical vagus nerve may be injected with an AAV vector solution through exposure of the nerve in the neck. Once in the nerve fascicle, the vector may be configured to preferentially enter the relevant nerve fibers that are the mediators of the therapeutic effect of vagus electric nerve stimulation for depression.

As mentioned above, injection into the ganglion may be utilized to target the neural cell bodies of peripheral nerves. Ganglia consist of sensory neurons of the peripheral nervous system, as well as autonomic neurons of the parasympathetic and sympathetic nervous system. A needle may be inserted into the ganglion which contains the cell bodies and a vector solution injected through the needle, where it may diffuse throughout the tissue and be taken up by the cell bodies (100s to 1000s of cells). In one embodiment, a dose of approximately 0.1 mL saline containing from $1\times10^{11}$ vg to $1\times10^{14}$ vg of AAV may be used per ganglion. There are different types of ganglia that may be targeted. Dorsal root ganglion of the spinal cord may be injected in a similar method that is used during selective dorsal rhizotomy (i.e. injection via the intrathecal subarachnoid space of the spinal cord), except rather than cutting the nerves, the dorsal root ganglia may be injected. Other ganglia not in the abdominal cavity, such as the nodose ganglion of the vagus nerve, may be targeted by making an incision through the skin, and then exposing the ganglia through separation of muscles, fascia and tendons. Ganglia in the abdominal cavity, such as the ganglia of the renal plexus, may be injected through laparoscopic techniques, wherein one or more small incisions may be made through the skin and abdominal wall to allow insertion of the surgical apparatus (camera, needle, tools, etc.) to locations facilitating access and imaging of the pertinent targeted tissue. The needle may be guided into the ganglia (as visualized through a camera or other imaging device, such as ultrasound or fluoroscopy). In all cases, the vector solution may be injected as a single bolus dose, or slowly through an infusion pump (0.001 to 0.1 mL/min).

These ranges are illustrative, and doses are tested for each virus-promoter-opsin construct pairing them with the targeted neurons.

In one particular example of ganglion injection, the dorsal root ganglia mediating clinical neuropathic pain may be injected with an AAV vector solution, preferably containing an AAV vector that has tropism for cell body.

In another particular example of ganglion injection, the dorsal root ganglia mediating undesired muscular spasticity may be injected with an AAV vector solution. An AAV vector that has tropism for cell body may be used towards this goal.

In another particular example of ganglion injection, the nodose ganglion may be exposed and injected with an AAV vector solution to address clinical epilepsy symptoms. An AAV vector that has tropism for cell body may be used towards this goal to infect specifically the afferent cells that are thought to mediate the therapeutic effect of vagus nerve stimulation. In one embodiment the AAV vector is injected into a cell body. In another embodiment the AAV vector is injected into a target tissue and retrogradely transported to a cell body. Embodiments of the invention include optical stimulation at a cell body or along an axon.

In another particular example of ganglion injection, the nodose ganglion may be exposed and injected with an AAV vector solution. An AAV vector that has tropism for cell body may be used towards this goal to infect specifically the afferent cells that are thought to mediate the therapeutic effect of vagus nerve stimulation.

In another particular example of ganglion injection, ganglion of the renal plexus may be injected for hypertension treatment. Laparoscopic surgery may be performed to target the ganglion of the renal plexus. Ganglia adjacent to the kidneys and on the renal arteries may be identified and then injected individually and directly with one objective being to infect the cell bodies of the renal plexus efferent neurons.

As noted above, direct injection of vascular structures such as artery walls may also be utilized to deliver genetic material for optogenetic therapy. For example, in one embodiment, portions of one or more of the renal arteries may be directly injected to infect the nearby renal plexus to address hypertension (the renal arteries are surrounded by a neural plexus that mediates control of blood pressure via the kidneys, as described in further detail below). A small incision may be made through the skin and abdominal wall to allow insertion of a laparoscopic surgical system (camera, needle, tools, etc.). A needle may be guided into the renal plexus (as visualized through the camera or other imaging device). The needle may be placed in multiple sites around the circumference of the renal arteries. The vector solution is injected through the needle where it may diffuse throughout the arterial wall and be taken up through by the adjacent renal plexus nerve fibers via diffusion across intact membranes (or transiently disrupted membranes). In all cases, the vector solution may be injected as a single bolus dose, or slowly through an infusion pump (0.001 to 0.1 mL/min). Multiple injections of a dose of approximately 0.1 mL saline containing $1 \times 10^{11}$ vg of AAV may be used at different sites around the circumference and length of the renal arteries (in the vicinity of the renal plexus), with the goal being to infect the axons of the renal plexus efferent neurons. The amount of virus is illustrative of such transfection but optimum dosing will vary depending on the target neuron paired with a specific virus-promoter-opsin construct.

Finally, as noted above, internal topical injection or application to a tissue structure surface may be utilized to deliver genetic material for optogenetic therapy. Recombinant vectors are capable of diffusing through membranes and infecting neural nerve endings following such topical application or exposure. Examples are the infection of sensory fibers following topical application on skin, which has been shown in pain treatment studies. Likewise, efficacy of topical application of viral vectors has been increased using vector solutions suspended in gels. In one embodiment, a vector may be suspended in a gel and applied (e.g., swabbed, painted, injected, or sprayed) to the surface of tissues that have high densities of targeted superficial nerve fibers. With such embodiment, vectors will diffuse through the gel and infect nerve fibers via diffusion across intact neural fiber membranes. Internal topical application may be achieved using laparoscopic techniques, wherein one or more small incisions may be made through the skin and other pertinent tissue structures (such as the abdominal wall) to allow insertion of the surgical apparatus (camera, needle, tools, etc.). A needle may be guided into the target tissue (as visualized through the camera or other imaging devices). In all cases, the vector may be mixed with the gel (e.g. the product sold under the tradename "KY Jelly" by Johnson & Johnson Corporation) and then sprayed onto, painted onto, or injected out upon the surface of the pertinent tissue. A dose of approximately 0.1 mL saline containing $1 \times 10^{11}$ vg of AAV may be used to cover each 1 $cm^2$ area. These ranges are illustrative, and doses are tested for each virus-promoter-opsin construct pairing them with the targeted neurons.

In one particular example of topical application, afferent nerve fibers of the stomach wall may be targeted and infected to address a clinical satiety challenge. Laparoscopic surgical techniques may be utilized to target the superficial nerve fibers that project into the stomach wall from the gastric and hepatic vagus nerve, with the clinical goal being to infect the fibers of the afferent stretch receptors in the stomach wall to facilitate optogenetic induction of satiety. Upon successful laparoscopic access, a solution or gel may be applied to infect the targeted nerve tissues.

In another particular example of topical application, hypertension may be addressed by topical application of vector solution or gel to the renal plexus from a laparoscopic approach to achieve transfer of optogenetic material to the pertinent nerves. Laparoscopic surgery may be performed to target the surface of the renal plexus directly. The renal arteries and kidneys may be identified using one or more imaging devices (such as a camera, ultrasound, fluoroscopy, radiography, etc.) and then the vector may be applied directly and topically at multiple sites to cover as much of the available nerve plexus surface as possible, the goal being to infect the axons of the renal plexus efferent neurons.

Prior to implantation or injection, patients may be started on a clear liquid diet on postoperative day 1. Following induction with general endotracheal anesthesia and the administration of a broad-spectrum prophylactic intravenous antibiotic and/or cystoscopy and/or retrograde pyelography may be performed, and a long indwelling optical therapeutic device, such as an applicator, and/or delivery segments, and/or a housing may be passed. A Foley catheter and orogastric tube may also be placed, by way of non-limiting examples. The patient may be placed in a 45-degree lateral decubitus position and secured to the operating table. Insufflation may be performed, for example, through a Veress needle, and laparoscopic ports may be passed into the peritoneal cavity. The ipsilateral colon may be reflected, and the proximal ureter and renal pelvis may be identified and fully mobilized. Dissection of an extensive length of proximal ureter may be avoided in an attempt to preserve any collateral vascular supply. If a crossing vessel is present, fibrotic bands between the vessels and collecting system may be divided to gain unobstructed access to the renal pelvis beyond the ureteropelvic junction (UBJ). The catheter may be cleared at this point, and the optical activator and/or delivery segments and/or housing then introduced into the renal pelvis. To close, a 5-mm closed suction drain, for example, may be placed through a posterior stab incision into the perinephric space adjacent to the UBJ. Hemostasis may be confirmed, the $CO_2$ may be evacuated, and the port sites may be closed. The orogastric tube may be removed prior to catheter removal.

The renal plexus (52) generally resides around the renal artery underneath a layer of renal fascia (64), as described in the following table.

| Distance From Outer Artery Surface (mm) | Cumulative % of Nerves |
|---|---|
| 0.5 | 9 |
| 1 | 25 |
| 1.5 | 51 |
| 2 | 99 |
| 2.5 | 100 |

The renal artery surface irradiance parameters are different from those of the target threshold irradiance because there are very few nerves in the outermost portions of the renal artery, most being located much closer to the intima between 1.5-2.0 mm beneath the outer surface. To compensate for irradiance diminution due to optical scattering, the irradiance delivered to the tissue surface is higher than that required for optical activation at the target depth. The scattering cross-section monotonically decreases with wavelength. As an illustrative example, although not rigorously analytical, reasonable approximations for the required surface irradiance relative to that required at the target depths shown in the above table grouped into spectral bands may be made, and are listed in the following table.

| Spectral Region | Irradiance Increase |
|---|---|
| 450-480 nm | 21 |
| 481-530 nm | 15 |
| 531-560 nm | 10 |
| 561-600 nm | 6 |

The optical parameters required to effectively activate specific optogenetic targets are listed in the following table.

| OPSIN | Pulse Duration (ms) | Duty Cycle (%) | Renal Surface Irradiance (mW/mm$^2$) |
|---|---|---|---|
| NpHR | 0.1-10 | 50-100 | 5-50 |
| eNpHR 3.0 | 0.1-10 | 50-100 | 5-50 |
| ARCH 3.0 | 0.1-10 | 50-100 | 10-100 |
| Mac 3.0 | 0.1-10 | 50-100 | 15-150 |
| ChR2 | 2-20 | 5-50 | 20-200 |
| VChR1 | 2-20 | 5-50 | 15-150 |
| CatCH | 2-20 | 5-50 | 20-200 |
| C1V1 | 2-20 | 5-50 | 20-200 |
| SFO | 0.1-10 | 0.1-1 | 15-150 |
| SSFO | 0.1-10 | 0.1-1 | 15-150 |

Figure 62A:
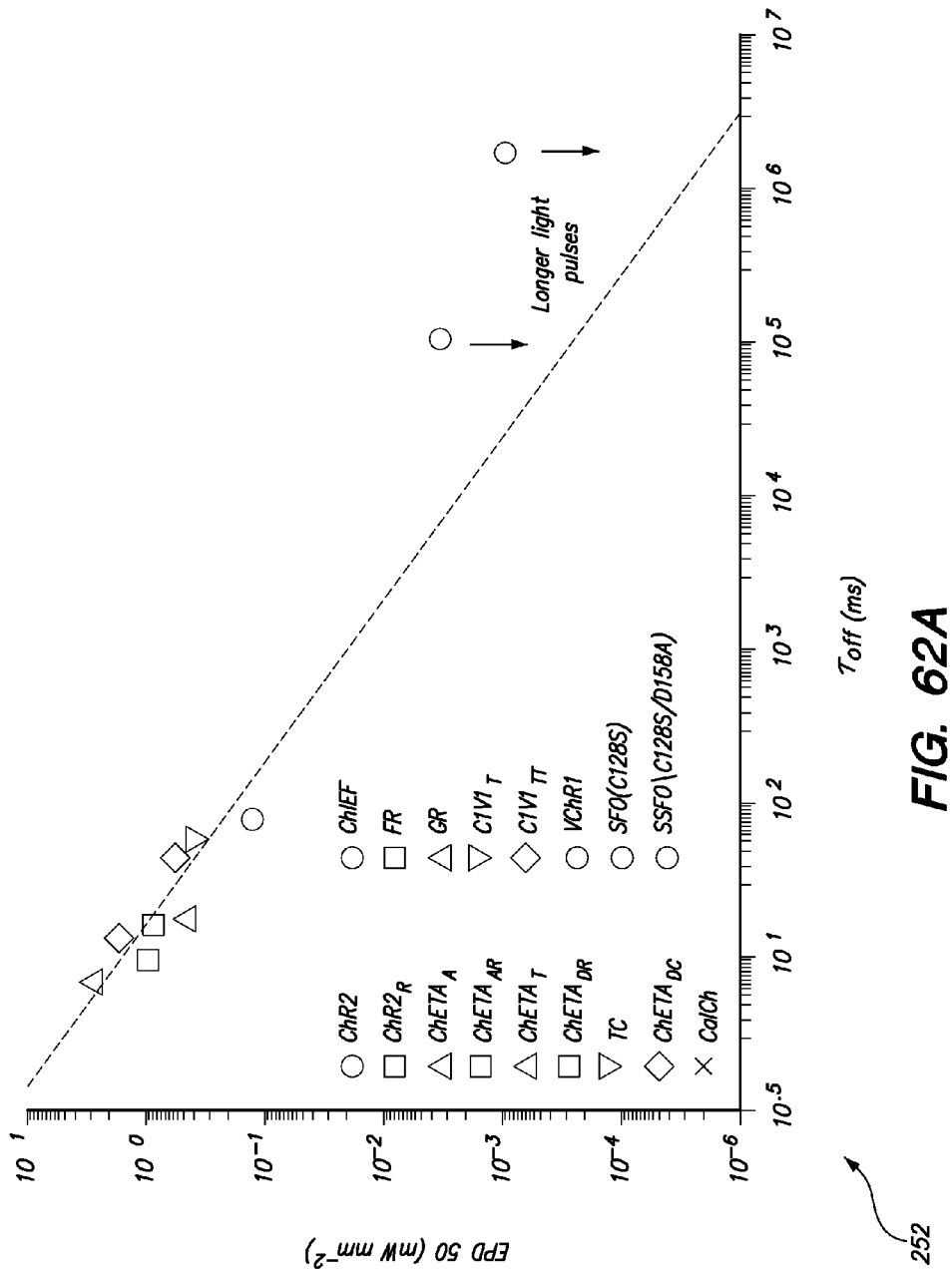
Figure 62C:
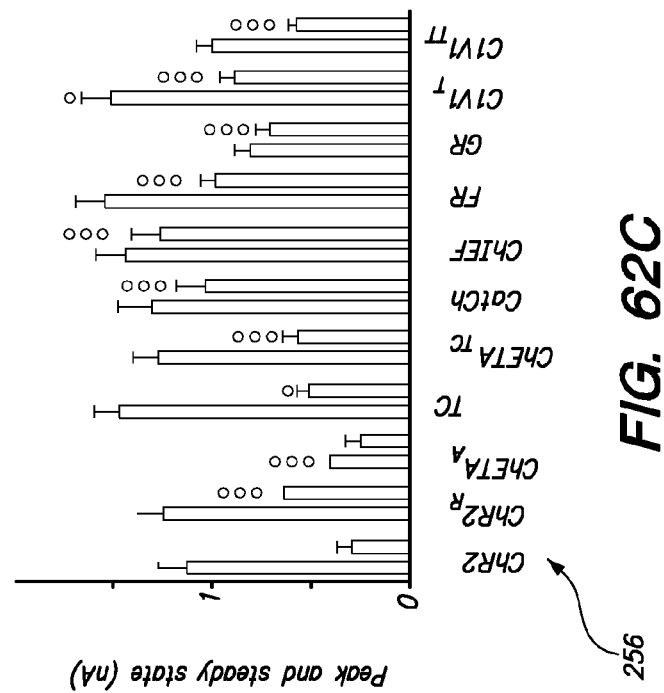
Figure 62B:
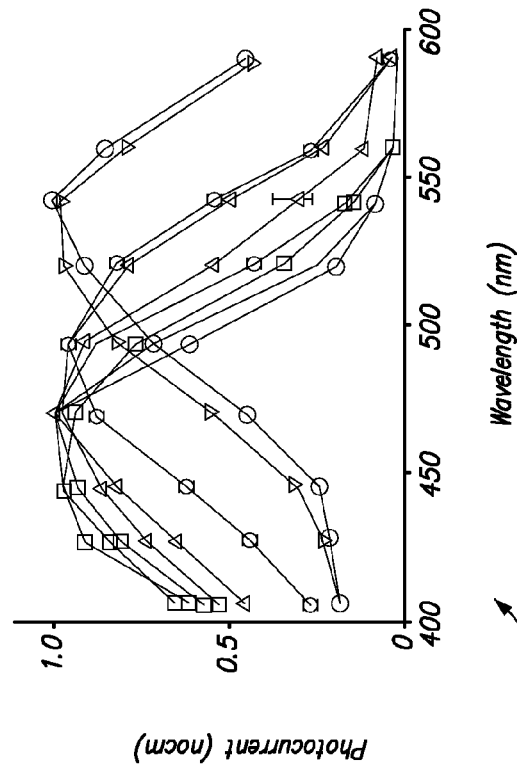

For Renal Nerve Inhibition, photosensitivity may be preferred over speed, or response time, of the opsin. Therefore, ChR2 opsins utilizing the C123S, and/or C128A, and/or C128S, and/or the D156A mutations, such as SFO and/or SSFO, may be used, as they may comprise the desired relatively high level of light sensitivity, although potentially with relatively lower temporal resolution. Alternately, mutations at analogous positions to ChR2 C123S, and/or C128A, and/or C128S, and/or the D156A in other may be added to other opsins. Alternately, the SFO and/or SSFO variants may be used with a 2-color illumination system, such as that shown in the exemplary system of FIG. 16, wherein light of a first color (such as blue light) may be used to activate the opsin, and light of a second wavelength (such as yellow light) may be used to de-activate the opsin, such as may be performed in an exemplary configuration for depolarization (hyperstimulation) block. Alternately, in a similar fashion, the C1V1 E122T, E162T, and/or E122T/E162T variants may comprise the desired relatively high level of light sensitivity. Alternately, ChIEF, and/or ChrFR, and/or ChrGr, including those with mutations analogous to the ChR2 SFO and/or SSFO mutations may be used in a configuration for depolarization (hyperstimulation) block. Alternately, opsins, such as, but not limited to, NpHR 3.0, and/or ARCH 3.0, may be for direct inhibition. An inhibitory opsin may be selected from those listed in FIGS. 62J-1 and 62J-2, by way of non-limiting examples. A stimulatory opsin may be selected from those listed in FIGS. 62J-1 and 62J-2, by way of non-limiting examples. An opsin may be selected from the group consisting of Opto-β2AR or Opto-α1AR, by way of non-limiting examples.

Any of the slab-type, and/or cuff-type, and/or spiral-type, and their respective systems herein described and shown in FIGS. 5, 8-14, and 17-28, or elsewhere herein, may be used to deliver therapeutic light to the exterior of the renal artery in order to reach the optogenetic targets within the renal nerve plexus. However, the blood residing in the renal artery is also an avid absorber of visible light and may render moot the light-recycling elements of those applicators for light that traverses the blood-filled lumen. It should be noted, however, that light-recycling still serves to increase the overall system efficiency for light that escapes otherwise and nominally avoids optical contact with blood.

Figure 25:
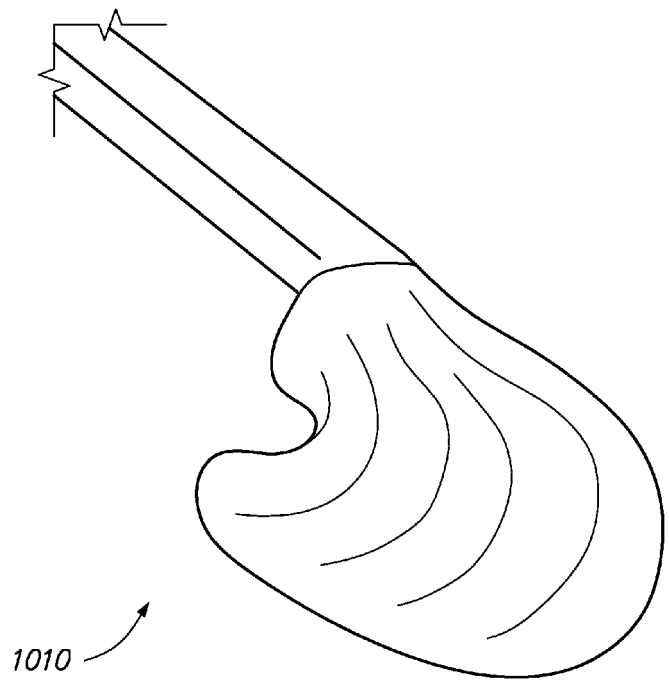
Figure 26:
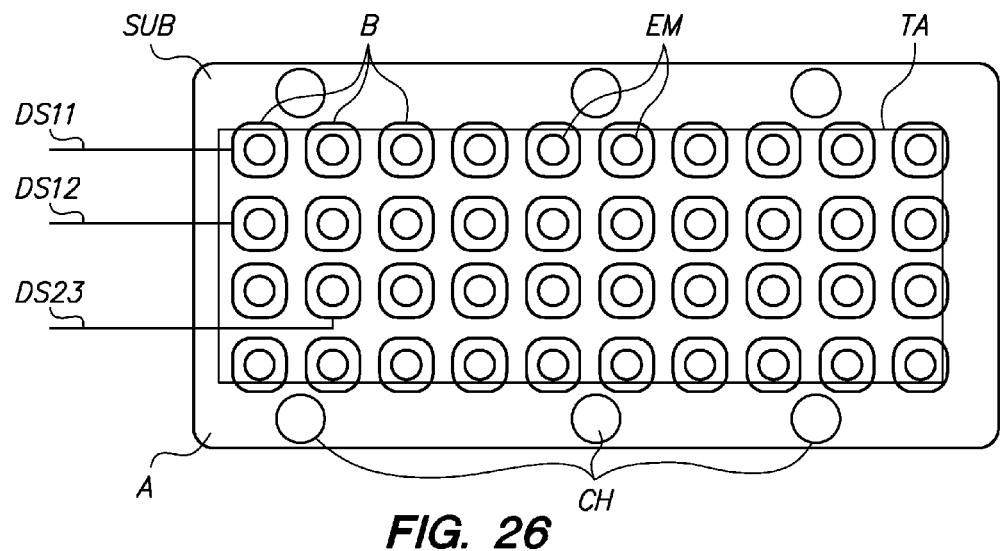
Figure 27A:
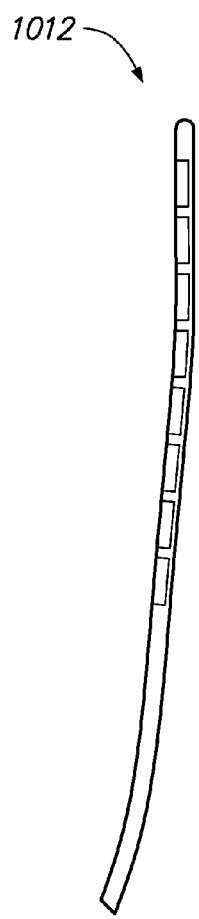
Figure 27B:
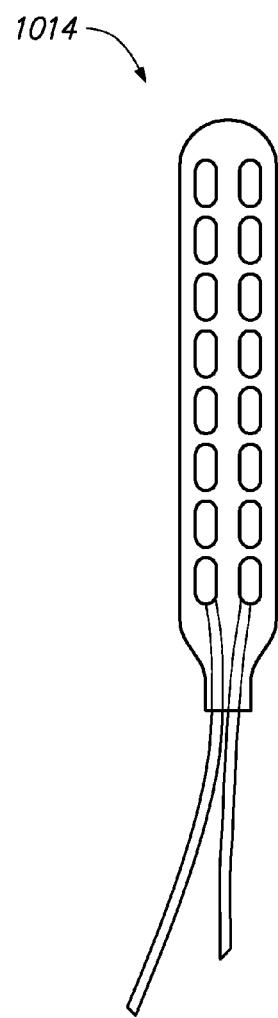
Figure 63:
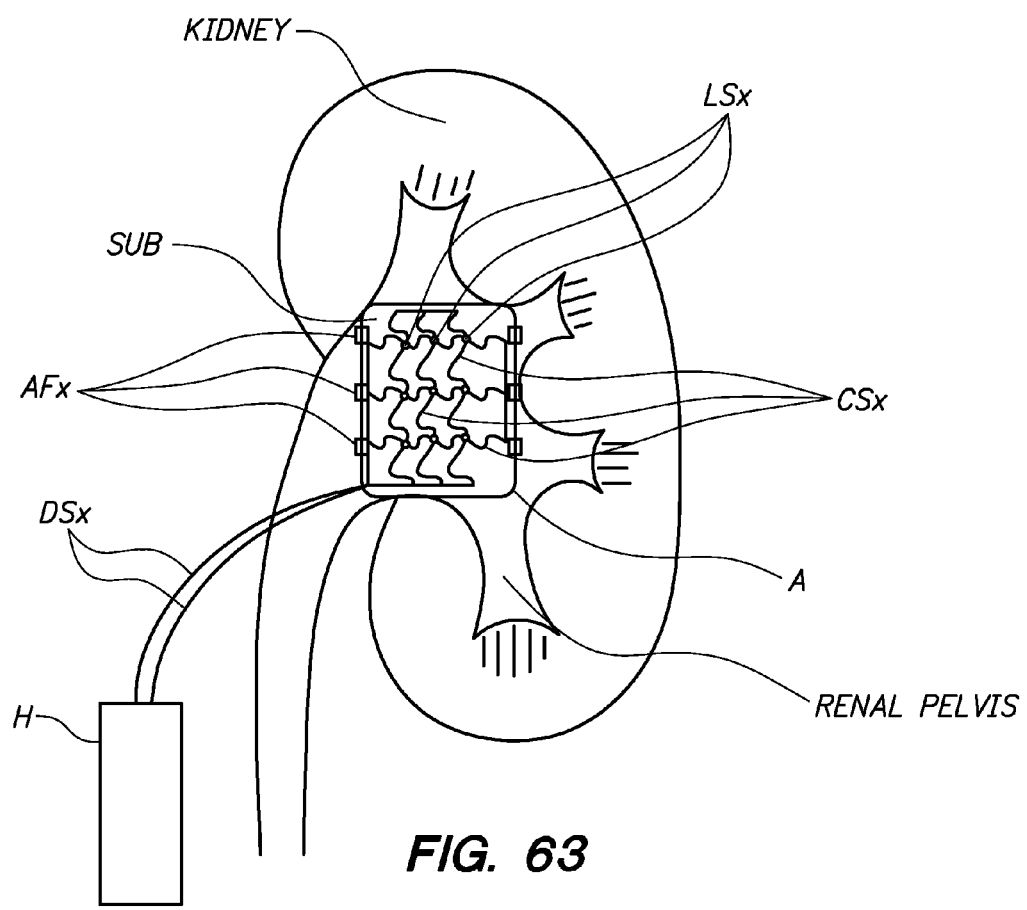
FIG. 63 depicts an embodiment of light delivery configurations for use when treating the renal pelvis connectors in accordance with the present invention.

FIG. 63 shows an alternate embodiment, where an Applicator A is similar to that shown in FIGS. 25-27, being further configured to comprise a web-like substrate SUB configured to lie on the outer surface of the kidney to illuminate the renal pelvis. In this exemplary embodiment, Applicator A comprises Substrate SUB, which is configured as a flexible web structure that may allow for it to be draped onto the target tissue, in this case a RENAL PELVIS of a KIDNEY. As has been described earlier, Delivery Segments DSx connect Applicator A to at least a portion of a system controller, shown here as Housing H. An illustrative example of a web-like Substrate SUB is shown in Kim, et al, "*Waterproof AlInGaP optoelectronics on stretchable substrates with applications in biomedicine and robotics*" Nature Materials 9, 929-937 (2010), which is incorporated herein by reference in its entirety. Anchoring Features AFx are also shown, and may provide means for the applicator to be affirmatively affixed and located on the target tissue. Anchoring Features AF may be, by way of non-limiting examples; tines, barbs, and/or closure holes (as described elsewhere herein).

Referring back to FIG. 1, after delivery of the polynucleotide to the targeted neuroanatomy (6), an expression time period generally is required to ensure that sufficient portions of the targeted neuroanatomy will express the light-responsive opsin protein upon exposure to light (8). This waiting period may, for example, comprise a period of between about 1 month and 4 months. After this period of time, light may be delivered to the targeted neuroanatomy to facilitate the desired therapy. Such delivery of light may take the form of many different configurations, including transcutaneous configurations, implantable configurations, configurations with various illumination wavelengths, pulsing configurations, tissue interfaces, etc., as described below in further detail.

Figure 2A:
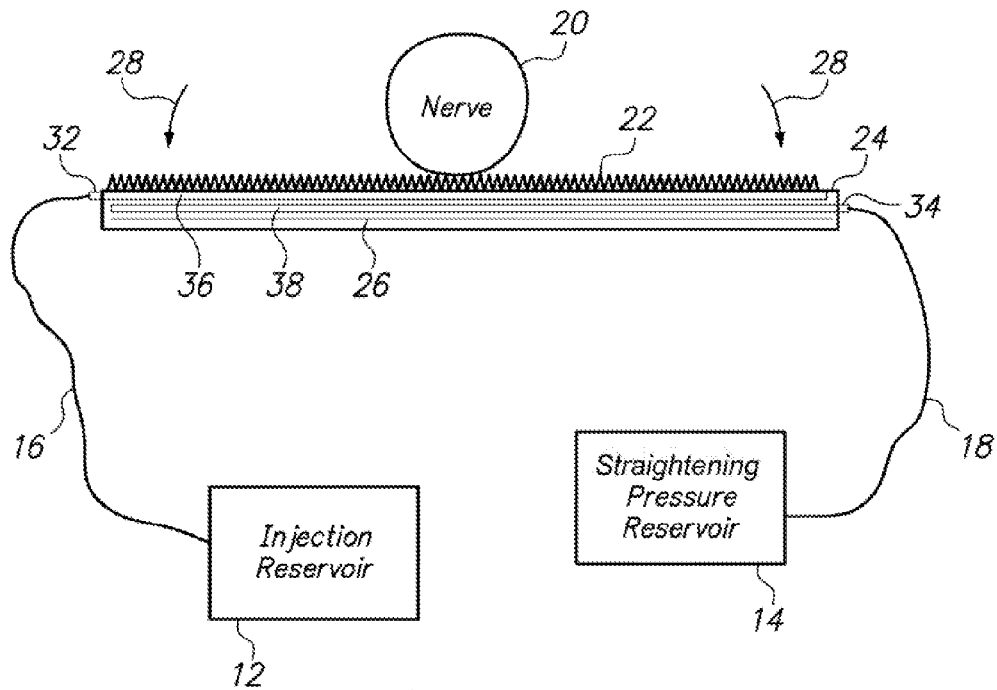
FIGS. 2A and 2B depict an embodiment of an injection configuration for optogenetic treatment of a human in accordance with the present invention.
Figure 2B:
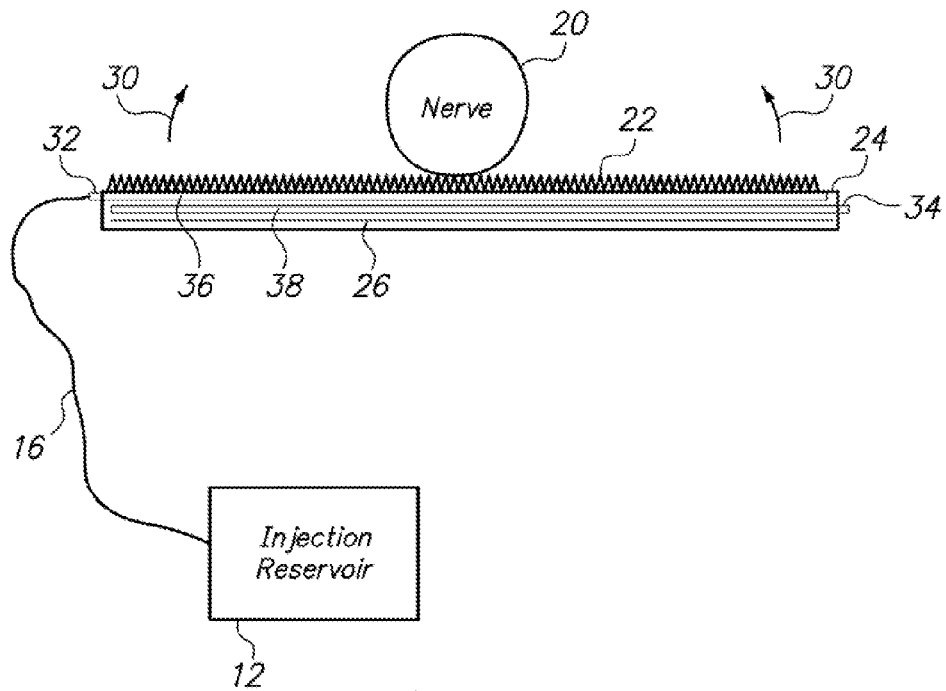

Referring to FIGS. 2A and 2B, both of which are end views showing a cross sectional anatomical face (N) and a cross sectional view of a treatment assembly which in orthogonal view may, for example, be rectangular, trapezoidal, or elliptical (i.e., so that it may provide a sufficient area of exposure to the anatomy N when in contact), a matrix of needles or needle-like injection structures (22) may be utilized to inject a vector solution or gel in a circumferential manner around a nerve (20), nerve bundle, vessel surrounded by nerve fibers, or other somewhat cylindrical targeted anatomic structure into which injection is desired. As shown in FIG. 2A, a flexible or deformable housing (24) may feature a bending spine member (26) configured to bias the housing into a cylindrical (i.e., like a cuff), arcuate, helical, or spiral shape without other counterbalancing loads. For example, the bending spine member may comprise a superalloy such as Nitinol, which may be configured through heat treatment to be pre-biased to assume such cylindrical, arcuate, helical, or spiral shape. The depicted embodiment of the housing (24) also features two embedded bladders—an injection bladder (36) which is fluidly coupled between the matrix of injection members (22) and an injection reservoir by a fluid conduit (16) such as a tube or flexible needle, and a mechanical straightening bladder (38), which is fluidly coupled to a straightening pressure reservoir (14) by a fluid conduit (18) such as a tube or flexible needle. Preferably both fluid conduits (16, 18) are removably coupled to the respective bladders (36, 38) by a removable coupling (32, 34) which may be decoupled by manually pulling the conduits (16, 18) away from the housing (24). The housing (24) may be inserted, for example, through a port in a laparoscopic tool, cannula, or catheter and inserted to a position as shown in FIG. 2A with the straightening bladder (38) fully pressurized to bias the housing into the shown flat condition with the ends rotated downward (28) due to the pressure applied through the straightening pressure reservoir (14), for example using an operatively coupled syringe or controllable pump, and functionally delivered through the associated conduit (18). With the straightened housing (24) in a desirable position relative to the targeted anatomic structure (20), preferably as confirmed using one or more visualization devices such as a laparoscopic camera, ultrasound transducer, fluoroscopy, or the like, the pressure within the straightening pressure reservoir (14) may be controllably decreased (for example, in one embodiment, the associated conduit 18 may simply be disconnected from the coupling 34) to allow the ends of the housing (24) to flex and rotate (30) up and around the anatomical structure (20) due to the now un-counterbalanced bending loads applied by the pre-bending-biased bending spine member (26). FIG. 2B depicts the ends starting to rotate up and around (30) the anatomical structure (20). With complete rotation, the flexible housing preferably will substantially surround at least a portion of the anatomical structure (20) in an arcuate, cuff, helical, or spiral configuration with the matrix of needles (22) interfaced directly against the outer surface of the anatomical structure (20), after which the pressure within the injection reservoir (12) may be controllably increased, for example using an infusion pump or syringe, to inject the anatomical structure (20) with the desired solution or gel. In one embodiment, it may be desirable to leave the housing in place as a prosthesis; in another embodiment it may be desirable to remove the housing after successful injection. In the former scenario, in one variation, the housing may also comprise a light delivery interface, such as is described below (i.e., in addition to a bending spine 26, a straightening bladder 38, an injection bladder 36, and a matrix of needles 22, the housing 24 may also comprise one or more light delivery fibers, lenses, and the like, as described below, to facilitate light therapy after injection of the pertinent genetic material). In the latter scenario, wherein the housing is to be removed after injection, the straightening pressure conduit (18) will remain coupled to the straightening bladder (38) so that after injection has been completed, the pressure within the straightening reservoir (14) may again be controllably increased, thereby rotating (28) the housing back out into a flat configuration as shown in FIG. 2A such that it may then be removed away from the subject anatomy (20). In one embodiment, the matrix of needles (22) may reside upon a movable or flexible membrane or layer relative to the supporting housing (24), and may be biased to recede inward toward the housing (24) when the injection pressure is not heightened, and to become more prominent relative to the supporting housing (24) when the injection pressure is increased; in other words, to assist with delivery and retraction (i.e., so that the housing 24 may be moved around relative to other nearby tissues without scratching, scraping, injuring, or puncturing such tissues without intention), when the injection pressure is relatively low, the injection structures may be configured to become recessed into the housing. It may also be desirable to have the matrix of needles (22) retract subsequent to injection to generally prevent tissue trauma upon exit of the housing (24) in the event that the housing (24) is to be removed, or to prevent fibrous tissue encapsulation of the targeted tissue structure (4) which may be associated with or accelerated by relatively abrasive or indwelling foreign body presence. Indeed, in one embodiment wherein the housing (24) is to remain in place (for example, as an illumination/light applicator platform), the matrix of needles (22) may comprise a bioresorbable material such as PLGA, which is commonly utilized in surgery for its resorbable qualities and may be configured to dissolve and/or resorb away within a short time period after injection has been completed.

Figure 3:
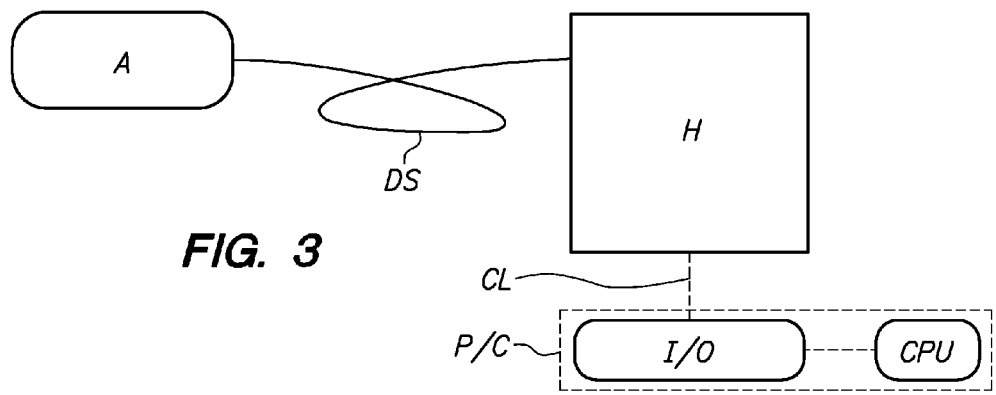
FIG. 3 depicts an embodiment of a system level componentry configuration for optogenetic treatment of a human in accordance with the present invention.

Referring to FIG. 3, a suitable light delivery system comprises one or more applicators (A) configured to provide light output to the targeted tissue structures. The light may be generated within the applicator (A) structure itself, or within a housing (H) that is operatively coupled to the applicator (A) via one or more delivery segments (DS). The one or more delivery segments (DS) serve to transport, or guide, the light to the applicator (A) when the light is not generated in the applicator itself. In an embodiment wherein the light is generated within the applicator (A), the delivery segment (DS) may simply comprise an electrical connector to provide power to the light source and/or other components which may be located distal to, or remote from, the housing (H). The one or more housings (H) preferably are configured to serve power to the light source and operate other electronic circuitry, including, for example, telemetry, communication, control and charging subsystems. External programmer and/or controller (P/C) devices may be configured to be operatively coupled to the housing (H) from outside of the patient via a communications link (CL), which may be configured to facilitate wireless communication or telemetry, such as via transcutaneous inductive coil configurations, between the programmer and/or controller (P/C) devices and the housing (H). The programmer and/or controller (P/C) devices may comprise input/output (I/O) hardware and software, memory, programming interfaces, and the like, and may be at least partially operated by a microcontroller or processor (CPU), which may be housed within a personal computing system which may be a stand-alone system, or be configured to be operatively coupled to other computing or storage systems.

Figure 4A:
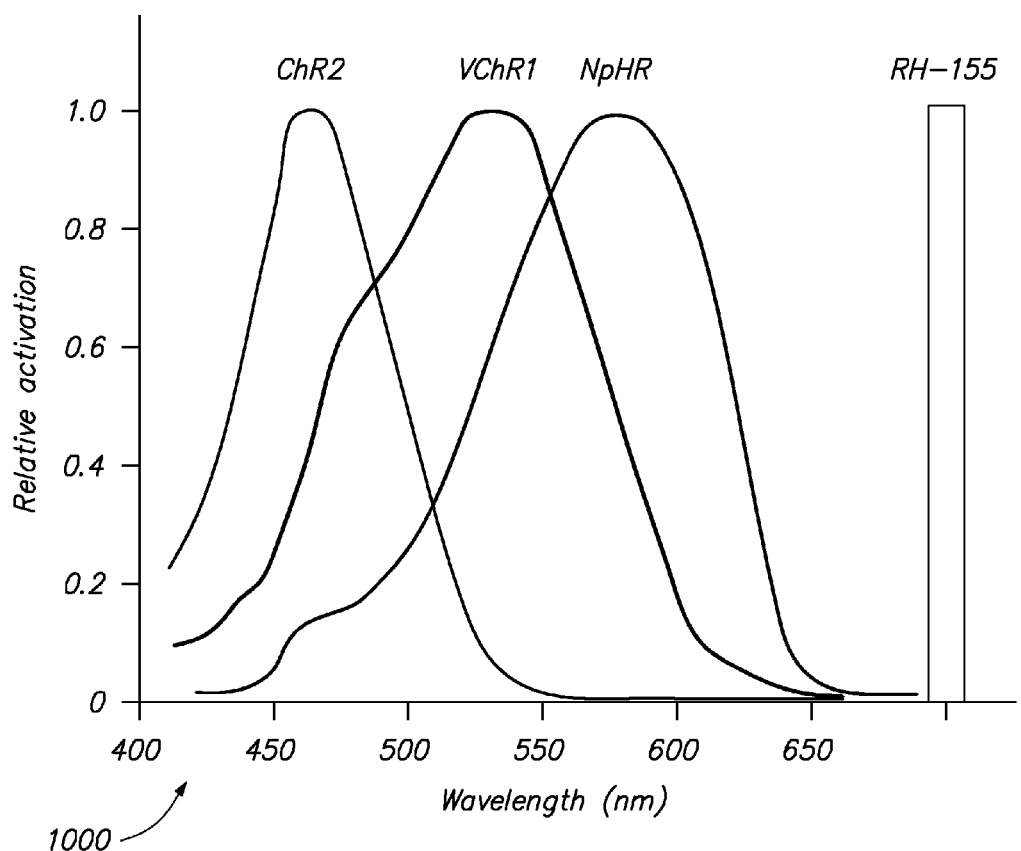
FIGS. 4A and 4B depict activation wavelength and timing charts for various opsin proteins that may be utilized in embodiments of the present invention.
Figure 4B:
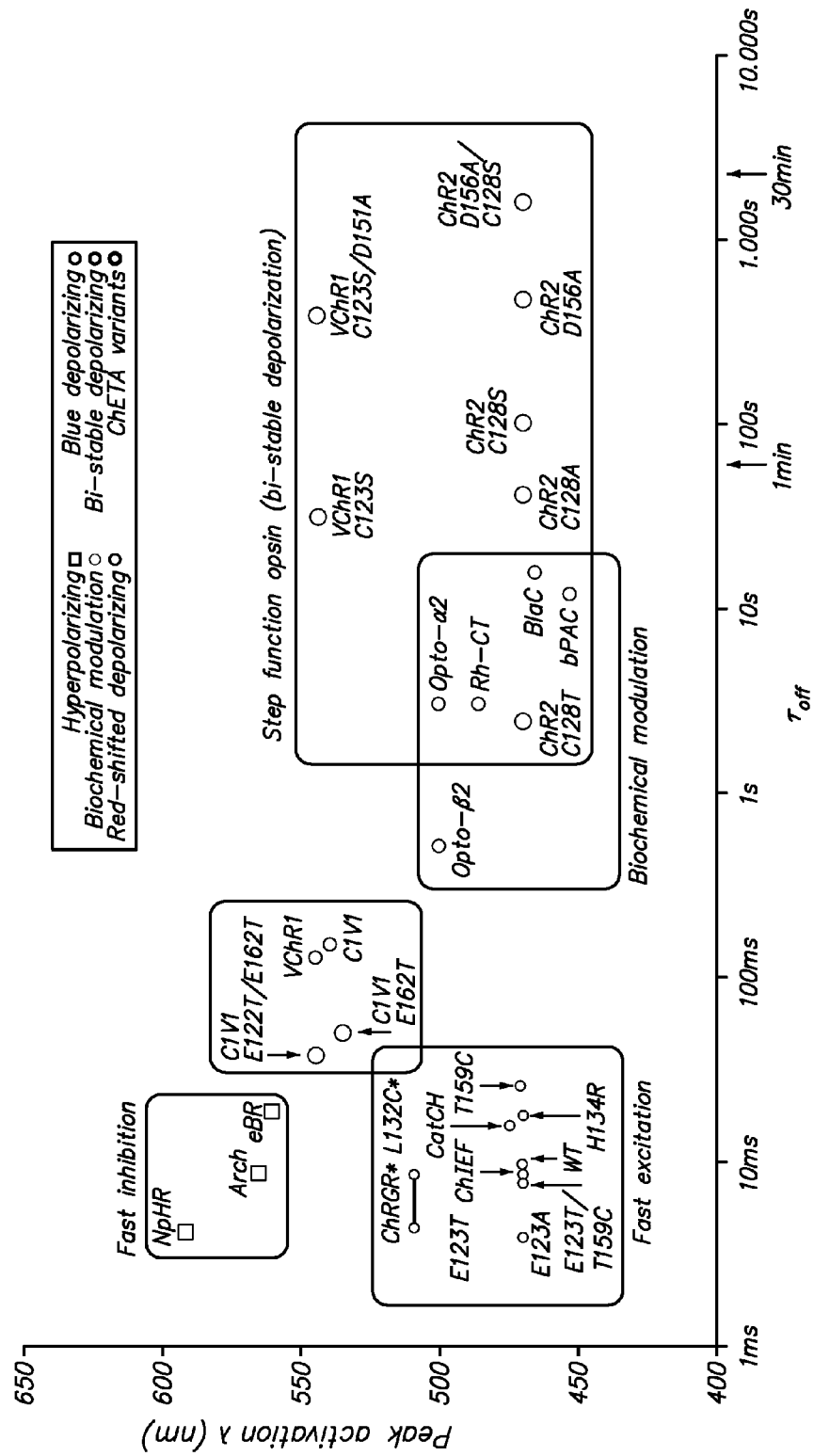

Referring to FIGS. 4A and 4B, as described above, various opsin protein configurations are available to provide excitatory and inhibitory functionality in response to light exposure at various wavelengths. FIG. 4A (1000) depicts wavelength vs. activation for three different opsins; FIG. 4B (1002) emphasizes that various opsins also have time domain activation signatures that may be utilized clinically; for example, certain step function opsins ("SFO") are known to have activations which last into the range of 30 minutes after stimulation with light.

Referring to FIGS. 4C-1 and 4C-2 (1004), a variety of light-emitting diodes (LED) are commercially available to provide illumination at relatively low power with various wavelengths. As described above in reference to FIG. 3, in one embodiment, light may be generated within the housing (H) and transported to the applicator (A) via the delivery segment (DS). Light may also be produced at or within the applicator (A) in various configurations. The delivery segments (DS) may consist of electrical leads or wires without light transmitting capability in such configurations. In other embodiments, light may be delivered using the delivery segments (DS) to be delivered to the subject tissue structures at the point of the applicator (A), or at one or more points along the deliver segment (DS) itself (for example, in one case the DS may be a fiber laser). Referring again to FIGS. 4C-1 and 4C-2 (1004), an LED (or alternatively, "ILED", to denote the distinction between this inorganic system and Organic LEDs) typically is a semiconductor light source, and versions are available with emissions across the visible, ultraviolet, and infrared wavelengths, with relatively high brightness. When a light-emitting diode is forward-biased (switched on), electrons are able to recombine with electron holes within the device, releasing energy in the form of photons. This effect is called electroluminescence and the color of the light (corresponding to the energy of the photon) is determined by the energy gap of the semiconductor. An LED is often small in area (less than 1 $mm^2$), and integrated optical components may be used to shape its radiation pattern. In one embodiment, for example, an LED variation manufactured by Cree Inc. and comprising a Silicon Carbide device providing 24 mW at 20 mA may be utilized as an illumination source.

Organic LEDs (or "OLED"s) are light-emitting diodes wherein the emissive electroluminescent layer is a film of organic compound that emits light in response to an electric current. This layer of organic semiconductor material is situated between two electrodes, which can be made to be flexible. At least one of these electrodes may be made to be transparent. The nontransparent electrode may be made to serve as a reflective layer along the outer surface on an optical applicator, as will be explained later. The inherent flexibility of OLEDs provides for their use in optical applicators such as those described herein that conform to their targets or are coupled to flexible or movable substrates, as described above in reference to FIGS. 2A-2B, and in further detail below. It should be noted, however, due to their relatively low thermal conductivity, OLEDs typically emit less light per area than an inorganic LED.

Other suitable light sources for embodiments of the inventive systems described herein include polymer LEDs, quantum dots, light-emitting electrochemical cells, laser diodes, vertical cavity surface-emitting lasers, and horizontal cavity surface-emitting lasers.

Polymer LEDs (or "PLED"s), and also light-emitting polymers ("LEP"), involve an electroluminescent conductive polymer that emits light when connected to an external voltage. They are used as a thin film for full-spectrum color displays. Polymer OLEDs are quite efficient and require a relatively small amount of power for the amount of light produced.

Quantum dots (or "QD") are semiconductor nanocrystals that possess unique optical properties. Their emission color may be tuned from the visible throughout the infrared spectrum. They are constructed in a manner similar to that of OLEDs.

A light-emitting electrochemical cell ("LEC" or "LEEC") is a solid-state device that generates light from an electric current (electroluminescence). LECs may be usually composed of two electrodes connected by (e.g. "sandwiching") an organic semiconductor containing mobile ions. Aside from the mobile ions, their structure is very similar to that of an OLED. LECs have most of the advantages of OLEDs, as well as a few additional ones, including:

The device does not depend on the difference in work function of the electrodes. Consequently, the electrodes can be made of the same material (e.g., gold). Similarly, the device can still be operated at low voltages;

Recently developed materials such as graphene or a blend of carbon nanotubes and polymers have been used as electrodes, eliminating the need for using indium tin oxide for a transparent electrode;

The thickness of the active electroluminescent layer is not critical for the device to operate, and LECs may be printed with relatively inexpensive printing processes (where control over film thicknesses can be difficult).

Semiconductor Lasers are available in a variety of output colors, or wavelengths. There are a variety of different configurations available that lend themselves to usage in the present invention, as well. Indium gallium nitride ($In_x Ga_{1-x}N$, or just InGaN) laser diodes have high brightness output at both 405, 445, and 485 nm, which are suitable for the activation of ChR2. The emitted wavelength, dependent on the material's band gap, can be controlled by the GaN/InN ratio; violet-blue 420 nm for 0.2 In/0.8 Ga, and blue 440 nm for 0.3 In/0.7 Ga, to red for higher ratios and also by the thickness of the InGaN layers which are typically in the range of 2-3 nm.

A laser diode (or "LD") is a laser whose active medium is a semiconductor similar to that found in a light-emitting diode. The most common type of laser diode is formed from a p-n junction and powered by injected electric current. The former devices are sometimes referred to as injection laser diodes to distinguish them from optically pumped laser diodes. A laser diode may be formed by doping a very thin layer on the surface of a crystal wafer. The crystal may be doped to produce an n-type region and a p-type region, one above the other, resulting in a p-n junction, or diode. Laser diodes form a subset of the larger classification of semiconductor p-n junction diodes. Forward electrical bias across the laser diode causes the two species of charge carrier—holes and electrons—to be "injected" from opposite sides of the p-n junction into the depletion region. Holes are injected from the p-doped, and electrons from the n-doped, semiconductor. (A depletion region, devoid of any charge carriers, forms as a result of the difference in electrical potential between n- and p-type semiconductors wherever they are in physical contact.) Due to the use of charge injection in powering most diode lasers, this class of lasers is sometimes termed "injection lasers" or "injection laser diodes" ("ILD"). As diode lasers are semiconductor devices, they may also be classified as semiconductor lasers. Either designation distinguishes diode lasers from solid-state lasers. Another method of powering some diode lasers is the use of optical pumping. Optically Pumped Semiconductor Lasers (or "OPSL") use a III-V semiconductor chip as the gain media, and another laser (often another diode laser) as the pump source. OPSLs offer several advantages over ILDs, particularly in wavelength selection and lack of interference from internal electrode structures. When an electron and a hole are present in the same region, they may recombine or "annihilate" with the result being spontaneous emission—i.e., the electron may re-occupy the energy state of the hole, emitting a photon with energy equal to the difference between the electron and hole states involved. (In a conventional semiconductor junction diode, the energy released from the recombination of electrons and holes is carried away as phonons, i.e., lattice vibrations, rather than as photons.) Spontaneous emission gives the laser diode below lasing threshold similar properties to an LED. Spontaneous emission is necessary to initiate laser oscillation, but it is one among several sources of inefficiency once the laser is oscillating. The difference between the photon-emitting semiconductor laser and conventional phonon-emitting (non-light-emitting) semiconductor junction diodes lies in the use of a different type of semiconductor, one whose physical and atomic structure confers the possibility for photon emission. These photon-emitting semiconductors are the so-called "direct bandgap" semiconductors. The properties of silicon and germanium, which are single-element semiconductors, have bandgaps that do not align in the way needed to allow photon emission and are not considered "direct." Other materials, the so-called compound semiconductors, have virtually identical crystalline structures as silicon or germanium but use alternating arrangements of two different atomic species in a checkerboard-like pattern to break the symmetry. The transition between the materials in the alternating pattern creates the critical "direct bandgap" property. Gallium arsenide, indium phosphide, gallium antimonide, and gallium nitride are all examples of compound semiconductor materials that may be used to create junction diodes that emit light.

Vertical-cavity surface-emitting lasers (or "VCSEL"s) have the optical cavity axis along the direction of current flow rather than perpendicular to the current flow as in conventional laser diodes. The active region length is very short compared with the lateral dimensions so that the radiation emerges from the surface of the cavity rather than from its edge as shown in the figure. The reflectors at the ends of the cavity are dielectric mirrors made from alternating high and low refractive index quarter-wave thick multilayer. VCSELs allow for monolithic optical structures to be produced.

Horizontal cavity surface-emitting lasers (or "HCSEL"s) combine the power and high reliability of a standard edge-emitting laser diode with the low cost and ease of packaging of a vertical cavity surface-emitting laser (VCSEL). They also lend themselves to use in integrated on-chip optronic, or photonic packages.

Figure 5:
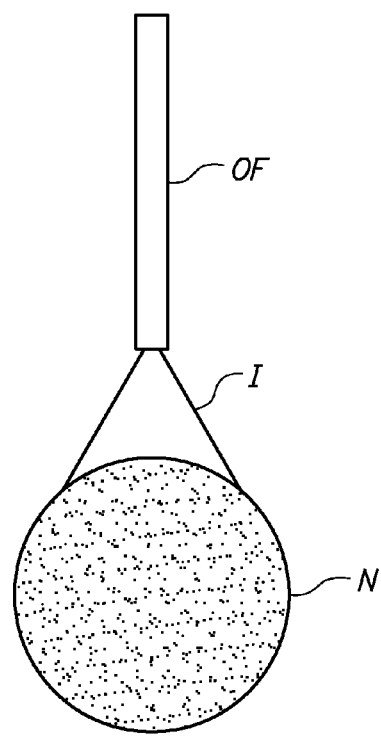
FIG. 5 depicts an embodiment of one portion of an illumination configuration for optogenetic treatment of a human in accordance with the present invention.

The irradiance required at the neural membrane in which the optogenetic channels reside is on the order of 0.05-2 mW/mm$^2$ and depends upon numerous elements, such as opsin channel expression density, activation threshold, etc. A modified channelrhodopsin-2 resident within a neuron may be activated by illumination of the neuron with green or blue light having a wavelength of between about 420 nm and about 520 nm, and in one example about 473 nm, with an intensity of between about 0.5 mW/mm$^2$ and about 10 mW/mm$^2$, such as between about 1 mW/mm$^2$ and about 5 mW/mm$^2$, and in one example about 2.4 mW/mm$^2$. Although the excitation spectrum may be different, similar exposure values hold for other opsins, such as NpHR, as well. Because most opsin-expressing targets are contained within a tissue or other structure, the light emitted from the applicator may need to be higher in order to attain the requisite values at the target itself. Light intensity, or irradiance, is lost predominantly due to optical scattering in tissue, which is a turbid medium. There is also parasitic absorption of endogenous chromophores, such as blood, that may also diminish the target exposure. Because of these effects, the irradiance range required at the output of an applicator is, for most of the cases described herein, between 1-100 mW/mm$^2$. Referring to FIG. 5, experiments have shown, for example, that for the single-sided exposure of illumination (I) from an optical fiber (OF) of a 1 mm diameter nerve bundle (N), the measured response (in arbitrary units) vs. irradiance (or Light Power Density, in mW/mm$^2$) is asymptotic, as shown in the graph depicted in FIG. 6 (1006). There is not appreciable improvement beyond 20 mW/mm$^2$ for this specific configuration of opsin protein, expression density, illumination geometry, and pulse parameters. However, we may use this result to scale the irradiance requirements to other targets with similar optical properties and opsin protein expression densities. The data in FIG. 6 (1006) may be used in a diffusion approximation optical model for neural materials, where the irradiance (I) obeys the following relation, $I=I_o e^{-(Q\mu z)}$. The resulting expression fits well with the following experimental data, and the result of this is given in the plot of FIG. 7 (1008). The details are further discussed below.

The optical penetration depth, δ, is the tissue thickness that causes light to attenuate to $e^{-1}$ (~37%) of its initial value, and is given by the following diffusion approximation.

$$\delta = \frac{1}{\sqrt{3\mu_a \mu_s'}},$$

where $\mu_a$ is the absorption coefficient, and $\mu_s'$ is the reduced scattering coefficient. The reduced scattering coefficient is a lumped property incorporating the scattering coefficient $\mu_s$ and the anisotropy g: $\mu_s' = \mu_s(1-g)$ [cm$^{-1}$]. The purpose of $\mu_s'$ is to describe the diffusion of photons in a random walk of step size of $1/\mu_s'$ [cm] where each step involves isotropic scattering. Such a description is equivalent to description of photon movement using many small steps $1/\mu_s$ that each involve only a partial deflection angle θ, if there are many scattering events before an absorption event, i.e., $\mu_a \ll \mu_s'$. The anisotropy of scattering, g, is effectively the expectation value of the scattering angle, θ. Furthermore, the "diffusion exponent," $\mu_{\mathit{eff}}$, is a lumped parameter containing ensemble information regarding the absorption and scattering of materials, $P_{\mathit{eff}} = \mathrm{Sqrt}(3\mu_a(\mu_a+\mu_s'))$. The cerebral cortex constitutes a superficial layer of grey matter (high proportion of nerve cell bodies) and internally the white matter, which is responsible for communication between axons. The white matter appears white because of the multiple layers formed by the myelin sheaths around the axons, which are the origin of the high, inhomogeneous and anisotropic scattering properties of brain, and is a suitable surrogate for use in neural tissue optics calculations with published optical properties, such as those below for feline white matter.

| $\lambda$ [νμ] | $\alpha_\alpha$ [χμ$^{-1}$] | $\alpha_\alpha$ [χμ$^{-1}$] | | $\alpha_{o\square}$ [χμ$^{-1}$] | $\alpha_{\epsilon\phi\phi}$ [χμ$^{-1}$] | $\delta$ [χμ] |
|---|---|---|---|---|---|---|
| 633 | 52.6 | 1.58 | .80 | 10.52 | 7.5 | 0.14 |
| 514 | — | — | | — | 10.9 | 0.091 |
| 488 | — | — | | — | 13.3 | 0.075 |

As was described earlier, the one-dimensional irradiance profile in tissue, I, obeys the following relation, $I=I_o e^{-(Q\mu z)}$, where Q is the volume fraction of the characterized material that is surrounded by an optically neutral substance such as interstitial fluid or physiologic saline. In the case of most nerves, Q=0.45 can be estimated from cross-sectional images. The optical transport properties of tissue yield an exponential decrease of the irradiance (ignoring temporal spreading, which is inconsequential for this application) through the target, or the tissue surrounding the target(s). The plot above contains good agreement between theory and model, validating the approach. It can be also seen that the optical penetration depth, as calculated by the above optical parameters agrees reasonably well with the experimental observations of measured response vs. irradiance for the example described above.

Furthermore, the use of multidirectional illumination, as has been described herein, may serve to reduce this demand, and thus the target radius may be considered as the limiting geometry, and not the diameter. For instance, if the above-mentioned case of illuminating a 1 mm nerve from 2 opposing sides instead of just the one, we can see that we will only need an irradiance of ~6 mW/mm$^2$ because the effective thickness of the target tissue is now ½ of what it was. It should be noted that this is not a simple linear system, or the irradiance value would have been 20/2=10 mW/mm$^2$. The discrepancy lies in the exponential nature of the photon transport process, which yields the severe diminution of the incident power at the extremes of the irradiation field. Thus, there is a practical limit to the number of illuminations directions that provide an efficiency advantage for deep, thick, and/or embedded tissue targets.

Figure 8:
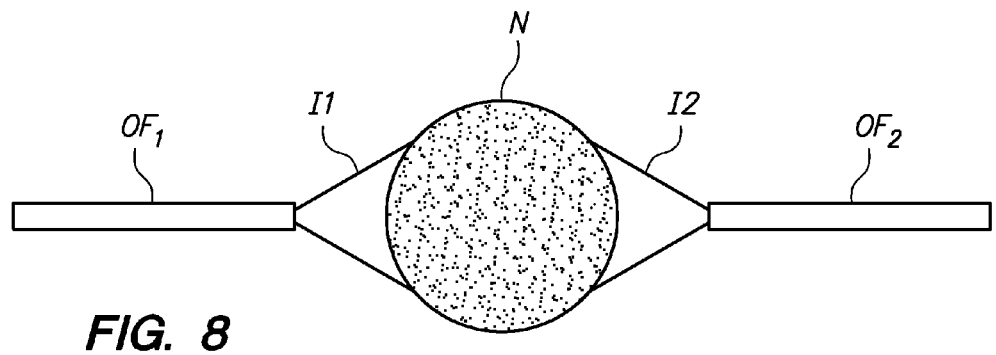
FIGS. 8-28 depict various aspects of embodiments of light delivery configurations which may be utilized for optogenetic treatment of a human in accordance with the present invention.

By way of non-limiting example, a 2 mm diameter nerve target may be considered a 1 mm thick target when illuminated circumferentially. Values of the sizes of a few key nerves follows as a set of non-limiting examples. The diameter of the main trunk of the pudendal nerve is 4.67±1.17 mm, whereas the branches of the ulnar nerve range in diameter from about 0.7-2.2 mm and the vagus nerve in the neck between 1.5-2.5 mm. Circumferential, and/or broad illumination may be employed to achieve electrically and optically efficient optogenetic target activation for larger structures and/or enclosed targets that cannot be addressed directly. This is illustrated in FIG. 8, where Optical Fibers OF1 and OF2 now illuminate the targeted tissue structure (N) from diametrically opposing sides with Illumination Fields I1 and I2, respectively. Alternately, the physical length of the illumination may be extended to provide for more photoactivation of expressed opsin proteins, without the commensurate heat build up associated with intense illumination limited to smaller area. That is, the energy may be spread out over a larger area to reduce localized temperature rises. In a further embodiment, the applicator may contain a temperature sensor, such as a resistance temperature detector (RTD), thermocouple, or thermistor, etc. to provide feedback to the processor in the housing to assure that temperature rises are not excessive, as is discussed in further detail below.

Figure 9:
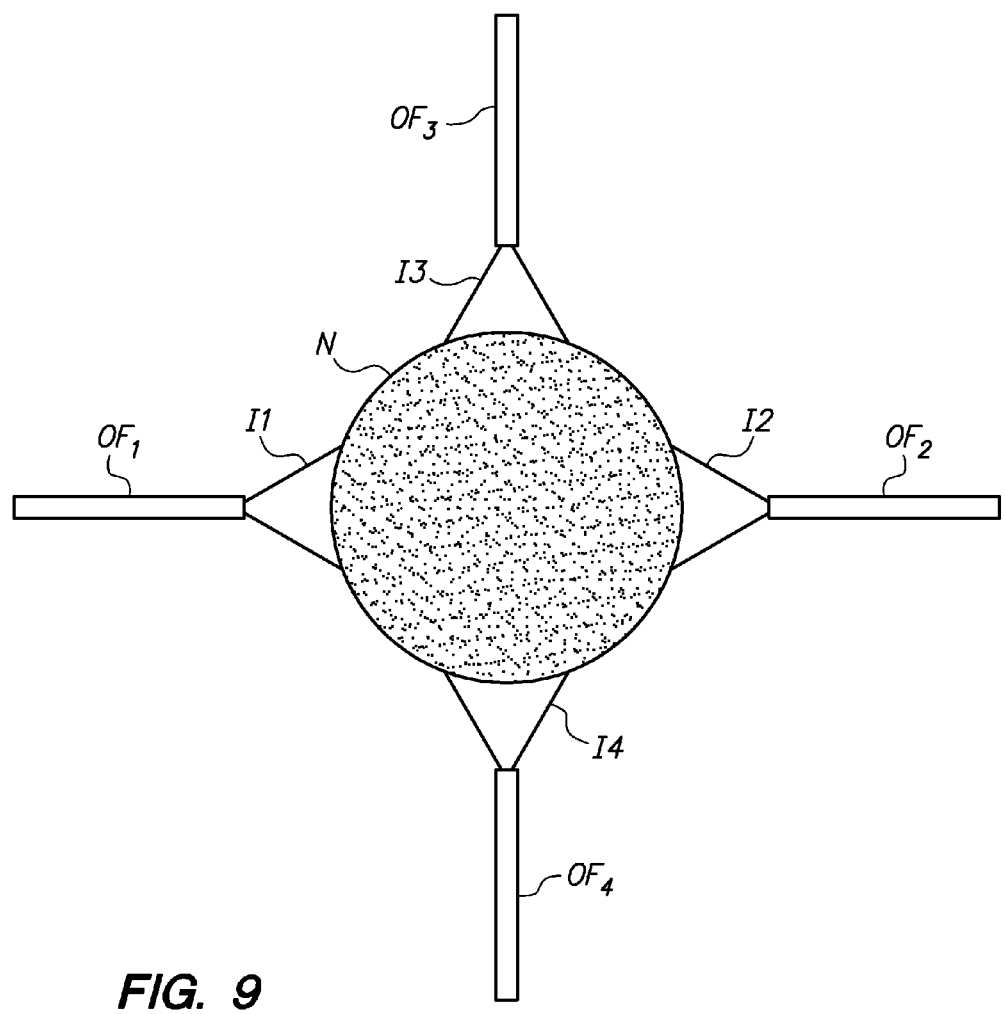

From the examples above, activation of a neuron, or set(s) of neurons within a 2.5 mm diameter vagus nerve may be nominally circumferentially illuminated by means of the optical applicators described later using an external surface irradiance of ≥5.3 mW/mm$^2$, as can be seen using the above curve when considering the radius as the target tissue thickness, as before. However, this is greatly improved over the 28 mW/mm$^2$ required for a 2.5 mm target diameter, or thickness. In this case, 2 sets of the opposing illumination systems from the embodiment above may be used, as the target surface area has increased, configuring the system to use Optical Fibers OF3 and OF4 to provide Illumination Fields I3 and I4, as shown in FIG. 9. There are also thermal concerns to be understood and accounted for in the design of optogenetic systems, and excessive irradiances will cause proportionately large temperature rises. Thus, it may be beneficial to provide more direct optical access to targets embedded in tissues with effective depths of greater than ~2 mm because of the regulatory limit applied to temperature rise allowed by conventional electrical stimulation, or "e-stim", devices of ΔT≤2.0° C.

Figure 10A:
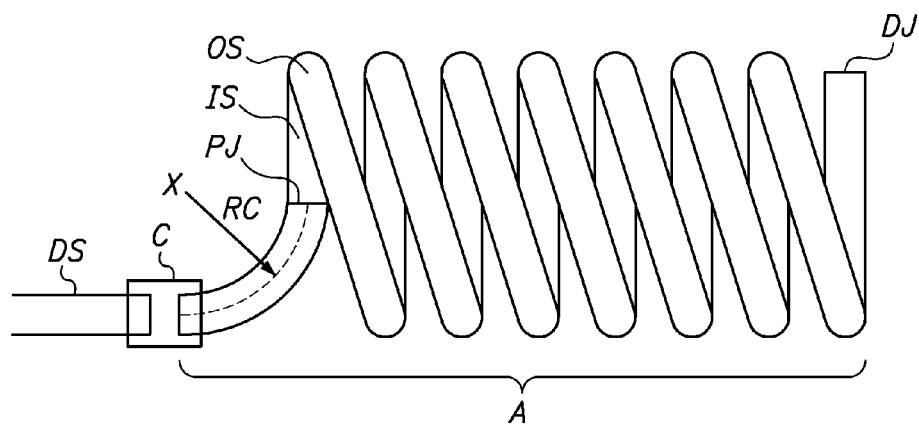
Figure 10B:
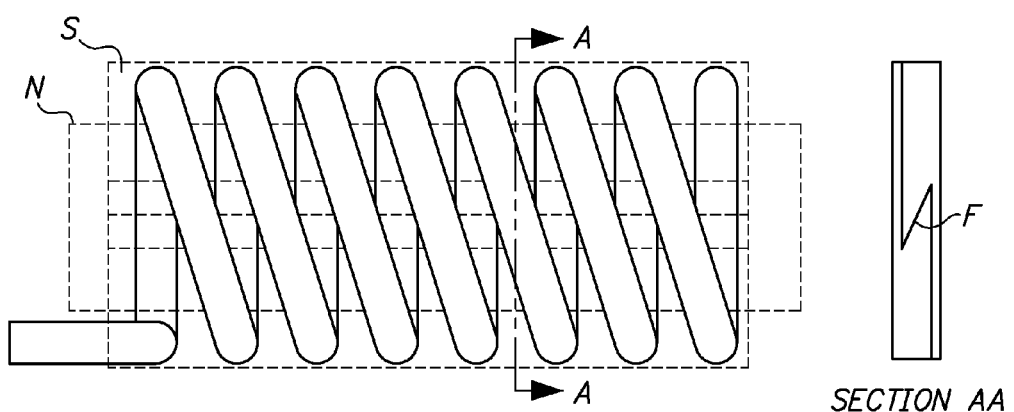
Figure 10C:

As described above, optical applicators suitable for use with the present invention may be configured in a variety of ways. Referring to FIGS. 10A-10C, a helical applicator with a spring-like geometry is depicted. Such a configuration may be configured to readily bend with, and/or conform to, a targeted tissue structure (N), such as a nerve, nerve bundle, vessel, or other structure to which it is temporarily or permanently coupled. Such a configuration may be coupled to such targeted tissue structure (N) by "screwing" the structure onto the target, or onto one or more tissue structures which surround or are coupled to the target. As shown in the embodiment of FIG. 10A, a waveguide may be connected to, or be a contiguous part of, a delivery segment (DS), and separable from the applicator (A) in that it may be connected to the applicator via connector (C). Alternately, it may be affixed to the applicator portion without a connector and not removable. Both of these embodiments are also described with respect to the surgical procedure described herein. Connector (C) may be configured to serve as a slip-fit sleeve into which both the distal end of Delivery Segment (DS) and the proximal end of the applicator are inserted. In the case where the delivery segment is an optical conduit, such an optical fiber, it preferably should be somewhat undersized in comparison to the applicator waveguide to allow for axial misalignment. For example, a 50 μm core diameter fiber may be used as delivery segment (DS) to couple to a 100 μm diameter waveguide in the applicator (A). Such 50 μm axial tolerances are well within the capability of modern manufacturing practices, including both machining and molding processes. The term waveguide is used herein to describe an optical conduit that confines light to propagate nominally within it, albeit with exceptions for output coupling of the light, especially to illuminate the target.

Figure 64:
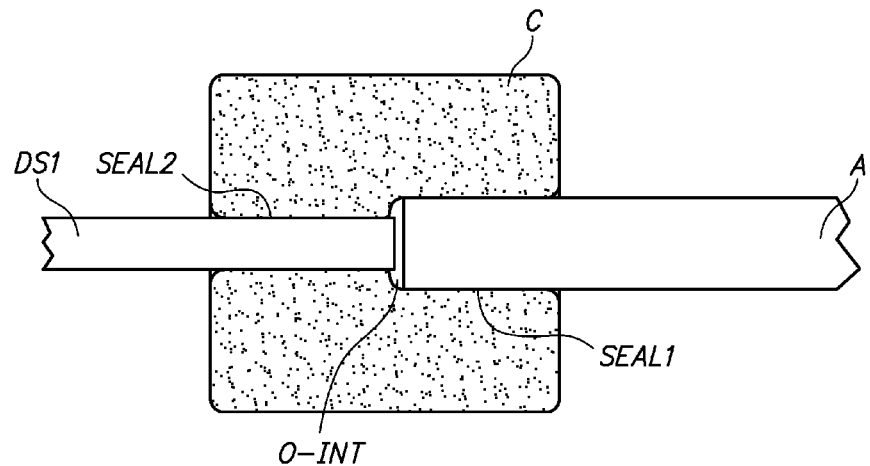
FIGS. 64-68 depict various aspects of embodiments of optical and/or electronic connectors in accordance with the present invention.

FIG. 64 shows an exemplary embodiment, wherein Connector C may comprise a single flexible component made of a polymer material to allow it to fit snugly over the substantially round cross-sectional Delivery Segment DS1, and Applicator A. These may be waveguides such as optical fibers and similar mating structures on the applicator, and/or delivery segment, and/or housing to create a substantially water-tight seal, shown as SEAL1 & SEAL2, that substantially prevents cells, tissues, fluids, and/or other biological materials from entering the Optical Interface O-INT.

Figure 65:
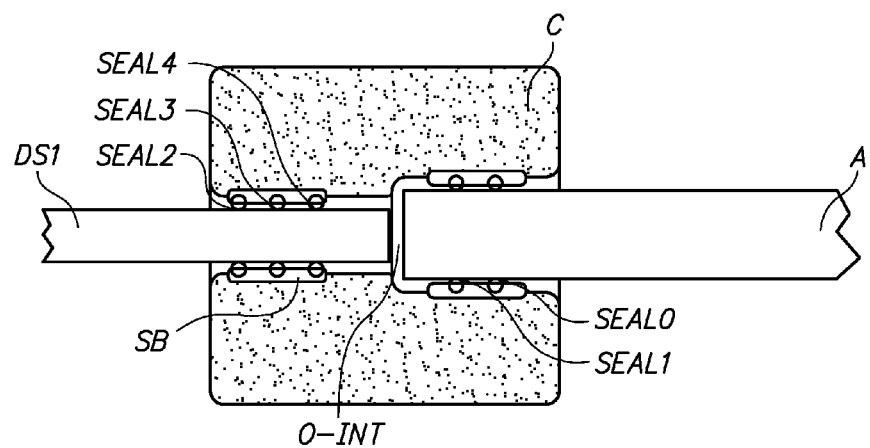

FIG. 65 shows an alternate exemplary embodiment, wherein Connector C may comprise a set of seals, shown as SEAL0 through SEAL 4, rather than rely upon the entire device to seal the optical connection. A variety of different sealing mechanisms may be utilized, such as, by way of non-limiting example, o-rings, single and dual lip seals, and wiper seals. The materials that may be used, by way of non-limiting example, are Nitrile (NBR, such as S1037), Viton, Silicone (VMQ, such as V1039, S1083 and S1146), Neoprene, Chloroprene (CR), Ethylene Propylene (EPDM, such as E1074 and E1080), Polyacrylic (ACM), Styrene Butadiene Rubber (SBR), and Fluorosilicone (FVMQ). SEAL0 through SEAL4 are shown in the exemplary embodiment to be resident within a Seal Bushing SB.

Alternately, the seal may be a component of the delivery segment and/or the housing, and/or the applicator, thus eliminating one insertion seal with a fixed seal, which may improve the robustness of the system. Such a hybrid system is shown in FIG. 66, where SEAL1 is shown as an integral seal permanently linking Applicator A with its subcomponent Connector C such that the connection at Optical Interface O-INT is established by inserting Delivery Segment DS1 into Connector C, and having seals SEAL2, SEAL3, and SEAL4 create the substantially water-tight seal about Delivery Segment DS1, while SEAL1 is integrated into Connector C.

Alternately, or in addition to the other embodiments, a biocompatible adhesive, such as, by way of non-limiting example, Loctite 4601, may be used to adhere the components being connected. Although other adhesives are considered within the scope of the present invention, cyanoacrylates such as Loctite 4601, have relatively low shear strength, and may be overcome by stretching and separating the flexible sleeve from the mated components for replacement without undue risk of patient harm. However, care must be taken to maintain clarity at Optical Interface O-INT.

Figure 67:
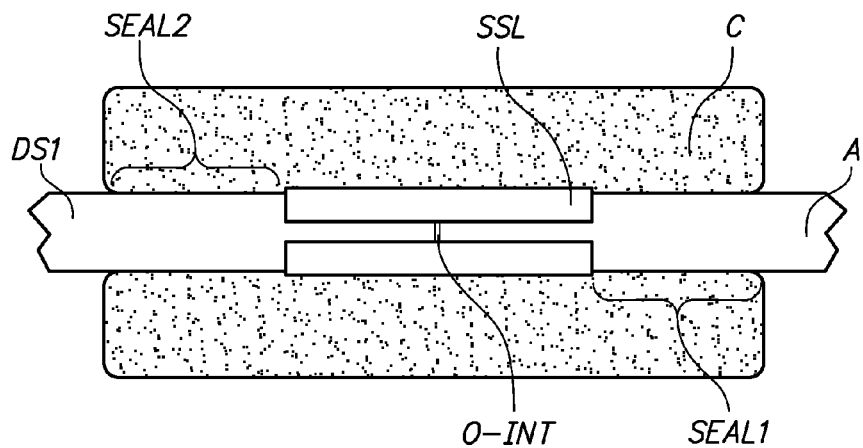

FIG. 67 shows an alternate exemplary embodiment, wherein Connector C may further comprise a high precision sleeve, Split Sleeve SSL, which is configured to axially align the optical elements at Optical Interface O-INT. By way of non-limiting example, split zirconia ceramic sleeves for coupling both Ø1.25 and Ø2.5 mm fiber optic ferrules, not shown, may be used to provide precision centration and all those components are available from Adamant-Kogyo. Similarly, other diameters may be accommodated using the same split sleeve approach to butt-coupling optical elements, such as optical fibers themselves.

Figure 66:
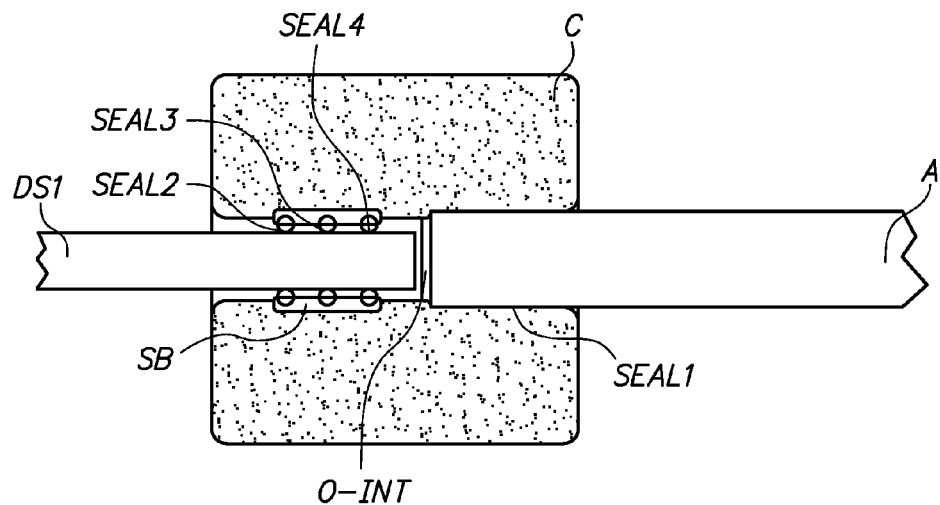
Figure 68:
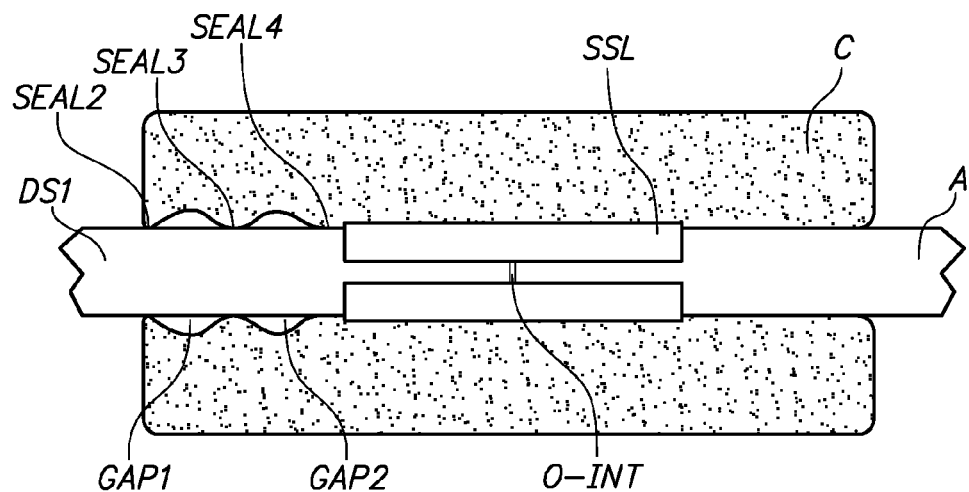

FIG. 68 shows an alternate exemplary embodiment, wherein the seals of FIGS. 66-67 of Connector C have been replaced by an integral sealing mechanism comprised of seals SEAL2 through SEAL4, that serve to fit about the circumference of Delivery Segment DS1, and create gaps GAP1 and GAP2. Rather than utilizing separate sealing elements, the sealing elements as shown are made to be part of an integrated sleeve.

Alternately, although not shown, the sealing mechanism may be configured to utilize a threaded mechanism to apply axial pressure to the sealing elements to create a substantially water-tight seal that substantially prevents cells, tissues, fluids, and/or other biological materials from entering the optical interfaces.

As shown in FIGS. 10A-10C and 64-68, the optical elements being connected by Connector C may be optical fibers, as shown in the exemplary embodiments. They may also be other portions of the therapeutic system, such as the delivery segments, an optical output from the housing, and an applicator itself.

Biocompatible adhesive may be applied to the ends of connector (C) to ensure the integrity of the coupling. Alternately, connector (C) may be configured to be a contiguous part of either the applicator or the delivery device. Connector (C) may also provide a hermetic electrical connection in the case where the light source is located at the applicator. In this case, it may also serve to house the light source, too. The light source may be made to butt-couple to the waveguide of the applicator for efficient optical transport. Connector (C) may be contiguous with the delivery segment or the applicator. Connector (C) may be made to have cross-sectional shape with multiple internal lobes such that it may better serve to center the delivery segment to the applicator.

The applicator (A) in this embodiment also comprises a Proximal Junction (PJ) that defines the beginning of the applicator segment that is in optical proximity to the target nerve. That is, PJ is the proximal location on the applicator optical conduit (with respect to the direction the light travels into the applicator) that is well positioned and suited to provide for light output onto the target. The segment just before PJ is curved, in this example, to provide for a more linear aspect to the overall device, such as might be required when the applicator is deployed along a nerve, and is not necessarily well suited for target illumination. Furthermore, the applicator of this exemplary embodiment also comprises a Distal Junction (DJ), and Inner Surface (IS), and an Outer Surface (OS). Distal Junction (DJ) represents the final location of the applicator still well positioned and suited to illuminate the target tissue(s). However, the applicator may extend beyond DJ, no illumination is intended beyond DJ. DJ may also be made to be a reflective element, such as a mirror, retro-reflector, diffuse reflector, a diffraction grating, A Fiber Bragg Grating ("FBG"—further described below in reference to FIG. 12), or any combination thereof. An integrating sphere made from an encapsulated "bleb" of $BaSO_4$, or other such inert, non-chromophoric compound may serve a diffuse reflector when positioned, for example, at the distal and of the applicator waveguide. Such a scattering element should also be placed away from the target area, unless light that is disallowed from waveguiding due to its spatial and/or angular distribution is desired for therapeutic illumination.

Figure 11A:
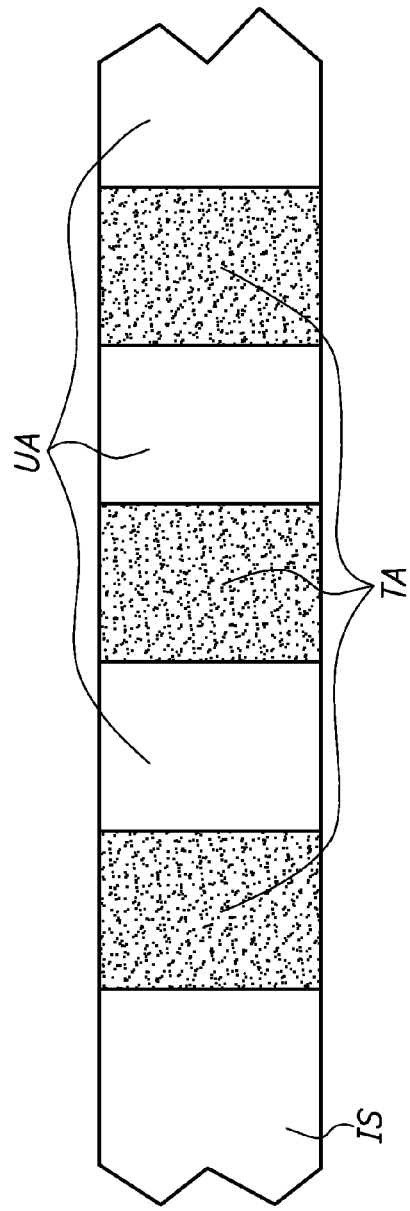

Inner Surface (IS) describes the portion of the applicator that "faces" the target tissue, shown here as Nerve (N). That is, N lies within the coils of the applicator and is in optical communication with IS. That is, light exiting IS is directed towards N. Similarly, Outer Surface (OS) describes that portion of the applicator that is not in optical communication with the target. That is, the portion that faces outwards, away from the target, such a nerve that lies within the helix. Outer Surface (OS) may be made to be a reflective surface, and as such will serve to confine the light within the waveguide and allow for output to the target via Inner Surface (IS). The reflectivity of OS may be achieved by use of a metallic or dielectric reflector deposited along it, or simply via the intrinsic mechanism underlying fiber optics, total internal reflection ("TIR"). Furthermore, Inner Surface (IS) may be conditioned, or affected, such that it provides for output coupling of the light confined within the helical waveguide. The term output coupling is used herein to describe the process of allowing light to exit the waveguide in a controlled fashion, or desired manner. Output coupling may be achieved in various ways. One such approach may be to texture IS such that light being internally reflected no longer encounters a smooth TIR interface. This may be done along IS continuously, or in steps. The former is illustrated in FIG. 11A in a schematic representation of such a textured applicator, as seen from IS. Surface texture is synonymous with surface roughness, or rugosity. It is shown in the embodiment of FIG. 11A as being isotropic, and thus lacking a definitive directionality. The degree of roughness is proportional to the output coupling efficiency, or the amount of light removed form the applicator in proportion to the amount of light encountering the Textured Area. In one embodiment, the configuration may be envisioned as being akin to what is known as a "matte finish", whereas OS will may be configured to have a more planar and smooth finish, akin to what is known as a "gloss finish". A Textured Area may be an area along or within a waveguide that is more than a simple surface treatment. It might also comprise a depth component that either diminishes the waveguide cross sectional area, or increases it to allow for output coupling of light for target illumination.

In this non-limiting example, IS contains areas textured with Textured Areas TA correspond to output couplers (OCs), and between them are Untextured Areas (UA). Texturing of textured Areas (TA) may be accomplished by, for example, mechanical means (such as abrasion) or chemical means (such as etching). In the case where optical fiber is used as the basis for the applicator, one may first strip buffer and cladding layers which may be coupled to the core, to expose the core for texturing. The waveguide may lay flat (with respect to gravity) for more uniform depth of surface etching, or may be tilted to provide for a more wedge-shaped etch.

Figure 11B:
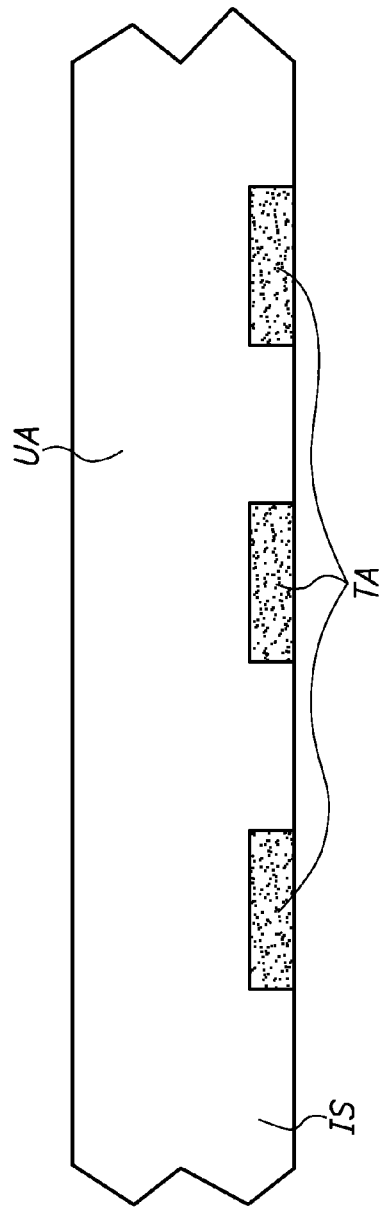

Referring to the schematic representation of FIG. 11B, an applicator is seen from the side with IS facing downward, and TA that do not wrap around the applicator to the outer surface (OS). Indeed, in such embodiment, they need not wrap even halfway around: because the texture may output couple light into a broad solid angle, Textured Areas (TA) need not be of large radial angular extent.

In either case, the proportion of light coupled out to the target also may be controlled to be a function of the location along the applicator to provide more uniform illumination output coupling from IS to the target, as shown in FIGS. 11A-12 and 20-23. This may be done to account for the diminishing proportion of light encountering later (or distal) output coupling zones. For example, if we consider the three (3) output coupling zones represented by Textured Areas (TA) in the present non-limiting example schematically illustrated in FIG. 11B, we now have TA1, TA2, and TA3. In order to provide equal distribution of the output coupled energy (or power) the output coupling efficiencies would be as follows: TA1=33%, TA2=50%, TA3=100%. Of course, other such portioning schemes may be used for different numbers of output coupling zones TAx, or in the case where there is directionality to the output coupling efficiency and a retro-reflector is used in a two-pass configuration, as is described in further detail below.

Referring to FIG. 11C, in the depicted alternate embodiment, distal junction (DJ) is identified to make clear the distinction of the size of TA with respect to the direction of light propagation.

In another embodiment, as illustrated in FIG. 11D, Textured Areas TA1, TA2 and TA3 are of increasing size because they are progressively more distal with the applicator. Likewise, Untextured Areas UA1, UA2 and UA3 are shown to become progressively smaller, although they also may be made constant. The extent (or separation, size, area, etc.) of the Untextured Areas (UAx) dictates the amount of illumination zone overlap, which is another means by which the ultimate illumination distribution may be controlled and made to be more homogeneous in ensemble. Note that Outer Surface (OS) may be made to be reflective, as described earlier, to prevent light scattered from a TA to escape the waveguide via OS and enhance the overall efficiency of the device. A coating may be used for the reflective element. Such coating might be, for example, metallic coatings, such as, Gold, Silver, Rhodium, Platinum, Aluminum. Alternately, a diffusive coating of a non-chromophoric substance, such as, but not limited to, $BaSO_4$ may be used as a diffuse reflector.

In a similar manner, the surface roughness of the Textured Areas (TA) may be changed as a function of location along the applicator. As described above, the amount of output coupling is proportional to the surface rugosity, or roughness. In particular, it is proportional to the first raw moment ("mean") of the distribution characterizing the surface rugosity. The uniformity in both it spatial and angular emission are proportional to the third and fourth standardized moments (or "skewness" and "kurtosis"), respectively. These are values that may be adjusted, or tailored, to suit the clinical and/or design need in a particular embodiment. Also, the size, extent, spacing and surface roughness may each be employed for controlling the amount and ensemble distribution of the target illumination.

Alternately, directionally specific output coupling maybe employed that preferentially outputs light traveling in a certain direction by virtue of the angle it makes with respect to IS. For example, a wedge-shaped groove transverse to the waveguide axis of IS will preferentially couple light encountering it when the angle incidence is greater than that required for TIR. If not, the light will be internally reflected and continue to travel down the applicator waveguide.

Figure 12:
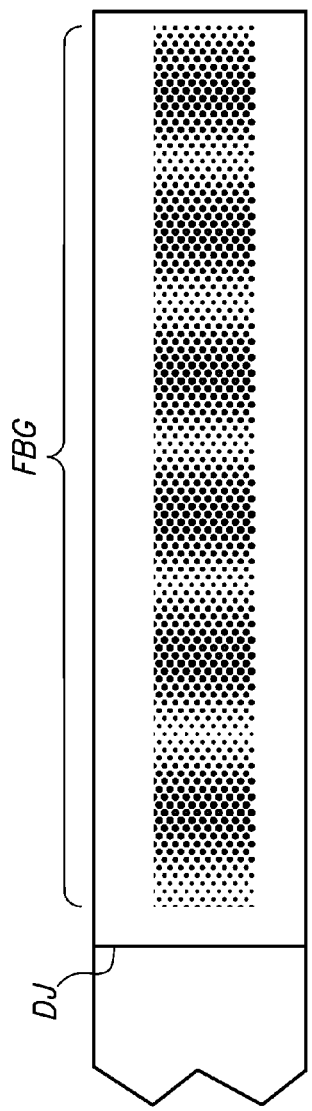

Furthermore, in such a directionally specific output coupling configuration, the applicator may utilize the above-mentioned retro-reflection means distal to DJ. FIG. 12 illustrates an example comprising a FBG retro-reflector.

A waveguide, such as a fiber, can support one or even many guided modes. Modes are the intensity distributions that are located at or immediately around the fiber core, although some of the intensity may propagate within the fiber cladding. In addition, there is a multitude of cladding modes, which are not restricted to the core region. The optical power in cladding modes is usually lost after some moderate distance of propagation, but can in some cases propagate over longer distances. Outside the cladding, there is typically a protective polymer coating, which gives the fiber improved mechanical strength and protection against moisture, and also determines the losses for cladding modes. Such buffer coatings may consist of acrylate, silicone or polyimide. For long-term implantation in a body, it may be desirable to keep moisture away from the waveguide to prevent refractive index changes that will alter the target illumination distribution and yield other commensurate losses. Therefore, for long-term implantation, a buffer layer (or region) may be applied to the Textured Areas TAx of the applicator waveguide. In one embodiment, "long-term" may be defined as greater than or equal to 2 years. The predominant deleterious effect of moisture absorption on optical waveguides is the creation of hydroxyl absorption bands that cause transmission losses in the system. This is a negligible for the visible spectrum, but an issue for light with wavelengths longer than about 850 nm. Secondarily, moisture absorption may reduce the material strength of the waveguide itself and lead to fatigue failure. Thus, while moisture absorption is a concern, in certain embodiments it is more of a concern for the delivery segments, which are more likely to undergo more motion and cycles of motion than the applicator.

Furthermore, the applicator maybe enveloped or partially enclosed by a jacket, such as Sleeve S shown in FIG. 10B. Sleeve S may be made to be a reflector, as well, and serve to confine light to the intended target. Reflective material(s), such as Mylar, metal foils, or sheets of multilayer dielectric thin films may be located within the bulk of Sleeve S, or along its inner or outer surfaces. While the outer surface of Sleeve S also may be utilized for reflective purposes, in certain embodiments such a configuration is not preferred, as it is in more intimate contact with the surrounding tissue than the inner surface. Such a jacket may be fabricated from polymeric material to provide the necessary compliance required for a tight fit around the applicator. Sleeve S, or an adjunct or alternative to, may be configured such that its ends slightly compress the target over a slight distance, but circumferentially to prevent axial migration, infiltration along the target surface. Sleeve S may also be made to be highly scattering (white, high albedo) to serve as diffusive retro-reflector to improve overall optical efficiency by redirecting light to the target.

Fluidic compression may also be used to engage the sleeve over the applicator and provide for a tighter fit to inhibit proliferation of cells and tissue ingrowth that may degrade the optical delivery to the target. Fluidic channels may be integrated into Sleeve S and filled at the time of implantation. A valve or pinch-off may be employed to seal the fluidic channels. Further details are described herein.

Furthermore, Sleeve S may also be made to elute compounds that inhibit scar tissue formation. This may provide for increased longevity of the optical irradiation parameters that might otherwise be altered by the formation of a scar, or the infiltration of tissue between the applicator and the target. Such tissue may scatter light and diminish the optical exposure. However, the presence of such infiltrates could also be detected by means of an optical sensor placed adjacent to the target or the applicator. Such a sensor could serve to monitor the optical properties of the local environment for system diagnostic purposes. Sleeve S may also be configured to utilize a joining means that is self-sufficient, such as is illustrated in the cross-section of FIG. 10C, wherein at least a part of the applicator is shown enclosed in cross-section A-A. Alternately, Sleeve S may be joined using sutures or such mechanical or geometric means of attachment, as illustrated by element F in the simplified schematic of FIG. 10C.

Figure 14:
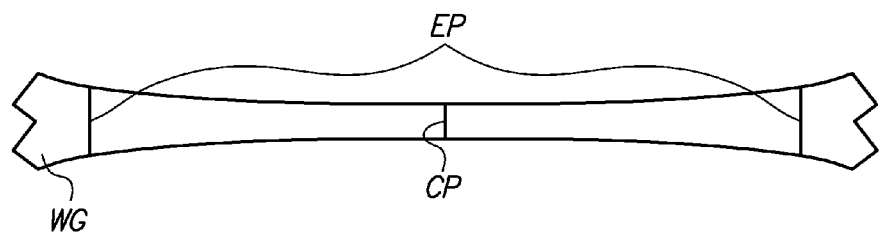

In a further embodiment, output coupling may be achieved by means of localized strain-induced effects with the applicator waveguide that serve to alter the trajectory of the light within it, or the bulk refractive index on the waveguide material itself, such as the use of polarization or modal dispersion. For example, output coupling may be achieved by placing regions (or areas, or volumes) of form-induced refractive index variation and/or birefringence that serve to alter the trajectory of the light within the waveguide beyond the critical angle required for spatial confinement and/or by altering the value of the critical angle, which is refractive-index-dependent. Alternately, the shape of the waveguide may be altered to output couple light from the waveguide because the angle of incidence at the periphery of the waveguide has been modified to be greater than that of the critical angle required for waveguide confinement. These modifications may be accomplished by transiently heating, and/or twisting, and/or pinching the applicator in those regions where output coupling for target illumination is desired. A non-limiting example is shown in FIG. 14, where a truncated section of Waveguide WG has been modified between Endpoints (EP) and Centerpoint (CP). The cross-sectional area and/or diameter of CP<EP. Light propagating through Waveguide WG will encounter a higher angle of incidence at the periphery of the waveguide due to the mechanical alteration of the waveguide material, resulting in light output coupling near CP in this exemplary configuration. It should be noted that light impinging upon the relatively slanted surface provided by the taper between EP and CP may output couple directly from the WG when the angle is sufficiently steep, and may require more than a single interaction with said taper before its direction is altered to such a degree that is ejected from the WG. As such, consideration may be given to which side of the WG is tapered, if it is not tapered uniformly, such that the output coupled light exiting the waveguide is directed toward the target, or incident upon an alternate structure, such as a reflector to redirect it to the target.

Figure 13:
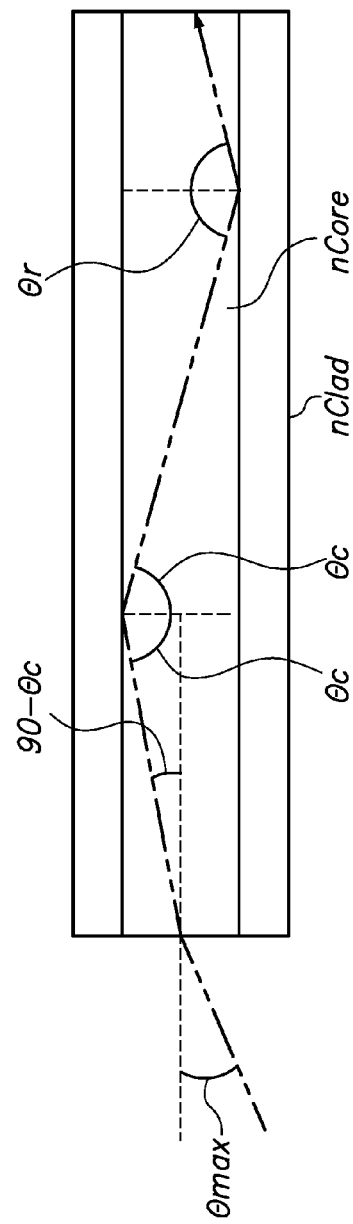

Referring to FIG. 13 and the description that follows, for contextual purposes an exemplary scenario is described wherein a light ray is incident from a medium of refractive index "n" upon a core of index "$n_{core}$" at a maximum acceptance angle, $\theta_{max}$, with Snell's law at the medium-core interface being applied. From the geometry illustrated in FIG. 13, we have:

From the geometry of the above figure we have:

$$\sin\theta_r = \sin(90° - \theta_c) = \cos\theta_c$$

where $$\theta_c = \sin^{-1}\frac{n_{clad}}{n_{core}}$$

is the critical angle for total internal reflection.
Substituting cos θc for sin Or in Snell's law we get:

$$\frac{n}{n_{core}}\sin\theta_{max} = \cos\theta_c.$$

By squaring both sides we get:

$$\frac{n^2}{n_{core}^2}\sin^2\theta_{max} = \cos^2\theta_c = 1 - \sin^2\theta_c = 1 - \frac{n_{clad}^2}{n_{core}^2}.$$

Solving, we find the formula stated above:

$$n \sin \theta_{max} = \sqrt{n_{core}^2 - n_{clad}^2},$$

This has the same form as the numerical aperture (NA) in other optical systems, so it has become common to define the NA of any type of fiber to be $$NA = \sqrt{n_{core}^2 - n_{clad}^2},$$

It should be noted that not all of the optical energy impinging at less than the critical angle will be coupled out of the system.

Alternately, the refractive index may be modified using exposure to ultraviolet (UV) light, such might be done to create a Fiber Bragg Grating (FBG). This modification of the bulk waveguide material will cause the light propagating through the waveguide to refractive to greater or lesser extent due to the refractive index variation. Normally a germanium-doped silica fiber is used in the fabrication of such refractive index variations. The germanium-doped fiber is photosensitive, which means that the refractive index of the core changes with exposure to UV light.

Alternately, and/or in combination with the abovementioned aspects and embodiments of the present invention, "whispering gallery modes" may be utilized within the waveguide to provide for enhanced geometric and/or strain-induced output coupling of the light along the length of the waveguide. Such modes of propagation are more sensitive to small changes in the refractive index, birefringence and the critical confinement angle than typical waveguide-filling modes because they are concentrated about the periphery of a waveguide. Thus, they are more susceptible to such means of output coupling and provide for more subtle means of producing a controlled illumination distribution at the target tissue.

Figure 15:
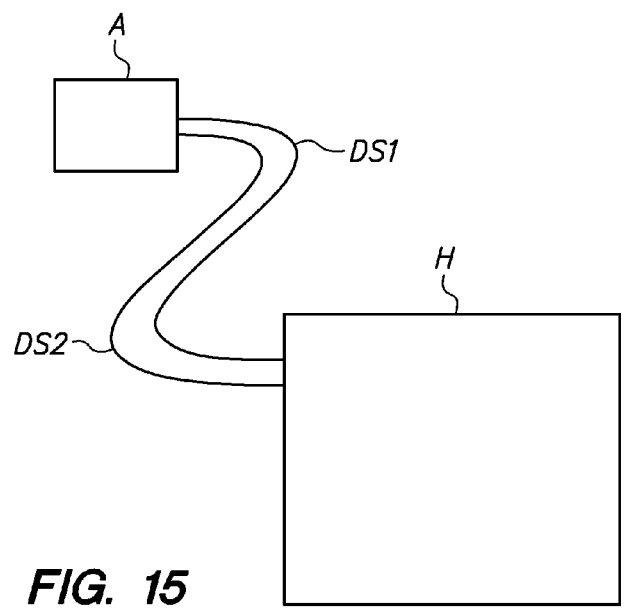

Alternately, more than a single Delivery Segment DS may be brought from the housing (H) to the applicator (A), as shown in FIG. 15. Here Delivery Segments DS1 and DS2 are separate and distinct. They may carry light from different sources (and of different color, or wavelength, or spectra) in the case where the light is created in housing (H), or they may be separate wires (or leads, or cables) in the case where the light is created at or near applicator (A).

In either case, the applicator may alternately further comprise separate optical channels for the light from the different Delivery Segments DSx (where x denotes the individual number of a particular delivery segment) in order to nominally illuminate the target area. A further alternate embodiment may exploit the inherent spectral sensitivity of the retro-reflection means to provide for decreased output coupling of one channel over another. Such would be the case when using a FBG retro-reflector, for instance. In this exemplary case, light of a single color, or narrow range of colors will be acted on by the FBG. Thus, it will retro-reflect only the light from a given source for bi-directional output coupling, while light from the other source will pass through largely unperturbed and be ejected elsewhere. Alternately, a chirped FBG may be used to provide for retro-reflection of a broader spectrum, allowing for more than a single narrow wavelength range to be acted upon by the FBG and be utilized in bi-directional output coupling. Of course, more than two such channels and/or Delivery Segments (DSx) are also within the scope of the present invention, such as might be the case when selecting to control the directionality of the instigated nerve impulse, as will be described in a subsequent section.

Alternately, multiple Delivery Segments may also provide light to a single applicator, or become the applicator(s) themselves, as is described in further detail below. For example, a single optical fiber deployed to the targeted tissue structure, wherein the illumination is achieved through the end face of the fiber is such a configuration, albeit a simple one. In this configuration, the end face of the fiber is the output coupler, or, equivalently, the emission facet, as the terms are interchangeable as described herein.

Figure 16:
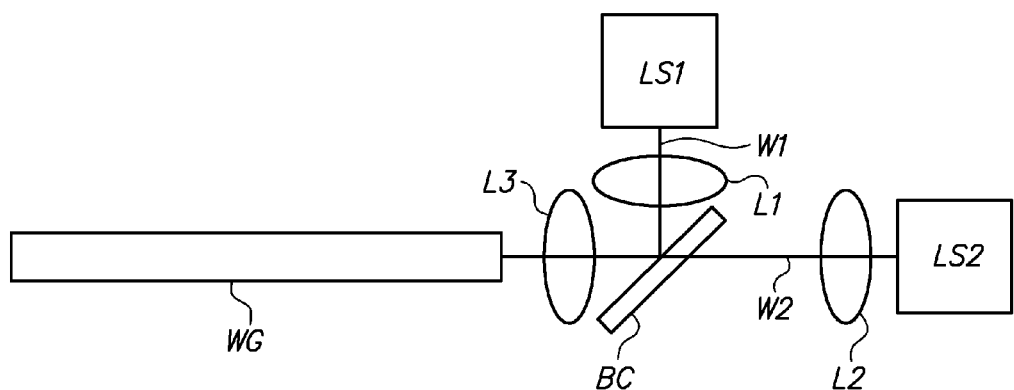

Alternately, a single delivery device may used to channel light from multiple light sources to the applicator. This may be achieved through the use of spliced, or conjoined, waveguides (such as optical fibers), or by means of a fiber switcher, or a beam combiner prior to initial injection into the waveguide, as shown in FIG. 16.

In this embodiment, Light Sources LS1 and LS2 output light along paths W1 and W2, respectively. Lenses L1 and L2 may be used to redirect the light toward Beam Combiner (BC), which may serve to reflect the output of one light source, while transmitting the other. The output of LS1 and LS2 may be of different color, or wavelength, or spectral band, or they may be the same. If they are different, BC may be a dichroic mirror, or other such spectrally discriminating optical element. If the outputs of Light Sources LS1 and LS2 are spectrally similar, BC may utilize polarization to combine the beams. Lens L3 may be used to couple the W1 and W2 into Waveguide (WG). Lenses L1 and L2 may also be replaced by other optical elements, such as mirrors, etc. This method is extensible to greater numbers of light sources.

The type of optical fiber that may be used as either delivery segments or within the applicators is varied, and may be selected from the group consisting of: Step-index, GRIN ("gradient index"), Power-Law index, etc. Alternately, hollow-core waveguides, photonic crystal fiber (PCF), and/or fluid filled channels may also be used as optical conduits. PCF is meant to encompass any waveguide with the ability to confine light in hollow cores or with confinement characteristics not possible in conventional optical fiber. More specific categories of PCF include photonic-bandgap fiber (PBG, PCFs that confine light by band gap effects), holey fiber (PCFs using air holes in their cross-sections), hole-assisted fiber (PCFs guiding light by a conventional higher-index core modified by the presence of air holes), and Bragg fiber (PBG formed by concentric rings of multilayer film). These are also known as "microstructured fibers". End-caps or other enclosure means may be used with open, hollow waveguides such as tubes and PCF to prevent fluid infill that would spoil the waveguide.

PCF and PBG intrinsically support higher numerical aperture (NA) than standard glass fibers, as do plastic and plastic-clad glass fibers. These provide for the delivery of lower brightness sources, such as LEDs, OLEDs, etc. This is notable for certain embodiments because such lower brightness sources are typically more electrically efficient than laser light sources, which is relevant for implantable device embodiments in accordance with the present invention that utilize battery power sources. Configurations for to creating high-NA waveguide channels are described in greater detail herein.

Figure 17A:
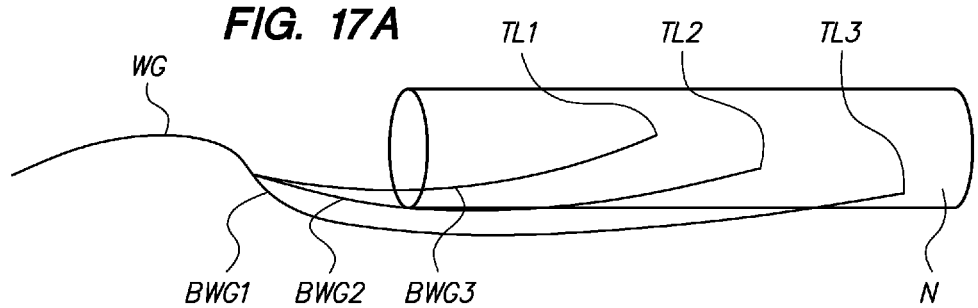

Alternately, a bundle of small and/or single mode (SM) optical fibers/waveguides may be used to transport light as delivery segments, and/or as an applicator structure, such as is shown in a non-limiting exemplary embodiment in FIG. 17A. In this embodiment, Waveguide (WG) may be part of the Delivery Segment(s) (DS), or part of the applicator (A) itself. As shown in the embodiment of FIG. 17A, the waveguide (WG) bifurcates into a plurality of subsequent waveguides, BWGx. The terminus of each BWGx is Treatment Location (TLx). The terminus may be the area of application/target illumination, or may alternately be affixed to an applicator for target illumination. Such a configuration is appropriate for implantation within a distributed body tissue, such as, by way of non-limiting example, the liver, pancreas, or to access cavernous arteries of the corpora cavernosa (to control the degree of smooth muscle relaxation in erection inducement).

Figure 17B:
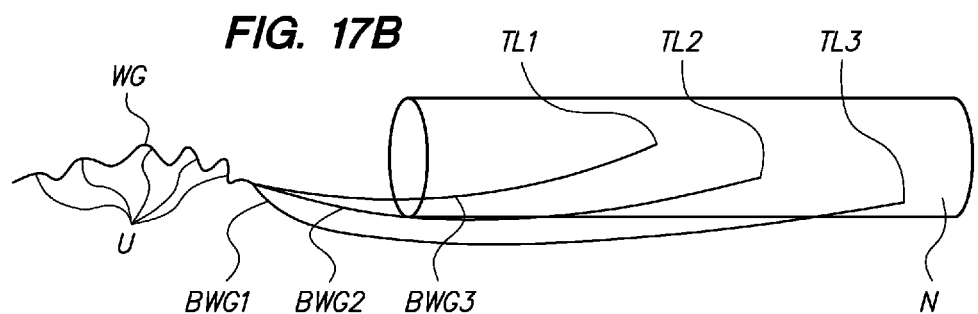

Referring to FIG. 17B, the waveguide (WG) may also be configured to include Undulations (U) in order to accommodate possible motion and/or stretching/constricting of the target tissues, or the tissues surrounding the target tissues, and minimize the mechanical load (or "strain") transmitted to the applicator from the delivery segment and vice versa. . . Undulations (U) may be pulsed straight during tissue extension and/or stretching. Alternately, Undulations (U) may be integral to the applicators itself, or it may be a part of the Delivery Segments (DS) supplying the applicator (A).

The Undulations (U) may be made to areas of output coupling in embodiments when the Undulations (U) are in the applicator. This may be achieved by means of similar processes to those described earlier regarding means by which to adjust the refractive index and/or the mechanical configuration(s) of the waveguide for fixed output coupling in an applicator. However, in this case, the output coupling is achieved by means of tissue movement that causes such changes. Thus, output coupling is nominally only provided during conditions of tissue extension and/or contraction and/or motion. The Undulations (U) may be configured of a succession of waves, or bends in the waveguide, or be coils, or other such shapes. Alternately, DS containing Undulations (U) may be enclosed in a protective sheath or jacket to allow DS to stretch and contract without encountering tissue directly.

A rectangular slab waveguide may be configured to be like that of the aforementioned helical-type, or it can have a permanent waveguide (WG) attached/inlaid. For example, a slab may be formed such that is a limiting case of a helical-type applicator, such as is illustrated in FIG. 18 for explanatory purposes and to make the statement that the attributes and certain details of the aforementioned helical-type applicators are suitable for this slab-like as well and need not be repeated.

Figure 18:
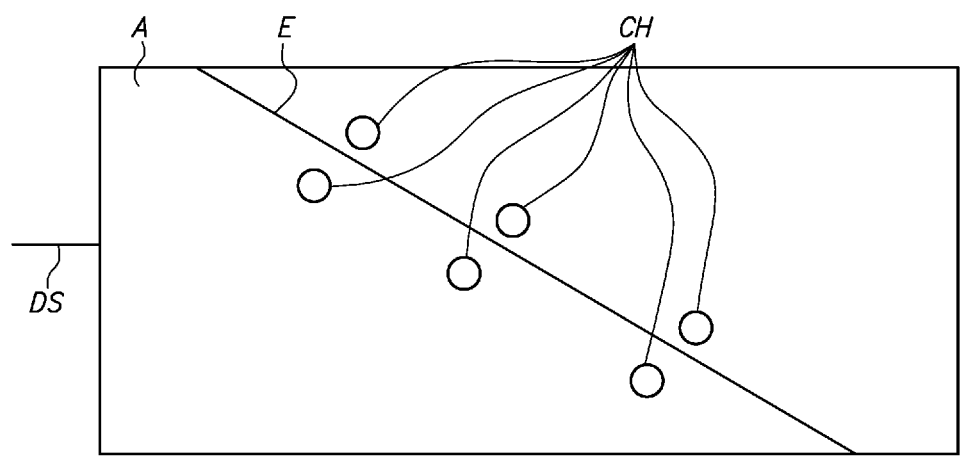

In the embodiment depicted in FIG. 18, Applicator (A) is fed by Delivery Segment (DS) and the effectively half-pitch helix is closed along the depicted edge (E), with closure holes (CH) provided, but not required. Of course, this is a reduction of the geometries discussed previously, and meant to convey the abstraction and interchangeability of the basic concepts therein and between those of the slab-type waveguides to be discussed.

Figure 19A:
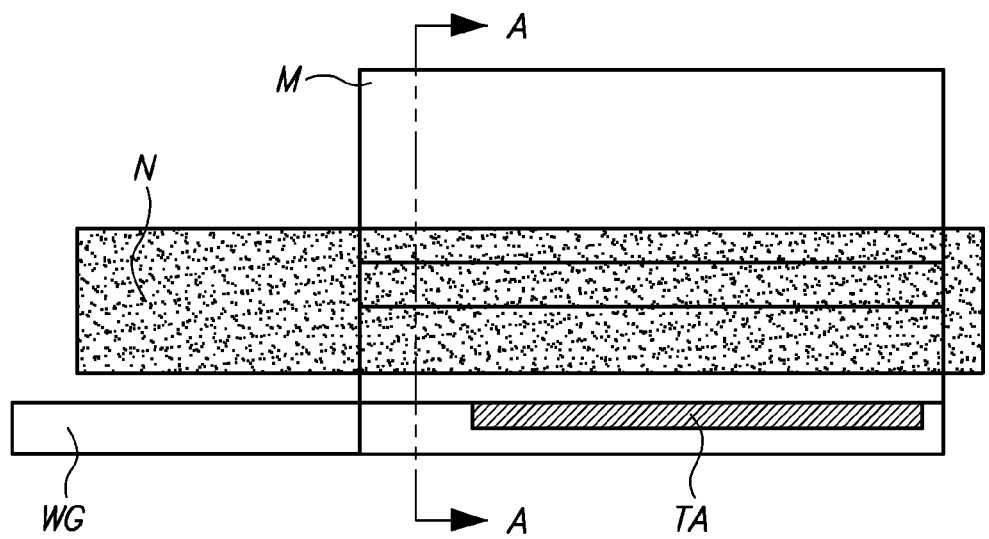

It should also be understood that the helical-type applicator described herein may also be utilized as a straight applicator, such as may be used to provide illumination along a linear structure like a nerve, etc. A straight applicator may also be configured as the helical-type applicators described herein, such as with a reflector to redirect stray light toward the target, as is illustrated in FIG. 19A by way of non-limiting example.

Figure 19B:
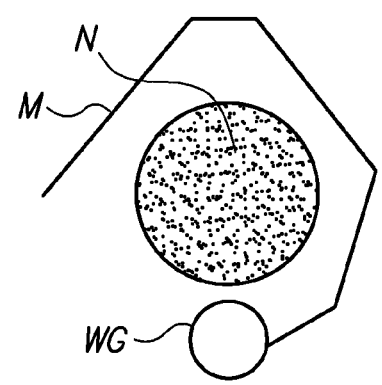
Figure 20:
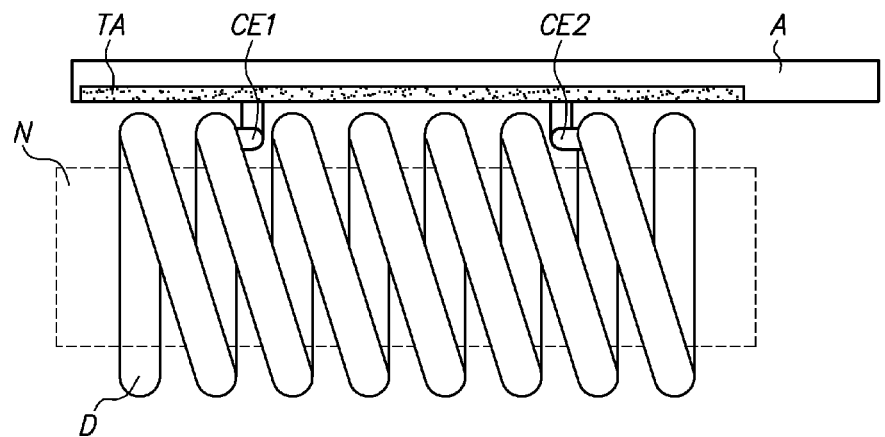

Here Waveguide (WG) contains Textured Area (TA), and the addition of Reflector (M) that at least partially surrounds target anatomy (N). This configuration provides for exposure of the far side of the target by redirecting purposefully exposed and scattered light toward the side of the target opposite the applicator. FIG. 19B illustrates the same embodiment, along cross-section A-A, showing schematically the use of a mirror (as Reflector M) surrounding Target (N.) Although not shown, WG and M may be affixed to a common casing (not shown) that forms part of the applicator. Reflector (M) is shown as being comprised of a plurality of linear faces, but need not be. In one embodiment it may be made to be a smooth curve, or in another embodiment, a combination of the two.

In another alternate embodiment, a straight illuminator may be affixed to the target, or tissue surrounding or adjacent or nearby to the target by means of the same helix-type ("helical") applicator. However, in this case the helical portion is not the illuminator, it is the means to position and maintain another illuminator in place with respect to the target. The embodiment illustrated in FIG. 20 utilizes the target-engaging feature(s) of the helical-type applicator to locate straight-type Applicator (A) in position near Target (N) via Connector Elements CE1 and CE2, which engage the Support Structure (D) to locate and maintain optical output. Output illumination is shown as being emitted via Textured Area (TA), although, as already discussed, alternate output coupling means are also within the scope of the present invention. The generality of the approach and the interchangeability of the different target-engaging means described herein (even subsequent to this section) are also applicable to serve as such Support Structures (D), and therefore the combination of them is also within the scope of the present invention.

Figure 21A:
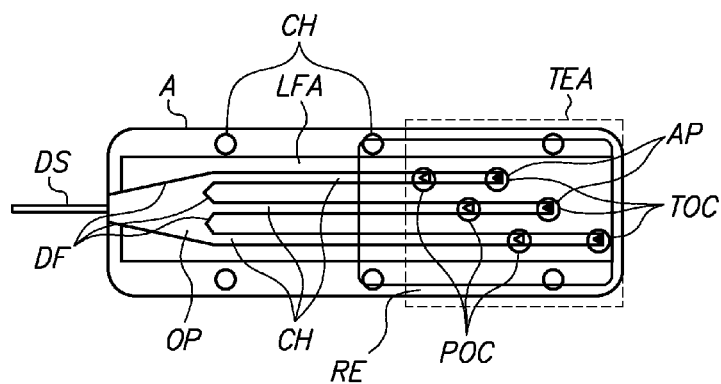
Figure 21B:
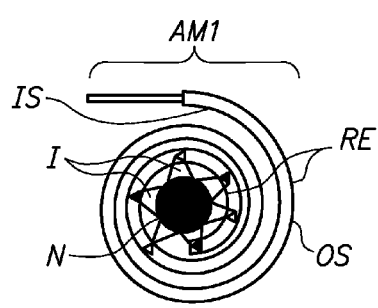
Figure 21C:
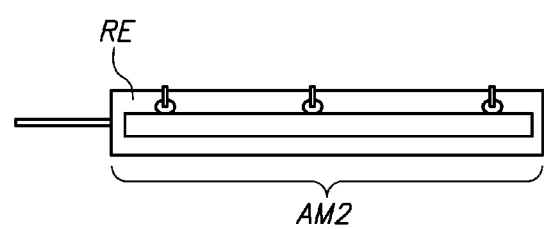

Slab-type ("slab-like") geometries of Applicator A, such as thin, planar structures, can be implanted, or installed at, near, or around the tissue target or tissue(s) containing the intended target(s). An embodiment of such a slab-type applicator configuration is illustrated in FIGS. 21A-21C. It may be deployed near or adjacent to a target tissue, and it may also be rolled around the target tissue, or tissues surrounding the target(s). It may be rolled axially, as illustrated by element AM1 in FIG. 21B, (i.e. concentric with the long axis of the targeted tissue structure N), or longitudinally, as illustrated by element AM2 in FIG. 21C (i.e. along the long axis of target N), as required by the immediate surgical situation, as shown in the more detailed figure below. The lateral edges that come into contact with each other once deployed at the target location could be made with complementary features to assure complete coverage and limit the amount of cellular infiltrate (i.e. limit scar tissue or other optical perturbations over time to better assure an invariant target irradiance, as was described in the earlier section pertaining to the helical-type applicator). Closure Holes (CH) are provided for this purpose in the figure of this non-limiting example. The closure holes (CH) may be sutured together, of otherwise coupled using a clamping mechanism (not shown). It may also provide different output coupling mechanisms than the specific helical-type waveguides described above, although, it is to be understood that such mechanisms are fungible, and may be used generically. And vice versa, that elements of output coupling, optical recirculation and waveguiding structures, as well as deployment techniques discussed in the slab-type section maybe applicable to helical-type, and straight waveguides.

The slab-type applicator (A) illustrated in FIGS. 21A-21C is comprised of various components, as follows. In the order "seen" by light entering the applicator, first is an interface with the waveguide of the delivery segment (DS). Alternately, the waveguide may be replaced by electrical wires, in the case where the emitter(s) is(are) included near or within the applicator. An Optical Plenum (OP) structure may be present after the interface to segment and direct light propagation to different channels CH using distribution facets (DF), whether it comes from the delivery segments (DS), or from a local light source. The optical plenum (OP) may also be configured to redirect all of the light entering the light entering it, such as might be desirable when the delivery segment (DS) should lie predominantly along the same direction as the applicator (A). Alternately, it may be made to predominantly redirect the light at angle to provide for the applicator to be directed differently than the delivery segment(s) (DS). Light propagating along the channel(s) (CH) may encounter an output coupling means, such as Partial Output Coupler (POC) and Total Output Coupler (TOC). The proximal output couplers (POC) redirect only part of the channeled light, letting enough light pass to provide adequate illumination to more distal targets, as was discussed previously. The final, or distal-most, output coupler (TOC) may be made to redirect nominally all of the impinging light to the target. The present embodiment also contains provisions for outer surface reflectors to redirect errant light to the target. It is also configured to support a reflector (RE) on or near the inner surface (IS) of applicator (A), with apertures (AP) to allow for the output coupled light to escape, that serves to more readily redirect any errant or scattered light back toward the target (N). Alternately, such a reflector (RE) may be constructed such that it is not covering the output coupler area, but proximal to it in the case of longitudinally rolled deployment such that it nominally covers the intended target engagement area (TEA). Reflector (RE) may be made from biocompatible materials such as platinum, or gold if they are disposed along the outside of the applicator (A). Alternately, such metallic coatings may be functionalized in order to make them bioinert, as is discussed below. The output couplers POC and TOC are shown in FIG. 21A as being located in the area of the applicator (A) suitable for longitudinal curling about the target (N) (FIG. 21B), or tissues surrounding the target (N), but need not be, as would be the case for deployments utilizing the unrolled and axially rolled embodiments (AM1). Any such surface (or sub-surface) reflector (RE) should be present along (or throughout) a length sufficient to provide at least complete circumferential coverage once the applicator is deployed. As used herein the terms optical conduit and channel member are equivalent.

The current embodiment utilizes PDMS, described below, or some other such well-qualified polymer, as a substrate (SUB) that forms the body of the applicator (A), for example as in FIG. 21A. For example, biological materials such as hyaluronan, elastin, and collagen, which are components of the native extracellular matrix, may also be used alone or in combination with inorganic compounds to form the substrate (SUB). Hydrogel may also be used, as it is biocompatible, may be made to elute biological and/or pharmaceutical compounds, and has a low elastic modulus, making it a compliant material. Likewise polyethylene, and/or polypropylene may also be used to fro Substrate SUB.

A material with a refractive index lower than that of the substrate (SUB) (PDMS in this non-limiting example) may used as filling (LFA) to create waveguide cladding where the PDMS itself acts as the waveguide core. In the visible spectrum, the refractive index of PDMS is ~1.4. Water, and even PBS and saline have indices of ~1.33, making them suitable for cladding materials. They are also biocompatible and safe for use in an illumination management system as presented herein, even if the integrity of the applicator (A) is compromised and they are released into the body.

Alternately, a higher index filling may be used as the waveguide channel. This may be thought of as the inverse of the previously described geometry, where in lieu of the polymer comprising substrate (SUB), you have a liquid filling (LFA) acting as the waveguide core medium, and the substrate (SUB) material acting as the cladding. Many oils have refractive indices of ~1.5 or higher, making them suitable for core materials.

Alternately, a second polymer of differing refractive index may be used instead of the aforementioned liquid fillings. A high-refractive-index polymer (HRIP) is a polymer that has a refractive index greater than 1.50. The refractive index is related to the molar refractivity, structure and weight of the monomer. In general, high molar refractivity and low molar volumes increase the refractive index of the polymer. Sulfur-containing substituents including linear thioether and sulfone, cyclic thiophene, thiadiazole and thianthrene are the most commonly used groups for increasing refractive index of a polymer in forming a HRIP. Polymers with sulfur-rich thianthrene and tetrathiaanthrene moieties exhibit n values above 1.72, depending on the degree of molecular packing.

Such materials may be suitable for use as waveguide channels within a lower refractive polymeric substrate. Phosphorus-containing groups, such as phosphonates and phosphazenes, often exhibit high molar refractivity and optical transmittance in the visible light region. Polyphosphonates have high refractive indices due to the phosphorus moiety even if they have chemical structures analogous to polycarbonates. In addition, polyphosphonates exhibit good thermal stability and optical transparency; they are also suitable for casting into plastic lenses. Organometallic components also result in HRIPs with good film forming ability and relatively low optical dispersion. Polyferrocenylsilanes and polyferrocenes containing phosphorus spacers and phenyl side chains show unusually high n values (n=1.74 and n=1.72), as well, and are also candidates for waveguides.

Hybrid techniques which combine an organic polymer matrix with highly refractive inorganic nanoparticles may be employed to produce polymers with high n values. As such, PDMS may also be used to fabricate the waveguide channels that may be integrated to a PDMS substrate, where native PDMS is used as the waveguide cladding. The factors affecting the refractive index of a HRIP nanocomposite include the characteristics of the polymer matrix, nanoparticles, and the hybrid technology between inorganic and organic components. Linking inorganic and organic phases is also achieved using covalent bonds. One such example of hybrid technology is the use of special bifunctional molecules, such as 3-Methacryloxypropyltrimethoxysilane (MEMO), which possess a polymerisable group as well as alkoxy groups. Such compounds are commercially available and can be used to obtain homogeneous hybrid materials with covalent links, either by simultaneous or subsequent polymerization reactions.

The following relation estimates the refractive index of a nanocomposite, $$n_{comp} = \varphi_p n_p + \varphi_{org} n_{org}$$

where, $n_{comp}$, $n_p$ and $n_{org}$ stand for the refractive indices of the nanocomposite, nanoparticle and organic matrix, respectively, while $\varphi_p$ and $\varphi_{org}$ represent the volume fractions of the nanoparticles and organic matrix, respectively.

The nanoparticle load is also important in designing HRIP nanocomposites for optical applications, because excessive concentrations increase the optical loss and decrease the processability of the nanocomposites. The choice of nanoparticles is often influenced by their size and surface characteristics. In order to increase optical transparency and reduce Rayleigh scattering of the nanocomposite, the diameter of the nanoparticle should be below 25 nm. Direct mixing of nanoparticles with the polymer matrix often results in the undesirable aggregation of nanoparticles—this may be avoided by modifying their surface, or thinning the viscosity of the liquid polymer with a solvent such as xylene; which may later be removed by vacuum during ultrasonic mixing of the composite prior to curing. Nanoparticles for HRIPs may be chosen from the group consisting of: $TiO_2$ (anatase, n=2.45; rutile, n=2.70), $ZrO_2$ (n=2.10), amorphous silicon (n=4.23), PbS (n=4.20) and ZnS (n=2.36). Further materials are given in the table below. The resulting nanocomposites may exhibit a tunable refractive index range, per the above relation.

| Substance | n (413.3 nm) | n (619.9 nm) |
|---|---|---|
| Os | 4.05 | 3.98 |
| W | 3.35 | 3.60 |

-continued

| Substance | n (413.3 nm) | n (619.9 nm) |
|---|---|---|
| Si crystalline | 5.22 | 3.91 |
| Si amorphous | 4.38 | 4.23 |
| Ge | 4.08 | 5.59-5.64 |
| GaP | 4.08 | 3.33 |
| GaAs | 4.51 | 3.88 |
| InP | 4.40 | 3.55 |
| InAs | 3.20 | 4.00 |
| InSb | 3.37 | 4.19 |
| PbS | 3.88 | 4.29 |
| PbSe | 1.25-3.00 | 3.65-3.90 |
| PbTe | 1.0-1.8 | 6.40 |
| Ag | 0.17 | 0.13 |
| Au | 1.64 | 0.19 |
| Cu | 1.18 | 0.27 |

In one exemplary embodiment, a HRIP preparation based on PDMS and PbS, the volume fraction of particles needs to be around 0.2 or higher to yield $n_{comp} \geq 1.96$, which corresponds to a weight fraction of at least 0.8 (using the density of PbS of 7.50 g cm$^{-3}$ and of PDMS of 1.35 g cm$^{-3}$). Such a HRIP can support a high numerical aperture (NA), which is useful when coupling light from relatively low brightness sources such as LEDs. The information given above allows for the recipe of other alternate formulations to be readily ascertained.

There are many synthesis strategies for nanocomposites. Most of them can be grouped into three different types. The preparation methods are all based on liquid particle dispersions, but differ in the type of the continuous phase. In melt processing particles are dispersed into a polymer melt and nanocomposites are obtained by extrusion. Casting methods use a polymer solution as dispersant and solvent evaporation yields the composite materials, as described earlier. Particle dispersions in monomers and subsequent polymerization result in nanocomposites in the so-called in situ polymerization route.

In a similar way, low refractive index composite materials have may also be prepared. As suitable filler materials, metals with low refractive indices below 1, such as gold (shown in the table above) may be chosen, and the resulting low index material used as the waveguide cladding.

Figure 22:
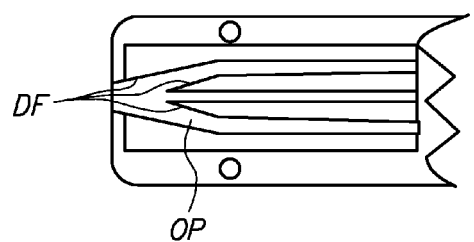

There are a variety of optical plenum configurations for capturing light input and creating multiple output channels. As shown in FIGS. 21A-21C and 22 the facets are comprised of linear faces, although other configurations are within the scope of the invention. The angle of the face with respect to the input direction of the light dictates the numerical aperture (NA). Alternately, curved faces may be employed for nonlinear angular distribution and intensity homogenization. A parabolic surface profile may be used, for example. Furthermore, the faces need not be planar. A three-dimensional surface may similarly be employed. The position of these plenum distribution facets DF may be used to dictate the proportion of power captured as input to a channel, as well. Alternately, the plenum distribution facets DF may spatially located in accordance with the intensity/irradiance distribution of the input light source. As a non-limiting example, in a configuration utilizing an input with a Lambertian irradiance distribution, such as that which may be output by an LED, the geometry of the distribution facets DF may be tailored to limit the middle channel to have ⅓ of the emitted light, and the outer channels evenly divide the remaining ⅔, such as is shown in FIG. 22 by way of non-limiting example.

Figure 23:
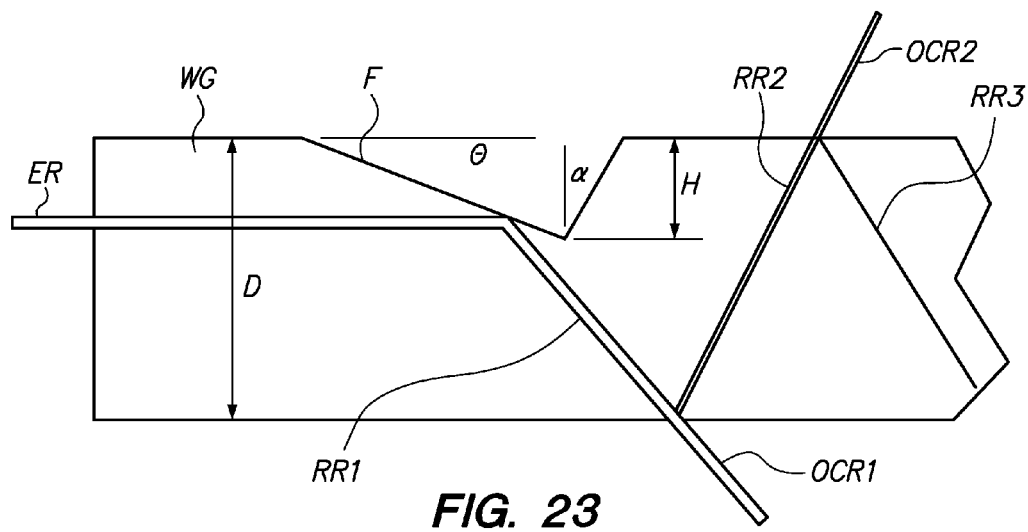

Output Coupling may be achieved many ways, as discussed earlier. Furthering that discussion, and to be considered as part thereof, scattering surfaces in areas of intended emission may be utilized. Furthermore, output coupling facets, such as POC and TOC shown previously, may also be employed. These may include reflective, refractive, and/or scattering configurations. The height of facet may be configured to be in proportion to the amount or proportion of light intercepted, while the longitudinal position dictates the output location. As was also discussed previously, for systems employing multiple serial OCs, the degree of output coupling of each may be made to be proportional to homogenize the ensemble illumination. A single-sided facet within the waveguide channel may be disposed such that it predominantly captures light traveling one way down the waveguide channel (or core). Alternately, a double-sided facet that captures light traveling both ways down the waveguide channel (or core) to provide both forward and backward output coupling. This would be used predominantly with distal retroreflector designs. Such facets may be shaped as, by way of non-limiting example; a pyramid, a ramp, an upward-curved surface, a downward-curved surface, etc. FIG. 23 illustrates output coupling for a ramp-shaped facet.

Light Ray ER enters (or is propagated within) Waveguide Core WG. It impinges upon Output Coupling Facet F and is redirected to the opposite surface. It becomes Reflected Ray RR1, from which Output Coupled Ray OCR1 is created, as is Reflected Ray RR2. OCR1 is directed at the target. OCR2 and RR3 are likewise created from RR2. Note that OCR2 is emitted from the same surface of WG as the facet. If there is no target or reflector on that side, the light is lost. The depth of F is H, and the Angle θ. Angle θ dictates the direction of RR1, and its subsequent rays. Angle α may be provided in order to allow for mold release for simplified fabrication. It may also be used to output couple light traversing in the opposite direction as ER, such as might be the case when distal retro-reflectors are used.

Alternately, Output Coupling Facet F may protrude from the waveguide, allowing for the light to be redirected in an alternate direction, but by similar means.

The descriptions herein regarding optical elements, such as, but limited to, Applicators and Delivery Segments may also be utilized by more than a single light source, or color of light, such as may be the case when using SFO, and/or SSFO opsins, as described in more detail elsewhere herein.

The waveguide channel(s) may be as described above. Use of fluidics may also be employed to expand (or contract) the applicator to alter the mechanical fit, as was described above regarding Sleeve S. When used with the applicator (A), it may serve to decrease infiltrate permeability as well as to increase optical penetration via pressure-induced tissue clearing. Tissue clearing, or optical clearing as it is also known, refers to the reversible reduction of the optical scattering by a tissue due to refractive index matching of scatterers and ground matter. This may be accomplished by impregnating tissue with substances ("clearing agents") such as, x-ray contrast agents (e.g. Verografin, Trazograph, and Hypaque-60), glucose, propylene glycol, polypropylene glycol-based polymers (PPG), polyethylene glycol (PEG), PEG-based polymers, and glycerol by way of non-limiting examples. It may also be accomplished by mechanically compressing the tissue.

Fluidic channels incorporated into the applicator substrate may also be used to tune the output coupling facets. Small reservoirs beneath the facets may be made to swell and in turn distend the location and/or the angle of the facet in order to adjust the amount of light and/or the direction of that light.

Figure 24:
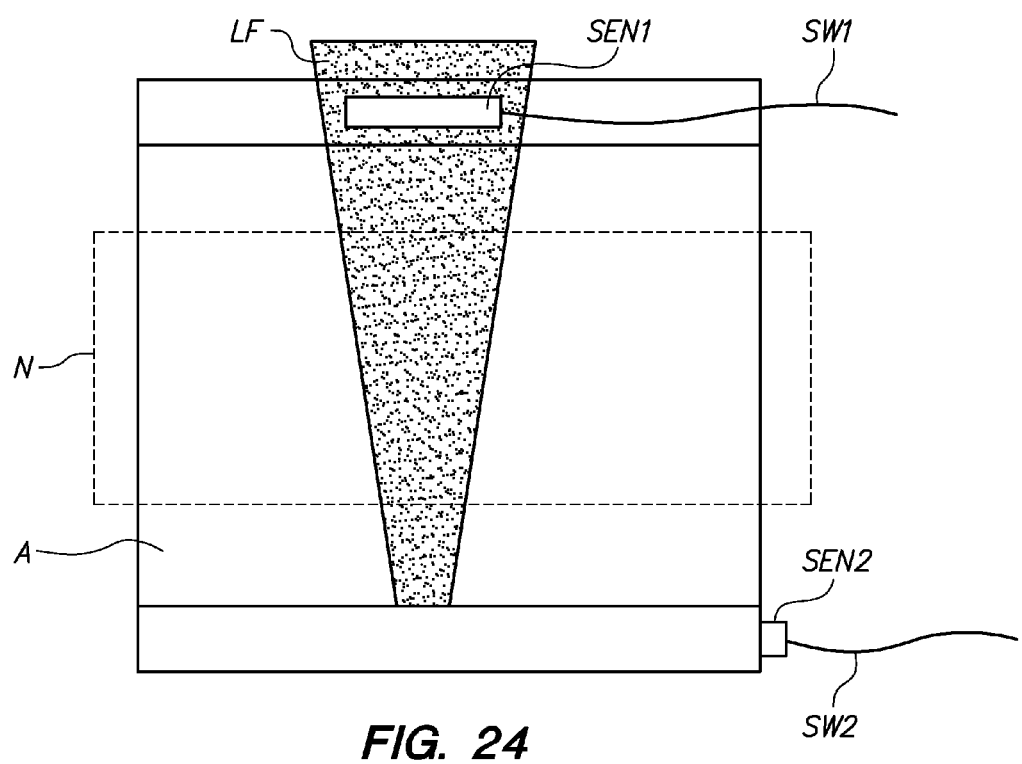

Captured light may also be used to assess efficiency or functional integrity of the applicator and/or system by providing information regarding the optical transport efficiency of the device/tissue states. The detection of increased light scattering may be indicative of changes in the optical quality or character of the tissue and or the device. Such changes may be evidenced by the alteration of the amount of detected light collected by the sensor. It may take the form of an increase or a decrease in the signal strength, depending upon the relative positions of the sensor and emitter(s). An opposing optical sensor may be employed to more directly sample the output, as is illustrated in FIG. 24. In this non-limiting embodiment, Light Field LF is intended to illuminate the Target (N) via output coupling from a waveguide within Applicator A, and stray light is collected by Sensor SEN1. SEN1 may be electrically connected to the Housing (not shown) via Wires SW1 to supply the Controller with information regarding the intensity of the detected light. A second Sensor SEN2 is also depicted. Sensor SEN2 may be used to sample light within a (or multiple) waveguides of Applicator A, and its information conveyed to a controller (or processor) via Wires SW2. This provides additional information regarding the amount of light propagating within the Waveguide(s) of the Applicator. This additional information may be used to better estimate the optical quality of the target exposure by means of providing a baseline indicative of the amount of light energy or power that is being emitted via the resident output coupler(s), as being proportional to the conducted light within the Waveguide(s).

Alternately, the temporal character of the detected signals may be used for diagnostic purposes. For example, slower changes may indicate tissue changes or device aging, while faster changes could be strain, or temperature dependent fluctuations. Furthermore, this signal may be used for closed loop control by adjusting power output over time to assure more constant exposure at the target. The detected signal of a Sensor such as SEN1 may also be used to ascertain the amount of optogenetic protein matter present in the target. If such detection is difficult to the proportionately small effects on the signal, a heterodyned detection scheme may be employed for this purpose. Such an exposure may be of insufficient duration or intensity to cause a therapeutic effect, but made solely for the purposes of overall system diagnostics.

Alternately, an applicator may be fabricated with individually addressable optical source elements to enable adjustment of the intensity and location of the light delivery, as is shown in the embodiment of FIG. 25 (1010). Such applicators may be configured to deliver light of a single wavelength to activate or inhibit nerves. Alternately, they may be configured to deliver light of two or more different wavelengths, or output spectra, to provide for both activation and inhibition in a single device, or a plurality of devices.

An alternate example of such an applicator is shown in FIG. 26, where Applicator A is comprised of Optical Source Elements LSx, may be comprised of Emitters (EM), mounted on Bases B; element "DS"xx represents the pertinent delivery segments as per their coordinates in rows/columns on the applicator (A); element "SUB" represents the substrate, element "CH" represents closure holes, and element "TA" a textured area, as described above.

The optical sensors described herein are also known as photodetectors, and come in different forms. These may include, by way of non-limiting examples, photovoltaic cells, photodiodes, pyroelectrics, photoresistors, photoconductors, phototranisistors, and photogalvanic devices. A photogalvanic sensor (also known as a photoelectrochemical sensor) may be constructed by allowing a conductor, such as stainless steel or platinum wire, to be exposed on, at, or adjacent to a target tissue. Light being remitted from the target tissue that impinges upon the conductor will cause it undergo a photogalvanic reaction that produces a electromotive force, or "EMF", with respect to another conductor, or conductive element, that is at least substantially in the same electrical circuit as the sensor conductor, such as it may be if immersed in the same electrolytic solution (such as is found within the body). The EMF constitutes the detector response signal. That signal may then be used as input to a system controller in order to adjust the output of the light source to accommodate the change. For example, the output of the light source may be increased, if the sensor signal decreases and vice versa.

In an alternate embodiment, an additional sensor, SEN2, may also be employed to register signals other than those of sensor SEN1 for the purposes of further diagnosing possible causes of systemic changes.

For example, the target opacity and/or absorbance may be increasing if SEN2 maintains a constant level indicating that the optical power entering the applicator is constant, but sensor SEN1 shows a decreasing level. A commensurate decrease in the response of sensor SEN2 would indicate that the electrical power to the light source should be increased to accommodate a decline in output and/or efficiency, as might be experienced in an aging device. Thus, an increase in optical power and/or pulse repetition rate delivered to the applicator may mitigate the risk of underexposure to maintain a therapeutic level.

Changes to the optical output of the light source may be made to, for example, the output power, exposure duration, exposure interval, duty cycle, pulsing scheme For the exemplary configuration shown in FIG. 24, the following table may be used to describe exemplary programming for the controller in each case of sensor response changes.

| SEN1 Response Change | SEN2 Response Change | Possible Cause(s) | Possible Action(s) |
| --- | --- | --- | --- |
| Decrease | Decrease | Light source output or overall optical system efficiency diminishing. | Increase electrical input power to light source to increase optical output power and regain expected signal from SEN1 and/or SEN2, and/or monitor therapeutic outcome. Otherwise, replacement of the light source is possibly indicated. |
| Decrease | Constant | Change in target optical characteristics, such as tissue or | Increase electrical input power to light source to |

-continued

| SEN1 Response Change | SEN2 Response Change | Possible Cause(s) | Possible Action(s) |
|---|---|---|---|
| | | cellular ingrowth between the applicator and target tissue, or relative movement between applicator and target. | increase optical output power and regain expected signal from SEN1 while resetting baseline for SEN2 signal level, and/or monitor therapeutic outcome. Otherwise, replacement of the applicator is possibly indicated. |
| Decrease | Increase | The amount of light diverted to SEN2 increasing. | Increase electrical input power to light source to increase optical output power and regain expected signal from SEN1 while resetting baseline for SEN2 signal level, and/or monitor therapeutic outcome. Otherwise, replacement of the applicator is possibly indicated. |
| Constant | Decrease | Change in target optical characteristics, such as tissue or cellular ingrowth between the applicator and target tissue. | Maintain light source output level while resetting baseline for SEN2 signal level, and/or monitor therapeutic outcome. |
| Constant | Increase | Change in the optical delivery efficiency of the applicator. | Maintain light source output level while resetting baseline for SEN2 signal level. |
| Increase | Decrease | Change in target optical characteristics, or movement of applicator with respect to target tissue. | Maintain light source output level while resetting baseline for SEN1 and SEN2 signal levels, and/or monitor therapeutic outcome. |
| Increase | Constant | Change in target optical characteristics, or movement of applicator with respect to target tissue. | Maintain light source output level while resetting baseline for SEN1 signal level, and/or monitor therapeutic outcome. |
| Increase | Increase | Change in the optical output and/or delivery efficiency of the system. | Decrease electrical input power to light source to increase optical output power and regain expected signal from SEN1 while resetting baseline for SEN2 signal level, if original setting is not achieved, and/or monitor therapeutic outcome. Otherwise, replacement of the applicator is possibly indicated. |

Figure 6:
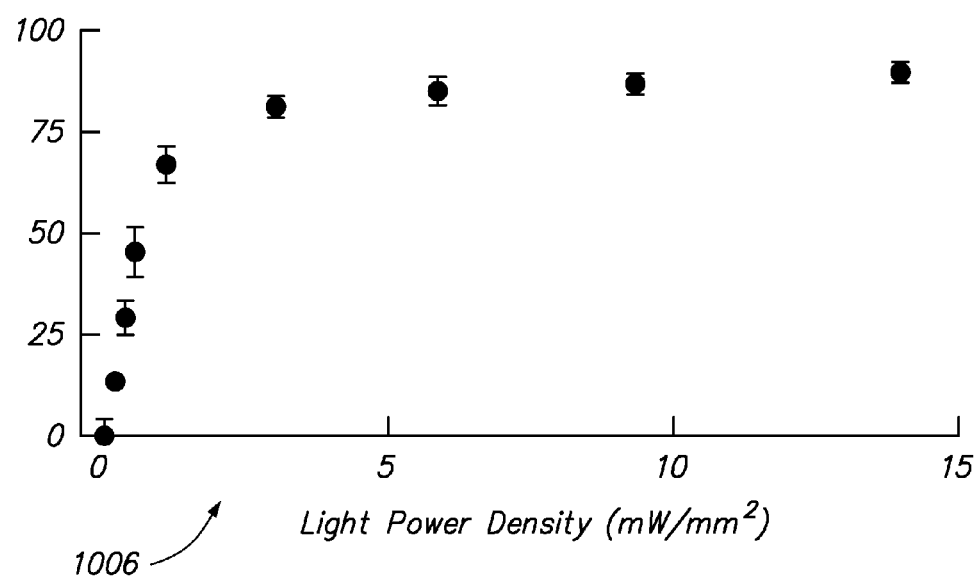
FIG. 6 depicts a light power density chart that may be applied in embodiments of the present invention.
Figure 7:
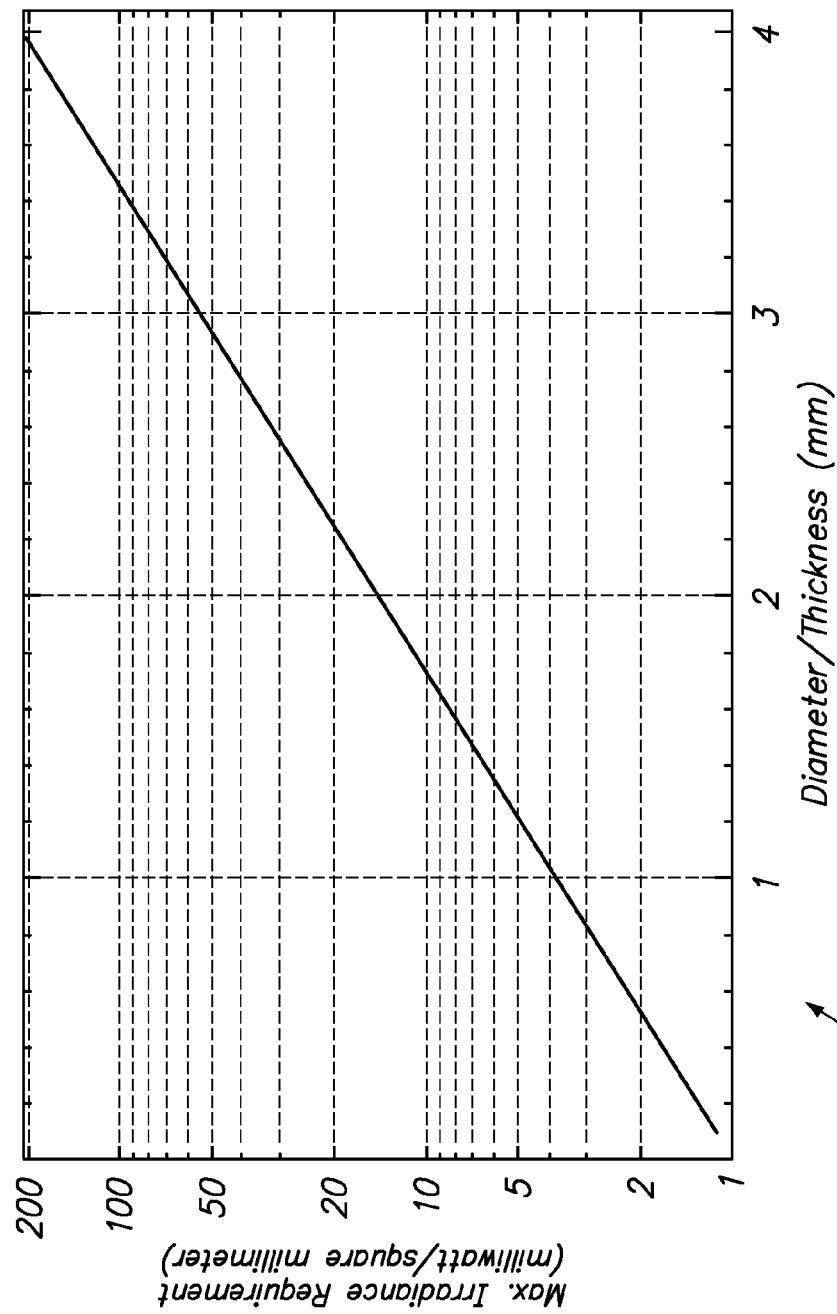
FIG. 7 depicts an irradiance versus geometry chart that may be applied in embodiments of the present invention.

It is to be understood that the term "constant" does not simply imply that there is no change in the signal or its level, but maintaining its level within an allowed tolerance. Such a tolerance may be of the order of ±20% on average. However, patient and other idiosyncrasies may also be need to be accounted and the tolerance band adjusted on a per patient basis where a primary and/or secondary therapeutic outcome and/or effect is monitored to ascertain acceptable tolerance band limits. As is shown in FIG. 6, an overexposure is not expected to cause diminished efficacy. However, the desire to conserve energy while still assuring therapeutic efficacy compels that overexposures be avoided to increase both battery lifetime and the recharge interval for improved patient safety and comfort.

Alternately, SEN2 may be what we will refer to as a therapeutic sensor configured to monitor a physical therapeutic outcome directly, or indirectly. Such a therapeutic sensor may be, by way of non-limiting example, an ENG probe, an EMG probe, a pressure transducer, a chemical sensor, an EKG sensor, or a motion sensor. A direct sensor is considered to be one that monitors a therapeutic outcome directly, such as the aforementioned examples of chemical and pressure sensors. An indirect sensor is one that monitors an effect of the treatment, but not the ultimate result. Such sensors are the aforementioned examples of ENG, EKG, and EMG probes, as are also discussed elsewhere herein.

Alternately, the therapeutic sensor may be a patient input device that allows the patient to at least somewhat dictate the optical dosage and/or timing. Such a configuration may be utilized, by way of non-limiting example, in cases such as muscle spasticity, where the patient may control the optical dosage and/or timing to provide what they deem to be the requisite level of control for a given situation.

In an alternate embodiment, an additional optical sensor may be located at the input end of the delivery segment near to the light source. This additional information may assist in diagnosing system status by allowing for the optical efficiency of the delivery segments to be evaluated. For example, the delivery segments and/or their connection to the applicator may be considered to be failing, if the output end sensor registers a decreasing amount of light, while the input end sensor does not. Thus, replacing the delivery segments and/or the applicator may be indicated.

Figure 69:
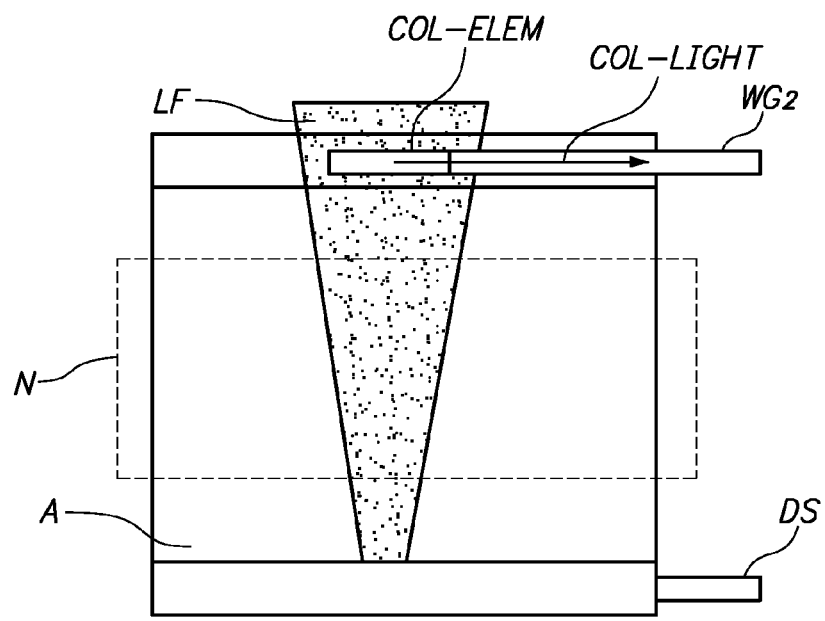
FIG. 69 depicts an embodiment of optical sensing in accordance with the present invention.

In an alternate embodiment, SEN1 may further be configured to utilize a collector, such as an optical fiber, or an t least an aspect of the Applicator itself, that serves to collect and carry the optical signal from, or adjacent to the Applicator to a remote location. By way of non-limiting example, light may be sampled at or near the target tissue, but transferred to the controller for detection and processing. Such a configuration is shown in FIG. 69, where Delivery Segment DS provides light to Applicator A, creating Light Field LF. Light Field LF is sampled by Collection Element COL-ELEM, which may be, by way of non-limiting example, a prism, a rod, a fiber, a side-firing fiber, a cavity, a slab, a mirror, a diffractive element, and/or a facet. Collected Light COL-LIGHT is transmitted by Waveguide WG2 to SEN1, not shown.

Alternately, the Delivery Segment itself, or a portion thereof, may be used to transmit light to the remote location of SEN1 by means of spectrally separating the light in the housing. This configuration may be similar to that shown in FIG. 16, with the alterations, that LS2 becomes SEN1, and Beamcombiner BC is configured such that it allows light from the target tissue to be transmitted to SEN1, while still allowing substantially all of the light form LS1 to be injected into Waveguide WG for therapeutic and diagnostic purposes. Such a configuration may be deployed when SEN1 may be a chemometric sensor, for example, and a fluorescence signal may be the desired measurand.

Alternate configurations are shown in FIGS. 27A (1012) and 27B (1014), wherein applicators configured as linear and planar arrays of emitters, or alternately output couplers, are shown.

Figure 28:
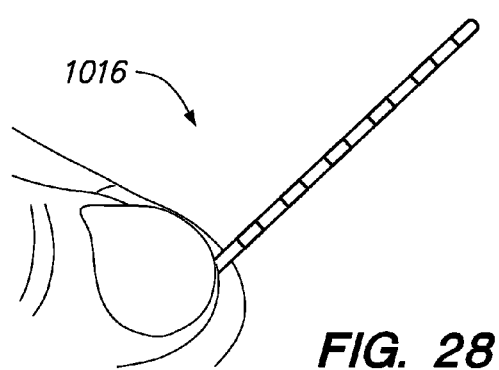

A linear array optogenetic light applicator (A), which also may be termed an "optarray", may be inserted into the intrathecal space to deliver light to the sacral roots, and/or the cell bodies of the nerves located within the dorsal and ventral horns of the spine, and/or nerve ganglia located near or about the sline, for optogenetic modulation of neurons involved in bowel, bladder, and erectile function. Alternately, it may be inserted higher in the spinal column for pain control applications, such as those described elsewhere in this application. Either the linear or matrix array optarray(s) may be inserted into the anterior intrathecal anatomy to control motor neurons and/or into the posterior intrathecal anatomy to control sensory neurons. A single optical element may be illuminated for greater specificity, or multiple elements may be illuminated. FIG. 28 (1016) illustrates an alternative view of an exemplary linear array.

The system may be tested at the time of implantation, or subsequent to it. The tests may provide for system configurations, such as which areas of the applicator are most effective, or efficacious, by triggering different light sources alone, or in combination, to ascertain their effect on the patient. This may be utilized when a multi-element system, such as an array of LEDs, for example, or a multiple output coupling method is used. Such diagnostic measurements may be achieved by using an implanted electrode that resides on, in or near the applicator, or one that was implanted elsewhere, as will be described in another section. Alternately, such measurements maybe made at the time of implantation using a local nerve electrode for induced stimulation, and/or an electrical probe to query the nerve impulses intraoperatively using a device such as the Stimulator/Locator sold under the tradename CHECKPOINT® from NDI and Checkpoint Surgical, Inc. to provide electrical stimulation of exposed motor nerves or muscle tissue and in turn locate and identify nerves as well to test their excitability. Once obtained, an applicator illumination configuration may be programmed into the system for optimal therapeutic outcome using an external Programmer/Controller (P/C) via a Telemetry Module (TM) into the Controller, or Processor/CPU of the system Housing (H), as are defined further below.

Figure 29A:
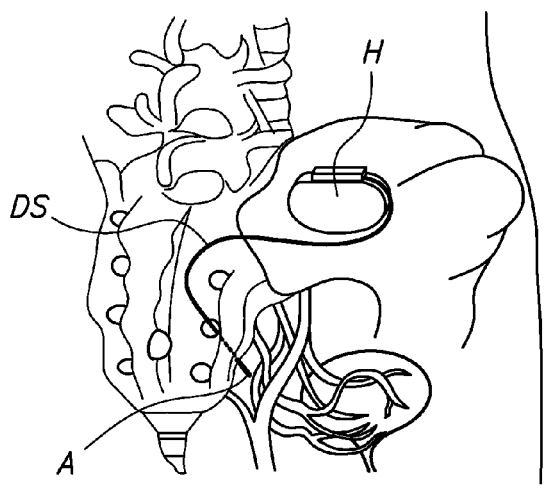
FIGS. 29A and 29B illustrate system level deployments of optogenetic treatment systems for nerve root intervention in accordance with the present invention.

FIG. 29A illustrates the gross anatomical location of an implantation/installation configuration wherein a controller housing (H) is implanted adjacent the pelvis, and is operatively coupled (via the delivery segment DS) to an applicator (A) positioned to stimulate one or more of the sacral nerve roots.

Figure 29B:
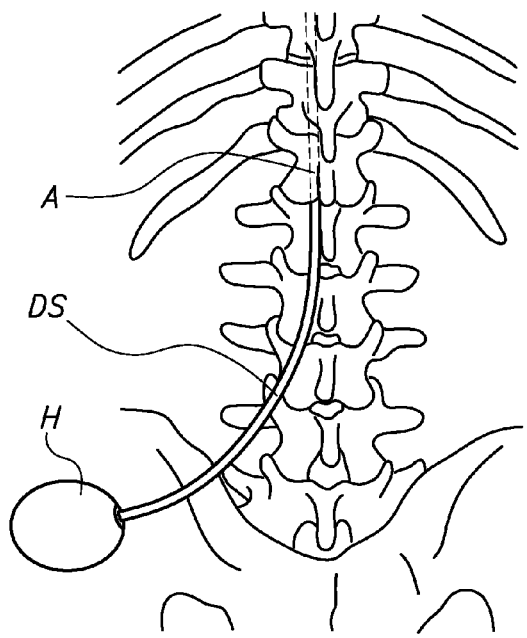

FIG. 29B illustrates the gross anatomical location of an implantation/installation configuration wherein a controller housing (H) is implanted adjacent the pelvis, and is operatively coupled (via the delivery segment DS) to an applicator (A) positioned to stimulate one or more of the lumbar, thoracic, or cervical nerve roots, such as by threading the delivery segment and applicator into the intrathecal space to reach the pertinent root anatomy.

The electrical connections for devices such as these where the light source is either embedded within, on, or located nearby to the applicator, may be integrated into the applicators described herein. Materials like the product sold by NanoSonics, Inc. under the tradename Metal Rubber™ and/or mc10's extensible inorganic flexible circuit platform may be used to fabricate an electrical circuit on or within an applicator. Alternately, the product sold by DuPont, Inc., under the tradename PYRALUX®, or other such flexible and electrically insulating material, like polyimide, may be used to form a flexible circuit; including one with a copper-clad laminate for connections. PYRALUX® in sheet form allows for such a circuit to be rolled. More flexibility may be afforded by cutting the circuit material into a shape that contains only the electrodes and a small surrounding area of polyimide.

Such circuits then may be encapsulated for electrical isolation using a conformal coating. A variety of such conformal insulation coatings are available, including by way of non-limiting example, parlene (Poly-Para-Xylylene) and parlene-C (parylene with the addition of one chlorine group per repeat unit), both of which are chemically and biologically inert. Silicones and polyurethanes may also be used, and may be made to comprise the applicator body, or substrate, itself. The coating material can be applied by various methods, including brushing, spraying and dipping. Parylene-C is a bio-accepted coating for stents, defibrillators, pacemakers and other devices permanently implanted into the body.

In a particular embodiment, biocompatible and bio-inert coatings may be used to reduce foreign body responses, such as that may result in cell growth over or around an applicator and change the optical properties of the system. These coatings may also be made to adhere to the electrodes and to the interface between the array and the hermetic packaging that forms the applicator.

By way of non-limiting example, both parylene-C and poly(ethylene glycol) (PEG, described herein) have been shown to be biocompatible and may be used as encapsulating materials for an applicator. Bioinert materials non-specifically downregulate, or otherwise ameliorate, biological responses. An example of such a bioinert material for use in an embodiment of the present invention is phosphoryl choline, the hydrophilic head group of phospholipids (lecithin and sphingomyelin), which predominate in the outer envelope of mammalian cell membranes. Another such example is Polyethylene oxide polymers (PEO), which provide some of the properties of natural mucous membrane surfaces. PEO polymers are highly hydrophilic, mobile, long chain molecules, which may trap a large hydration shell. They may enhance resistance to protein and cell spoliation, and may be applied onto a variety of material surfaces, such as PDMS, or other such polymers. An alternate embodiment of a biocompatible and bioinert material combination for use in practicing the present invention is phosphoryl choline (PC) copolymer, which may be coated on a PDMS substrate. Alternately, a metallic coating, such as gold or platinum, as were described earlier, may also be used. Such metallic coatings may be further configured to provide for a bioinert outer layer formed of self-assembled monolayers (SAMs) of, for example, D-mannitol-terminated alkanethiols. Such a SAM may be produced by soaking the intended device to be coated in 2 mM alkanethiol solution (in ethanol) overnight at room temperature to allow the SAMs to form upon it. The device may then be taken out and washed with absolute ethanol and dried with nitrogen to clean it.

A variety of embodiments of light applicators are disclosed herein. There are further bifurcations that depend upon where the light is produced (i.e., in or near the applicator vs. in the housing or elsewhere). FIGS. 30A and 30B illustrate these two configurations.

Referring to FIG. 30A, in a first configuration, light is generated in the housing and transported to the applicator via the delivery segment. The delivery segment(s) may be optical waveguides, selected from the group consisting of round fibers, hollow waveguides, holey fibers, photonic bandgap devices, and/or slab configurations, as have described previously. Multiple waveguides may also be employed for different purposes. As a non-limiting example, a traditional circular cross-section optical fiber may be used to transport light from the source to the applicator because such fibers are ubiquitous and may be made to be robust and flexible. Alternately, such a fiber may be used as input to another waveguide, this with a polygonal cross-section providing for regular tiling. Such waveguides have cross-sectional shapes that pack together fully, i.e. they form an edge-to-edge tiling, or tessellation, by means of regular congruent polygons. That is, they have the property that their cross-sectional geometry allows them to completely fill (pack) a two-dimensional space. This geometry yields the optical property that the illumination may be made to spatially homogeneous across the face of such a waveguide. Complete homogeneity is not possible with other geometries, although they may be made to have fairly homogeneous irradiation profiles nonetheless. For the present application, a homogenous irradiation distribution may be utilized because it may provide for uniform illumination of the target tissue. Thus, such regular-tiling cross-section waveguides may be useful. It is also to be understood that this is a schematic representation and that multiple applicators and their respective delivery segments may be employed. Alternately, a single delivery segment may service multiple applicators. Similarly, a plurality of applicator types may also be employed, based upon the clinical need.

Referring to the configuration of FIG. 30B, light is in the applicator. The power to generate the optical output is contained within the housing and is transported to the applicator via the delivery segment. It is to be understood that this is a schematic representation and that multiple applicators and their respective delivery segments may be employed. Similarly, a plurality of applicator types may also be employed.

The size(s) of these applicators may be dictated by the anatomy of the target tissue. By way of non-limiting example, a fluidic channel slab-type (or, equivalently, "slab-like") applicator may be configured to comprise a parallel array of 3 rectangular HRIP waveguides that are 200 μm on a side, the applicator may be between 1-10 mm in width and between 5-100 mm in length, and provide for multiple output couplers along the length of each channel waveguide to provide a distributed illumination of the target tissue.

The pertinent delivery segments may be optical waveguides, such as optical fibers, in the case where the light is not generated in or near the applicator(s). Alternately, when the light is generated at or near the applicator(s), the delivery segments may be electrical wires. They may be further comprised of fluidic conduits to provide for fluidic control and/or adjustment of the applicator(s). They may also be any combination thereof, as dictated by the specific embodiment utilized, as have been previously described.

Figure 31:
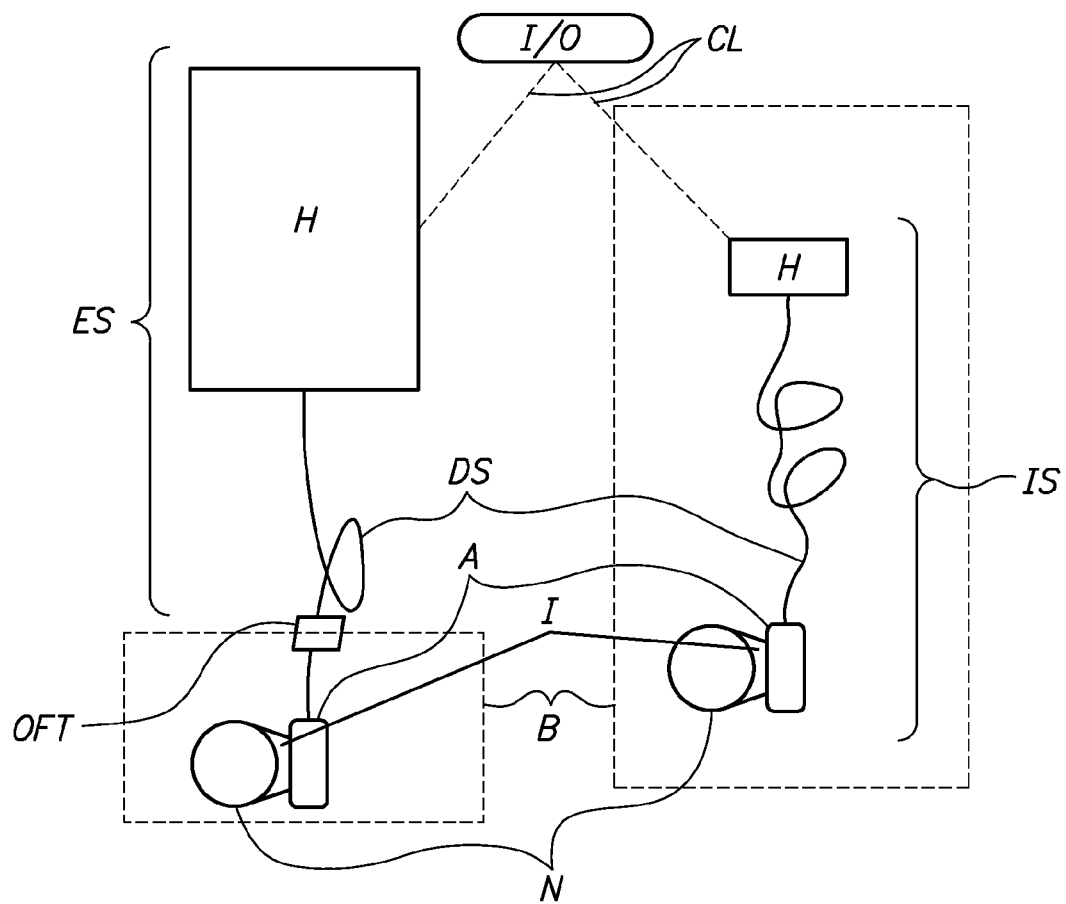

Embodiments of the subject system may be partially, or entirely, implanted in the body of a patient. FIG. 31 illustrates this, wherein the left hand side of the illustration schematically depicts the partially implanted system, and the right hand side of the illustration the fully implanted device. The housing H may be implanted, carried, or worn on the body (B), along with the use of percutaneous feedthroughs or ports for optical and/or electrical conduits that comprise the delivery segments (various embodiments/denotations of DS, or "DSx", as per the Figures) that connect to Applicator(s) A implanted to irradiate target tissue(s) N. In this exemplary embodiment, a Transcutaneous Optical Feedthrough COFT may be coupled to the Delivery Segments affixed to Housing H, located in Extracorporeal Space ES, while Applicator A is in the Intracorporeal Space IS along with Target Tissue N.

Figure 70:
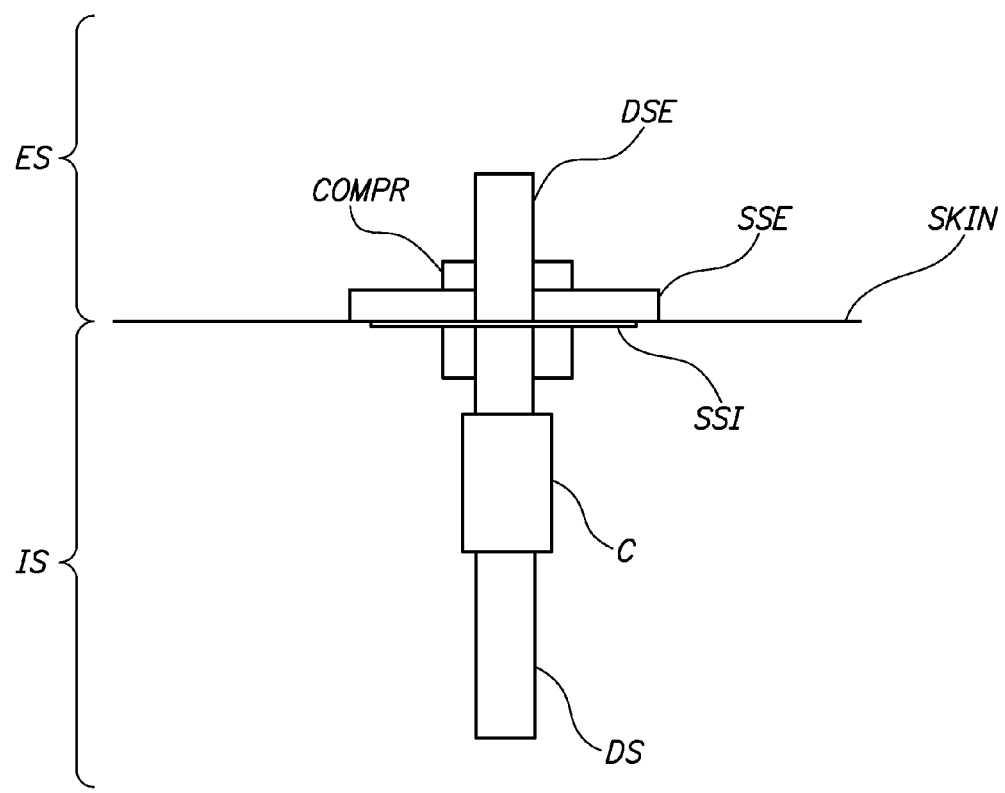
FIG. 70 depicts an embodiment of a percutaneous feedthrough in accordance with the present invention.

FIG. 70 shows an embodiment of a transcutaneous optical feedthrough, or port, comprising, by way of non-limiting example, an External Delivery Segment DSE, which in turn is routed through a seal, comprised of, External Sealing Element SSE that resides in the extracorporeal space ES, and Internal Sealing Element SSI that resides in the intracorporeal space IS. These sealing elements may held together by means of Compression Element COMPR to substantially maintain an infection-free seal for Transcutaneous Optical Feedthrough COFT. Internal Seal SSI, may comprise a medical fabric sealing surface along with a more rigid member coupled thereto to more substantially impart the compressive force from Compression Element COMPR when forming a percutaneous seal. The medical fabric/textile may be selected from the list consisting of, by way of non-limiting examples; dacron, polyethylene, polypropylene, silicone, nylon, and PTFE. Woven and/or non-woven textiles may be used as a component of Internal Seal SSI. The fabric, or a component thereon, may also be made to elute compounds to modulate wound healing and improve the character of the seal. Such compounds, by way of non-limiting examples, may be selected from the list consisting of; Vascular Endothelial Growth Factor (VEGF), glycosaminoglycans (Gags), and other cytokines. Applicable medical textiles may be available from vendors, such as Dupont and ATEX Technologies, for example. Delivery Segment DS may be connected to the optical and/or electrical connections of Applicator A, not shown for purposes of clarity, not shown. External Delivery Segment DSE may be may be connected to the optical and/or electrical output of Housing H, not shown for purposes of clarity. The surface of the patient, indicated in this example as Skin SKIN, may offer a natural element by way of the epidermis onto which the seal may be formed. Details regarding the means of sealing External Delivery Segment DES, which passes through the Skin SKIN, to Compression Element COMPR are discussed elsewhere herein in regards to optical feedthroughs within Housing H, such as are shown in FIGS. 73A-75.

Figure 71A:
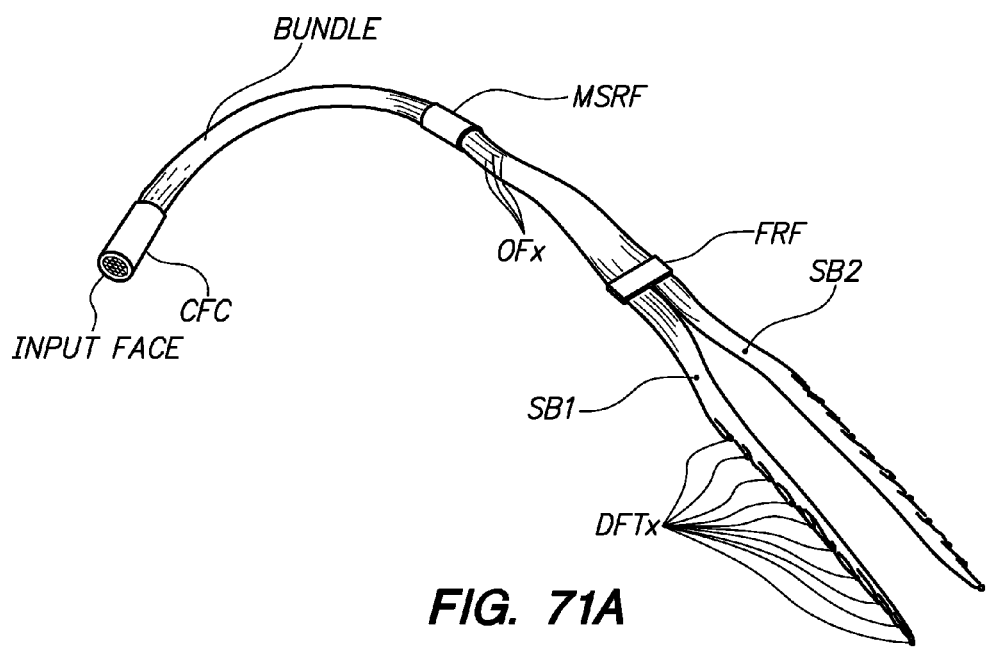
FIGS. 71A-72B depict various aspects of embodiments of configurations which may be utilized for optogenetic treatment of the spine in accordance with the present invention.
Figure 71B:
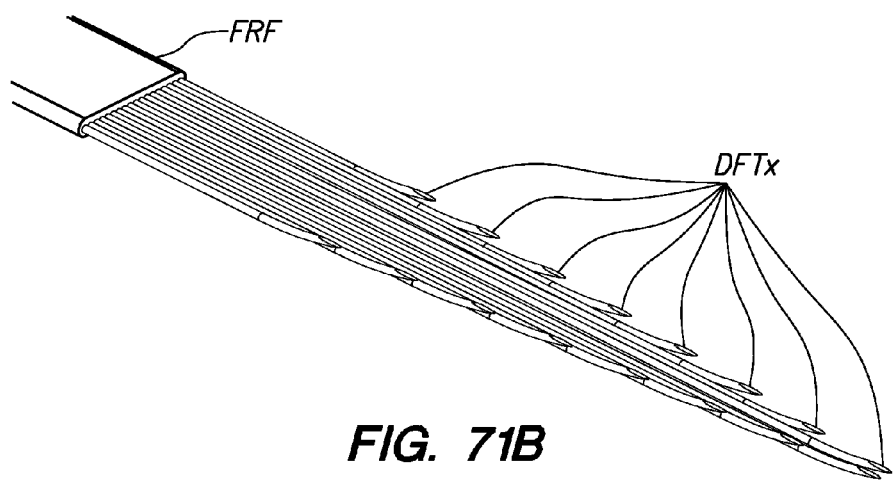
Figure 71C:
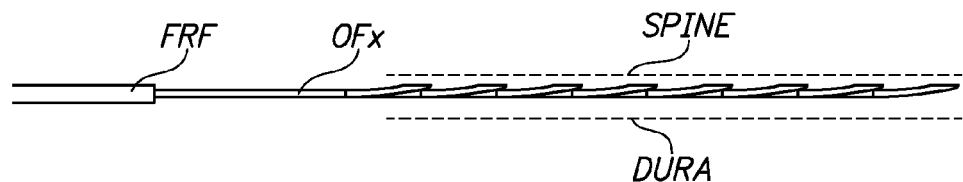

FIGS. 71A-C show an alternate embodiment, wherein a plurality of waveguides, such as, but not limited to fibers, may be bundled together for ease of capturing the light at input face INPUT FACE from a single light source, such as, by way of non-limiting examples, an LED or a laser and distributing it to a target tissue within the spine of a patient. The fibers, OFx may be connectorized at the input face INPUT FACE using circular ferrule connector CFC to form bundle BUNDLE. The bundle may then be further dressed using mid-section retaining ferrule MSRF. It may then splay out into a one-dimensional array by utilizing Flat Retaining Ferrule FRF to dispose the array to shine light on or over a desired area(s), such as, by way of non-limiting example, the left and right portions of the ventral spinal cord between L5 and L6 in order to target the roots pudendal nerve, via lateral sections SB1 and SB2. The distal tips DFTx of the individual Optical Fibers OFx within a Fiber Bundle FBx may be bent in the direction of desired illumination, or ground and coated to fire the light sideways, or have a optical element, such as, by way of non-limiting example, a mirror, lens, or prism, located distal to the output face to ultimately direct the light to the target tissue, such as has been described elsewhere herein regarding the optical output of applicators. The output ends DFTx may then be encapsulated in a permanent transparent coating to hold them in the desired position. Radio-opaque markings may be placed at, on, or along the applicator to improve placement accuracy relative to the target tissue under fluoroscopic guidance.

A non-limiting example of how such a bundled fiber light delivery segment may be constructed follows. All fibers at the input end of the bundle may be grouped together inside a temporary ferrule with a removable adhesive. This ferrule may be round, rectangular, or other shape. One embodiment holds all fibers in a single layer between two flat pieces of material, to be ground and polished at a desired angle, such as 45°. These angled ends of the fibers may be plated with a reflective coating, as mentioned earlier. The fibers may then be routed through a removable length guide which holds each fiber or group of fibers at individual lengths to create a range of lengths, such that they are spaced to fit the finished configuration of Applicator A. Optical Fibers OFx may be bundled, or re-bundled in another temporary or permanent ferrule or other fixing member with a removable or permanent adhesive at or near their Output Ends DFTx. Output Ends DFTx may then be removed from the length guide and Output Ends DFTx pulled tight and then bundled in a third permanent circular, square, rectangular or other shaped ferrule with a permanent adhesive at the desired length. This output end may then be cut and polished. The fiber bundle may then be removed from the distal ferrule and adhesive. At this point the distal ends of the fibers should straighten and project linearly from the most distal ferrule at the range of lengths defined by the length guide. The angled polished (and possibly coated) ends should all be made to point in approximately the same direction, and/or at the same point in space depending upon the final configuration for Applicator A. The output ends may then be encapsulated in a permanent transparent coating to hold them in the desired position using fixtures if necessary. Some non-limiting examples of this coating are over-molded, cast or dipped silicone, polyimide tape with silicone or acrylic adhesive or two layers of polyethylene heat-welded together.

Figure 72A:
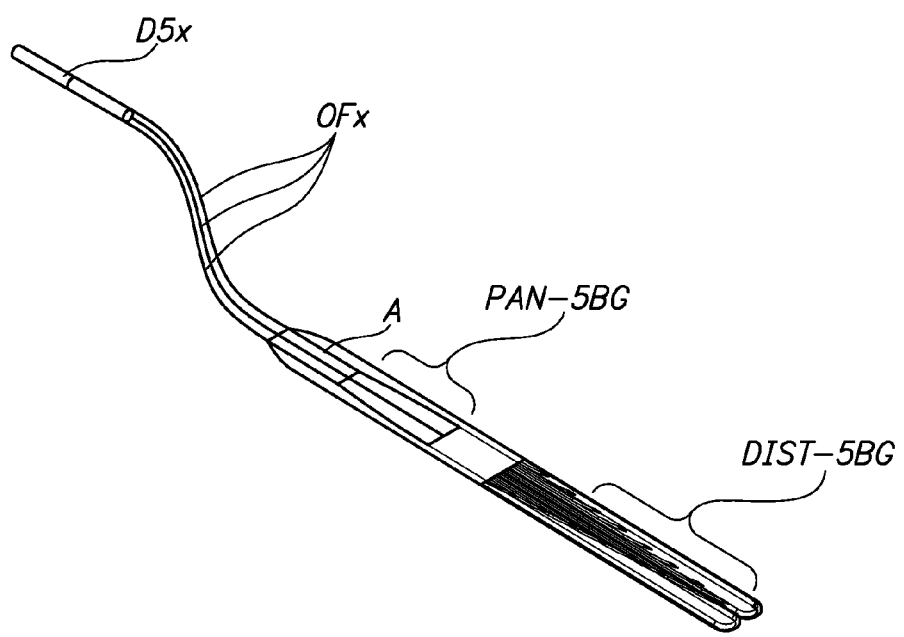
Figure 72B:
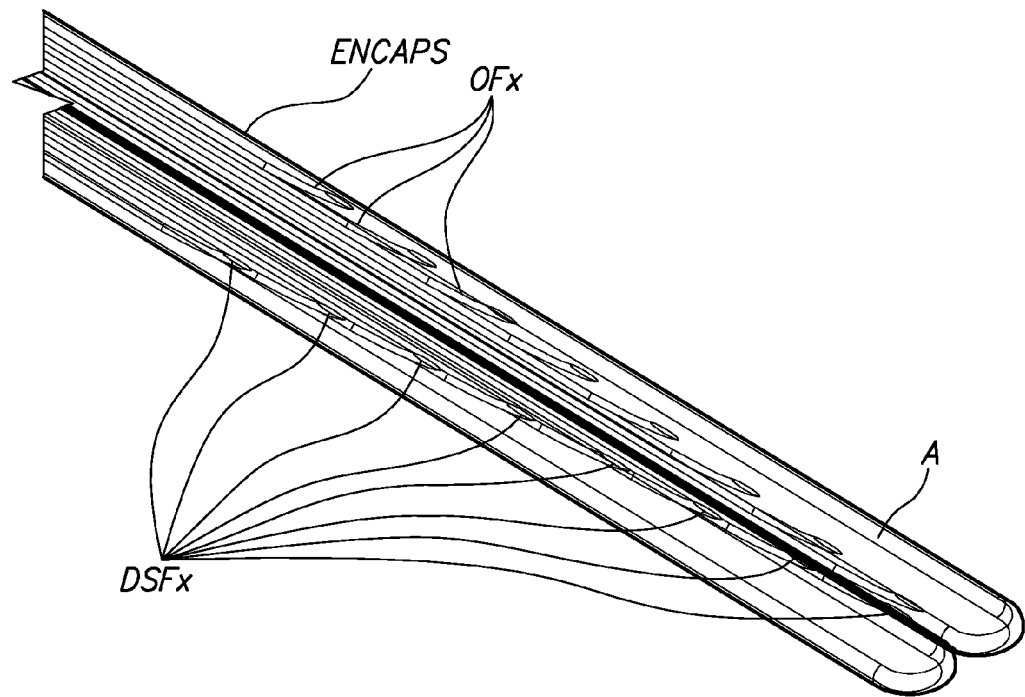

FIGS. 72A and 72B show an alternate embodiment of the present invention in which the Applicator A is configured to encapsulate the lateral sections SB1 and SB2 containing Distal Tips DFTx of individual Optical Fibers OFx within Fiber Bundle FBx that comprises Delivery Segment DS. Optical Fibers OFx are separated within Fan Segment FAN-SEG and disposed at a Distal Segment DIST-SEG within Applicator A for treatment at the spine, or other such predominantly linear anatomical location, of a patient. Similar to FIG. 1B, Figure CC-B shows a more detailed view of the Distal Segment DIST-SEG, in which the addition of Encapsulant ENCAPS is shown with Distal Tips DFTx of individual Optical Fibers OFx.

Figure 73A:
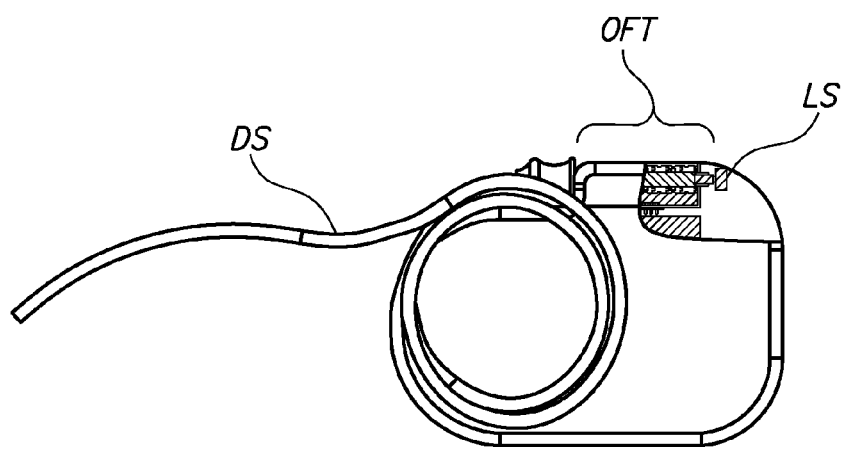
FIGS. 73A-75 depict various aspects of embodiments of configurations of optical feedthroughs in accordance with the present invention.
Figure 73B:
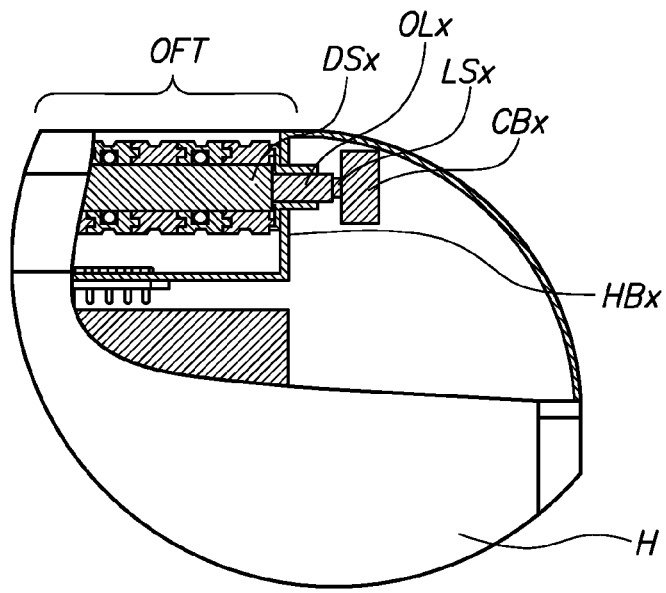

FIGS. 73A AND 73B show an alternate embodiment of an implantable, hermetically sealed Housing H comprising an optical feed-through OFT, wherein Delivery Segment DSx may be coupled to Housing H. The system further may comprise a configuration such that Delivery Segment DSx may be coupled to Housing H via a plurality of electrical connections and at least one optical connection via Connector C, which in this exemplary embodiment is shown as a component of Delivery Segment DS, but alternate configurations are within the scope of the present invention. Also shown are hidden line views of the Housing H, Delivery Segment DSx, and Connector C that reveal details of an embodiment, such as Circuit Board CBx, Light Source LSx, Optical Lens OLx, the proximal portion of the Delivery Segment DSx, and a Hermetic Barrier HBx. Light Source LSx may be mounted to and electrical delivered thereto by Circuit Board CBx. Optical Lens OLx may be a sapphire rod lens that serves to transmit light to Delivery Segment DSx.

Figure 74:
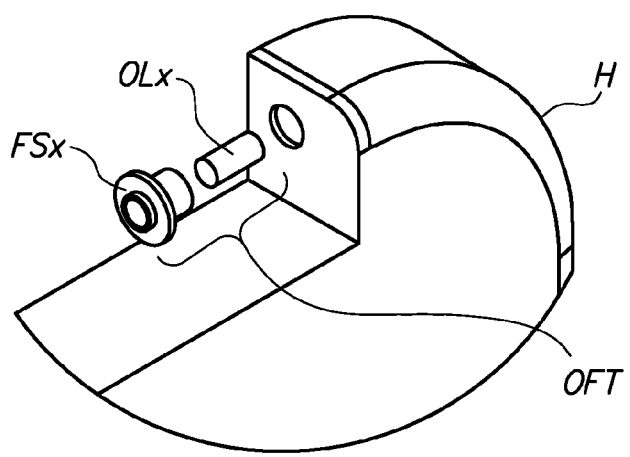

FIG. 74 shows an enlarged view of the implantable Housing H and the optical feed-through OFT, comprised of the Optical Lens OLx and the Flanged Seal FSx. In an exemplary embodiment, the outer cylindrical surface of the sapphire lens may be coated with high purity gold, for example, and brazed to a flanged seal, such as a titanium seal, in a brazing furnace. This may create a biocompatible hermetic connection between Optical Lens OLx and the Flanged Seal FSx. The exemplary lens-seal combination may then be inserted into a hole in the outer surface of Housing H, which may also be comprised of titanium, and Flanged Seal FSx welded at least partially about the perimeter of a complementary hole in Housing H. This may create a completely biocompatible hermetically sealed assembly through which light from Light Source LSx may be coupled from within Housing H and transmit light outside of Housing H for use by Delivery Segments DS, and/or an Applicator A for treatment at a target tissue, as has been described elsewhere herein.

Figure 75:
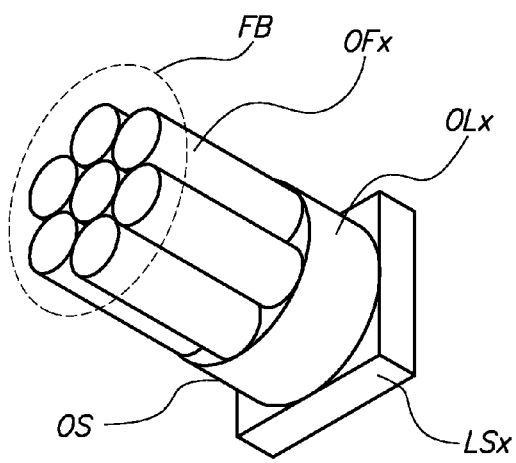

FIG. 75 shows an isometric view of an embodiment of the present invention, in which Light Source LSx may be at least partially optically coupled to fiber bundle FBx via Optical Lens OLx interposed between the two. Optically index-matched adhesive may be used to affix Optical Lens OLx onto Light Source LSx directly. It should be understood that the light source may be contained within a hermetically sealed implantable housing, not shown for clarity, and that Optical Lens OLx crosses the wall of the hermetically sealed implantable Housing H wherein a portion of Optical Lens OLx resides within Housing H and another portion of Optical Lens OLx resides outside of Housing H and is hermetically sealed around at least a portion of its Outer Surface OS, and that a Fiber Bundle FB may reside outside the hermetically sealed implantable Housing H and may be coupled to Optical Lens OLx. For instance, if a single source Light Source LS is used, such as an LED, a bundle of 7 Optical Fibers OFx may be used to capture the output of Light Source LS, which may be, for example, a 1 mm×1 mm LED. Fiber Bundle FB may have an outer diameter of 1 mm to assure that all Optical Fibers OFx are exposed to the output of Light Source LS. Using fibers of 0.33 mm outer (cladding) diameter is the most efficient way of packing 7 fibers into a circular cross section using a hexagonal close-packed (HCP) configuration to approximate a 1 mm diameter circle. The ultimate optical collection efficiency will scale from the filling ratio, the square of the fiber core/cladding ratio, and in further proportion to the ratio of the fiber étendue to that of the LED output as the numerical apertures are considered. These sub-fibers, or sub-bundles as the case may be, may be seperated and further routed, trimmed, cut, polished, and/or lensed, depending upon the desired configuration. Brazing of Optical Lens OLx and the Flanged Seal FSx should be performed prior to the use of adhesives.

| Number of Fibers | Circular Filling % | Square Filling % |
| --- | --- | --- |
| 7 | 78 | 61 |
| 19 | 80 | 63 |
| 37 | 81 | 63.5 |
| 55 | 81.5 | 64 |
| 85 | 82 | 64.5 |

The above table describes several different possibilities for coupling light from a single source into a plurality of fibers (a bundle) in a spatially efficient manner. For circular fibers, the HCP configuration has a maximum filling ratio of ~90.7%. It should be understood that even more efficient bundles may be constructed using hexagonal or otherwise shaped individual fibers and the Fiber Bundles FBx shown are merely for exemplary purposes. The plurality of fibers may be separated in to smaller, more flexible sub-bundles. Fiber Bundles FBx may be adhesively bonded together and/or housed within a sheath, not shown for clarity. Multiple smaller Optical Fibers OFx may be used to provide an ultimately more flexible Fiber Bundle FBx, and may be flexibly routed through tortuous pathways to access target tissue. Additionally, Optical Fibers OFx may be separated either individually or in sub groups to be routed to more than one target tissue site. For instance, if a seven fiber construct is used, these seven fibers may be routed to seven individual targets. Similarly, if a 7×7 construction is used, the individual bundles of 7 fibers may be similarly routed to seven individual targets and may be more flexible than the alternative 1×7 construct fiber bundle and hence routed to the target more easily.

Figure 76A:
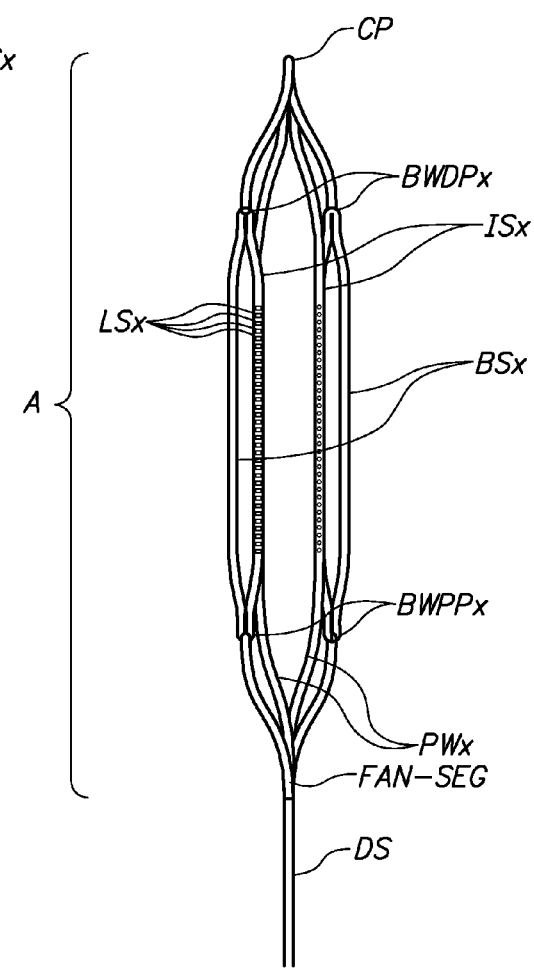

FIG. 76A shows an embodiment of the present invention similar to that shown in FIGS. 26-28, wherein an Applicator A is now configured for intrathecal spinal illumination, where a Pull Wire(s) PWx may be coupled to Biasing Segments BSx and Illumination Segments ISx, such that Applicator A expands to fill the intrathecal space when force is applied to pull the Pull Wire(s) PWx, Delivery Segments DSx separate to form Fan Segment FAN-SEG. Pull Wire(s) PWx are then coupled to the distal sections of the Biasing Segments BSx at Distal Pivot Element BWDPx. Common Pivot CP is located at the distal-most end of the applicator. Proximal Pivot Element(s) BWPPx may serve to distribute the load from Pull Wire(s) PWx. Pull Wires PWx may be routed off axis, substantially at or near the Distal and/or Proximal locations of the Biasing or Illumination segments, BWDPx and BWPPx, respectively, such that asymmetrical axial loads are placed on the segments, thereby imparting a bending moment within the Biasing Segments BSx and Illumination Segments ISx.

Figure 76B:
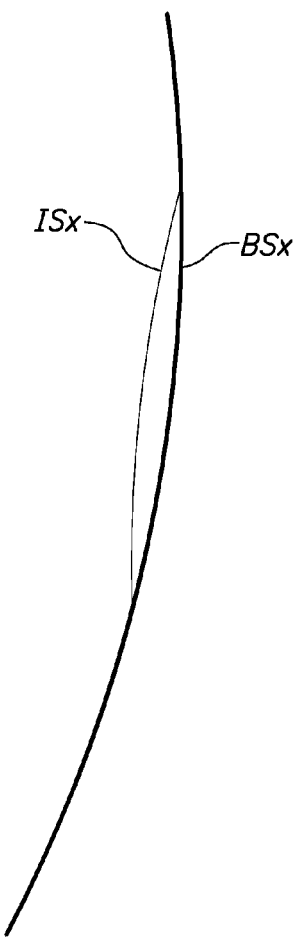

As configured, pulling on Pull Wire(s) PWx may cause the Light Sources LSx located on or about Illumination Segment(s) ISx to move in one direction and Biasing Segments BSx to move in the opposite direction, as shown in FIG. 76B. In this fashion Light Sources LSx are deployed against the spinal cord and the Biasing Segments BSx is placed against the wall of the spinal dura. This design may provide for the application of low and even pressure while accommodating the geometry of the intrathecal space, as is shown in the alternate view of this exemplary configuration in FIG. 76B, where Biasing Segment(s) BSx are located dorsally for illumination of the dorsal roots and ventrally for illumination of the ventral roots. The amount of movement, or translocation, of the Illumination Segments ISx and Biasing Segments BSx is proportional to the amount of Pull Wire(s) movement (and therefore force applied to the pull wire).

A structure may be comprised of a flexible material, such as silicone (as has been described elsewhere herein), which may be compressed via rolling or folding to fit through a small introducer, such as; an endoscope, a laproscope, a cannula, or a catheter. It may be further configured to expand and fit securely in the intradural space of the spinal column when removed from the introducer. The structure may have a location for the mounting LEDs such that when the device is deployed in the spinal column, the LED outputs being directed toward the target tissue. The structure may be fabricated of conductive wires or traces and insulated so that the structure forms the circuitry used to power the LEDs. Additionally, control wires can be included so that the location of the LEDs may be adjusted relative to the location of the securing features. The entire structure may be shaped in 3 dimensions to minimize any pressure applied to the spinal cord or any other tissue. The structure may be shaped and or adjusted through control wires to place a small amount of pressure holding the LEDs against the target to maximize light transmission to the targeted cells within the target tissue.

Figure 77:
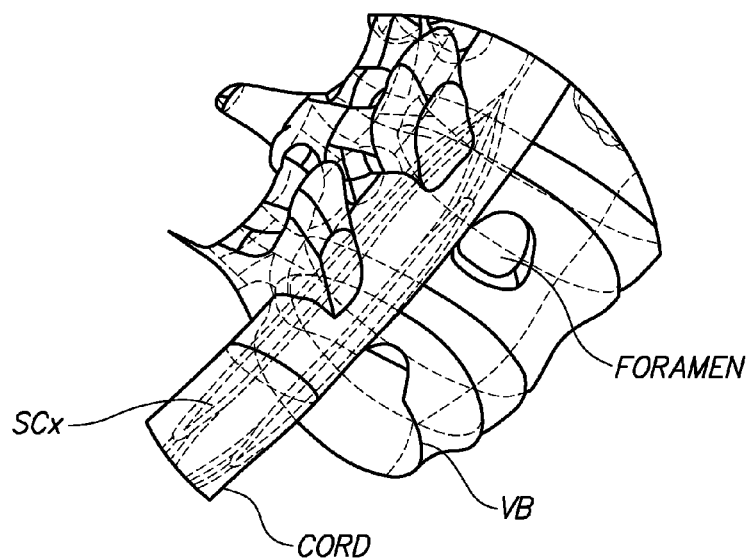

FIG. 77 shows details regarding the therapeutic placement of the intrathecal Applicator A for illumination of the dorsal aspect of the Spinal Cord CORD, and illustrates the locations anatomical elements FORAMEN, and Vertebral Body VB for anatomic reference.

FIG. 78 shows the exemplary embodiment of FIGS. 76A & FIG. 76B in a state for insertion into the intrathecal space of the patient, as described earlier, where Pull Wires PWx are in their relaxed state, which may cause the individual segments of Applicator A, such as Bias Segments BSx and Illumination Segments ISx to be substantially adjacent, and/or overlapped to present a minimal cross-sectional area. For the purposes of these embodiments, the term Lighting Segment may be used to describe the segment of the Applicator for illuminating the spine using either proximal or distal Light Sources LSx, (e.g. LEDs on the lighting segment(s), and/or waveguides transmitting light from a remote light source).

FIG. 79 illustrates an embodiment of the present invention, wherein an Applicator A may be used to illuminate a target tissue N with using at least one Light Source LSx.

Light Source(s) LSx may be LEDs or laser diodes. Light Source(s) LSx may be located at or adjacent to the target tissue, and reside at least partially within an Applicator A, and be electrically connected by Delivery Segment(s) DS to their power supply and controller that reside, for example, inside a Housing H.

FIG. 80 shows such an exemplary system configuration. In this illustrative embodiment, a single strip of LEDs is encased in an optically clear and flexible silicone, such as the low durometer, unrestricted grade implantable materials MED-4714 or MED4-4420 from NuSil, by way of non-limiting examples. This configuration provides a relatively large surface area for the dissipation of heat. For example, a 0.2 mm×0.2 mm 473 nm wavelength LED, such as those used in the picoLED devices by Rohm, or the die from the Luxeon Rebel from Phillips, may produce about 1.2 mW of light. In the exemplary embodiment being described, there are 25 LEDs utilized, producing a total of about 30 mW of light, and in turn generate about 60 mW of heat. They are nominally between 30-50% efficient. The heat generated by the LEDs may be dissipated over the relatively large surface area afforded by the present invention of 15 mm$^2$, or a heat flux of 4 mW/mm$^2$ at the surface of Applicator A. Implantable (unrestricted) grade silicone has a thermal conductivity of about 0.82 Wm$^{-1}$ K$^{-1}$, and a thermal diffusivity of about 0.22 mm$^2$s$^{-1}$ and distributing the heat over a larger area and/or volume of this material decreases the peak temperature rise produced at the tissue surface.

Figure 81:
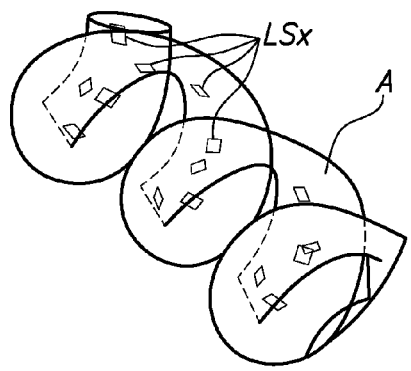

FIG. 81 illustrates an alternate configuration of the embodiment of FIG. 79, with the addition of a spiral, or helical design for Applicator A is utilized. Such a configuration may allow for greater exposure extent of the target tissue. This may also be useful to allow slight misplacement of the applicator with respect to the target tissue, if the longitudinal exposure length is greater than that intended for the target tissue and the deployed location of Applicator A also subsumes the target tissue by a reasonable margin. A reasonable margin for most peripheral applications is about ±2 mm. Applicator A must provide an inner diameter (ID) that is at least slightly larger than the outer diameter (OD) of the target tissue for the target tissue with Applicator A to move axially without undue stress. Slightly larger in the case of most peripheral nerves may provide that the ID of Applicator A be 5-10% larger than the target tissue OD.

Fiber and or protective coverings on or containing a waveguide, such as, but not limited to optical fiber may be shaped to provide a strain-relieving geometry such that forces on the applicator are much reduced before they are transmitted to the target tissue. By way of non-limiting example, shapes for a flexible fiber to reduce forces on the target tissue include; serpentine, helical, spiral, dual non-overlapping spiral (or "bowtie"), cloverleaf, or any combination of these.

Figure 82A:
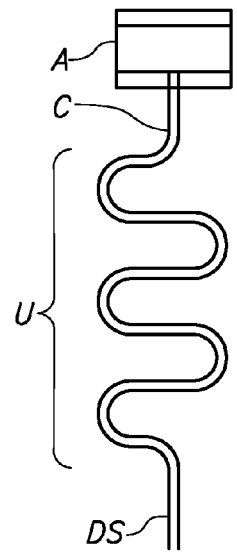
Figure 82B:
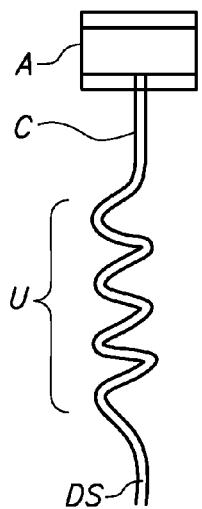
Figure 82C:
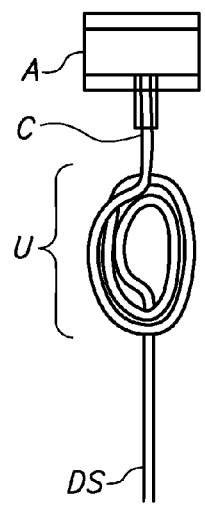

FIGS. 82A-82D illustrate a few of these different configurations in which Undulations U are configured to create a strain relief section of optical waveguide Delivery Segment DS prior to its connection to Applicator A via Connector C. FIG. 82A illustrates a Serpentine section of Undulations U for creating a strain relief section within Delivery Segment DS and/or Applicator A. FIG. 82B illustrates a Helical section of Undulations U for creating a strain relief section within Delivery Segment DS and/or Applicator A. FIG. 82C illustrates a Spiral section of Undulations U for creating a strain relief section within Delivery Segment DS and/or Applicator A. FIG. 82D illustrates a Bowtie section of Undulations U for creating a strain relief section within Delivery Segment DS and/or Applicator A. Target Tissue resides within Applicator in these exemplary embodiments, but other configurations, as have been described elsewhere herein, are also within the scope of the present invention.

FIG. 83 shows an alternate embodiment, wherein Applicator A may be configured such that it is oriented at an angle relative the Delivery Segment DS, and not normal to it as was illustrated in the earlier exemplary embodiments. Such an angle might be required, for example, in order to accommodate anatomical limitations, such as the target tissue residing in a crevice or pocket, as may the case for certain peripheral nerves. Another bend, or Undulation U, in either the Delivery Segment DS or in an element of Applicator A, such as an output coupler, as has been described elsewhere herein, may be utilized to create the angle.

In an alternate embodiment, an optical feature may be incorporated into the system at the distal end of the Delivery Segment DS, or the proximal end of the optical input of Applicator A to reflect the light an angle relative to the direction of the fiber to achieve the angle.

Plastic optical fiber such as 100 μm core diameter ESKA SK-10 from Mitsubishi may be routed and/or shaped in a jig and then heat-set to form Undulations U directly. Alternately, a covering may be used over the waveguide, and that covering may be fabricated to create Undulations U in the waveguide indirectly. An alternate exemplary plastic fiber waveguide may be constructed from a PMMA (n=1.49) core material with a cladding of THV (n−1.35) to provide an NA of 0.63. A polyethylene tube, such as, PE10 from Instech Solomon, may be used as a cover, shaped in a jig and heat-set to create Undulations U while using a silica optical fiber within the tube. Heat-setting for these two exemplary embodiments may be accomplished by routing the element to be shaped in a jig or tool to maintain the desired shape, or one approximating it, and then heating the assembly in an oven at 70° C. for 30 minutes. Alternately, the bends may be created in more gradual steps, such that only small bends are made at each step and the final heating (or annealing) provides the desired shape. This approach may better assure that no stress-induced optical changes are ingendered, such as refractive index variations, which might result in transmission loss. Although optical fiber has been discussed in the previous examples, other delivery segment and applicator configurations are within the scope of the present invention.

Light transmission through tissue such as skin is diffusive, and scattering the dominant process. Scattering diminishes the directionality and brightness of light illuminating tissue. Thus, the use of highly directional and/or bright sources is rendered moot. This may limit the depth in tissue that a target may be affected. An in-vivo light collector may used within the tissue of a patient in cases where straightforward transcutaneous illumination cannot be used to adequately irradiate a target due to irradiance reduction, and a fully implanted system may be deemed too invasive.

In one embodiment, an at least partially implanted system for collecting light from an external source may be placed in-vivo and/or in-situ within the skin of a patient to capture and transmit light between the external light source and an implanted applicator. Such applicators have been described elsewhere herein.

Alternately, an at least partially implanted system for collecting light from an external source may be placed in-vivo and/or in-situ within the skin of a patient to capture and transmit light between the external light source and direct it to the target tissue directly, without the use of a separate applicator.

The light collection element of the system may be constructed, for example, from a polymer material that has an outer layer of a nominally different index of refraction than that of the body or core material, such as is done in fiber optics. While the index of refraction of skin and other tissues is about equal to that of water, corresponding to a range of 1.33-1.40 in the visible spectrum, and would provide a functional cladding that may yield an NA as high as 0.56 when PMMA is used is the unclad core material. However, native chromophores within tissues such as skin that may be avid absorbers of the light from the external light source, especially visible light. Examples of such native chromophores are globins (e.g. oxy-, deoxy-, and met-hemoglobin), melanins (e.g. neuro-, eu-, and pheo-melanin), and xanthophylls (e.g. carotenol fatty acid esters). The evanescent wave present in an insufficiently clad or unclad collection device may be coupled into absorption by these native pigments that potentially causes unintended and/or collateral heating that not only diminishes the amount of light conducted to the target, but also may create a coating on the collector that continually degrades its performance. For example, there may be melanin resident at the dermal-epidermal junction, and blood resident in the capillary bed of the skin.

In one embodiment, the depth of the surface of the implantable light conductor is placed between 100 and 1000 μm beneath the tissue surface. In the case of cutaneous implantation, this puts that surface below the epidermis.

The implantable light collector/conductor may be made of polymeric, glass, or crystalline material. Some non-limiting examples are; PMMA, Silicones, such as MED-4714 or MED4-4420 from NuSil, PDMS, and High-Refractive-Index Polymers (HRIPs), as are described elsewhere herein.

A cladding layer may also be used on the implantable light collector to improve reliability, robustness and overall performance. By way of non-limiting example, THV (a low index fluoropolymer blend), Fluorinated ethylene propylene (FEP), and/or polymethylpentene may be used to construct cladding layers about a core material. These materials are biocompatible and possess relatively low indices of refraction (n=1.35-1.4). Thus, they provide for light collection over a wide numerical aperture (NA).

In addition to the use of a cladding layer on the implantable light conductor/collector, a coating may be disposed to the outer surface of the conductor/collector to directly confine the light within the conductor, and/or to keep the maintain the optical quality of the outer surface to avoid absorption by native chromophores in the tissue at or near the outer surface of the collector because the evanescent wave present in a waveguide may still interact with the immediate environment. Such coating might be, for example, metallic coatings, such as, Gold, Silver, Rhodium, Platinum, Aluminum. A dielectric coating may also be used. Examples being; $SiO_2$, $Al_2O_3$ for protecting a metallic coating, or a layered dielectric stack coating to improve reflectivity, or a simple single layer coating to do likewise, such as quarter-wave thickness of $MgF_2$.

Alternately, the outer surface of the implantable light collector may be configured to utilize a pilot member for the introduction of the device into the tissue. This pilot member may be configured to be a cutting tool and/or dilator, from which the implantable light conductor may be removably coupled for implantation.

Implantation may be performed, by way of non-limiting example, using pre-operative and/or intra-operative imaging, such as radiography, fluoroscopy, ultrasound, magnetic resonance imaging (MRI), computed tomography (CT), optical imaging, microscopy, confocal microscopy, endoscopy, and optical coherence tomography (OCT).

Alternately, the pilot member may also form a base into which the implantable light collector is retained while implanted. As such, the pilot member may be a metal housing that circumscribes the outer surface of the implantable light collector and provides at least a nominally sheltered environment. In such cases replacement of the light collector may be made easier by leaving in place the retaining member (as the implanted pilot member may be known) and exchanging the light collector only. This may be done, for example, in cases where chronic implantation is problematic and the optical quality and/or efficiency of the light collector diminishes.

Alternately, the outer surface of the implantable collector may be made more bioinert by utilizing coatings of: Gold or Platinum, parylene-C, poly(ethylene glycol) (PEG), phosphoryl choline, Polyethylene oxide polymer, self-assembled monolayers (SAMs) of, for example, D-mannitol-terminated alkanethiols, as has been described elsewhere herein.

The collection element may be comprised of, by way of non-limiting example, an optical fiber or waveguide, a lightpipe, or plurality of such elements. For example, considering only scattering effects, a single 500 μm diameter optical fiber with an intrinsic numerical aperture (NA) of 0.5 that is located 300 μm below the skin surface may be able to capture at most about 2% of the light from a Ø1 mm beam of collimated light incident upon the skin surface. Thus, a 1 W source power may be required in order to capture 20 mW, and require a surface irradiance of 1.3 $W/mm^2$. This effect improves additively for each such fiber included in the system. For example, 4 such fibers may lower the surface incident optical power required by the same factor of 4 and still capture 20 mW. Of course, this does not increase the delivered brightness at the target, but may provide for more power to be delivered and distributed at the target, such as might be done in circumferential illumination. It should be known that it is a fundamental law of physics that brightness cannot be increased without adding energy to a system. Multiple fibers, such as those described, may be used to supply light to an applicator via multiple delivery segments, as are described elsewhere herein.

Larger numbers of light collecting elements, such as the optical fiber waveguides described in the embodiments above are also within the scope of the present invention.

Figure 38:
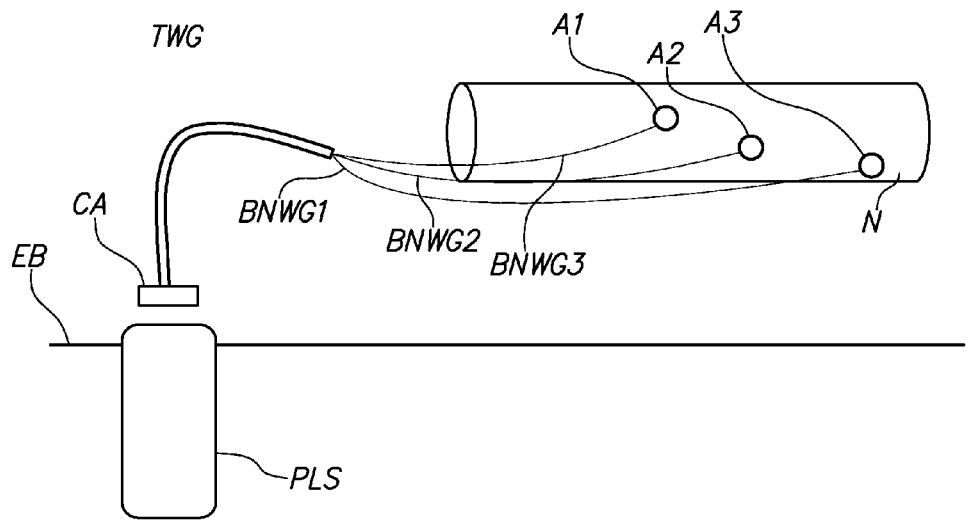

Similar to the embodiment of FIG. 38, an alternate embodiment is shown in FIG. 84. Light Rays LR from External Light Source ELS are shown in the illustrative exemplary embodiment to exit External Light Source ELS, encounter External Boundary EB (such as the skin's stratum corneum and/or epidermis and subsequently traverse the Dermal-Epidermal Junction DEJ) to reach the proximal surface of Implantable Light Collector PLS, where the proximal collection surface is divided into individual sections that each provide input for waveguides and/or delivery segments DSx that are operatively coupled to an Applicator A in order to illuminate target tissue N.

Figure 85:
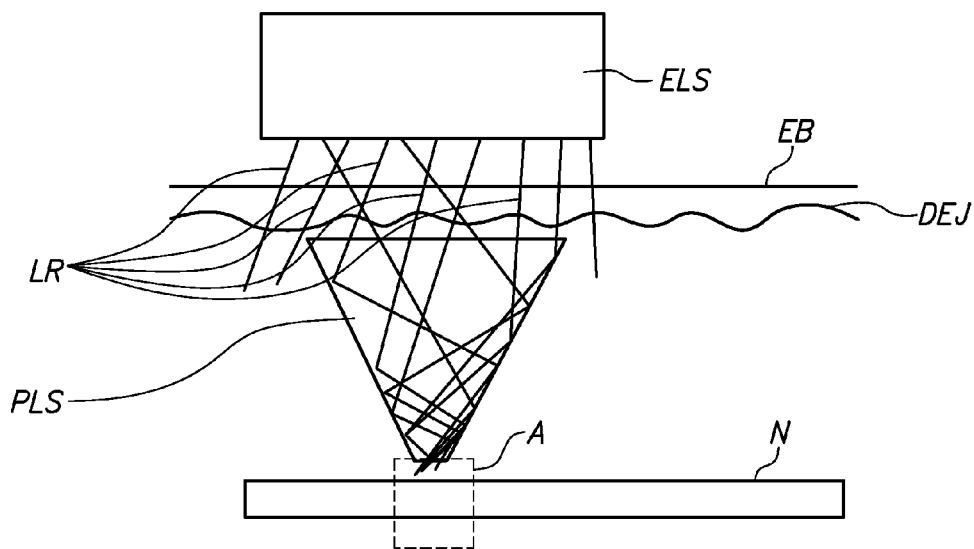

FIG. 85 illustrates an alternate embodiment similar to that of FIG. 84, where Implantable Light Collector PLS is not subdivided into separate sections, but instead supplies light to Applicator A via a single input channel. Delivery Segments DSx are not shown, but may be utilized in a further embodiment.

Surface cooling techniques and apparatus may be used in further embodiments of the present invention to mitigate the risk of collateral thermal damage that may be caused by optical absorption by the melanin located at the dermal-epidermal junction. Basic skin-cooling approaches have been described elsewhere. Such as, by way on non-limiting example, those described by U.S. Pat. Nos. 5,486,172; 5,595,568; and 5,814,040; which are incorporated herein in their entirety.

Figure 86:
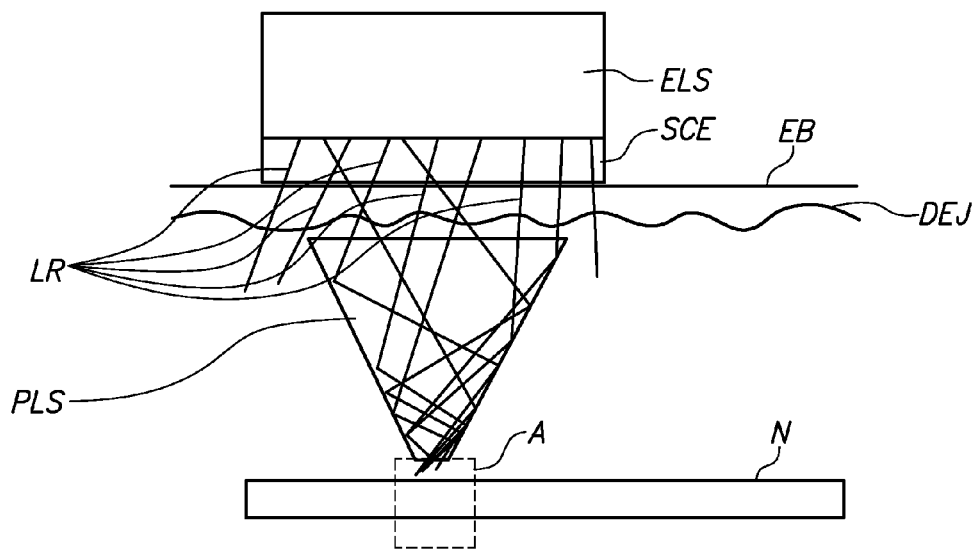

FIG. 86 illustrates an alternate embodiment of the present invention similar to that of FIG. 85, but with the addition of Skin Cooling Element SCE. Skin Cooling Element SCE is shown in direct contact with the skin surface, but need not be, as has been described in the aforementioned references immediately above. Similar to External Light Source ELS, Skin Cooling Element SCE may also be connected to a system controller and power supply. The user may program the parameters of Skin Cooling Element SCE to improve comfort and efficacy by adjusting the amount and/or temperature of the cooling, as well as its duration and timing relative to the illumination light from External Light Source ELS. External is understood to be equivalent to extracorporeal.

In an alternate embodiment, a tissue clearing agent, such as those described elsewhere herein, may be used to improve the transmission of light through tissue for collection by an implanted light collection device. The following tissue clearing agents may be used, by way of non-limiting examples; glycerol, polypropylene glycol-based polymers, polyethylene glycol-based polymers (such as PEG200 and PEG400), polydimethylsiloxane, 1,4-butanediol, 1,2-propanediol, certain radiopaque x-ray contrast media (such as Reno-DIP, Diatrizoate meglumine). For example, topical application of PEG-400 and Thiazone in a ratio of 9:1 for between 15-60 minutes may be used to decrease the scattering of human skin to improve the overall transmission of light via an implantable light collector.

Figure 32:
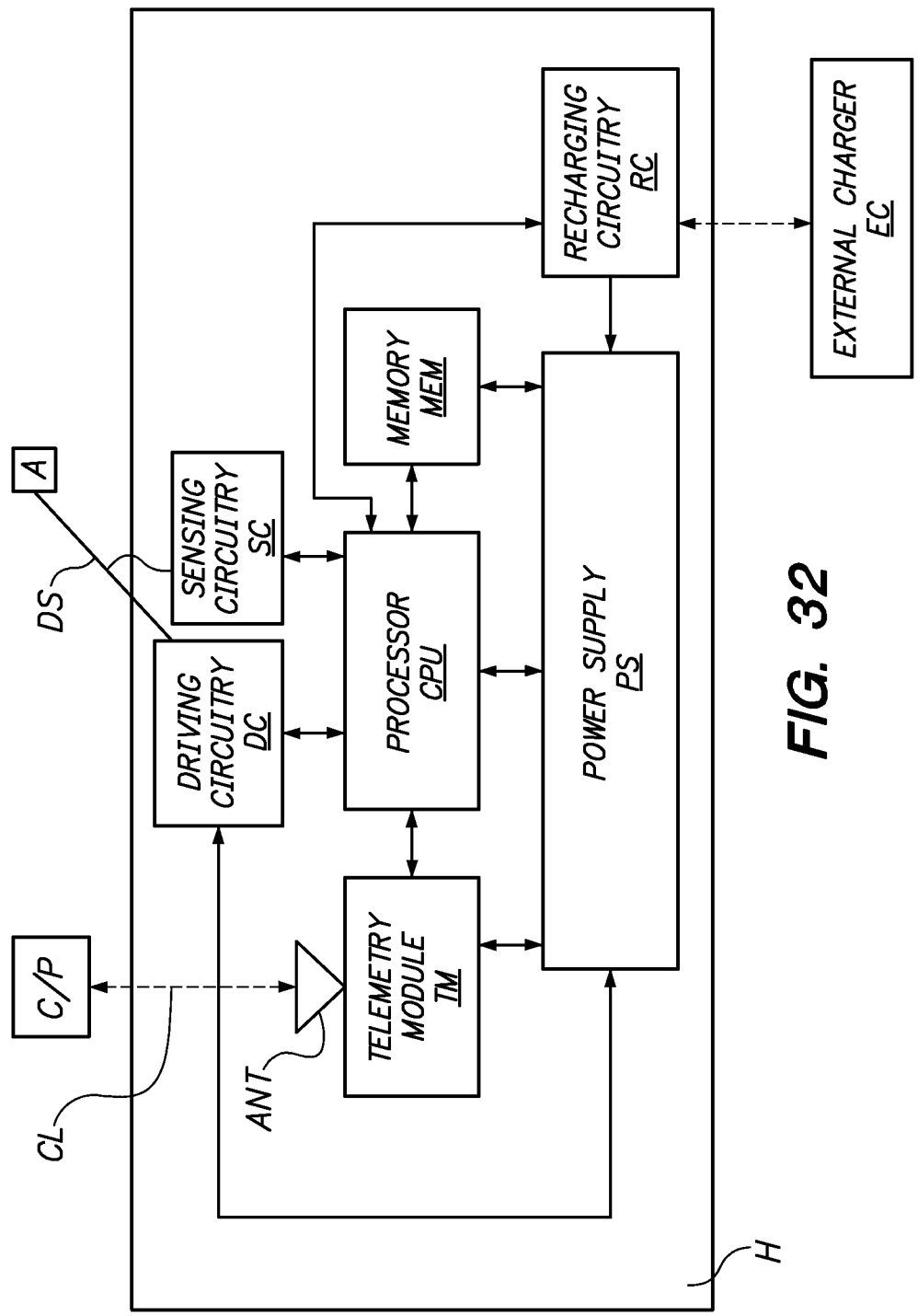

Referring to FIG. 32, a block diagram is depicted illustrating various components of an example implantable housing H. In this example, implantable stimulator includes processor CPU, memory MEM, power supply PS, telemetry module TM, antenna ANT, and the driving circuitry DC for an optical stimulation generator (which may or may not include a light source, as is described elsewhere herein). The Housing H is coupled to one Delivery Segments DSx, although it need not be. It may be a multi-channel device in the sense that it may be configured to include multiple optical paths (e.g., multiple light sources and/or optical waveguides or conduits) that may deliver different optical outputs, some of which may have different wavelengths. More or less delivery segments may be used in different implementations, such as, but not limited to, one, two, five or more optical fibers and associated light sources may be provided. The delivery segments may be detachable from the housing, or be fixed.

Memory (MEM) may store instructions for execution by Processor CPU, optical and/or sensor data processed by sensing circuitry SC, and obtained from sensors both within the housing, such as battery level, discharge rate, etc., and those deployed outside of the Housing (H), possibly in Applicator A, such as optical and temperature sensors, and/or other information regarding therapy for the patient. Processor (CPU) may control Driving Circuitry DC to deliver power to the light source (not shown) according to a selected one or more of a plurality of programs or program groups stored in Memory (MEM). The Light Source may be internal to the housing H, or remotely located in or near the applicator (A), as previously described. Memory (MEM) may include any electronic data storage media, such as random access memory (RAM), read-only memory (ROM), electronically-erasable programmable ROM (EEPROM), flash memory, etc. Memory (MEM) may store program instructions that, when executed by Processor (CPU), cause Processor (CPU) to perform various functions ascribed to Processor (CPU) and its subsystems, such as dictate pulsing parameters for the light source.

Electrical connections may be through Housing H via an Electrical Feedthrough EFT, such as, by way of non-limiting example, The SYGNUS® Implantable Contact System from Bal-SEAL.

In accordance with the techniques described in this disclosure, information stored in Memory (MEM) may include information regarding therapy that the patient had previously received. Storing such information may be useful for subsequent treatments such that, for example, a clinician may retrieve the stored information to determine the therapy applied to the patient during his/her last visit, in accordance with this disclosure. Processor CPU may include one or more microprocessors, digital signal processors (DSPs), application-specific integrated circuits (ASICs), field-programmable gate arrays (FPGAs), or other digital logic circuitry. Processor CPU controls operation of implantable stimulator, e.g., controls stimulation generator to deliver stimulation therapy according to a selected program or group of programs retrieved from memory (MEM). For example, processor (CPU) may control Driving Circuitry DC to deliver optical signals, e.g., as stimulation pulses, with intensities, wavelengths, pulse widths (if applicable), and rates specified by one or more stimulation programs. Processor (CPU) may also control Driving Circuitry (DC) to selectively deliver the stimulation via subsets of Delivery Segments (DSx), and with stimulation specified by one or more programs. Different delivery segments (DSx) may be directed to different target tissue sites, as was previously described.

Telemetry module (TM) may include, by way of non-limiting example, a radio frequency (RF) transceiver to permit bi-directional communication between implantable stimulator and each of a clinician programmer module and/or a patient programmer module (generically a clinician or patient programmer, or "C/P"). A more generic form is described above in reference to FIG. 3 as the input/output (I/O) aspect of a controller configuration (P/C). Telemetry module (TM) may include an Antenna (ANT), of any of a variety of forms. For example, Antenna (ANT) may be formed by a conductive coil or wire embedded in a housing associated with medical device. Alternatively, antenna (ANT) may be mounted on a circuit board carrying other components of implantable stimulator or take the form of a circuit trace on the circuit board. In this way, telemetry module (TM) may permit communication with a programmer (C/P). Given the energy demands and modest data-rate requirements, the Telemetry system may be configured to use inductive coupling to provide both telemetry communications and power for recharging, although a separate recharging circuit (RC) is shown in FIG. 32 for explanatory purposes. An alternate configuration is shown in FIG. 33.

Figure 33:
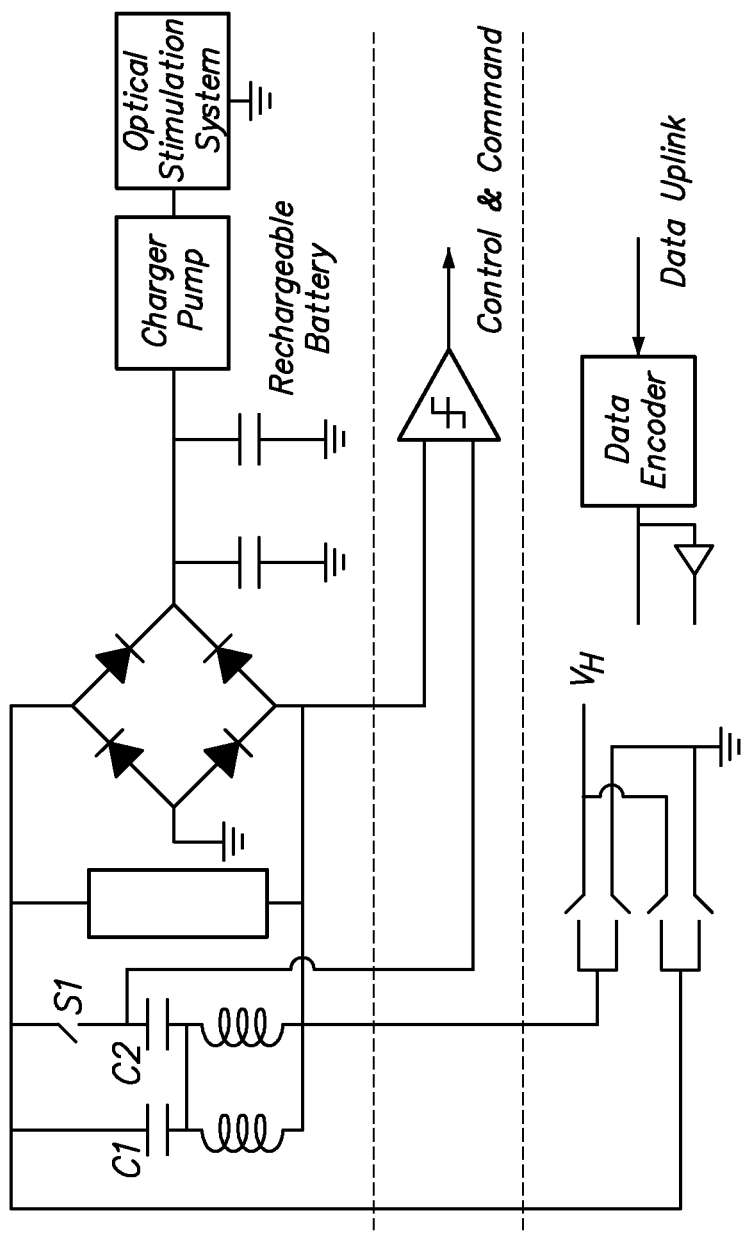

Referring to FIG. 33, a telemetry carrier frequency of 175 kHz aligns with a common ISM band and may use on-off keying at 4.4 kbps to stay well within regulatory limits. Alternate telemetry modalities are discussed elsewhere herein. The uplink may be an H-bridge driver across a resonant tuned coil. The telemetry capacitor, C1, may be placed in parallel with a larger recharge capacitor, C2, to provide a tuning range of 50-130 kHz for optimizing the RF-power recharge frequency. Due to the large dynamic range of the tank voltage, the implementation of the switch, S1, employs a nMOS and pMOS transistor connected in series to avoid any parasitic leakage. When the switch is OFF, the gate of pMOS transistor is connected to battery voltage, VBattery, and the gate of nMOS is at ground. When the switch is ON, the pMOS gate is at negative battery voltage, −VBattery, and the nMOS gate is controlled by charge pump output voltage. The ON resistance of the switch is designed to be less than 5Ω to maintain a proper tank quality factor. A voltage limiter, implemented with a large nMOS transistor, may be incorporated in the circuit to set the full wave rectifier output slightly higher than battery voltage. The output of the rectifier may then charge a rechargeable battery through a regulator.

Figure 34:
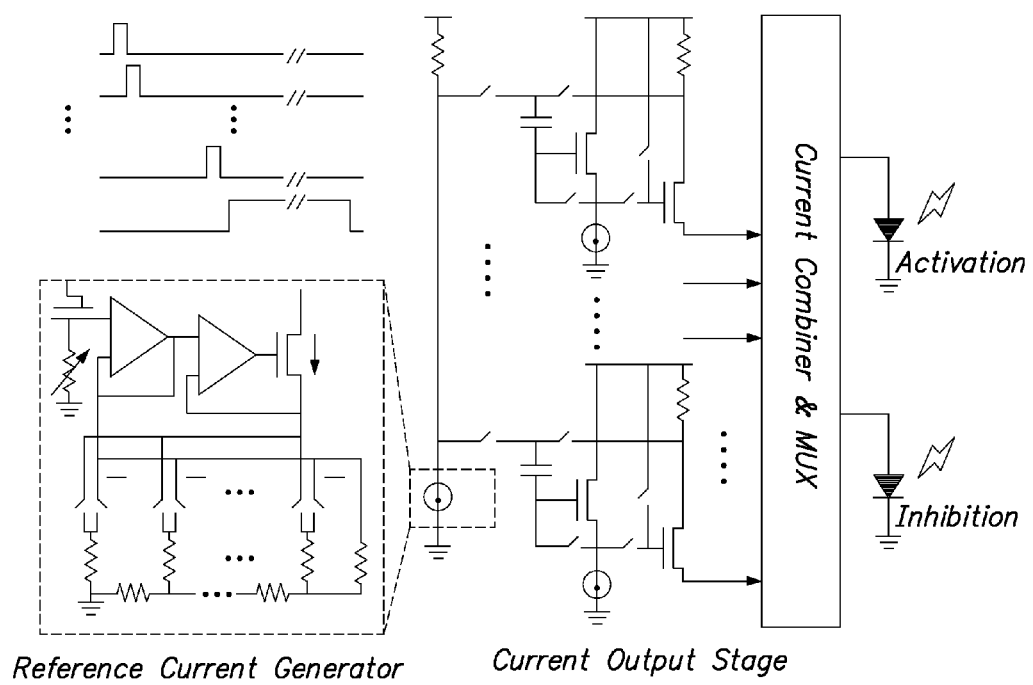

FIG. 34 relates to an embodiment of the Driving Circuitry DC, and may be made to a separate integrated circuit (or "IC"), or application specific integrated circuit (or "ASIC"), or a combination of them.

The control of the output pulse train, or burst, may be managed locally by a state-machine, as shown in this non-limiting example, with parameters passed from the microprocessor. Most of the design constraints are imposed by the output drive DAC. First, a stable current is required to reference for the system. A constant current of 100 nA, generated and trimmed on chip, is used to drive the reference current generator, which consists of an R-2Rbased DAC to generate an 8-bit reference current with a maximum value of 5 A. The reference current is then amplified in the current output stage with the ratio of $R_o$ and $R_{ref}$, designed as a maximum value of 40. An on-chip sense-resistor-based architecture was chosen for the current output stage to eliminate the need to keep output transistors in saturation, reducing voltage headroom requirements to improve power efficiency. The architecture uses thin-film resistors (TFRs) in the output driver mirroring to enhance matching. To achieve accurate mirroring, the nodes X and Y may be forced to be the same by the negative feedback of the amplifier, which results in the same voltage drop on $R_o$ and $R_{ref}$. Therefore, the ratio of output current, $I_o$, and the reference current, $I_{ref}$, equals to the ratio of and $R_{ref}$ and $R_o$.

The capacitor, C, retains the voltage acquired in the precharge phase. When the voltage at Node Y is exactly equal to the earlier voltage at Node X, the stored voltage on C biases the gate of P2 properly so that it balances $I_{bias}$. If, for example, the voltage across $R_o$ is lower than the original $R_{ref}$ voltage, the gate of P2 is pulled up, allowing $I_{bias}$ to pull down on the gate on P1, resulting in more current to $R_o$. In the design of this embodiment, charge injection is minimized by using a large holding capacitor of 10 pF. The performance may be eventually limited by resistor matching, leakage, and finite amplifier gain. With 512 current output stages, the optical stimulation IC may drive two outputs for activation and inhibition (as shown in FIG. 34) with separate sources, each delivering a maximum current of 51.2 mA.

Alternatively, if the maximum back-bias on the optical element can withstand the drop of the other element, then the devices can be driven in opposite phases (one as sinks, one as sources) and the maximum current exceeds 100 mA. The stimulation rate can be tuned from 0.153 Hz to 1 kHz and the pulse or burst duration(s) can be tuned from 100 s to 12 ms. However, the actual limitation in the stimulation output pulse-train characteristic is ultimately set by the energy transfer of the charge pump, and this generally should be considered when configuring the therapeutic protocol.

The Housing H (or applicator, or the system via remote placement) may further contain an accelerometer to provide sensor input to the controller resident in the housing. This may be useful for modulation and fine control of a hypertension device, for example, or for regulation of a pacemaker. Remote placement of an accelerometer may be made at or near the anatomical element under optogenetic control, and may reside within the applicator, or nearby it. In times of notable detected motion, the system may alter it programming to accommodate the patient's intentions and provide more or less stimulation and/or inhibition, as is required for the specific case at hand.

The Housing H may still further contain a fluidic pump (not shown) for use with the applicator, as was previously described herein.

External programming devices for patient and/or physician can be used to alter the settings and performance of the implanted housing. Similarly, the implanted apparatus may communicate with the external device to transfer information regarding system status and feedback information. This may be configured to be a PC-based system, or a stand-alone system. In either case, the system generally should communicate with the housing via the telemetry circuits of Telemetry Module (TM) and Antenna (ANT). Both patient and physician may utilize controller/programmers (C/P) to tailor stimulation parameters such as duration of treatment, optical intensity or amplitude, pulse width, pulse frequency, burst length, and burst rate, as is appropriate.

Once the communications link (CL) is established, data transfer between the MMN programmer/controller and the housing may begin. Examples of such data are:
1. From housing to controller/programmer:
    a. Patient usage
    b. Battery lifetime
    c. Feedback data
        i. Device diagnostics (such as direct optical transmission measurements by an emitter-opposing photosensor)
2. From controller/programmer to housing:
    a. Updated illumination level settings based upon device diagnostics
    b. Alterations to pulsing scheme
    c. Reconfiguration of embedded circuitry
        i. such as field programmable gate array (FPGA), application specific integrated circuit (ASIC), or other integrated or embedded circuitry By way of non-limiting examples, near field communications, either low power and/or low frequency; such as ZigBee, may be employed for telemetry. The tissue(s) of the body have a well-defined electromagnetic response(s). For example, the relative permittivity of muscle demonstrates a monotonic log-log frequency response, or dispersion. Therefore, it is advantageous to operate an embedded telemetry device in the frequency range of ≤1 GHz. In 2009 (and then updated in 2011), the US FCC dedicated a portion of the EM Frequency spectrum for the wireless biotelemetry in implantable systems, known as The Medical Device Radiocommunications Service (known as "MedRadio"). Devices employing such telemetry may be known as "medical micropower networks" or "MMN" services. The currently reserved spectra are in the 401-406, 413-419, 426-432, 438-444, and 451-457 MHz ranges, and provide for these authorized bandwidths:
    401-401.85 MHz: 100 kHz
    401.85-402 MHz: 150 kHz
    402-405 MHz: 300 kHz
    405-406 MHz: 100 kHz
    413-419 MHz: 6 MHz
    426-432 MHz: 6 MHz
    438-444 MHz: 6 MHz
    451-457 MHz: 6 MHz The rules do not specify a channeling scheme for MedRadio devices. However, it should be understood that the FCC stipulates that:

MMNs should not cause harmful interference to other authorized stations operating in the 413-419 MHz, 426-432 MHz, 438-444 MHz, and 451-457 MHz bands.

MMNs must accept interference from other authorized stations operating in the 413-419 MHz, 426-432 MHz, 438-444 MHz, and 451-457 MHz bands.

MMN devices may not be used to relay information to other devices that are not part of the MMN using the 413-419 MHz, 426-432 MHz, 438-444 MHz, and 451-457 MHz frequency bands.

An MMN programmer/controller may communicate with a programmer/controller of another MMN to coordinate sharing of the wireless link.

Implanted MMN devices may only communicate with the programmer/controller for their MMN.

An MMN implanted device may not communicate directly with another MMN implanted device.

An MMN programmer/controller can only control implanted devices within one patient.

Interestingly, these frequency bands are used for other purposes on a primary basis such as Federal government and private land mobile radios, Federal government radars, and remote broadcast of radio stations. It has recently been shown that higher frequency ranges are also applicable and efficient for telemetry and wireless power transfer in implantable medical devices.

An MMN may be made not to interfere or be interfered with by external fields by means of a magnetic switch in the implant itself. Such a switch may be only activated when the MMN programmer/controller is in close proximity to the implant. This also provides for improved electrical efficiency due to the restriction of emission only when triggered by the magnetic switch. Giant Magnetorestrictive (GMR) devices are available with activation field strengths of between 5 and 150 Gauss. This is typically referred to as the magnetic operate point. There is intrinsic hysteresis in GMR devices, and they also exhibit a magnetic release point range that is typically about one-half of the operate point field strength. Thus, a design utilizing a magnetic field that is close to the operate point will suffer from sensitivities to the distance between the housing and the MMN programmer/controller, unless the field is shaped to accommodate this. Alternately, one may increase the field strength of the MMN programmer/controller to provide for reduced sensitivity to position/distance between it and the implant. In a further embodiment, the MMN may be made to require a frequency of the magnetic field to improve the safety profile and electrical efficiency of the device, making it less susceptible to errant magnetic exposure. This can be accomplished by providing a tuned electrical circuit (such as an L-C or R-C circuit) at the output of the switch.

Alternately, another type of magnetic device may be employed as a switch. By way of non-limiting example, a MEMS device may be used. A cantilevered MEMS switch may be constructed such that one member of the MEMS may be made to physically contact another aspect of the MEMS by virtue of its magnetic susceptibility, similar to a miniaturized magnetic reed switch. The suspended cantilever may be made to be magnetically susceptible by depositing a ferromagnetic material (such as, but not limited to Ni, Fe, Co, NiFe, and NdFeB) atop the end of the supported cantilever member. Such a device may also be tuned by virtue of the cantilever length such that it only makes contact when the oscillations of the cantilever are driven by an oscillating magnetic field at frequencies beyond the natural resonance of the cantilever.

Figure 35:
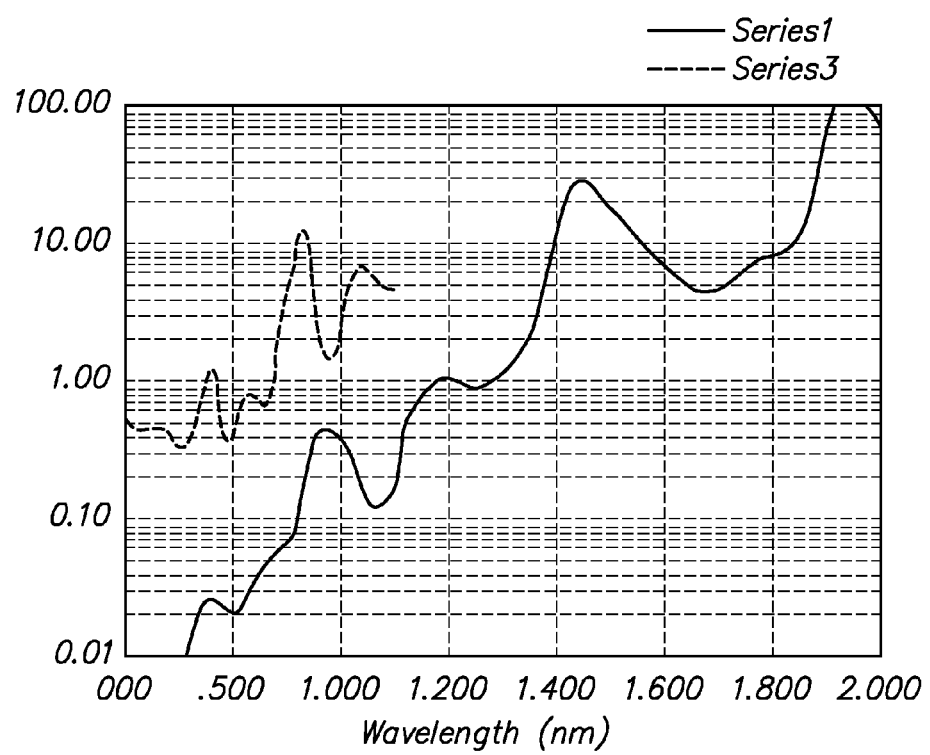

Alternately, an infrared-sensitive switch might be used. In this embodiment of this aspect of the present invention, a photodiode or photoconductor may be exposed to the outer surface of the housing and an infrared light source used to initiate the communications link for the MMN. Infrared light penetrates body tissues more readily than visible light due to its reduced scattering. However, water and other intrinsic chromophores have avid absorption, with peaks at 960, 1180, 1440, and 1950 nm, as are shown in the spectra of FIG. 35 (1018), where the water spectrum runs form 700-2000 nm and that of adipose tissue runs from 600-1100 nm.

Figure 36:
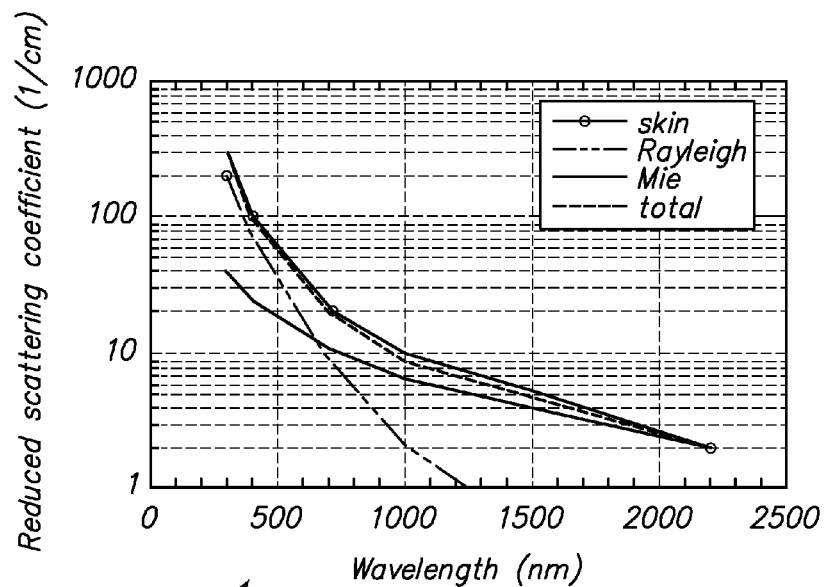

However, the penetration depth in tissue is more influenced by its scattering properties, as shown in the spectrum of FIG. 36 (1020), which displays the optical scattering spectrum for human skin, including the individual components from both Mie (elements of similar size to the wavelength of light) and Rayleigh (elements of smaller size than the wavelength of light) scattering effects.

This relatively monotonic reduction in optical scattering far outweighs absorption, when the abovementioned peaks are avoided. Thus, an infrared (or near-infrared) transmitter operating within the range of 800-1300 nm may be preferred. This spectral range is known as the skin's "optical window."

Figure 37:
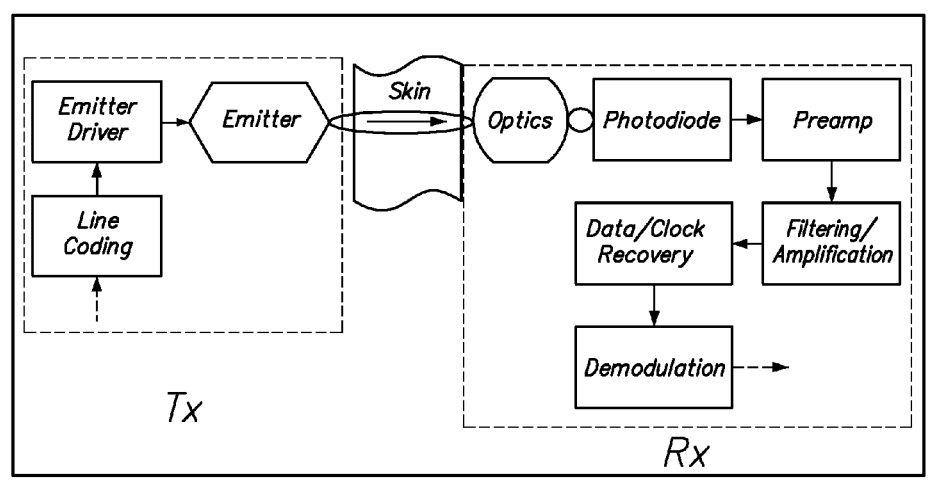

Such a system may further utilize an electronic circuit, such as that shown in FIG. 37 (1022), for telemetry, and not just a sensing switch. Based upon optical signaling, such a system may perform at high data throughput rates.

Generically, the signal-to-noise ratio (SNR) of a link is defined as, $$SNR_i = \frac{I_s}{I_N} = \frac{P_s R}{I_{N_{elec}} + P_{N_{amb}} R}$$

where $I_s$ and $I_N$ are the photocurrents resulting from incident signal optical power and photodiode noise current respectively, $P_s$ is the received signal optical power, R is the photodiode responsivity (A/W), $I_{Nelec}$ is the input referred noise for the receiver and $P_{Namb}$ is the incident optical power due to interfering light sources (such as ambient light). $P_s$ can be further defined as $$P_s = \int_{A_T} P_{Tx} J_{Rx\lambda} \eta_\lambda dA$$

where $P_{Tx}$ (W) is the optical power of the transmitted pulse, $J_{Rx\lambda}$ (cm$^{-2}$) is the tissue's optical spatial impulse response flux at wavelength $\lambda$, $\eta_\lambda$ is an efficiency factor ($\eta_\lambda \leq 1$) accounting for any inefficiencies in optics/optical filters at $\lambda$ and $A_T$ represents the tissue area over which the receiver optics integrate the signal.

The abovementioned factors that affect the total signal photocurrent and their relationship to system level design parameters include emitter wavelength, emitter optical power, tissue effects, lens size, transmitter-receiver misalignment, receiver noise, ambient light sources, photodiode responsivity, optical domain filtering, receiver signal domain filtering, line coding and photodiode and emitter selection. Each of these parameters can be independently manipulated to ensure that the proper signal strength for a given design will be achieved.

Most potentially-interfering light sources have signal power that consists of relatively low frequencies (e.g. Daylight: DC; Fluorescent lights: frequencies up to tens or hundreds of kilohertz), and can therefore be rejected by using a high-pass filter in the signal domain and using higher frequencies for data transmission.

The emitter may be chosen from the group consisting of, by way of non-limiting example, a VCSEL, an LED, a HCSEL. VCSELs are generally both higher brightness and more energy efficient than the other sources and they are capable of high-frequency modulation. An example of such a light source is the device sold under the model identifier "HFE 4093-342" from Finisar, Inc., which operates at 860 nm and provides ≤5 mW of average power. Other sources are also useful, as are a variety of receivers (detectors). Some non-limiting examples are listed in the following table.

| 820-850 nm | Agilent HFBR-1412 | Agilent HFBR-2412 |
| --- | --- | --- |
| | Agilent HFBR-1416 | Agilent HFBR-2416 |
| | Hamamatsu L1915 | Hamamatsu GT4176 |
| | Hamamatsu L5128 | |
| | Hamamatsu L5871 | |
| | Hamamatsu L6486 | |
| 950 nm | Infineon SFH 4203 | Infineon SFH 203 |
| | Infineon SFH 4301 | Infineon SFH 5400 |
| | Infineon SFH 4502 | Infineon SFH 5440 |
| | Infineon SFH 4503 | Infineon SFH5441 |
| 1300 nm | Agilent HFBR-1312 | Agilent HFBR-2316 |
| | Hamamatsu L7866 | |
| | Hamamatsu L7850 | |

Alignment of the telemetry emitter to receiver may be improved by using a non-contact registration system, such as an array of coordinated magnets with the housing that interact with sensors in the controller/programmer to provide positional information to the user that the units are aligned. In this way, the overall energy consumption of the entire system may be reduced.

Although glycerol and polyethylene glycol (PEG) reduce optical scattering in human skin, their clinical utility has been very limited. Penetration of glycerol and PEG through intact skin is very minimal and extremely slow, because these agents are hydrophilic and penetrate the lipophilic stratum corneum poorly. In order to enhance skin penetration, these agents need to be either injected into the dermis or the stratum corneum has to be removed, mechanically (e.g., tape stripping, light abrasion) or thermally (e.g., erbium: yttrium-aluminum-garnet (YAG) laser ablation), etc. Such methods include tape stripping, ultrasound, iontophoresis, electroporation, microdermabrasion, laser ablation, needle-free injection guns, and photomechanically driven chemical waves (such as the process known as "optoporation"). Alternately, microneedles contained in an array or on a roller (such as the Dermaroller® microneedling device) may be used to decrease the penetration barrier. The Dermaroller® micro-needling device is configured such that each of its 192 needles has a 70 μm diameter and 500 μm height. These microneedles are distributed uniformly atop a 2 cm wide by 2 cm diameter cylindrical roller. Standard use of the microneedle roller typically results in a perforation density of 240 perforations/cm$^2$ after 10 to 15 applications over the same skin area. While such microneedle approaches are certainly functional and worthwhile, clinical utility would be improved if the clearing agent could simply be applied topically onto intact skin and thereafter migrate across the stratum corneum and epidermis into the dermis. Food and Drug Administration (FDA) approved lipophilic polypropylene glycol-based polymers (PPG) and hydrophilic PEG-based polymers, both with indices of refraction that closely match that of dermal collagen (n=1.47) are available alone and in a combined pre-polymer mixture, such as polydimethylsiloxane (PDMS). PDMS is optically clear, and, in general, is considered to be inert, non-toxic and non-flammable. It is occasionally called dimethicone and is one of several types of silicone oil (polymerized siloxane), as was described in detail in an earlier section. The chemical formula for PDMS is $CH_3[Si(CH_3)_2O]_nSi(CH_3)_3$, where n is the number of repeating monomer $[SiO(CH_3)_2]$ units. The penetration of these optical clearing agents into appropriately treated skin takes about 60 minutes to achieve a high degree of scattering reduction and commensurate optical transport efficiency. With that in mind, a system utilizing this approach may be configured to activate its illumination after a time sufficient to establish optical clearing, and in sufficient volume to maintain it nominally throughout or during the treatment exposure. Alternately, the patient/user may be instructed to treat their skin a sufficient time prior to system usage.

Alternately, the microneedle roller may be configured with the addition of central fluid chamber that may contain the tissue clearing agent, which is in communication with the needles. This configuration may provide for enhanced tissue clearing by allowing the tissue clearing agent to be injected directly via the microneedles.

A compression bandage-like system could push exposed emitters and/or applicators into the tissue containing a subsurface optogenetic target to provide enhanced optical penetration via pressure-induced tissue clearing in cases where the applicator is worn on the outside of the body; as might be the case with a few of the clinical indications described herein, like micromastia, erectile dysfunction, and neuropathic pain. This configuration may also be combined with tissue clearing agents for increased effect. The degree of pressure tolerable is certainly a function of the clinical application and the site of its disposition. Alternately, the combination of light source compression into the target area may also be combined with an implanted delivery segment, or delivery segments, that would also serve to collect the light from the external source for delivery to the applicator(s). Such an example is shown in FIG. 38, where External Light Source PLS (which may the distal end of a delivery segment, or the light source itself) is placed into contact with the External Boundary EB of the patient. The PLS emits light into the body, which it may be collected by Collection Apparatus CA, which may be a lens, a concentrator, or any other means of collecting light, for propagation along Trunk Waveguide TWG, which may a bundle of fibers, or other such configuration, which then bifurcates into separate interim delivery segments BNWGx, that in turn deliver the light to Applicators Ax that are in proximity to Target N.

Figure 87:
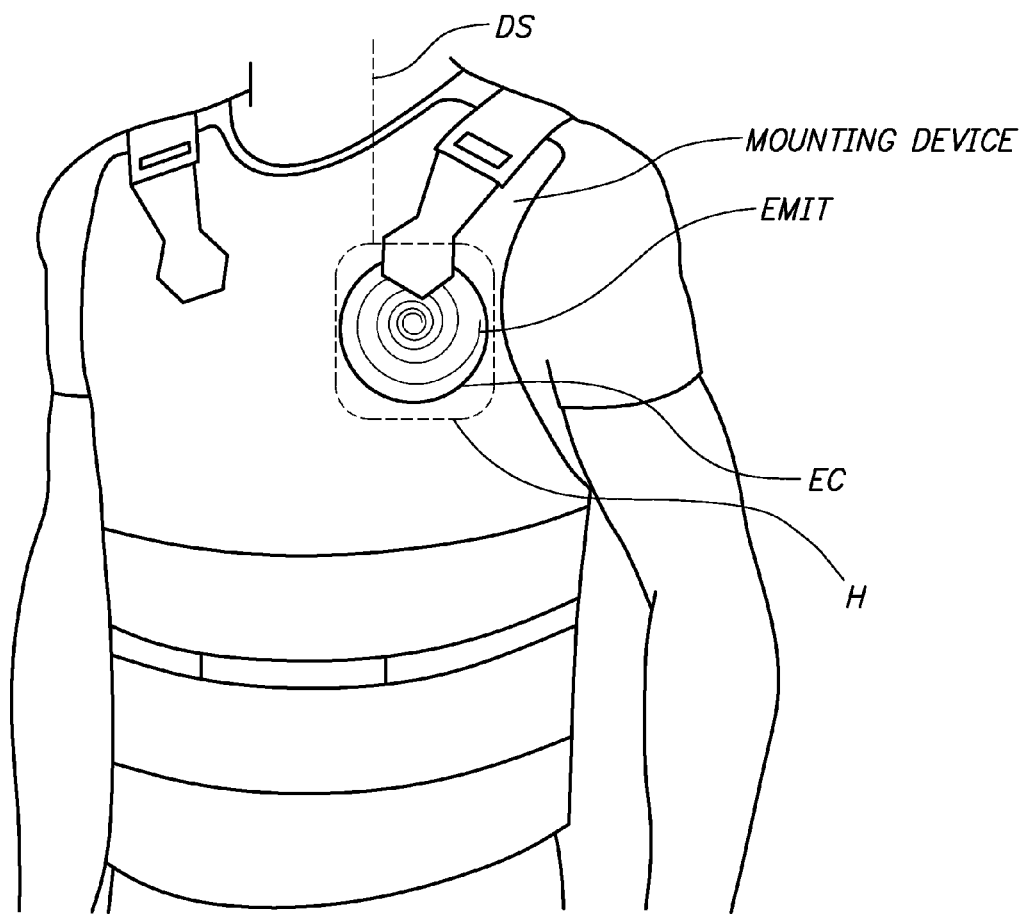
FIG. 87 depicts an embodiment for mounting an external charging device of a percutaneous feedthrough in accordance with the present invention.

FIG. 87 illustrates an embodiment, where an external charging device is mounted onto clothing for simplified use by a patient, comprising a Mounting Device MOUNTING DEVICE, which may be selected from the group consisting of, but not limited to: a vest, a sling, a strap, a shirt, and a pant. Mounting Device MOUNTING DEVICE further comprising a Wireless Power Transmission Emission Element EMIT, such as, but not limited to, a magnetic coil, or electrical current carrying plate, that is located substantially nearby an implanted power receiving module, such as is represented by the illustrative example of Housing H, which is configured to be operatively coupled to Delivery Segment(s) DS. Within Housing H, may be a power supply, light source, and controller, such that the controller activates the light source by controlling current thereto. Alternately, the power receiving module may be located at the applicator (not shown), especially when the Applicator is configured to contain a Light Source.

An electrical synapse is a mechanical and electrically conductive link between two abutting neurons that is formed at a narrow gap between the pre- and postsynaptic neurons known as a gap junction. At gap junctions, such cells approach within about 3.5 nm of each other, a much shorter distance than the 20 to 40 nm distance that separates cells at a chemical synapse. In many systems, electrical synapse systems co-exist with chemical synapses.

Compared to chemical synapses, electrical synapses conduct nerve impulses faster, but unlike chemical synapses they do not have gain (the signal in the postsynaptic neuron is the same or smaller than that of the originating neuron). Electrical synapses are often found in neural systems that require the fastest possible response, such as defensive reflexes and in cases where a concerted behavior of a subpopulation of cells is required (such as in propagation of calcium waves in astrocytes, etc.). An important characteristic of electrical synapses is that most of the time, they are bidirectional, i.e. they allow impulse transmission in either direction. However, some gap junctions do allow for communication in only one direction.

Normally, current carried by ions could travel in either direction through this type of synapse. However, sometimes the junctions are rectifying synapses, containing voltage-dependent gates that open in response to a depolarization and prevent current from traveling in one of the two directions. Some channels may also close in response to increased calcium ($Ca^{2+}$) or hydrogen (H+) ion concentration so as not to spread damage from one cell to another.

Certain embodiments of the present invention relate to systems, methods and apparatuses that provide for optogenetic control of synaptic rectification in order to offer improved control for both optogenetic and electrical nerve stimulation.

Nerve stimulation, such as electrical stimulation ("e-stim"), may cause bidirectional impulses in a neuron, which may be characterized as antidromic and/or orthodromic stimulation. That is, an action potential may trigger pulses that propagate in both directions along a neuron. However, the coordinated use of optogenetic inhibition in combination with stimulation may allow only the intended signal to propagate beyond the target location by suppression or cancellation of the errant signal using optogenetic inhibition. This may be achieved in multiple ways using what we will term "multi-applicator devices" or "multi-zone devices". The function and characteristics of the individual elements utilized in such devices were defined earlier.

Figure 39A:
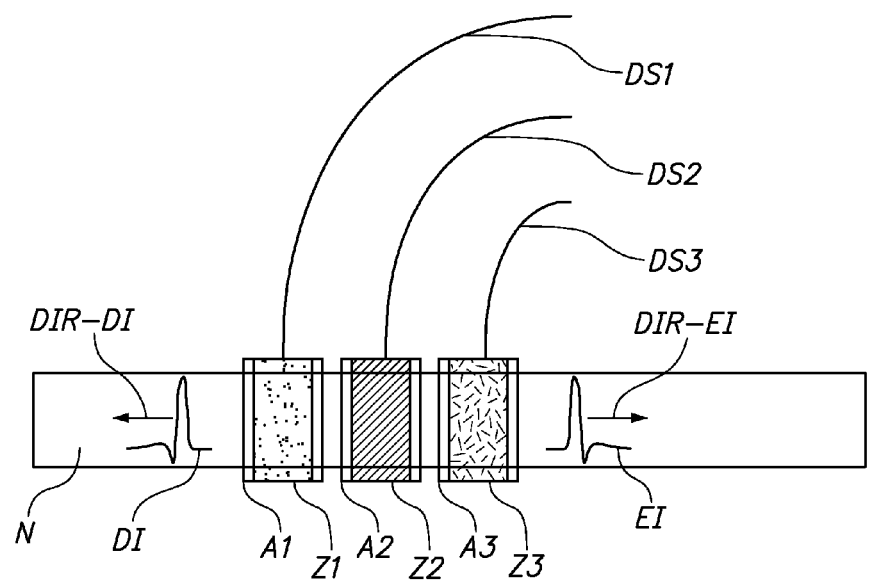

In a first embodiment, a multi-applicator device is configured to utilize separate applicators Ax for each interaction zone Zx along the target nerve N, as is shown in FIG. 39A. One example is the use optogenetic applicators on both ends (A1, A3) and an electrical stimulation device (A2) in the middle. This example was chosen to represent a generic situation wherein the desired signal direction may be on either side of the excitatory electrode. The allowed signal direction may be chosen by the selective application of optogenetic inhibition from the applicator on the opposite side of the central Applicator A2. In this non-limiting example, the Errant Impulse EI is on the RHS of the stimulation cuff A2, traveling to the right, as indicated by arrow DIR-EI, and passing through the portion f the target covered by A3 and the Desired Impulse DI is on the LHS of A2, travelling to the left, as indicated by arrow DIR-DI, and, passing through the portion f the target covered by A1.

Activation of A3 may serve to disallow transmission of EI via optogenetic inhibition of the signal, suppressing it. Similarly, activation of A1 instead of A3 would serve to suppress the transmission of the Desired Impulse DI and allow the Errant Impulse EI to propagate. Therefore, bi-directionality is maintained in this triple applicator configuration, making it a flexible configuration for Impulse direction control. Such flexibility may not always be clinically required, and simpler designs may be used, as is explained in subsequent paragraphs. This inhibition/suppression signal may accompany or precede the electrical stimulation, as dictated by the specific kinetics of the therapeutic target. Each optical applicator may also be made such that it is capable of providing both optogenetic excitation and inhibition by utilizing two spectrally distinct light sources to activate their respective opsins in the target. In this embodiment, each applicator, Ax, is served by its own Delivery Segment, DSx. These Delivery Segments, DS1, DS2, and DS3 serve as conduits for light and/or electricity, as dictated by the type of applicator present. As previously described, the Delivery Segment(s) connect(s) to a Housing containing the electrical and/or electro-optical components required to provide for power supply, processing, feedback, telemetry, etc. Alternately, Applicator A2 may be an optogenetic applicator and either Applicators A1 or A3 may be used to suppress the errant signal direction.

Alternately, as mentioned above, only a pair of applicators may be required when the therapy dictates that only a single direction is required. Referring to the embodiment of FIG. 39B, the directionality of the Desired Impulse DI and Errant Impulse EI described above is maintained. However, Applicator A3 is absent because the directionality of the Desired Impulse DI is considered to be fixed as leftward, and Applicator A2 is used for optogenetic suppression of the Errant Impulse EI, as previously described.

Figure 39B:
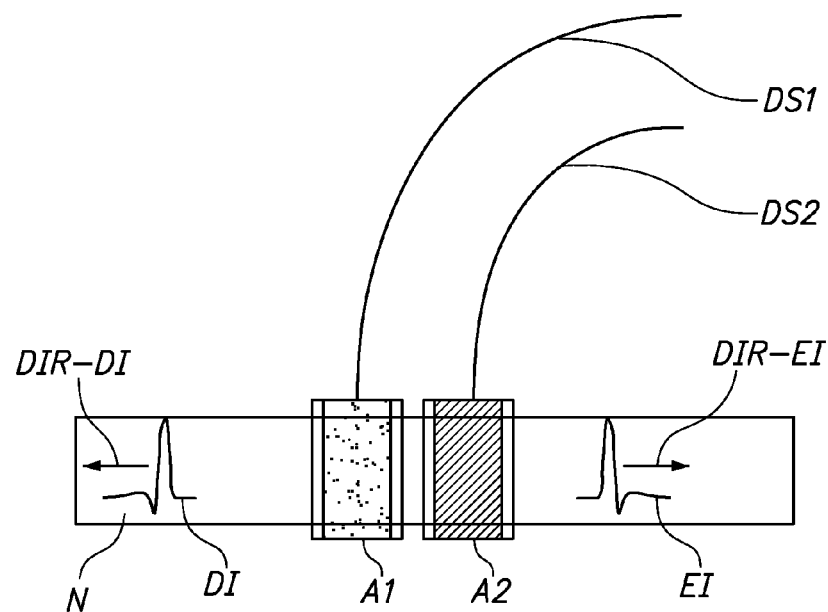
Figure 39C:
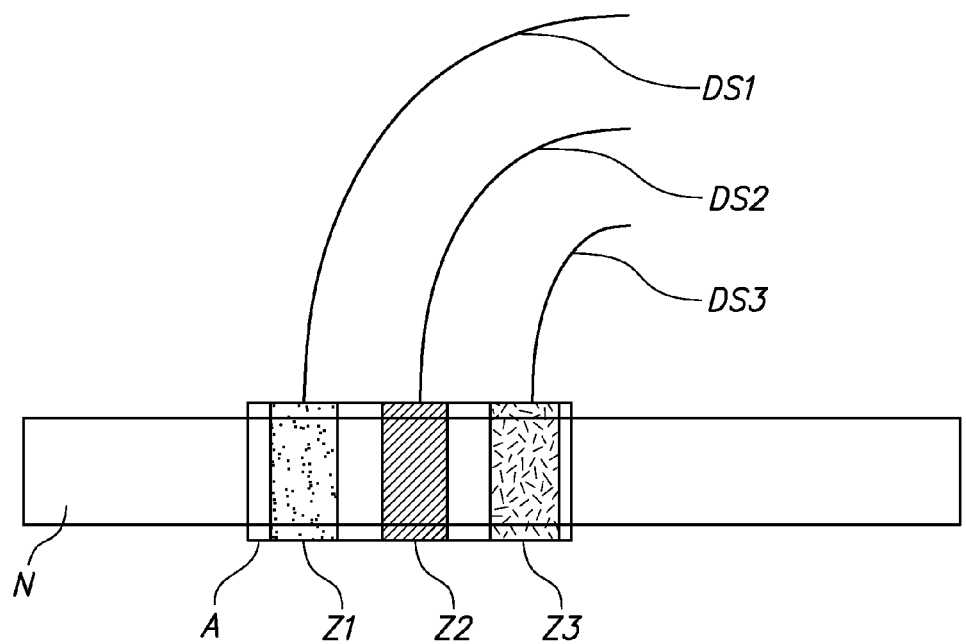

Alternately, referring to the embodiment of FIG. 39C, a single applicator may be used, wherein the electrical and optical activation zones Z1, Z2, and Z3 are spatially separated, but still contained within a single applicator A.

Furthermore, the combined electrical stimulation and optical stimulation described herein may also be used for intraoperative tests of inhibition in which an electrical stimulation is delivered and inhibited by the application of light to confirm proper functioning of the implant and optogenetic inhibition. This may be performed using the applicators and system previously described for testing during the surgical procedure, or afterwards, depending upon medical constraints and/or idiosyncrasies of the patient and/or condition under treatment. The combination of a multiple-applicator, or multiple-zone applicator, or multiple applicators, may also define which individual optical source elements within said applicator or applicators may be the most efficacious and/or efficient means by which to inhibit nerve function. That is, an e-stim device may be used as a system diagnostic tool to test the effects of different emitters and/or applicators within a multiple emitter, or distributed emitter, system by suppressing, or attempting to suppress, the induced stimulation via optogenetic inhibition using an emitter, or a set of emitters and ascertaining, or measuring, the patient, or target, response(s) to see the optimal combination for use. That optimal combination may then be used as input to configure the system via the telemetric link to the housing via the external controller/programmer. Alternately, the optimal pulsing characteristics of a single emitter, or set of emitters, may be likewise ascertained and deployed to the implanted system.

In one embodiment, a system may be configured such that both the inhibitory and excitatory probes and/or applicators are both optical probes used to illuminate cells containing light-activatable ion channels that reside within a target tissue. In this configuration, the cells may be modified using optogenetic techniques, such as has been described elsewhere herein, especially with regard to therapy for cardiac hypertension.

One further embodiment of such a system may be to attach an optical applicator, or applicators, on the Vagus nerve to send ascending stimulatory signals to the brain, while suppressing the descending signals by placing the excitatory applicator proximal to the CNS and the inhibitory applicator distal to the excitatory applicator. The excitatory applicator may, for example, supply illumination in the range of 10-100 mW/mm$^2$ of nominally 450±50 nm light to the surface of the nerve bundle to activate cation channels in the cell membrane of the target cells within the Vagus nerve while the inhibitory applicator supplies illumination in the range of 10-100 mW/mm$^2$ of nominally 590±50 nm light to activate Cl$^-$ ion pumps in the cell membrane of the target cells to suppress errant descending signals from reaching the PNS.

In an alternate embodiment, the inhibitory probe may be activated prior to the excitatory probe to bias the nerve to suppress errant signals. For example, activating the inhibitory probe at least 5 ms prior to the excitatory probe allows time for the Cl— pumps to have cycled at least once for an opsin such as eNpHR3.0, thus potentially allowing for a more robust errant signal inhibition. Other opsins have different time constants, as described elsewhere herein, and subsequently different pre-excitation activation times.

Alternately, a system may be configured such that only either the inhibitory or excitatory probes and/or applicators are optical probes used to illuminate cells containing light-activatable ion channels that reside within a target tissue while other probe is an electrical probe. In the case of the stimulation applicator being an electrical probe, typical neurostimulation parameters, such as those described in U.S. patent application Ser. Nos. 13/707,376 and 13/114,686, which are expressly incorporated herein by reference, may be used. The operation of a stimulation probe, including alternative embodiments of suitable output circuitry for performing the same function of generating stimulation pulses of a prescribed amplitude and width, is described in U.S. Pat. Nos. 6,516,227 and 6,993,384, which are expressly incorporated herein by reference. By way of non-limiting example, parameters for driving an electrical neuroinhibition probe, such as those described in U.S. patent application Ser. No. 12/360,680, which is expressly incorporated herein by reference, may be used. When the neuroinhibition is accomplished using an electrical probe, the device may be operated in a mode that is called a "high frequency depolarization block". By way of non-limiting example, for details regarding the parameters for driving a high frequency depolarization block electrical probe reference can be made to Kilgore K L and Bhadra N, *High Frequency Mammalian Nerve Conduction Block: Simulations and Experiments*, Engineering in Medicine and Biology Society, 2006. EMBS '06. 28th Annual International Conference of the IEEE, pp. 4971-4974, which is expressly incorporated herein by reference.

In further embodiments, sensors may be used to ascertain the amount of errant signal suppression in a closed-loop manner to adjust the inhibitory system parameters. An example of such a system is shown in FIG. 39B or 39C, where a sensor SEN is located passed the inhibition probe ascertain the degree of errant nerve signal suppression. Sensor SEN may be configured to measure the nerve signal by using an ENG probe, for example. It alternately be a therapeutic sensor configured to monitor a physical therapeutic outcome directly, or indirectly. Such a therapeutic sensor may be, by way of non-limiting example, an ENG probe, an EMG probe, a pressure transducer, a chemical sensor, an EKG sensor, or a motion sensor. A direct sensor is considered to be one that monitors a therapeutic outcome directly, such as the aforementioned examples of chemical and pressure sensors. An indirect sensor is one that monitors an effect of the treatment, but not the ultimate result. Such sensors are the aforementioned examples of ENG, EKG, and EMG probes, as has been described elsewhere herein with respect to therapy for cardiac hypertension.

Alternately, the therapeutic sensor may be a patient input device that allows the patient to at least somewhat dictate the optical dosage and/or timing. Such a configuration may be utilized, by way of non-limiting example, in cases such as muscle spasticity, where the patient may control the optical dosage and/or timing to provide what they deem to be the requisite level of control for a given situation.

As described herein with regard to probe and/or applicator placement, distal refers to more peripheral placement, and proximal refers to more central placement along a nerve. As such, an inhibition probe that is located distally to an excitation probe may be used to provide ascending nerve signals while suppressing descending nerve signals. Equivalently, this configuration may be described as an excitation probe that is located proximally to an inhibition probe. Similarly, an excitation probe that is located distally to an inhibition probe may be used to provide descending nerve signals while suppress ascending nerve signals. Equivalently, this configuration may be described as an inhibition probe that is located proximally to an excitation probe. Descending signals travel in the efferent direction away from the CNS towards the PNS, and vice versa ascending signals travel in the afferent direction.

Excitatory opsins useful in the invention may include red-shifted depolarizing opsins including, by way of non-limiting examples, C1V1 and C1V1 variants C1V1/E162T and C1V1/E122T/E162T; blue depolarizing opsins including ChR2/L132C and ChR2/T159C and combinations of these with the ChETA substitutions E123T and E123A; and SFOs including ChR2/C128T, ChR2/C128A, and ChR2/C128S. These opsins may also be useful for inhibition using a depolarization block strategy. Inhibitory opsins useful in the invention may include, by way of non-limiting examples, NpHR, Arch, eNpHR3.0 and eArch3.0. Opsins including trafficking motifs may be useful. An inhibitory opsin may be selected from those listed in FIGS. 62J-1 and 62J-2, by way of non-limiting examples. A stimulatory opsin may be selected from those listed in FIGS. 62J-1 and 62J-2, by way of non-limiting examples. An opsin may be selected from the group consisting of Opto-β2AR or Opto-α1AR, by way of non-limiting examples.

Figure 40A:
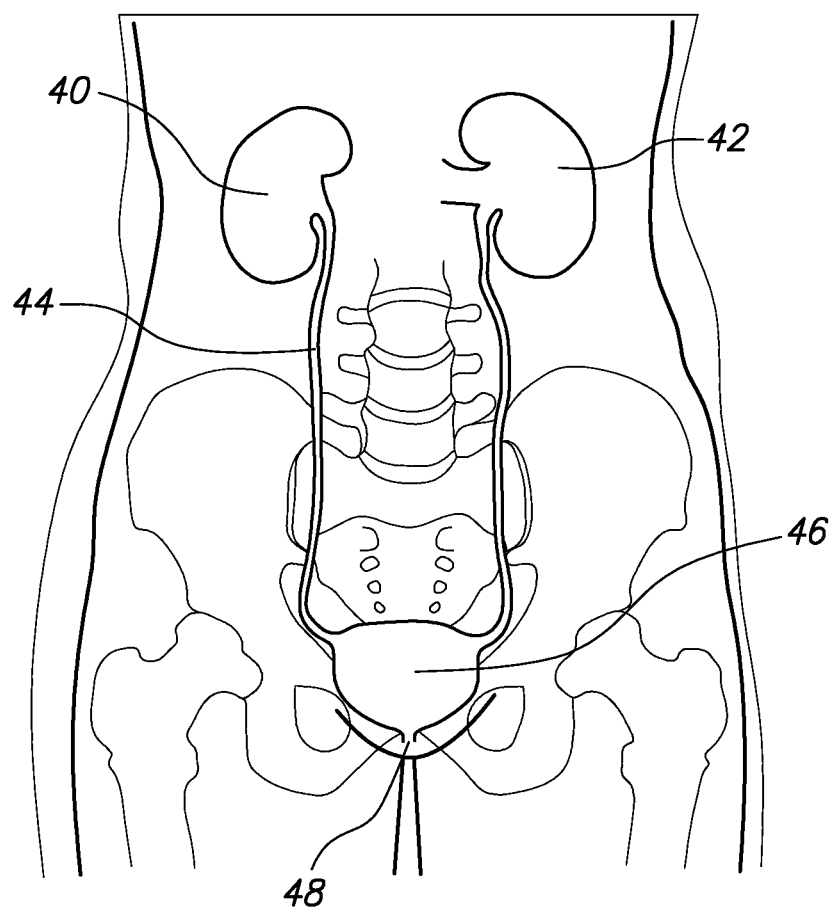
FIGS. 40A-50 depict various aspects of embodiments of configurations which may be utilized for optogenetic treatment of a hypertension using neuromodulation of the renal plexus in accordance with the present invention.
Figure 40B:
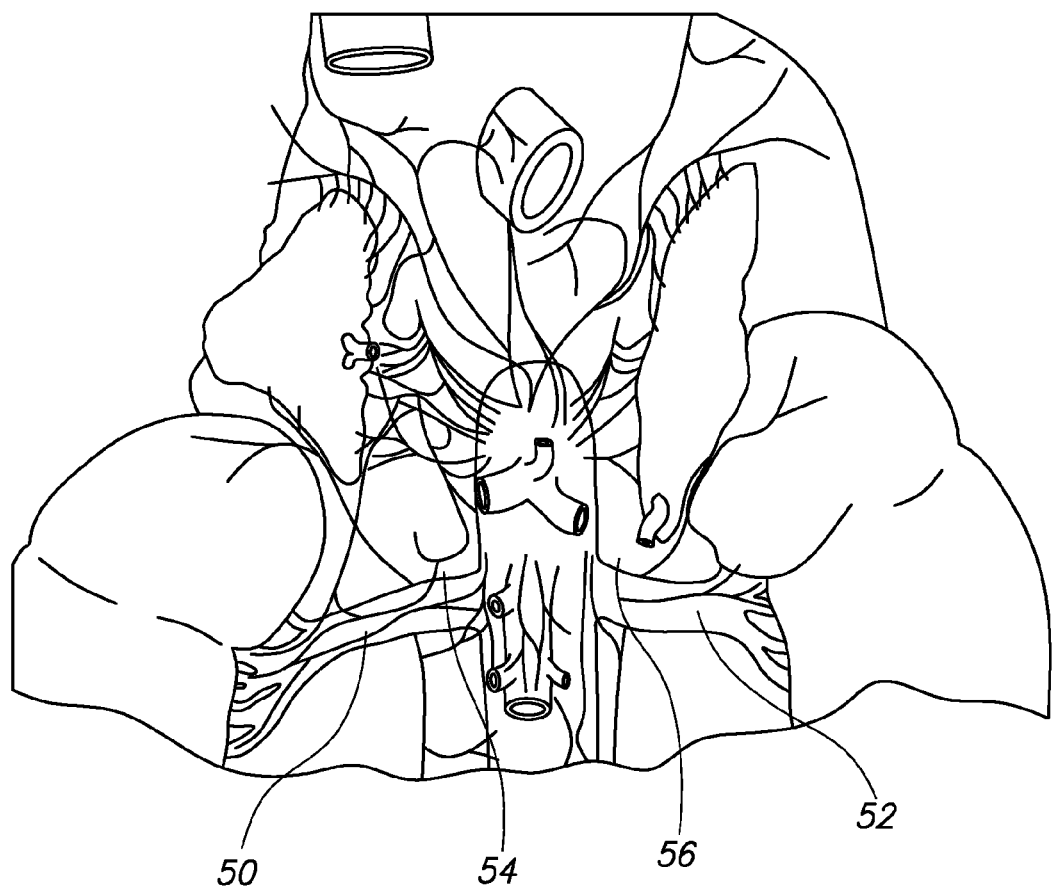
Figure 41:
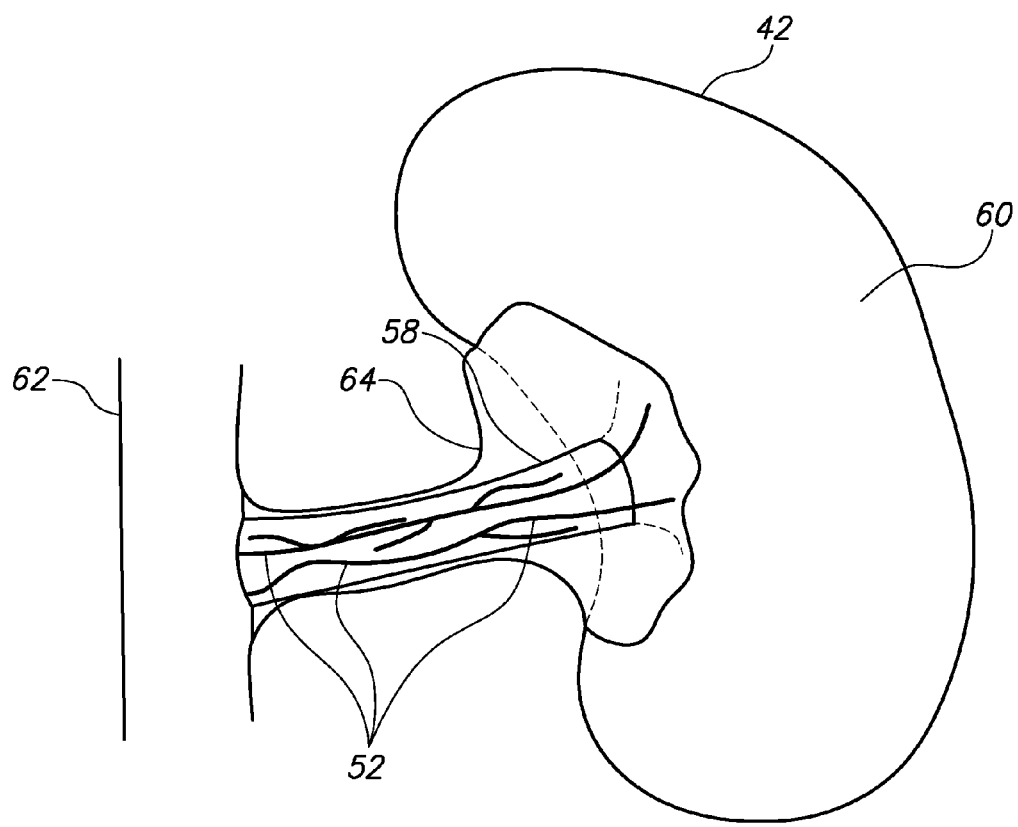

In one embodiment, an optogenetic treatment system may be installed and utilized to control cardiovascular hypertension by selectively and controllably modulating the activity of the renal nerve plexus. Referring to FIGS. 40A-40B and 41, certain aspects of the human urinary system anatomy are depicted, including the right kidney (40), left kidney (42; shown in partial sectional view in FIG. 40A), a right ureter (44), the bladder (46), and urethra (48). FIG. 40B illustrates that the renal nerve plexus typically at least partially envelops each of the renal arteries. The right renal plexus (50) cascades down in a weblike fashion around the right renal artery and generally includes a right renal ganglion (54); similarly, the left renal plexus (52) generally cascades down in a weblike fashion around the left renal artery and generally includes a left renal ganglion (56). FIG. 41 illustrates a close-up partial anatomical schematic view depicting the renal artery (58) as the main vascular intercoupling between the kidney (42) and the aorta (62). The renal plexus (52) generally resides around the renal artery underneath a thin layer of renal fascia (64).

Primary cardiovascular hypertension (the term "primary" used in reference to high blood pressure not caused by another illness) affects some 20-25% of the adult population worldwide, and persistently elevated blood pressure levels have been shown to lead to many harmful clinical consequences. Heretofore, methods for treating hypertension have primarily been pharmacologic, with common drug prescriptions including diuretics, adrenergic receptor antagonists, calcium channel blockers, renin inhibitors, ACE inhibitors, angiotensin II receptor antagonists, aldosterone antagonists, vasodilators, and alpha-2 agonists. For some patients, treatment with one or more of these drug classes succeeds in bringing their blood pressure into a normal range and therefore reduces their risk of hypertension's many consequences. Many patients, however, remain unresponsive to these drug therapies. Their hypertension persists despite an aggressive drug regimen, and they therefore continue on the pathway toward life-altering strokes, dementia, kidney failure, and heart failure. Among physicians, such patients are said to be suffering from "treatment-resistant hypertension."

Figure 42:
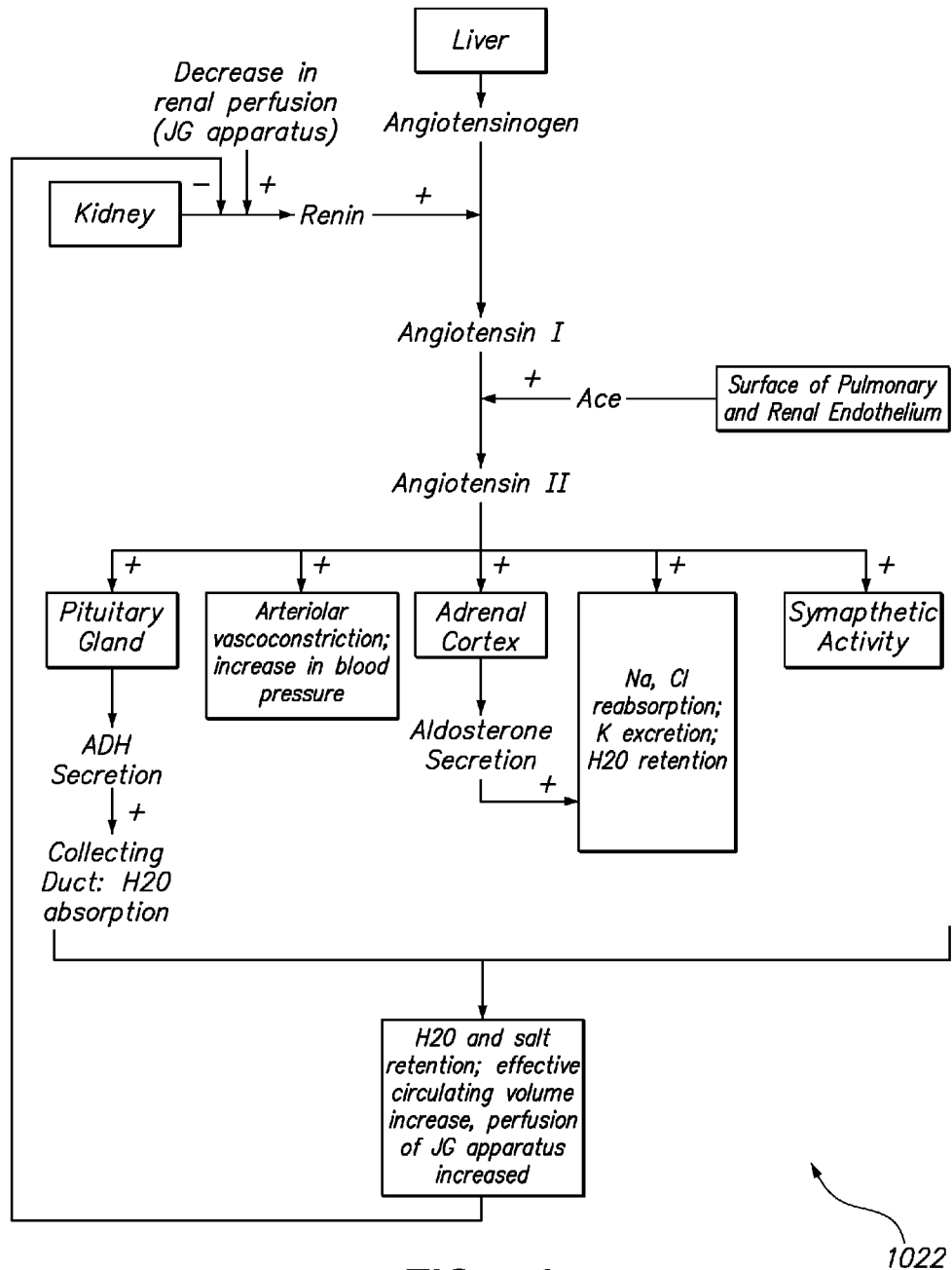

Since around 2008, a device-based treatment paradigm known as "renal denervation" or "ablative renal denervation" has been available for treatment-resistant hypertension patients. For example, certain aspects are described in U.S. Pat. No. 6,978,174, which is incorporated by reference herein in its entirety. Essentially this family of procedures involves utilizing a radiofrequency probe such as an endovascular catheter placed through the renal artery to ablatively destroy portions of the renal nerve plexus that are positioned adjacent the renal artery. The reason that this procedure has an impact upon hypertension is that the kidney normally receives nerve signals from the renal artery nerve plexus that set in motion a series of processes that raise blood pressure. Referring to FIG. 42, this series of inter-related bodily functions is known to physicians as the "renin-angiotensin-aldosterone system". Elements with "+" indications near them are indicative of a stimulatory signal to the system; elements with "−" indications near them are indicative of an inhibitory signal to the system. Blocking nerve impulses in the renal nerve plexus essentially places a stop in portions of this process to prevent it from occurring, thereby blocking one of the body's main methods of raising blood pressure. Specifically, when stretch receptors in the upper half of the heart (the atria) sense that blood pressure is low, they send nerve impulses down the spinal cord, through five spinal roots (T10-S2), through the renal artery nerve plexus, and into the kidneys, activating the juxtaglomerular apparatus (millions of individual juxtaglomerular apparatuses). The juxtaglomerular apparatuses respond to the nerve impulses by secreting a hormone known as renin, as shown in FIG. 42. Renin circulates in the bloodstream and acts as an enzyme that converts a protein produced by liver cells, angiotensinogen, into its mature form, angiotensin I. Angiotensin I also circulates in the bloodstream, and when it makes its way into the lungs, it encounters angiotensin converting enzyme (ACE) which converts it into angiotensin II. Angiotensin II circulates throughout the bloodstream and is recognized by receptors on the cells membranes of cells lining small arteries. When angiotensin II makes contact with these small-artery-lining cells, they react by triggering a contraction of the smooth muscle cells around the artery, causing the artery to constrict (become smaller). Hence, angiotensin II is known as a natural "vasoconstrictor." The effect of constricting millions of small blood vessels at the same time is to reduce the total volume of the cardiovascular system, which raises blood pressure. Angiotensin II also acts to raise blood pressure in other ways, including causing the kidney to retain more fluid than it otherwise would, and increasing the rate at which the heart beats.

Hence, by preventing the signal to secrete renin from reaching the cells in the kidney that produce renin, the entire system is blocked and the body is unable to raise blood pressure by its natural approach. Patients thus treated using renal denervation techniques may have effectively reduced their blood pressure and thereby reduced their risk of many ill-health consequences, but they also lack an important ability to raise blood pressure when needed (i.e., by permanently ablating or destroying portions of the subject nerve plexus, this functionality is gone—for better or worse—and these patients are at risk for the reverse problem: hypotension, or blood pressure that is too low). Hypotension can result in fainting, ischemic strokes, and an inability to exercise. Further, as with almost any kind of ablative treatment, the destruction of tissue can involve destruction of tissue that was intended to not be damaged in the procedure (radiofrequency ablation in a wet, close-quarters environment generally is not hyper-specific). So the renal denervation procedure that has been in use since 2008 may solve one problem (hypertension) but create other problems due to its lack of specificity and permanence. Thus there is a need for a configuration that can reversibly block the renin-angiotensin-aldosterone axis: one that can be turned on or off, be adjusted along a range of effect, and one that has specificity. This challenge may be addressed in a novel and unprecedented manner using optogenetic techniques.

Figure 45:
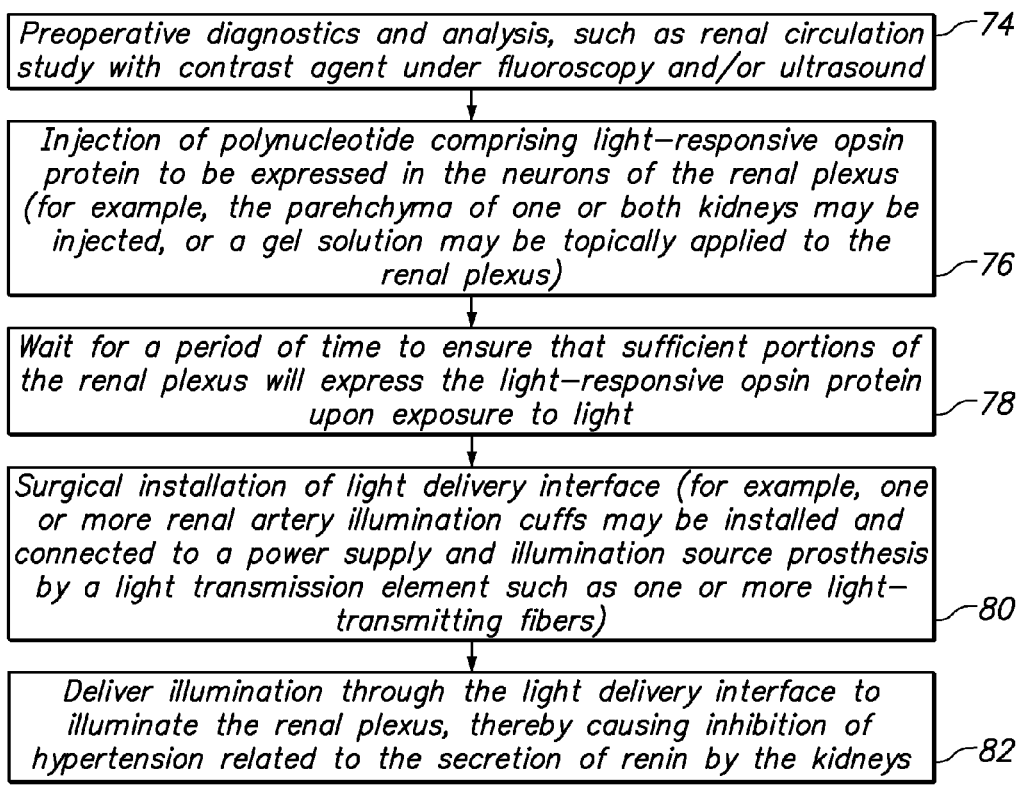

Referring ahead to FIG. 45, in one embodiment, a treatment configuration may comprise preoperative diagnostics and analysis, such as a renal circulation and/or anatomy study using fluoroscopy, radiography, ultrasound, laparoscopy, or other techniques to understand the vasculature and other structures in detail (74). A polynucleotide encoding a light-responsive opsin protein to be expressed in the neurons of the renal plexus may be injected (76), after which a waiting time for expression of the proteins may ensue (78). In an embodiment, opsins listed herein may be useful in optogenetic methods for treating hypertension.

Figure 48:
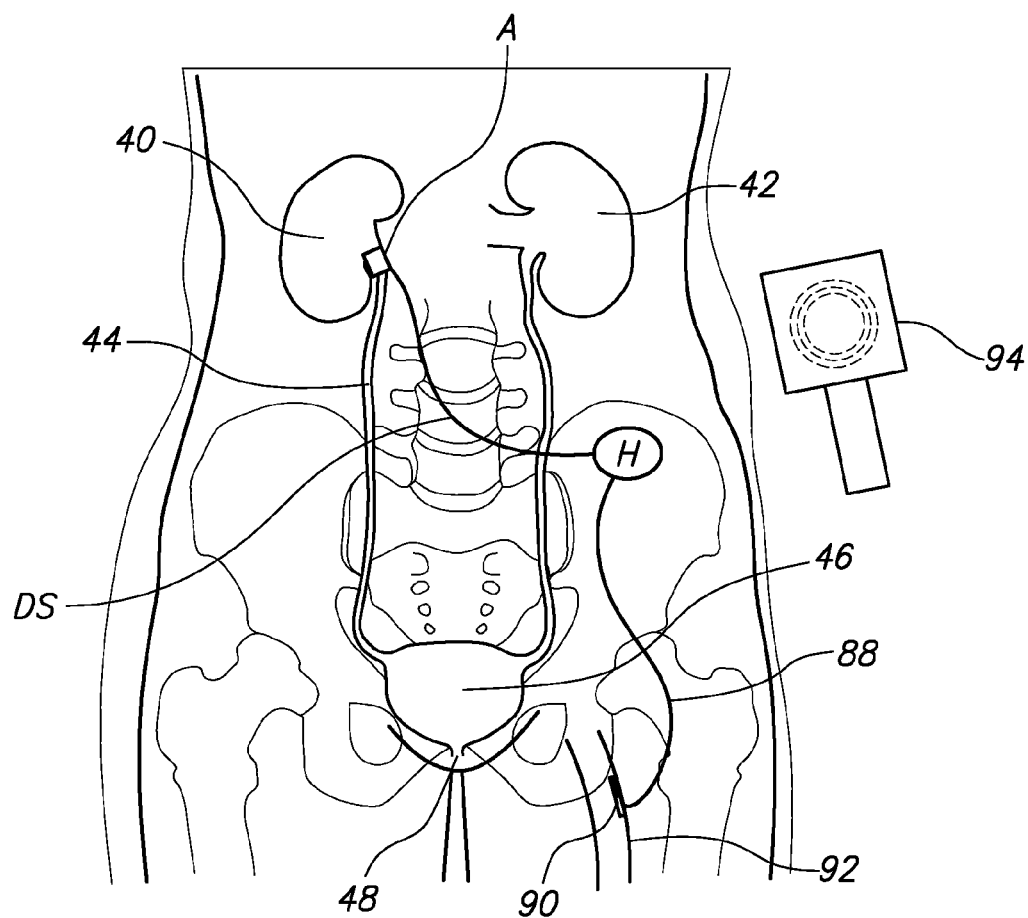

A light delivery interface or applicator configuration may then be installed (80) and illumination may be delivered through the applicator to cause inhibition of hypertension through the renal plexus in a specific and controllable manner (82). As described above, injection may take many forms, including injection directly into the parenchyma of the kidney (element 60 of FIG. 41) from a transcutaneous position with a syringe for transfective uptake into the renal plexus, direct injection using a syringe from a transcutaneous or laparoscopic platform into various branches of the renal plexus or ganglion, topical injection or application of a vector solution or gel onto various branches of the renal plexus or ganglion, or injection utilizing a movable housing or cuff with a matrix of needles, as described, for example, in reference to FIGS. 2A and 2B. Also as described above, the illumination configuration, delivery system, and main system housing may take several forms. Referring ahead to FIG. 48, in one embodiment, for example, the housing (H) comprises control circuitry and a power supply; the delivery system (DS) comprises an electrical lead to pass power and monitoring signals as the lead operatively couples the housing (H) to the applicator (A); the applicator (A) preferably comprises a cuff style applicator, akin to those described in reference to FIGS. 2A-2B but with an illuminating substrate or akin to those described in reference to FIGS. 21A-21C. Alternatively a configuration such as those described in reference to FIGS. 10A-10B may be utilized.

Generally the opsin configuration will be selected to facilitate controllable inhibitory neuromodulation of the associated renal nerve plexus in response to light application through the applicator. Thus in one embodiment an inhibitory opsin such as NpHR, eNpHR 3.0, ARCH 3.0, or ArchT, or Mac 3.0 may be utilized. In another embodiment, an inhibitory paradigm may be accomplished by utilizing a stimulatory opsin in a hyperactivation paradigm, as described above. Suitable stimulatory opsins for hyperactivation inhibition may include ChR2, VChR1, certain Step Function Opsins (ChR2 variants, SFO), ChR2/L132C (CatCH), excitatory opsins listed herein, or a red-shifted C1V1 variant (e.g., C1V1), the latter of which may assist with illumination penetration through fibrous tissues which may tend to creep in or encapsulate the applicator (A) relative to the targeted neuroanatomy of the renal plexus. In another embodiment, an SSFO may be utilized. An SFO or an SSFO is differentiated in that it may have a time domain effect for a prolonged period of minutes to hours, which may assist in the downstream therapy in terms of saving battery life (i.e., one light pulse may get a longer-lasting physiological result, resulting in less overall light application through the applicator A). As described above, preferably the associated genetic material is delivered via viral transfection in association with injection paradigm, as described above. An inhibitory opsin may be selected from those listed in FIGS. 62J-1 and 62J-2, by way of non-limiting examples. A stimulatory opsin may be selected from those listed in FIGS. 62J-1 and 62J-2, by way of non-limiting examples. An opsin may be selected from the group consisting of Opto-β2AR or Opto-α1AR, by way of non-limiting examples.

The virus used can be one of a number of available gene delivery vectors. Consideration of viral type used in the application to delivering opsins to the relevant neuronal sites innervating the kidney takes into account delivery to the neurons, selectivity to only these neurons, trafficking of viral cargoes, safety of the approach and ability to effectively express the opsin for prolonged periods such that therapeutic utility can be maintained. One viral type of use may be adeno-associated viruses (AAV), these viruses have an advantage compared to other potential viruses in that their DNA does not integrate randomly into the host cell genome, this being of benefit as it avoids the potential of oncogenic consequences. There are multiple serotypes of AAV that may be of utility in this application. AAV1 can be injected into the renal parenchyma or the artery itself where it will be taken up into the nerve terminals present therein; the virus will subsequently be retrogradely transported to the neuronal cell bodies such that the single stranded DNA that is delivered to the host cell nucleus will be converted to episomal concatamers that will be maintained for the life of the neuron. Other viral serotypes may be used in this application; the exact preference being combination of ability to be retrogradely transported to the neuronal cell body, cellular tropism and low level of immunogenicity. AAV2 has commonly been used, AAV6 displays lower immunogenicity while AAV1, 6, 8 and 9 show high levels of retrograde transport. The optimal AAV serotype could be determined by one skilled in the art by testing each available serotype and analyzing expression in neuronal cell bodies and axons.

Other viruses may also be used to deliver the transgene of interest; these include adenovirus, lentiviruses and pseudorabies or rabies virus. These viruses have an added advantage that they can be pseudotyped by replacing their envelope proteins with those of other viruses or with chimeric envelope proteins that can direct tropism to specific cellular populations. By use of pseudotyped viruses that can specifically transduce the neurons innervating the kidney, a greater specificity can be obtained which is of benefit, avoiding the expression of opsins in other cells such as the smooth muscle of the renal artery, which would otherwise be responsive to illumination and may influence the desired physiological function. Specificity may also be achieved by using cell-type-specific promoters to control the expression of the opsin, even if multiple cell types have been transduced with virus. Promoters which allow ubiquitous expression, with little differentiation between cell types such as the cytomegalovirus (CMV) promoter may be used in this therapeutic application. However greater selectivity may be achieved using a promoter that directs expression specifically to the neurons innervating the kidney. Examples of such promoters include, but are not limited to, human synapsin and neuronal specific enolase. For the promoter chosen there may be as restricted an expression as is necessary to prevent off target effects, along with sufficient expression of the opsin such that functional levels may be attained in the neuron. For specific neuronal cell types, a variety of promoters may be utilized. E.g. for motor neurons, promoter domains derived from chicken beta actin (CBA), the transcription factor Hb9, the "survival of motor neuron" (SMN1), methyl-CpG-binding protein-2 (MeCP2) and promoters of the transcription factors Pax6, Nkx6.1, Olig2, and Mnr2 may be utilized successfully. For sensory neurons, the latency-associated promoter 2 (LAP2), neuron-specific enolase (NSE) may be used. Other promoters as listed herein may also be useful.

Additional functionality in the constructs used in this application can be achieved by the use of specific trafficking and targeting sequences in the construct. As opsins are only functional when expressed on the plasma membrane of neurons addition of signal sequences that will promote the trafficking of opsin through the ER, Golgi apparatus and specifically to the plasma membrane can allow the most efficient expression. Furthermore, sequences can be incorporated that direct the opsin to specific compartments such as the cell body, axon or dendrites which can further increase the presence of opsin in the desired location.

Figure 43:
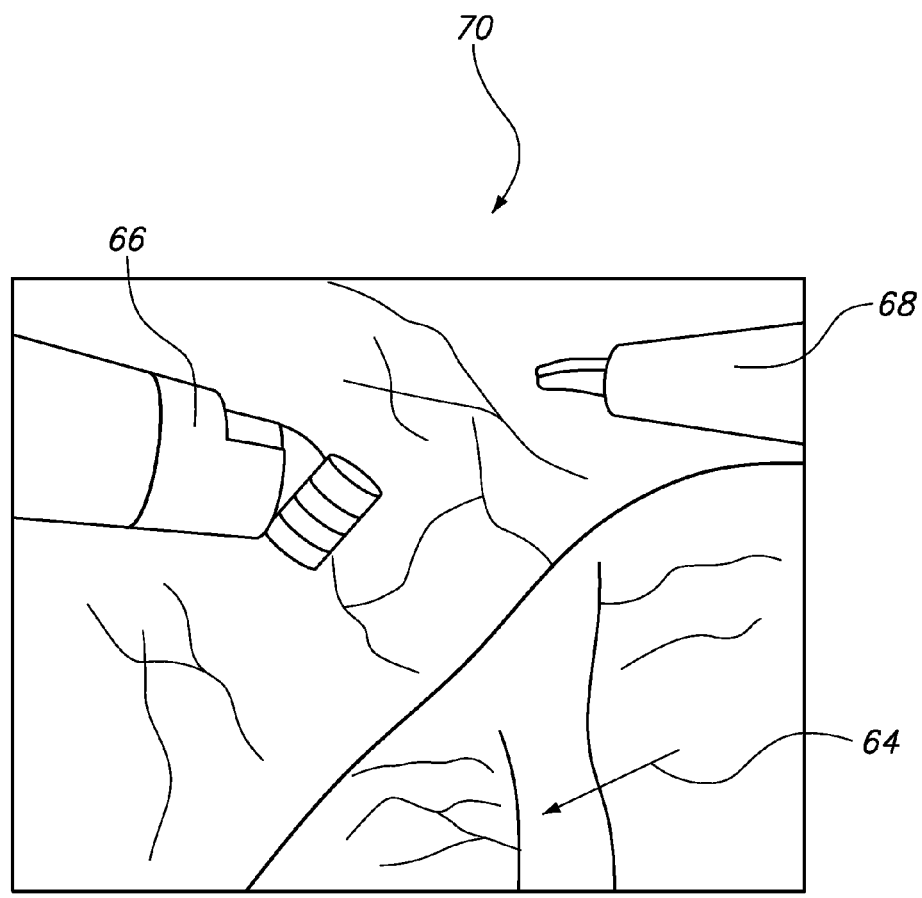
Figure 44:
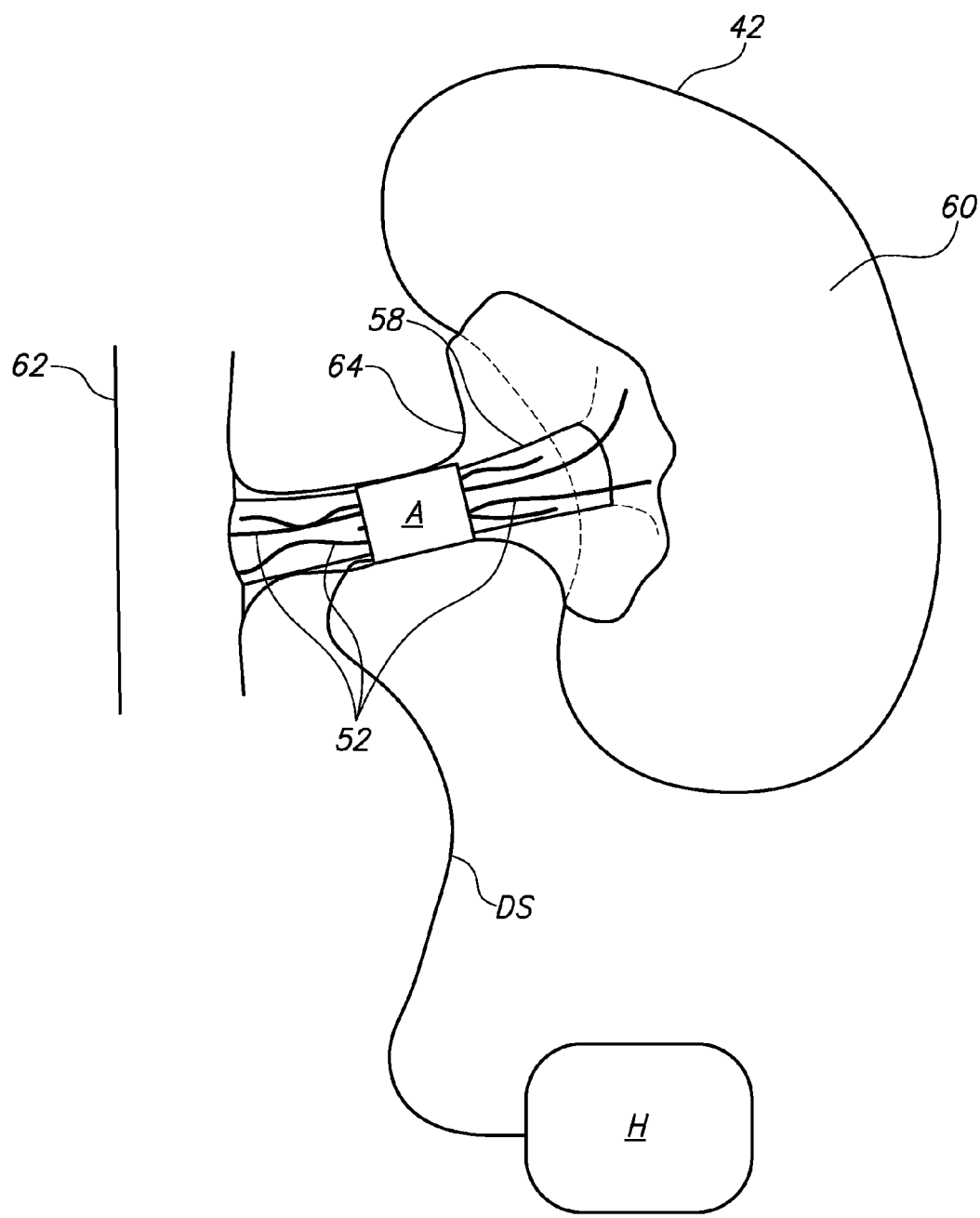
Figure 49:
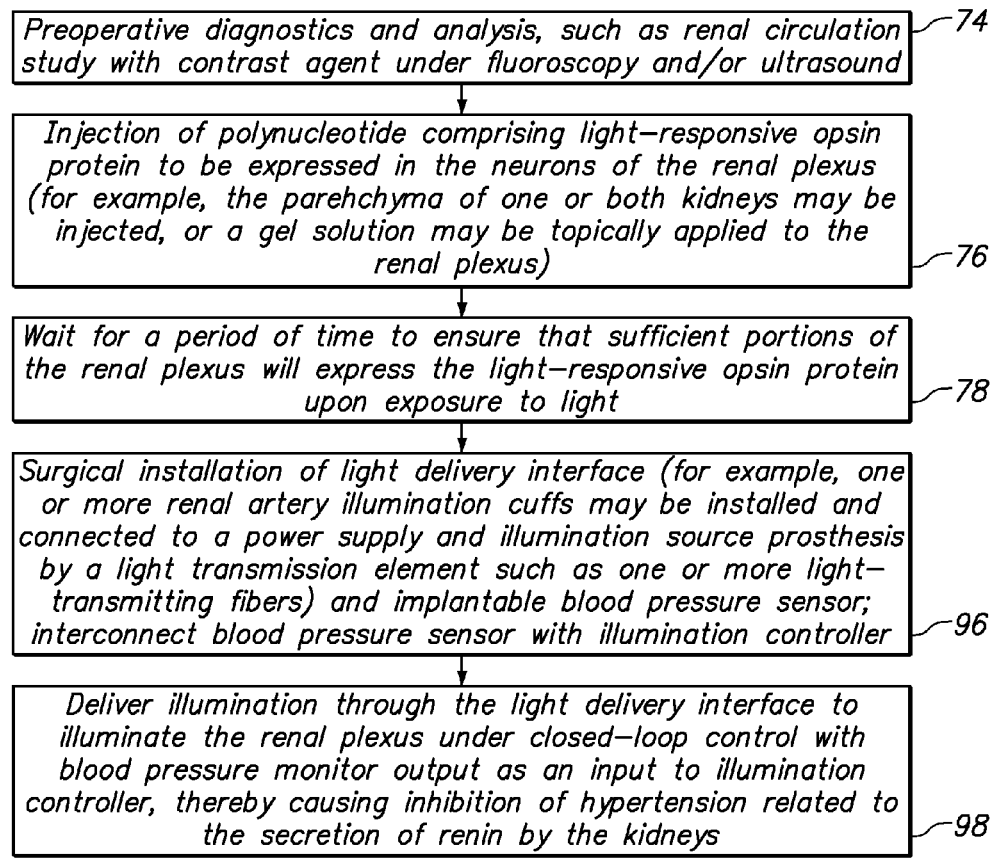

Referring to FIG. 43, the renal fascia (64) and underlying renal artery and renal nerve plexus may be reached using laparoscopic procedures, as shown in the laparoscopic camera view (70) which shows two small grasping/cutting tools extending into the subject anatomy through one or more relatively small transcutaneous port wounds. Referring to FIG. 44, a cuff-like applicator (A) is installed about the periphery of the renal artery (58) immediately adjacent portions of the renal plexus (52) to facilitate illumination, as directed by the intercoupled (DS) implantable system housing (H), which preferably is implanted within the patient as well, as shown, for example, in FIG. 48, wherein the housing (H) resides near the pelvis of the patient. The embodiment of FIG. 48 also shows an external programmer/communicator (94) which may be wirelessly connected (i.e., using inductive techniques) to the housing (H) for programming, exchanging data, or inductive battery charging. The embodiment of FIG. 48 also features an implantable endovascular pressure sensor (90), such as those available from Fraunhofer-Gesellschaft under the tradename "Hyper-IMS", which may be connected to the controller within the housing (H) via an electrical lead (88) to facilitate closed-loop hypertension control (i.e., blood pressure may be monitored using the sensor 90 and controlled using the optogenetic control system, H, DS, A), as described in FIG. 49, wherein a sensor may be installed (96) and utilized for closed-loop control of blood pressure (98).

Alternately, a system may be configured to utilize one or more wireless power transfer inductors/receivers that are implanted within the body of a patient that are configured to supply power to the implantable power supply.

There are a variety of different modalities of inductive coupling and wireless power transfer. For example, there is non-radiative resonant coupling, such as is available from Witricity, or the more conventional inductive (near-field) coupling seen in many consumer devices. All are considered within the scope of the present invention. The proposed inductive receiver may be implanted into a patient for a long period of time. Thus, the mechanical flexibility of the inductors may need to be similar to that of human skin or tissue. Polyimide that is known to be biocompatible was used for a flexible substrate.

By way of non-limiting example, a planar spiral inductor may be fabricated using flexible printed circuit board (FPCB) technologies into a flexible implantable device. There are many kinds of a planar inductor coils including, but not limited to; hoop, spiral, meander, and closed configurations. In order to concentrate a magnetic flux and field between two inductors, the permeability of the core material is the most important parameter. As permeability increases, more magnetic flux and field are concentrated between two inductors. Ferrite has high permeability, but is not compatible with microfabrication technologies, such as evaporation and electroplating. However, electrodeposition techniques may be employed for many alloys that have a high permeability. In particular, Ni (81%) and Fe (19%) composition films combine maximum permeability, minimum coercive force, minimum anisotropy field, and maximum mechanical hardness. An exemplary inductor fabricated using such NiFe material may be configured to include 200 µm width trace line width, 100 µm width trace line space, and have 40 turns, for a resultant self-inductance of about 25 µH in a device comprising a flexible 24 mm square that may be implanted within the tissue of a patient. The power rate is directly proportional to the self-inductance.

The radio-frequency protection guidelines (RFPG) in many countries such as Japan and the USA recommend the limits of current for contact hazard due to an ungrounded metallic object under the electromagnetic field in the frequency range from 10 kHz to 15 MHz. Power transmission generally requires a carrier frequency no higher than tens of MHz for effective penetration into the subcutaneous tissue.

In certain embodiments of the present invention, an implanted power supply may take the form of, or otherwise incorporate, a rechargeable micro-battery, and/or capacitor, and/or super-capacitor to store sufficient electrical energy to operate the light source and/or other circuitry within or associated with the implant when used along with an external wireless power transfer device. Exemplary microbatteries, such as the Rechargeable NiMH button cells available from VARTA, are within the scope of the present invention. Supercapacitors are also known as electrochemical capacitors.

Figure 46:
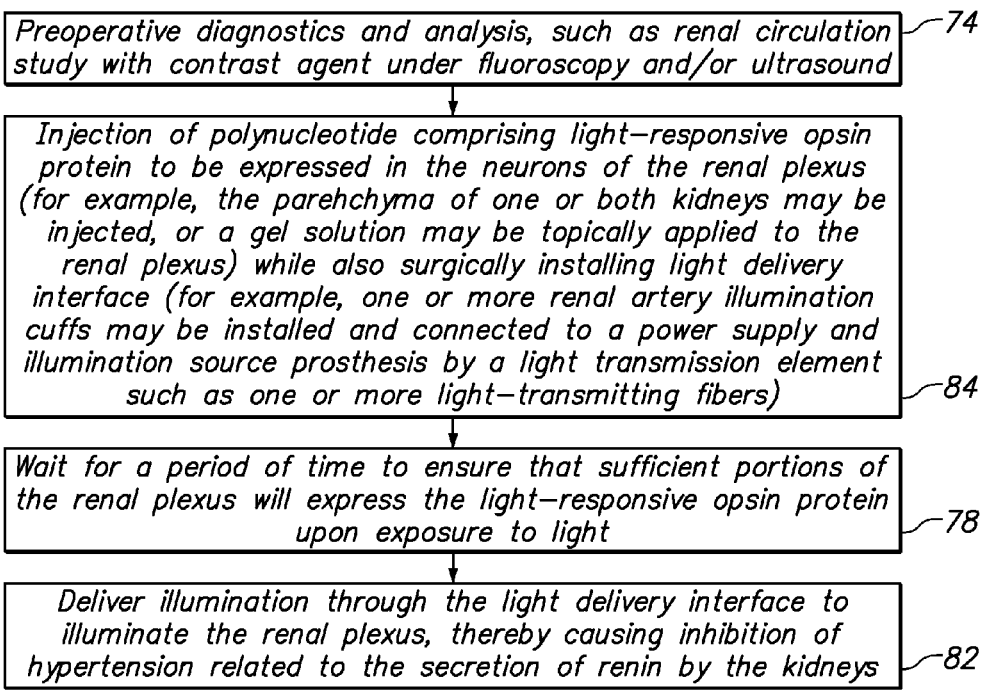

FIG. 46 illustrates an embodiment wherein the opsin genetic material and applicator are installed at the same time (84) to minimize the number of procedures to the patient.

Figure 47:
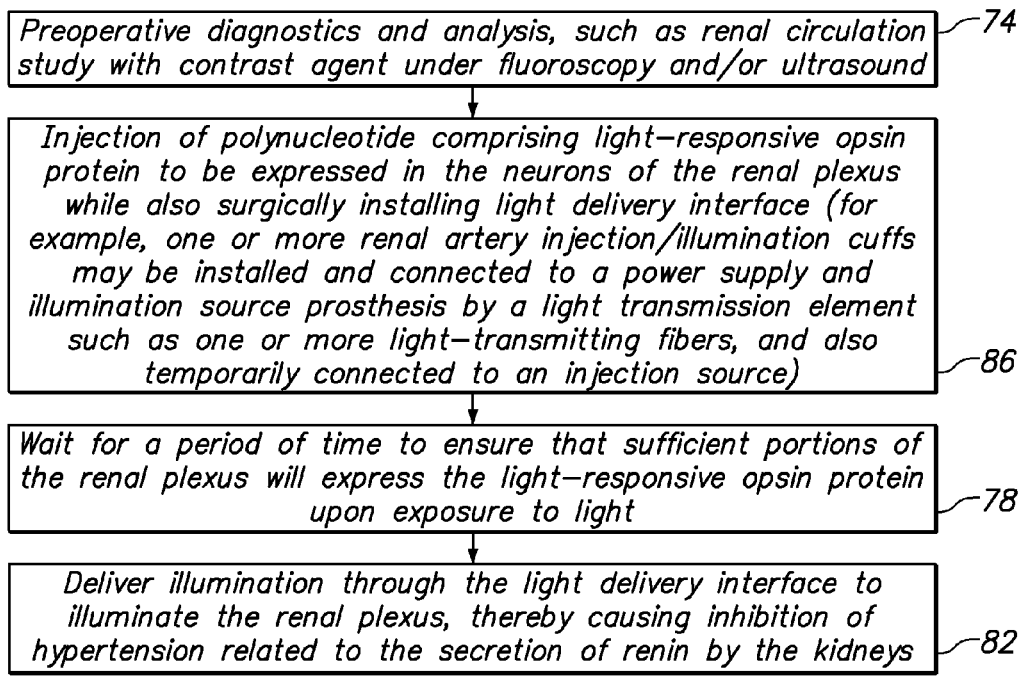

FIG. 47 illustrates an embodiment wherein the opsin genetic material and applicator are installed at the same time by virtue of an applicator which also functions as an injection means (86), as described, for example, in reference to FIGS. 2A and 2B above.

Figure 50:
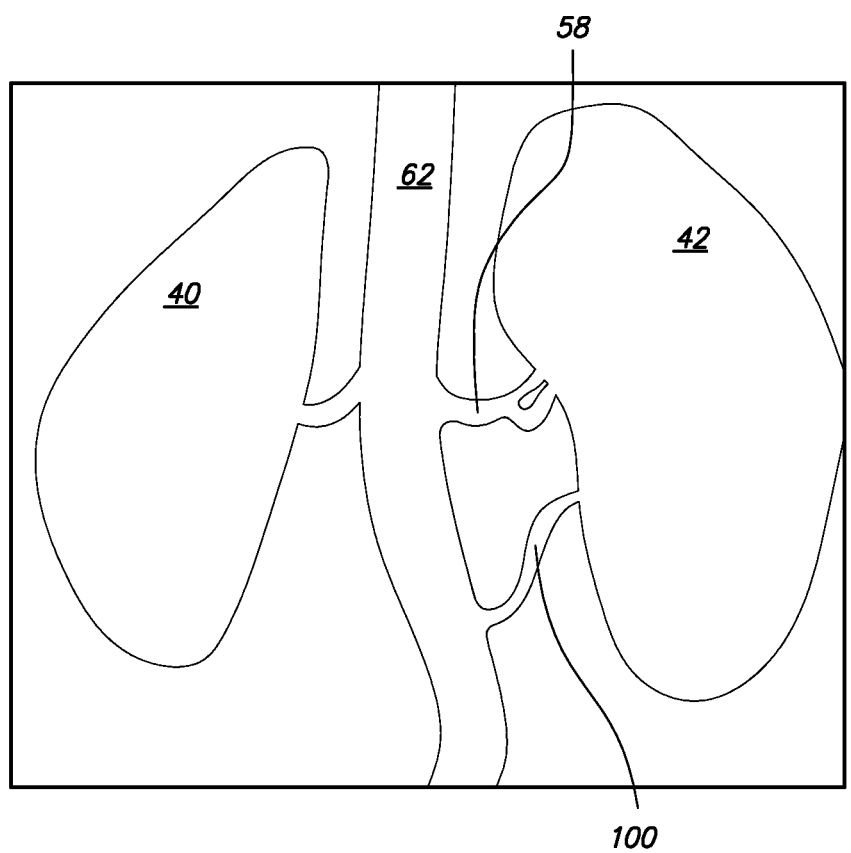

Referring to FIG. 50, anatomical variation generally may be accounted for in procedures such as those described herein, and therefore, it may be desirable in a case wherein a patient has an extra renal artery (100) to have three applicators placed at each of the renal arteries to control the associated portions of the renal plexus. An inhibitory opsin protein may be selected from the group consisting of, by way of non-limiting examples: NpHR, eNpHR 1.0, eNpHR 2.0, eNpHR 3.0, Mac, Mac 3.0, Arch, Arch3.0, and ArchT. An inhibitory opsin may be selected from those listed in FIGS. 62J-1 and 62J-2, by way of non-limiting examples. A stimulatory opsin protein may be selected from the group consisting of, by way of non-limiting examples: ChR2, C1V1-E122T, C1V1-E162T, C1V1-E122T/E162T, CatCh, VChR1-SFO, and ChR2-SFO. A stimulatory opsin may be selected from those listed in FIGS. 62J-1 and 62J-2, by way of non-limiting examples. An opsin may be selected from the group consisting of Opto-β2AR or Opto-α1AR, by way of non-limiting examples. The light source may be controlled to deliver a pulse duration between about 0.1 and about 20 milliseconds, a duty cycle between about 0.1 and 100 percent, and a surface irradiance of between about 5 milliwatts per square millimeter to about 200 milliwatts per square millimeter.

Figure 88A:
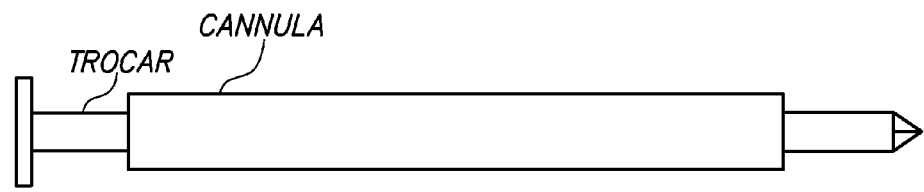
FIGS. 88A-89 depict embodiments of an elongate member for use in the surgical implantation of optogenetic therapeutic devices in accordance with the present invention.
Figure 88B:
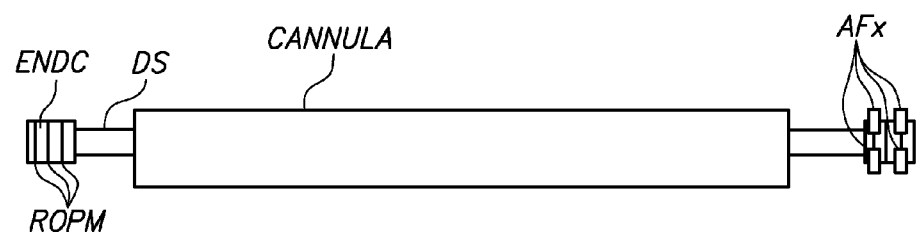

FIGS. 88A and 88B show an alternate embodiment of the present invention, where a Trocar and Cannula may be used to deploy an at least partially implantable system for optogenetic control of the renal nerve plexus for the control of cardiac hypertension. Trocar TROCAR may be used to create a tunnel through tissue between surgical access points that may correspond to the approximate intended deployment locations of elements of the present invention, such as applicators and housings. Cannula CANNULA may be inserted into the tissue of the patient along with, or after the insertion of the trocar. The trocar may be removed following insertion and placement of the cannula to provide an open lumen for the introduction of system elements. The open lumen of cannula CANNULA may then provide a means to locate delivery segment DS along the route between a housing and an applicator. The ends of delivery segment DS may be covered by end caps ENDC. End caps ENDC may be further configured to comprise radio-opaque markings ROPM to enhance the visibility of the device under fluoroscopic imaging and/or guidance. End Caps ENDC may provide a watertight seal to ensure that the optical surfaces of the Delivery Segment DS, or other system component being implanted, are not degraded. The cannula may be removed subsequent to the implantation of delivery segment DS. Subsequently, delivery segment DS may be connected to an applicator that is disposed to the target tissue and/or a housing, as have been described elsewhere herein. In a further embodiment, the End Caps ENDC, or the Delivery Segment DS itself may be configured to also include a temporary Tissue Fixation elements AFx, such as, but not limited to; hook, tines, and barbs, that allow the implanted device to reside securely in its location while awaiting further manipulation and connection to the remainder of the system.

Figure 89:
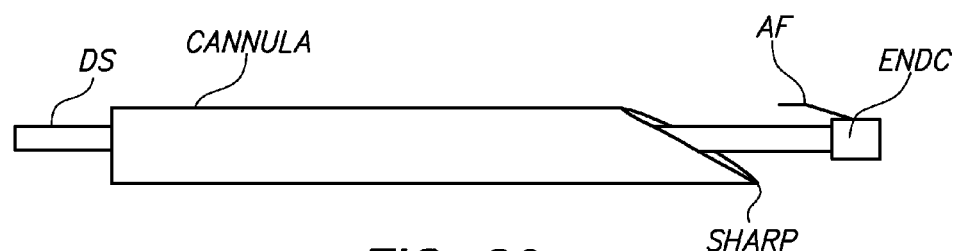

FIG. 89 illustrates an alternate embodiment, similar to that of FIGS. 88A&B, further configured to utilize a barbed Tissue Fixation Element AF that is affixed to End Cap ENDC. Tissue Fixation Element AF may be a barbed, such that it will remain substantially in place after insertion along with Cannula CANNULA, shown in this example as a hypodermic needle with sharp End SHARP being the leading end of the device as it is inserted into a tissue of a patient. The barbed feature(s) of Tissue Fixation Element AF insert into tissue, substantially disallowing Delivery Segment DS to be removed. In a still further embodiment, Tissue Fixation Element AF may be made responsive to an actuator, such as a trigger mechanism (not shown) such that it is only in the configuration to affirmatively remain substantially in place after insertion when activated, thus providing for the ability to be relocated more easily during the initial implantation, and utilized in conjunction with a forward motion of Delivery Segment DS to free the end from the tissue it has captured. Delivery Segment DS may be substantially inside the hollow central lumen of Cannula CANNULA, or substantially slightly forward of it, as is shown in the illustrative embodiment. As used herein, cannula also refers to an elongate member, or delivery conduit. The elongate delivery conduit may be a cannula. The elongate delivery conduit may be a catheter. The catheter may be a steerable catheter. The steerable catheter may be a robotically steerable catheter, configured to have electromechanical elements induce steering into the elongate delivery conduit in response to commands made by an operator with an electronic master input device that is operatively coupled to the electromechanical elements. The surgical method of implantation further may comprise removing the elongate delivery conduit, leaving the delivery segment in place between the first anatomical location and the second anatomical location.

An alternate embodiment of the invention may comprise the use of a SFO and/or a SSFO opsin in the cells of the target tissue to affect neural inhibition of the renal plexus for the treatment of cardiac hypertension, such a system may comprise a 2-color illumination system in order to activate and then subsequently deactivate the light sensitive protein. As is described elsewhere herein, the step function opsins may be activated using blue or green light, such as a nominally 450 nm LED or laser light source, and may be deactivated using a yellow or red light, such as a nominally 600 nm LED of laser light source. The temporal coordination of these colors may be made to produce a hyperstimulation (depolarization) block condition by pulsing the first light source for activation to create an activation pulse of a duration between 0.1 and 10 ms, then pulsing the second light source for deactivation to create a deactivation pulse of a duration between 0.1 to 10 ms at a time between 1 and 100 ms after the completion of the activation pulse from the first light source. Alternately, certain inhibitory opsins, such as, but not limited to, NpHR and Arch, may be similarly deactivated using blue light.

It is understood that systems for renal nerve inhibition may be configured from combinations of any of the applicators, controllers/housings, delivery segments, and other system elements described, and utilize therapeutic parameters defined herein. By way of non-limiting example, a system comprising a nominally 590 nm LED light source may be operatively coupled to a waveguide delivery segment, comprised of a bundle of 37 100 µm diameter optical fibers, via a hermetic optical feedthrough to transmit light from within an implantable housing, and controlled by a controller therein, to an axially rolled slab-type applicator, comprised of multiple output couplers and a fitted with a reflective sleeve, that may be disposed on or about the exterior of the renal artery to illuminate cells containing an NpHR opsin within the target tissue with a pulse duration of between 0.1-10 ms, a duty cycle of between 20-50%, and an irradiance of between 5-20 mW/mm$^2$ at the surface of the renal artery.

Figure 102:
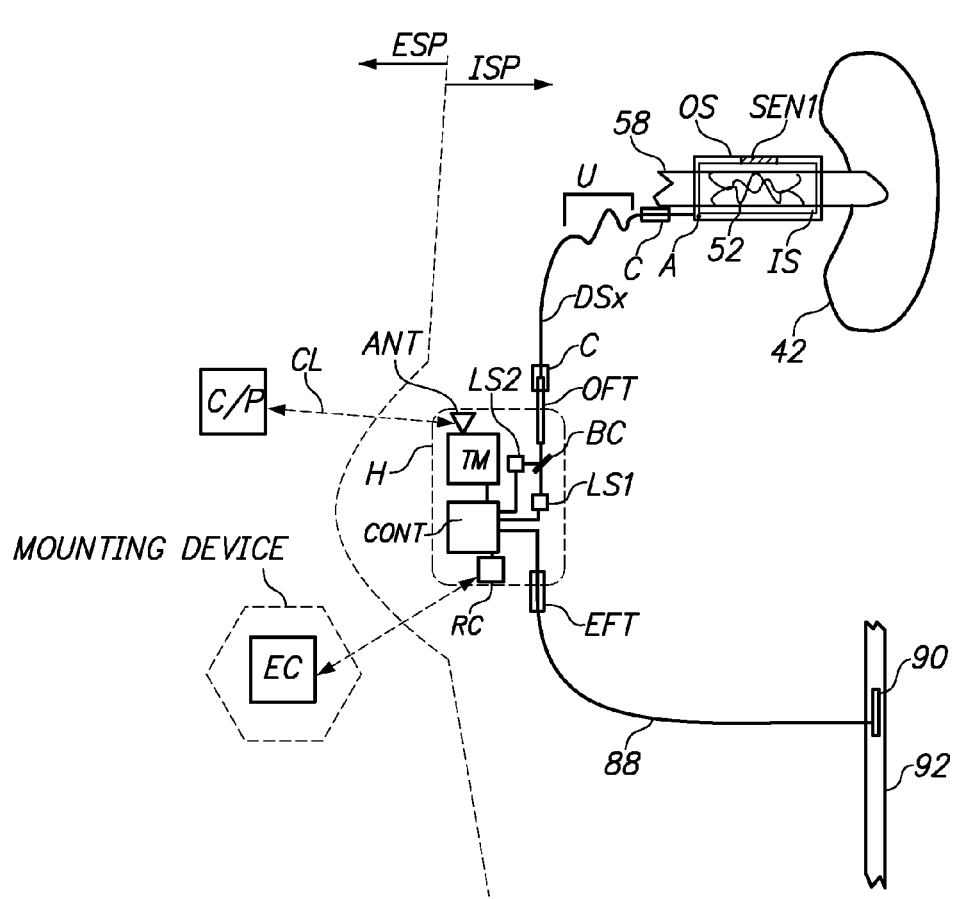
FIG. 102 depicts an embodiment of a system in accordance with the present invention.

FIG. 102 shows an alternate exemplary embodiment of a system for the treatment of cardiac hypertension via optogenetic inhibition of the renal nerve plexus, comprising elements, such as is described in more detail with respect to FIGS. 10A-26, 31-34, 37, 40A-50, 64-69, 73A-75, and 87-89. Applicator A, a rolled slab-type applicator that is 10 mm wide and 40 mm long when unrolled, such as is described in more detail with respect to FIGS. 18 and 21-23 is deployed about Renal Artery 58, which contains Renal Plexus 52, of Kidney 42, such as is described in more detail with respect to FIGS. 40A-50. Applicator A further comprises Inner Surface IS and Outer Surface OS, such as is described in more detail with respect to FIG. 21B, wherein Outer Surface OS may be at least a partially reflecting surface configured to recycle remitted light back into Target Tissue N (which, in this example, is Renal Plexus 52). Applicator A further comprises Sensor SEN1, such as is described in more detail with respect to FIGS. 24 and 69. Light is delivered to Applicator A via Delivery Segments DS, such as is described in more detail with respect to FIGS. 10A-21. Connector C is configured to operatively couple light from Delivery Segments DS to Applicator A, such as is described in more detail with respect to FIGS. 10A and 64-68. Delivery Segments DS further comprise Undulations U, such as is described in more detail with respect to FIGS. 17B and 82A-83. Delivery Segments DS are further configured to comprise Signal Wires SW between Sensor SEN1 and the Controller CONT of Housing H. As such, Connector C is further configured to provide the electrical connection, as well. Delivery Segments DS are operatively coupled to Housing H via Optical Feedthrough OFT, such as is described in more detail with respect to FIGS. 73A-75. Light is provided to Delivery Segments DS from Light Sources LS1 and LS2 within Housing H after being combined with Beam Combiner BC, such as is described in more detail with respect to FIG. 16. Light Sources LS1 and LS2 may be configured to LEDs, and/or lasers that provide spectrally different output to activate and/or deactivate the opsins resident within Target Tissue 52, such as is described in more detail elsewhere herein. The Controller CONT shown within Housing H is a simplification, for clarity, of that described in more detail with respect to FIGS. 32-34. External clinician programmer module and/or a patient programmer module C/P may communicate with Controller CONT via Telemetry module TM via Antenna ANT via Communications Link CL, such as is described in more detail with respect to FIGS. 31-32 and 39. Power Supply PS, not shown for clarity, may be wirelessly recharged using External Charger EC, such as is described in more detail with respect to FIGS. 31-334. Furthermore, External Charger EC may be configured to reside within a Mounting Device MOUNTING DEVICE, such as is described in more detail with respect to FIG. 87. Mounting Device MOUNTING DEVICE may be a pant, as is especially well configured for this exemplary embodiment. External Charger EC, as well as External clinician programmer module and/or a patient programmer module C/P and Mounting Device MOUNTING DEVICE may be located within the extracorporeal space ESP, while the rest of the system is implanted and may be located within the intracorporeal space ISP, such as is described in more detail with respect to FIGS. 31 and 70. The system may further comprise an implanted in-situ blood pressure sensor 90, resident within the Femoral Artery, such as is described in more detail with respect to FIG. 48. Implantable endovascular pressure sensor 90, such as those available from Fraunhofer-Gesellschaft under the tradename "Hyper-IMS", may be connected to the controller within the housing (H) via an electrical lead (88) to facilitate closed-loop hypertension control. Electrical Lead 88 may be connected to the Controller CONT of Housing H via an Electrical Feedthrough EFT, such as, by way of non-limiting example, The SYGNUS® Implantable Contact System from Bal-SEAL.

In certain scenarios wherein light sensitivity of opsin genetic material may be of paramount importance, it may be desirable to focus less on wavelength (as discussed above, certain "red-shifted" opsins may be advantageous due to the greater permeability of the associated radiation wavelengths through materials such as tissue structures) and more on a tradeoff that has been shown between response time and light sensitivity (or absorption cross-section). In other words, optimal opsin selection in many applications may be a function of system kinetics and light sensitivity. Referring to the plot (252) of FIG. 62A, for example, electrophysiology dose for a 50% response (or "EPD50"; lower EPD50 means more light-sensitive) is plotted versus temporal precision ("$\tau_{off}$", which represents the time constant with which an opsin deactivates after the illumination has been discontinued). These data are from Mattis et al, Nat Methods 2011, Dec. 10; 9(2): 159-172, which is incorporated by reference herein in its entirety, and illustrates the aforementioned tradeoff. In addition to EPD50 and $\tau_{off}$, other important factors playing into opsin selection optimization may include exposure density ("H-thresh") and photocurrent levels. H-thresh may be assessed by determining the EPD50 dose for an opsin; the longer the channel created by the opsin requires to "reset", the longer the associated membrane will remain polarized, and thus will block further depolarization. The following table features a few exemplary opsins with characteristics compared.

| Opsin | EPD50 [mW/ mm2] | Tau-off [ms] | Lambda Peak [nm] | Pentration Depth [normalized to 475 nm] | Peak Photo-current [nA] | SS Photo-current [nA] | Peak Potential [mV] |
|---|---|---|---|---|---|---|---|
| C1V1t | 0.3 | 75 | 540 | 1.67 | 1.5 | 1 | 30 |
| C1V1tt | 0.4 | 50 | 540 | 1.67 | 1.1 | 0.6 | 32 |
| CatCh | 0.3 | 60 | 475 | 1.00 | 1.25 | 1 | 38 |
| VChR1 | 0.1 | 100 | 550 | 1.80 | | | |

Figure 62D:
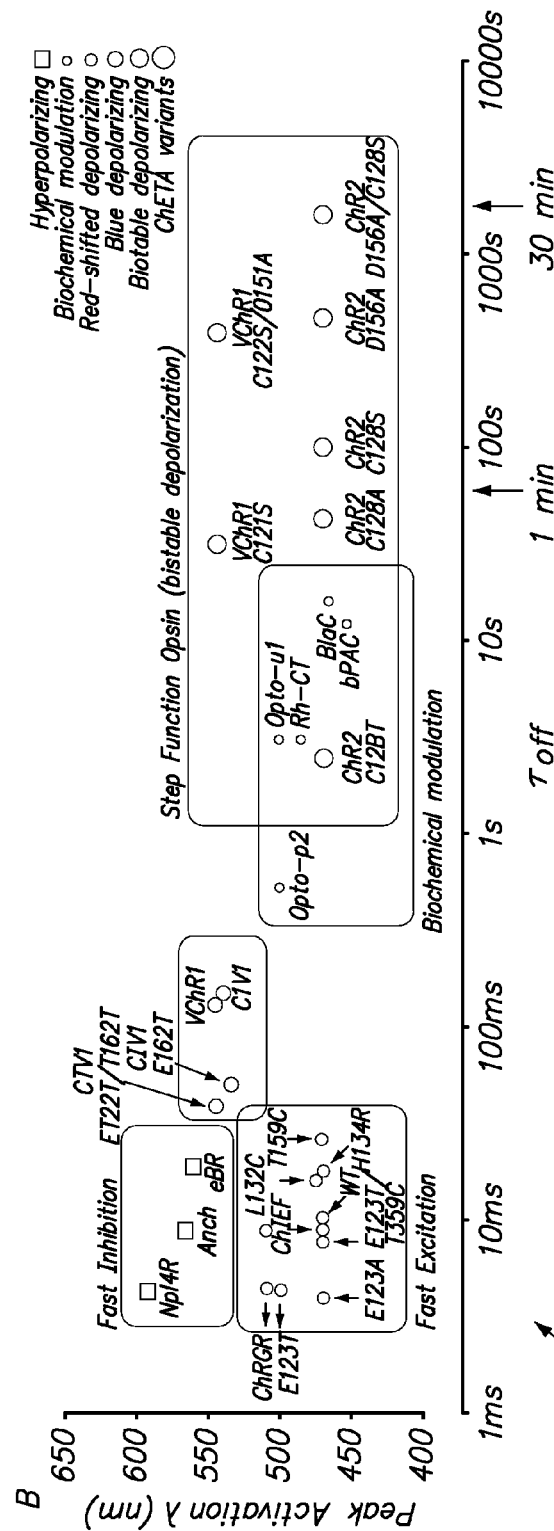
Figure 62E:
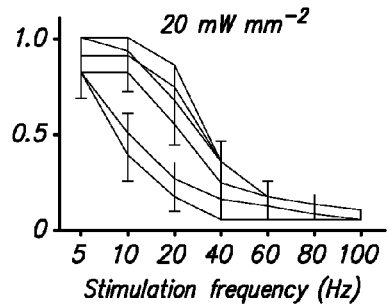
Figure 62F:
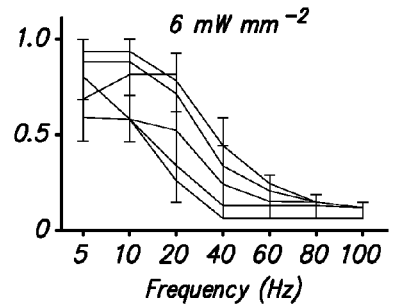
Figure 62G:
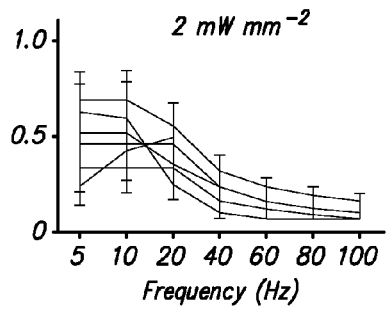
Figure 62H:
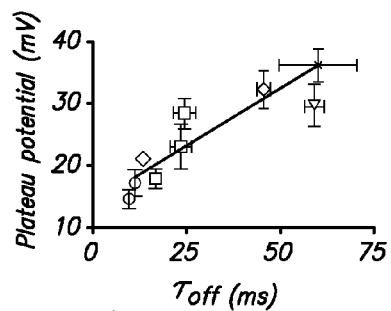
Figure 62I:
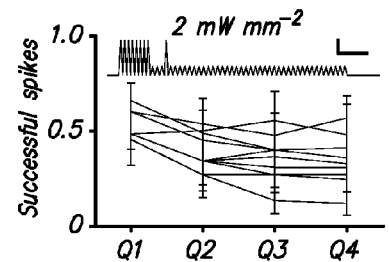

Thus, from an opsin protein selection perspective, the combination of low exposure density (H-thresh), long photorecovery time ($\tau_{off}$), and high photocurrent results in an opsin well-suited for applications that do not require ultra-temporal precision. As described above, a further consideration remains the optical penetration depth of the light or radiation responsible for activating the opsin. Tissue is a turbid medium, and predominantly attenuates the power density of light by Mie (elements of similar size to the wavelength of light) and Rayleigh (elements of smaller size than the wavelength of light) scattering effects. Both effects are inversely proportional to the wavelength, i.e. shorter wavelength is scattered more than a longer wavelength. Thus, a longer opsin excitation wavelength is preferred, but not required, for configurations where there is tissue interposed between the illumination source and the target. A balance may be made between the ultimate irradiance (optical power density and distribution) at the target tissue containing the opsin and the response of the opsin itself. The penetration depth in tissue (assuming a simple lambda$^{-4}$ scattering dependence) is listed in the table above. Considering all the abovementioned parameters, both C1V1 (E162T) and VChR1 may be desirable choices in many clinical scenarios, due to combination of low exposure threshold, long photorecovery time, and optical penetration depth. FIGS. 62B-62C and 62E-62I feature further plots (254, 256, 260, 262, 264, 266, 268, respectively) containing data from the aforementioned incorporated Mattis et al 2011 reference, demonstrating the interplay/relationships of various parameters of candidate opsins. FIG. 62D features a plot (258) similar to that shown in FIG. 4B, which contains data from Yizhar et al, Neuron. 2011 July; 72:9-34, which is incorporated by reference herein in its entirety. The table (270) of FIGS. 62J-1 and 62J-2 features data from the aforementioned incorporated Yizhar et al Neuron 2011 reference, in addition to Wang et al, 2009, Journal of Biological Chemistry, 284: 5625-5696; Gradinaru et al, 2010, Cell: 141:1-12; Wen et al., PLoS One. 2010; 5(9):e12893; Lin et al, Biophys J. 2009; 96(5):1803-14; Lin et al., Nat Neurosci. 2013 16(10):1499-1508, all of which are incorporated by reference herein in their entirety.

Amino acid sequences of exemplary opsins, as well as of exemplary signal peptides, signal sequences, ER export sequences, and a trafficking sequence, are shown in FIGS. 51A-61M-7. Information on exemplary opsins, signal peptides, signal sequences, ER export sequences, and trafficking sequences is also in published US patent applications 20130019325 and 2011011217, published PCT application WO/2013/126521, Yizhar et al, Nature. 2011; 477(7363): 171-8; Zhang F, et al., Cell. 2011; 147(7):1446-57; Mattis et al., Nat Methods. 2011; 9(2):159-72; and Fenno et al., Annu Rev Neurosci. 2011; 34:389-412, Prakash et al., 2012 Nature Methods 9(12):1171-1179; as well as in the GenBank records cited in FIGS. 51A-61M-7, all of which are incorporated by reference.

Figure 90:
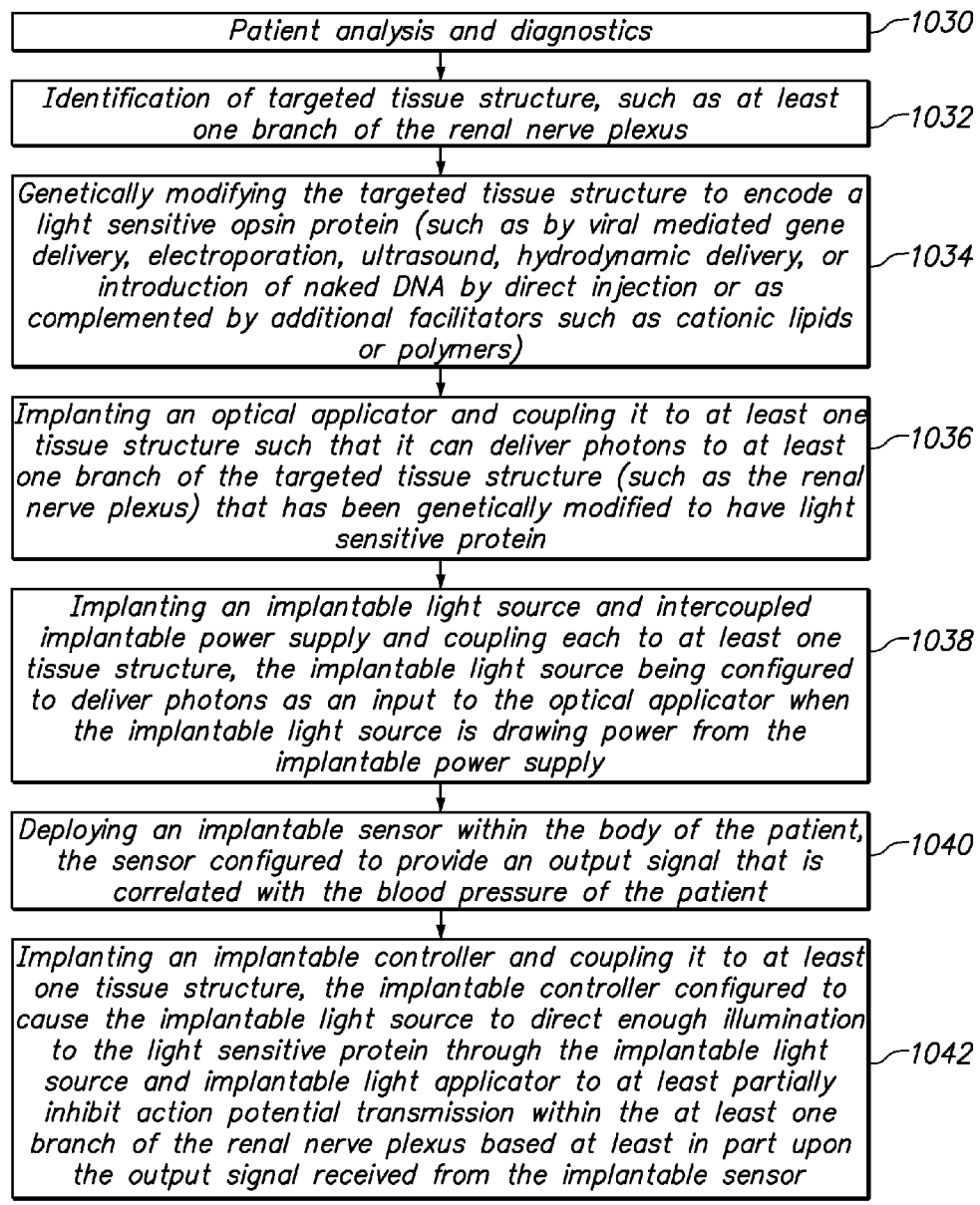
FIGS. 90-101 depict various configurations for conducting procedures featuring technologies such as those described herein.

Referring to FIGS. 90-101, various configurations for conducting procedures featuring technologies such as those described above are illustrated. Referring to FIG. 90, for example, one embodiment is illustrated for controlling hypertension of a patient via optogenetic intervention, wherein along with patient analysis and diagnostics (1030), such as blood pressure characterization, echocardiography, performance stress testing, and/or blood chemistry testing, a tissue structure such as the renal nerve pelvis may be targeted for intervention (1032). The targeted tissue structure may be genetically modified to encode a light sensitive protein (such as by such as by viral mediated gene delivery, electroporation, ultrasound, hydrodynamic delivery, or introduction of naked DNA by direct injection or as complemented by additional facilitators such as cationic lipids or polymers; 1034) and an optical applicator may be implanted and coupled to a tissue structure in a configuration allowing the optical applicator to deliver photons to at least one branch of the targeted tissue structure, such as the renal nerve plexus, which has been genetically modified to have the light sensitive protein (1036). An implantable light source and implantable power supply may be implanted and coupled to one or more tissue structures to provide stability, the implantable light source being configured to deliver photons as an input to the optical applicator when the implantable light source is drawing power from the implantable power supply (1038). In implantable sensor may be deployed within the body of the patient and configured to provide an output signal that is correlated with the blood pressure of the patient (1040). An implantable controller may be implanted and coupled to at least one tissue structure; the implantable controller may be configured to cause the implantable light source to direct enough illumination to the light sensitive protein through the implantable light source and implantable light applicator to at least partially inhibit action potential transmission within the at least one branch of the renal nerve plexus based at least in part upon the output signal received from the implantable sensor (1042). Thus a closed-loop hypertension control paradigm may be executed utilizing light sensitive proteins.

Figure 91:
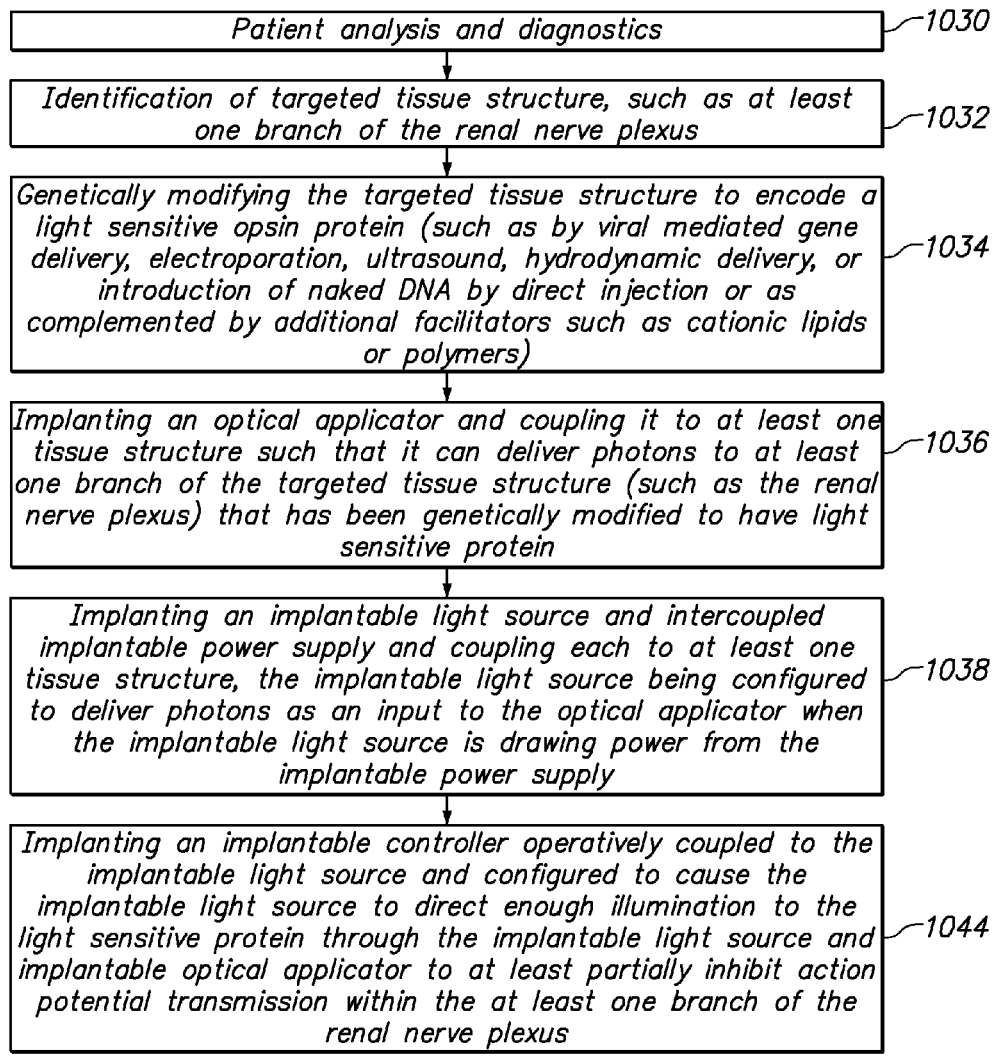

Referring to FIG. 91, an embodiment somewhat similar to that of FIG. 90 is illustrated, with the exception that the embodiment of FIG. 91 features an open-loop paradigm without a blood pressure sensor, such that along with patient analysis and diagnostics (1030), identification of a targeted tissue structure such as a branch of the renal nerve plexus (1032), genetic modification of the targeted tissue structure to encode a light sensitive opsin protein (1034), implantation of an optical applicator (1036) and implantable light source (1038), an implantable controller is implanted to be operatively coupled to the implantable light source and configured to cause the implantable light source to direct enough illumination to the light sensitive protein through the implantable light source and implantable optical applicator to at least partially inhibit action potential transmission within the at least one branch of the renal nerve plexus (1044). The controller may be configured to induce or cause chronic stimulation (i.e., over a long period of time, somewhat akin to a cardiac pacemaker pacing functionality, but in this example the pacing may be stimulating an inhibitory-opsin-encoding nerve to prevent the creation/propagation of action potentials) to prevent the renal plexus from elevating the patient's blood pressure.

Figure 92:
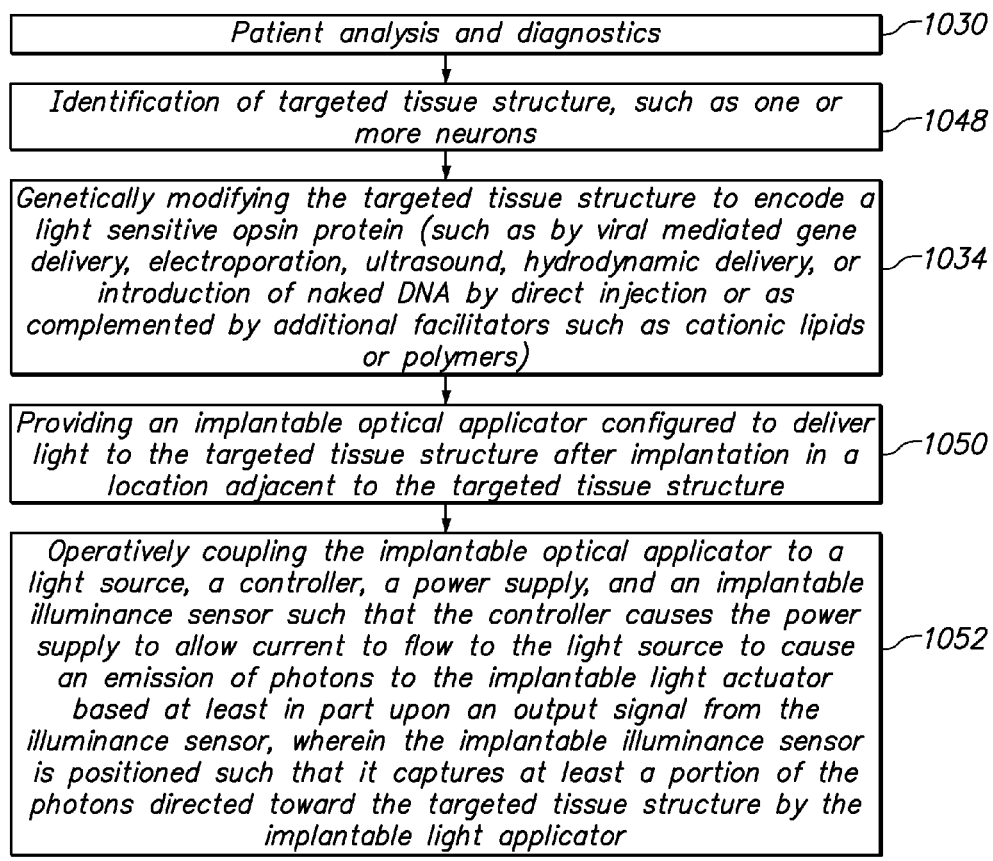

Referring to FIG. 92, a closed loop illuminance configuration is depicted wherein along with patient analysis and diagnostics (1030) and identification of a targeted tissue structure, such as one or more neurons or nerves (1048), the targeted tissue structure may be genetically modified to encode a light sensitive opsin protein (1034), and a implantable optical applicator may be provided to deliver light to the targeted tissue structure after implantation in a location adjacent to the targeted tissue structure (1050). The implantable optical applicator may be operatively coupled to a light source, a controller, a power supply, and an implantable illuminance sensor such that the controller causes the power supply to allow current to flow to the light source to cause an emission of photons to the implantable light actuator based at least in part upon an output signal from the implantable illuminance sensor, wherein the implantable illuminance sensor is positioned such that it captures at least a portion of the photons directed toward the targeted tissue structure by the implantable light applicator (1052).

Figure 93:
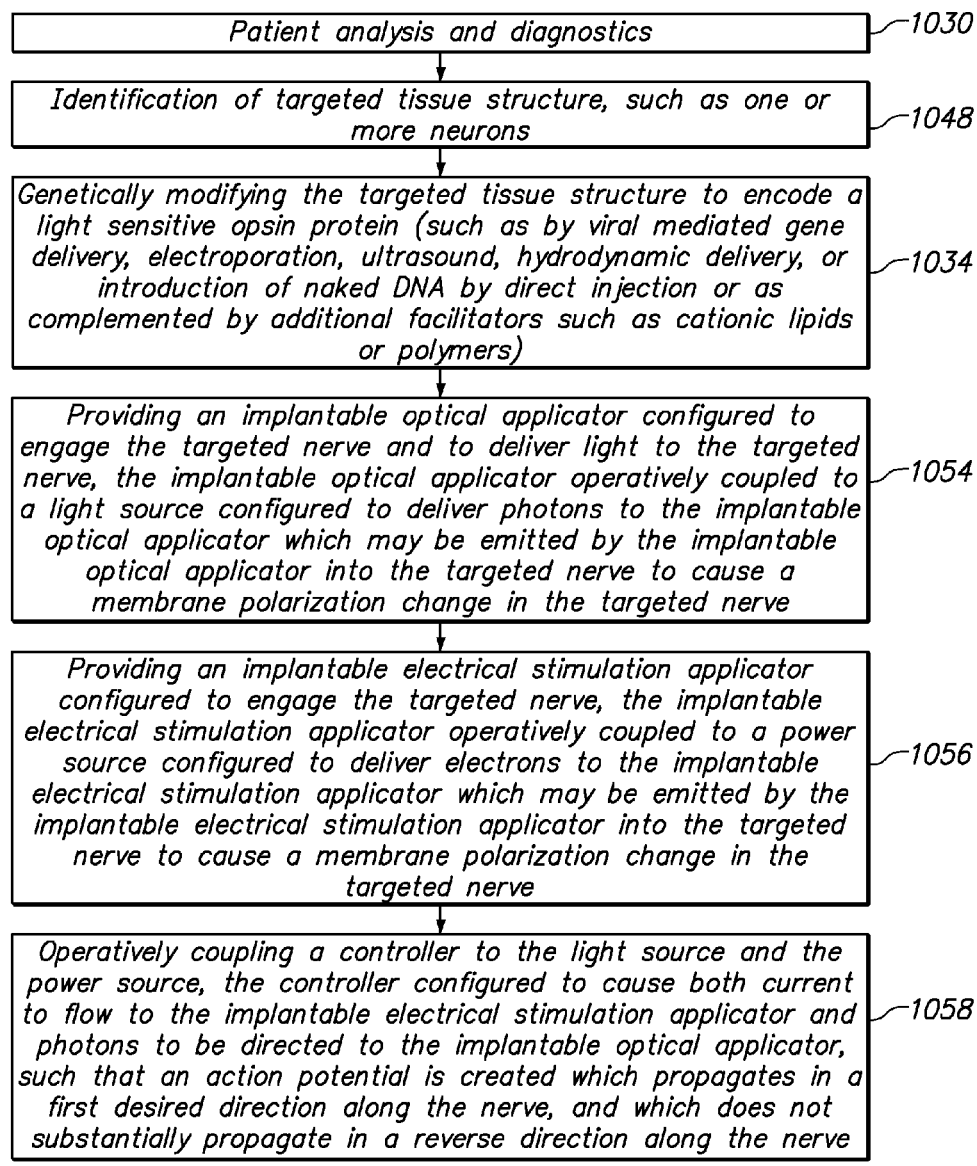

Referring to FIG. 93, a configuration is illustrated wherein directional control of an action potential may be achieved in a nerve comprising light sensitive protein. As shown in FIG. 93, along with patient analysis and diagnostics (1030) and identification of a targeted tissue structure, such as one or more neurons or nerves (1048), the targeted tissue structure may be genetically modified to encode a light sensitive opsin protein (1034), and an implantable optical applicator may be provided and configured to engage the targeted nerve and to deliver light to the targeted nerve, the implantable optical applicator operatively coupled to a light source configured to deliver photons to the implantable optical applicator which may be emitted by the implantable optical applicator into the targeted nerve to cause a membrane polarization change in the targeted nerve (1054). An implantable electrical stimulation applicator, such as an "e-stim" or electrical stimulation electrode, configured to engage and stimulate the targeted nerve may be provided, the implantable electrical stimulation applicator operatively coupled to a power source configured to deliver electrons to the implantable electrical stimulation applicator which may be emitted by the implantable electrical stimulation applicator into the targeted nerve to cause a membrane polarization change in the targeted nerve (1056). A controller may be operatively coupled to the light source and the power source, and configured to cause both current to flow to the implantable electrical stimulation applicator and photons to be directed to the implantable optical applicator, such that an action potential is created which propagates in a first desired direction along the nerve, and which does not substantially propagate in a reverse direction along the nerve (1058).

Figure 94:
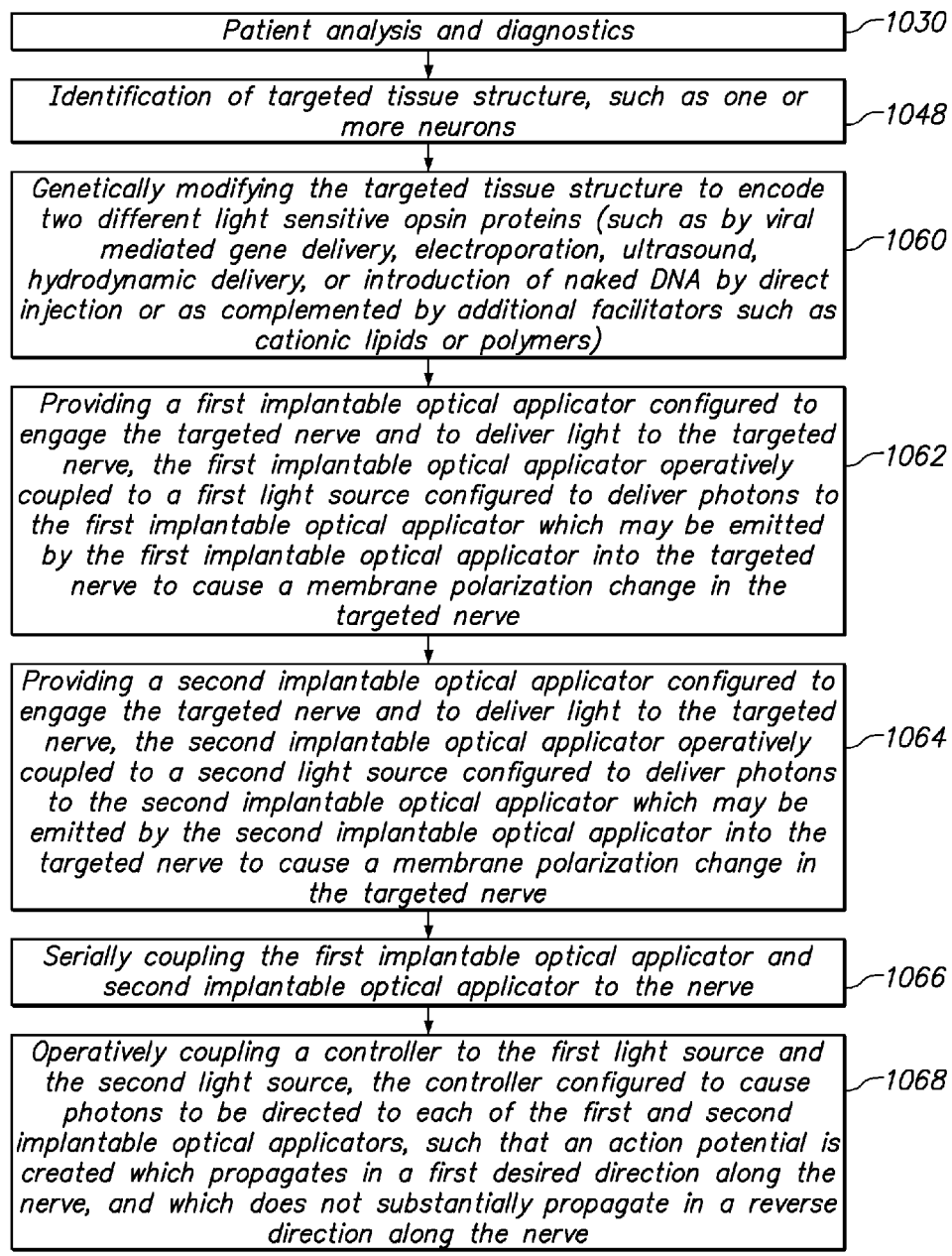

Referring to FIG. 94, another configuration is illustrated wherein directional control of an action potential may be achieved in a nerve comprising light sensitive protein. As shown in FIG. 94, along with patient analysis and diagnostics (1030) and identification of a targeted tissue structure, such as one or more neurons or nerves (1048), the targeted tissue structure may be genetically modified to encode two different light sensitive opsin proteins, such as by viral mediated gene delivery, electroporation, ultrasound, hydrodynamic delivery, or introduction of naked DNA by direct injection or as complemented by additional facilitators such as cationic lipids or polymers, as discussed above (1060). A first implantable optical applicator may be provided and configured to engage the targeted nerve and to deliver light to the targeted nerve, the first implantable optical applicator operatively coupled to a first light source configured to deliver photons to the first implantable optical applicator which may be emitted by the first implantable optical applicator into the targeted nerve to cause a membrane polarization change in the targeted nerve (1062). A second implantable optical applicator may be provided and configured to engage the targeted nerve and to deliver light to the targeted nerve, the second implantable optical applicator operatively coupled to a second light source configured to deliver photons to the second implantable optical applicator which may be emitted by the second implantable optical applicator into the targeted nerve to cause a membrane polarization change in the targeted nerve (1064). A controller may be operatively coupled to the first light source and second light source, the controller configured to cause photons to be directed to each of the first and second implantable optical applicators, such that, depending upon the particular types of opsin proteins selected and delivered to the pertinent nerve, an action potential is created which propagates in a first desired direction along the nerve, and which does not substantially propagate in a reverse direction along the nerve (1068).

Figure 95:
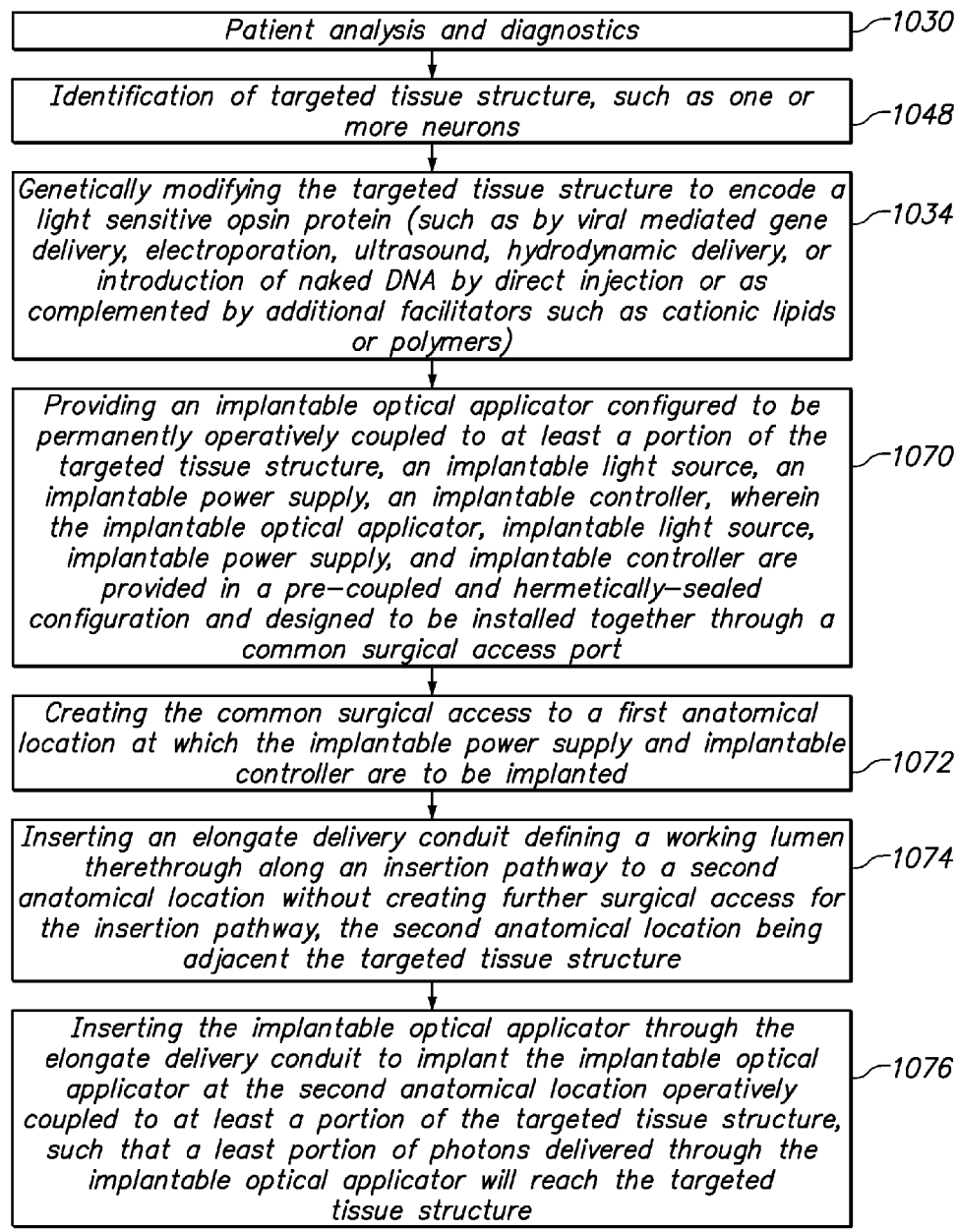

Referring to FIG. 95, a method for installing a system for stimulating a targeted tissue structure comprising light sensitive protein is illustrated, wherein certain components are pre-coupled. As shown in FIG. 95, along with along with patient analysis and diagnostics (1030) and identification of a targeted tissue structure, such as one or more neurons or nerves (1048), the targeted tissue structure may be genetically modified to encode a light sensitive opsin protein (1034), and an implantable optical applicator may be provided and configured to be permanently operatively coupled to at least a portion of the targeted tissue structure, an implantable light source, an implantable power supply, an implantable controller, wherein the implantable optical applicator, implantable light source, implantable power supply, and implantable controller are provided in a pre-coupled and hermetically-sealed configuration and designed to be installed together through a common surgical access port (1070). A common surgical access port to a first anatomical location may be created at which the implantable power supply and implantable controller are to be implanted (1072). An elongate delivery conduit defining a working lumen therethrough may be inserted along an insertion pathway to a second anatomical location without creating further surgical access for the insertion pathway, the second anatomical location being adjacent the targeted tissue structure (1074). The implantable optical applicator may be inserted through the elongate delivery conduit to implant the implantable optical applicator at the second anatomical location operatively coupled to at least a portion of the targeted tissue structure, such that a least a portion of photons delivered through the implantable optical applicator will reach the targeted tissue structure (1076).

Figure 96:
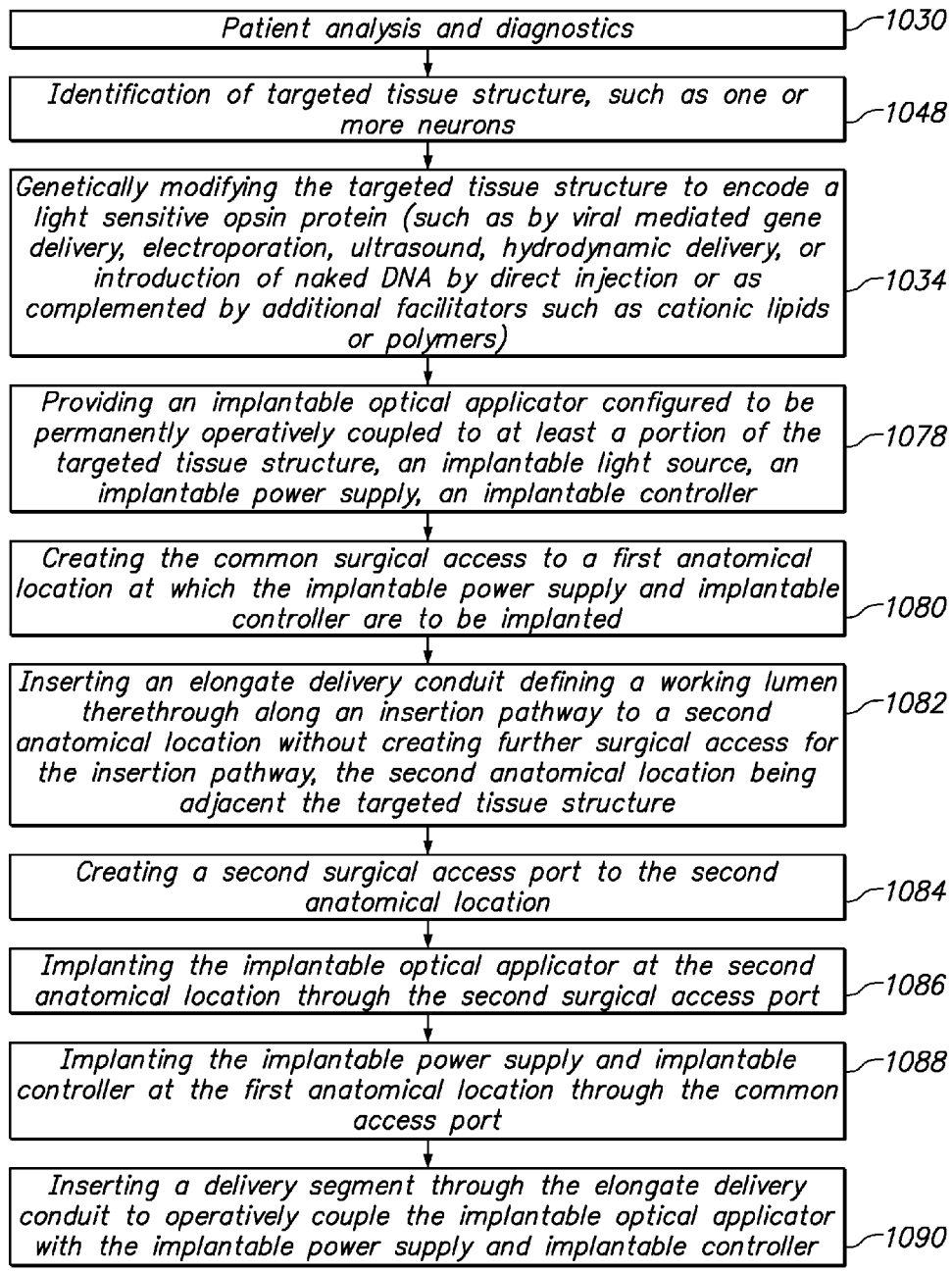

Referring to FIG. 96, a method for installing a system for stimulating a targeted tissue structure comprising light sensitive protein is illustrated, wherein certain components are coupled in-situ. As shown in FIG. 96, along with patient analysis and diagnostics (1030) and identification of a targeted tissue structure, such as one or more neurons or nerves (1048), the targeted tissue structure may be genetically modified to encode a light sensitive opsin protein (1034), and an implantable optical applicator may be provided and configured to be permanently operatively coupled to at least a portion of the targeted tissue structure, an implantable light source, an implantable power supply, an implantable controller (1078). A common surgical access port may be created to a first anatomical location at which the implantable power supply and implantable controller are to be implanted (1080). An elongate delivery conduit defining a working lumen therethrough may be inserted along an insertion pathway to a second anatomical location without creating further surgical access for the insertion pathway, the second anatomical location being adjacent the targeted tissue structure (1082). A second surgical access port to the second anatomical location may be created (1084), and the implantable optical applicator may be implanted at the second anatomical location through the second surgical access port (1086). The implantable power supply (such as an implantable/sealed battery) and implantable controller (such as a microcontroller, microprocessor, application specific integrated circuit, or field programmable gate array, for example) may be implanted at the first anatomical location through the common access port (1088) and a delivery segment may be inserted through the elongate delivery conduit to operatively couple the implantable optical applicator with the implantable power supply and implantable controller (1090).

Figure 97:
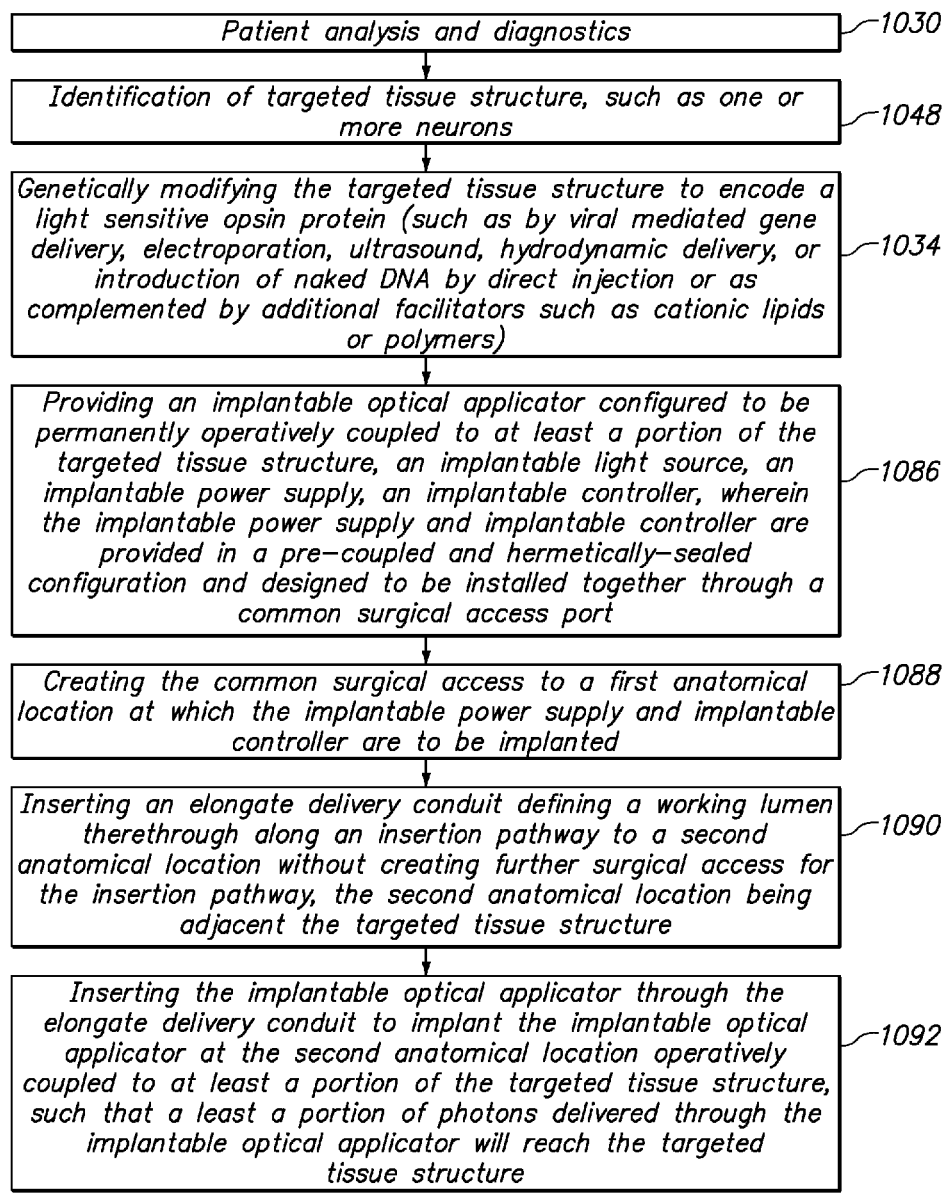

Referring to FIG. 97, a method for installing a system for stimulating a targeted tissue structure comprising light sensitive protein is illustrated, wherein certain components may be coupled in-situ and certain components may be pre-coupled. As shown in FIG. 97, along with patient analysis and diagnostics (1030) and identification of a targeted tissue structure, such as one or more neurons or nerves (1048), the targeted tissue structure may be genetically modified to encode a light sensitive opsin protein (1034), and an implantable optical applicator may be provided and configured to be permanently operatively coupled to at least a portion of the targeted tissue structure, an implantable light source, an implantable power supply, an implantable controller, wherein the implantable power supply and implantable controller are provided in a pre-coupled and hermetically-sealed configuration and designed to be installed together through a common surgical access port (1086). A common surgical access port may be created to a first anatomical location at which the implantable power supply and implantable controller are to be implanted (1088). An elongate delivery conduit defining a working lumen therethrough may be inserted along an insertion pathway to a second anatomical location without creating further surgical access for the insertion pathway, the second anatomical location being adjacent the targeted tissue structure (1090). The implantable optical applicator may be inserted through the elongate delivery conduit to implant the implantable optical applicator at the second anatomical location operatively coupled to at least a portion of the targeted tissue structure, such that a least a portion of photons delivered through the implantable optical applicator will reach the targeted tissue structure (1092).

Figure 98:
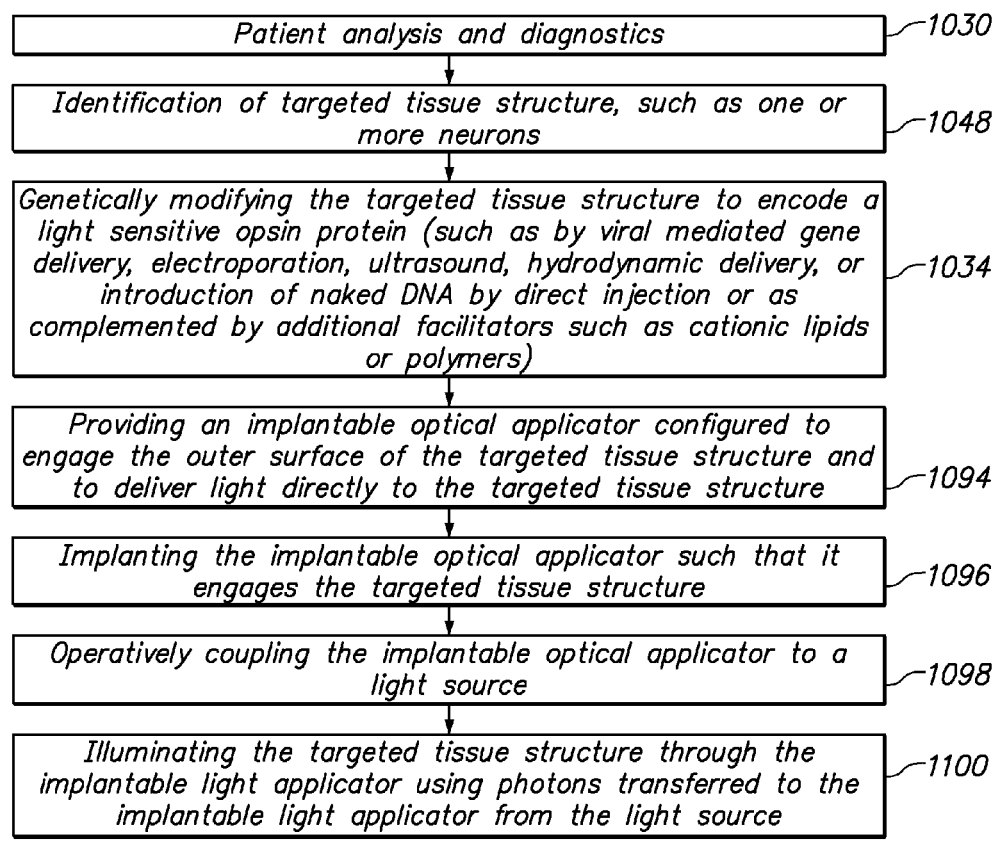

Referring to FIG. 98, a method for illuminating a targeted tissue structure of a patient is depicted. As shown in FIG. 98, along with patient analysis and diagnostics (1030) and identification of a targeted tissue structure, such as one or more neurons or nerves (1048), the targeted tissue structure may be genetically modified to encode a light sensitive opsin protein (1034), and an implantable optical applicator may be provided and configured to engage the outer surface of the targeted tissue structure and to deliver light directly to the targeted tissue structure (1094). The implantable optical applicator may be implanted such that it engages the targeted tissue structure (1096) and the implantable optical applicator may be operatively coupled to a light source (1098). The targeted tissue structure may be illuminated through the implantable light applicator using photons transferred to the implantable light applicator from the light source (1100).

Figure 99:
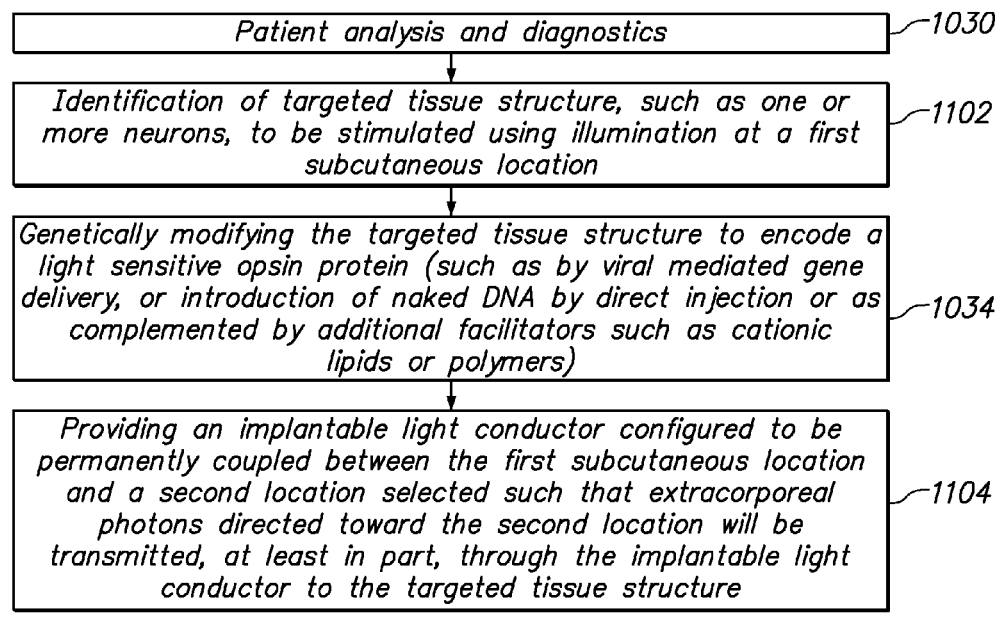

Referring to FIG. 99, a method for stimulating a tissue structure comprising light sensitive protein is illustrated. As shown in FIG. 99, along with patient analysis and diagnostics (1030) and identification of a targeted tissue structure, such as one or more neurons or nerves to be stimulated using illumination at a first subcutaneous location (1102), the targeted tissue structure may be genetically modified to encode a light sensitive opsin protein (1034), and an implantable light conductor, such as a light pipe or waveguide, may be provided and configured to be permanently coupled between the first subcutaneous location and a second location selected such that extracorporeal photons directed toward the second location will be transmitted, at least in part, through the implantable light conductor to the targeted tissue structure (1104).

Figure 100:
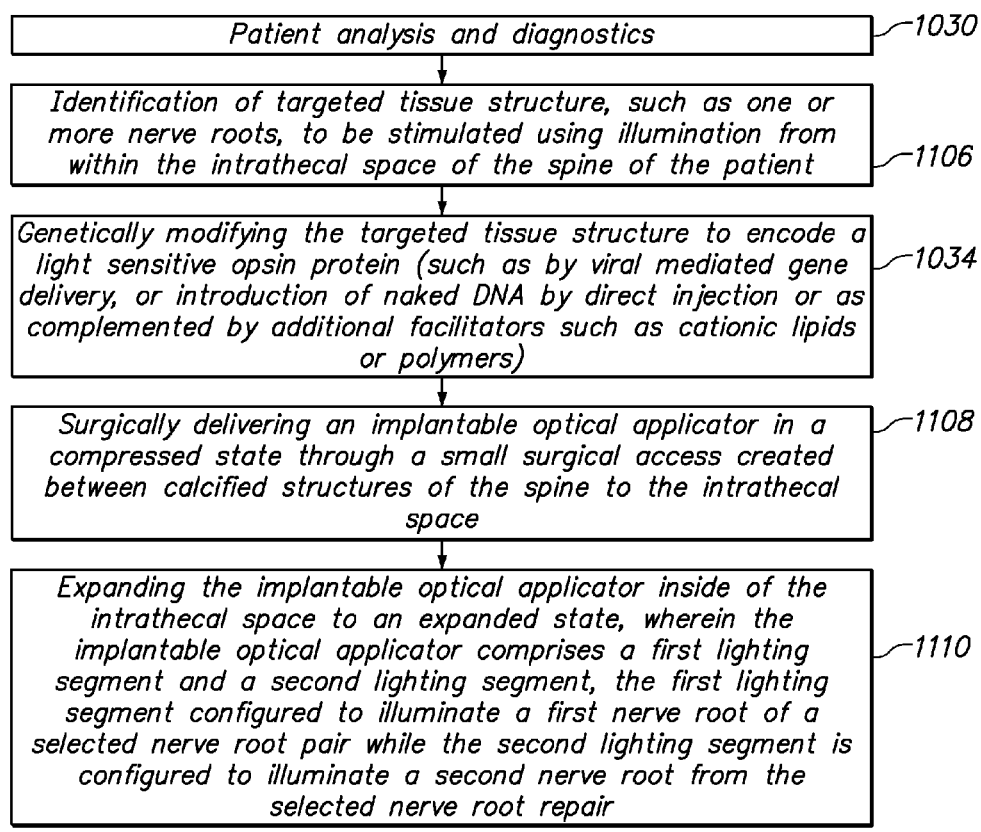

Referring to FIG. 100, a method for illuminating, from within the intrathecal space of a spine of a patient, a nerve root pair that has been genetically modified to comprise light sensitive protein is illustrated. As shown in FIG. 100, along with patient analysis and diagnostics (1030) and identification of a targeted tissue structure, such as one or more neurons, nerve roots, or nerves to be stimulated using illumination at a first subcutaneous location (1106), the targeted tissue structure may be genetically modified to encode a light sensitive opsin protein (1034), and an implantable optical applicator may be surgically delivered in a compressed state through a small surgical access created between calcified structures of the spine to the intrathecal space (1108). The implantable optical applicator may be expanded inside of the intrathecal space to an expanded state, wherein the implantable optical applicator comprises a first lighting segment and a second lighting segment, the first lighting segment configured to illuminate a first nerve root of a selected nerve root pair while the second lighting segment is configured to illuminate a second nerve root from the selected nerve root pair (1110).

Figure 101:
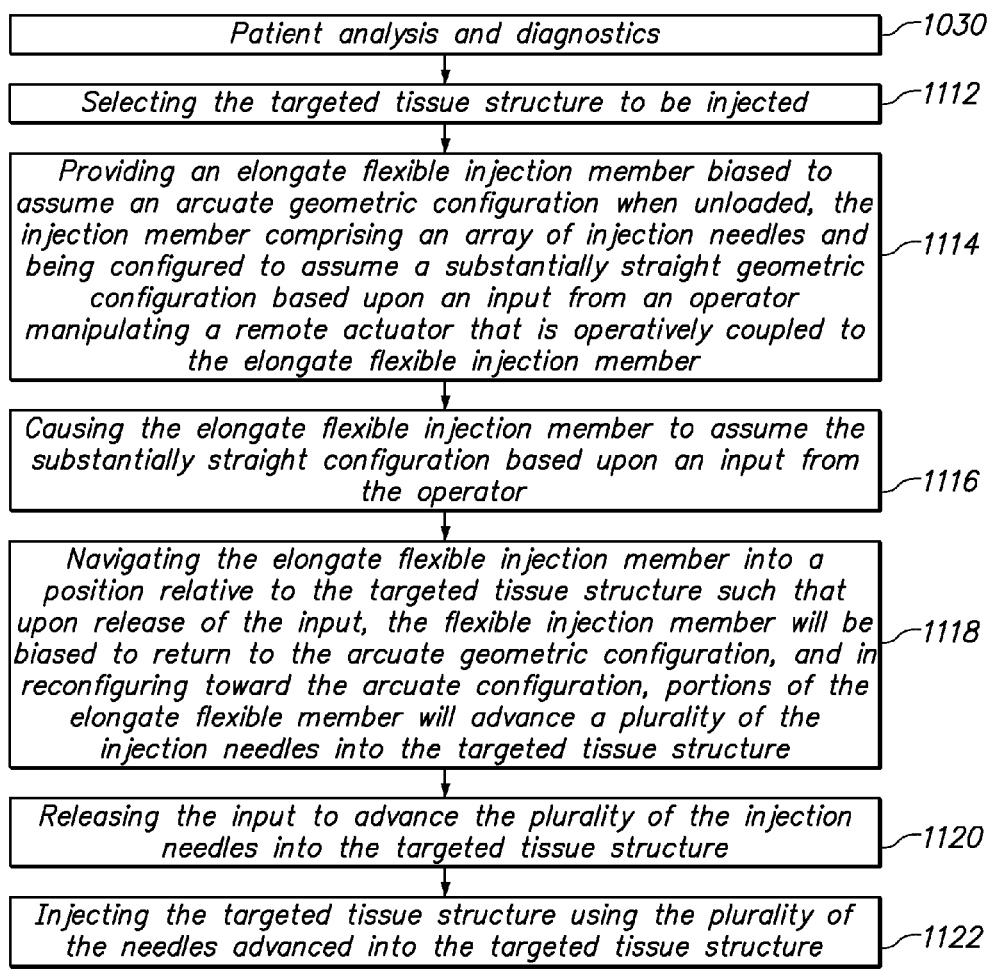

Referring to FIG. 101, a configuration for controllably injecting a targeted tissue structure is illustrated. As shown in FIG. 101, along with patient analysis and diagnostics (1030) and selection of a targeted tissue structure to be injected (1112; such as one or more neurons, nerve roots, or nerves to be stimulated using illumination after being genetically modified, such as by viral mediated gene delivery using an injection, as described above), an elongate flexible injection member biased to assume an arcuate geometric configuration when unloaded may be provided, the injection member comprising an array of injection needles and being configured to assume a substantially straight geometric configuration based upon an input from an operator manipulating a remote actuator that is operatively coupled to the elongate flexible injection member (1114). The flexible injection member may be caused to assume the substantially straight configuration based upon an input from the operator (1116) and may be navigated into a position relative to the targeted tissue structure such that upon release of the input, the flexible injection member will be biased to return to the arcuate geometric configuration, and in reconfiguring toward the arcuate configuration, portions of the elongate flexible member will advance a plurality of injection needles into the targeted tissue structure (1118). The input may be released to advance the plurality of the injection needles into the targeted tissue structure (1120) and the targeted tissue structure may be controllably injected using the plurality of the needles advanced into the targeted tissue structure (1122).

In some embodiments, the light-responsive protein can comprise an amino acid sequence at least about 90%, 91%, 92%, 93%, 94%, 95%, 96%, 97%, 98%, 99%, or 100% identical to the sequence shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:49. In an embodiment, the light-responsive protein can comprise an amino acid sequence at least about 90%, 91%, 92%, 93%, 94%, 95%, 96%, 97%, 98%, 99%, or 100% identical to a polypeptide encoded by SEQ ID NO:50.

An "individual" can be a mammal, including a human. Mammals include, but are not limited to, farm animals, sport animals, pets, primates, mice and rats. Individuals also include companion animals including, but not limited to, dogs and cats. In one aspect, an individual is a human. In another aspect, an individual is a non-human animal.

As used herein, "depolarization-induced synaptic depletion" occurs when continuous depolarization of a neural cell plasma membrane prevents the neural cell from sustaining high frequency action on efferent targets due to depletion of terminal vesicular stores of neurotransmitters.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which an amino acid residue is replaced with an amino acid residue having a chemically different side chain (i.e., replacing an amino acid having a basic side chain with an amino acid having an aromatic side chain).

The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

Light-responsive Opsin Proteins

Provided herein are optogenetic-based methods for selectively hyperpolarizing or depolarizing neurons.

Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms. Any microbial opsin that can be used to promote neural cell membrane hyperpolarization or depolarization in response to light may be used. For example, the Halorhodopsin family of light-responsive chloride pumps (e.g., NpHR, NpHR2.0, NpHR3.0, NpHR3.1) and the GtR3 proton pump can be used to promote neural cell membrane hyperpolarization in response to light. As another example, eARCH (a proton pump) or ArchT can be used to promote neural cell membrane hyperpolarization in response to light. Additionally, members of the Channelrhodopsin family of light-responsive cation channel proteins (e.g., ChR2, SFOs, SSFOs, C1V1s) can be used to promote neural cell membrane depolarization or depolarization-induced synaptic depletion in response to a light stimulus.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQ-IDINV (SEQ ID NO:37).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:37)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGAL-SAVGRELLFVTNPVVVNGS (SEQ ID NO:38))

2) the β2 subunit signal peptide of the neuronal nicotinic acetylcholine receptor (e.g., MAGHSNSMALFSFSLL-WLCSGVLGTEF (SEQ ID NO:39));

3) a nicotinic acetylcholine receptor signal sequence (e.g., MGLRALMLWLLAAAGLVRESLQG (SEQ ID NO:40)); and 4) a nicotinic acetylcholine receptor signal sequence (e.g., MRGTPLLLVVSLFSLLQD (SEQ ID NO:41)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a modified opsin of the present disclosure include, e.g., VXXSL (where X is any amino acid) [SEQ ID NO:42] (e.g., VKESL (SEQ ID NO:43); VLGSL (SEQ ID NO:44); etc.); NANSFCYENEVALTSK (SEQ ID NO:45); FXYENE (SEQ ID NO:46) (where X is any amino acid), e.g., FCYENEV (SEQ ID NO:47); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

Additional protein motifs which can enhance light-responsive protein transport to the plasma membrane of a cell are described in U.S. patent application Ser. No. 12/041,628, which is incorporated herein by reference in its entirety. In some embodiments, the signal peptide sequence in the protein can be deleted or substituted with a signal peptide sequence from a different protein.

Light-responsive Chloride Pumps

In some aspects of the methods provided herein, one or more members of the Halorhodopsin family of light-responsive chloride pumps are expressed on the plasma membranes of neural cells.

In some aspects, said one or more light-responsive chloride pump proteins expressed on the plasma membranes of the nerve cells described above can be derived from *Natronomonas pharaonis*. In some embodiments, the light-responsive chloride pump proteins can be responsive to amber light as well as red light and can mediate a hyperpolarizing current in the nerve cell when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 90%, 91%, 92%, 93%, 94%, 95%, 96%, 97%, 98%, 99%, or 100% identical to the sequence shown in SEQ ID NO:32. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions.

The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 32 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:46), where X can be any amino acid. In another embodiment, the ER export signal can comprise the amino acid sequence VXXSL, where X can be any amino acid [SEQ ID NO:42]. In some embodiments, the ER export signal can comprise the amino acid sequence FCYENEV (SEQ ID NO:47).

Endoplasmic reticulum (ER) export sequences that are suitable for use in a modified opsin of the present disclosure include, e.g., VXXSL (where X is any amino acid) [SEQ ID NO:42] (e.g., VKESL (SEQ ID NO:43); VLGSL (SEQ ID NO:44); etc.); NANSFCYENEVALTSK (SEQ ID NO:45); FXYENE (where X is any amino acid) (SEQ ID NO:46), e.g., FCYENEV (SEQ ID NO:47); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins provided herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 32 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:37).

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 32 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:48). In another embodiment, the light-responsive chloride pump protein comprises an amino acid sequence at least 95% identical to SEQ ID NO:33.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 32, wherein the N-terminal signal peptide of SEQ ID NO:32 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:34.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:32. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:32 and an endoplasmic reticulum (ER) export signal. In some embodiments, the amino acid sequence at least 95% identical to the sequence shown in SEQ ID NO:32 is linked to the ER export signal through a linker. In some embodiments, the ER export signal comprises the amino acid sequence FXYENE (SEQ ID NO:46), where X can be any amino acid. In another embodiment, the ER export signal comprises the amino acid sequence VXXSL, where X can be any amino acid [SEQ ID NO:42]. In some embodiments, the ER export signal comprises the amino acid sequence FCYENEV (SEQ ID NO:47). In some embodiments, the NpHR opsin protein comprises an amino acid sequence at least 95% identical to the sequence shown in SEQ ID NO:32, an ER export signal, and a membrane trafficking signal. In other embodiments, the NpHR opsin protein comprises, from the N-terminus to the C-terminus, the amino acid sequence at least 95% identical to the sequence shown in SEQ ID NO:32, the ER export signal, and the membrane trafficking signal. In other embodiments, the NpHR opsin protein comprises, from the N-terminus to the C-terminus, the amino acid sequence at least 95% identical to the sequence shown in SEQ ID NO:32, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence K S R I T S E G E Y I P L D Q I D I N V (SEQ ID NO:37). In some embodiments, the membrane trafficking signal is linked to the amino acid sequence at least 95% identical to the sequence shown in SEQ ID NO:32 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:33. In some embodiments, the light-responsive opsin protein comprises the amino acid sequence of SEQ ID NO:34.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:32, an ER export signal, and a membrane trafficking signal. In another embodiment, the polynucleotides comprise a sequence which encodes an amino acid at least 95% identical to SEQ ID NO:33 and SEQ ID NO:34. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-responsive Proton Pumps

In some aspects of the methods provided herein, one or more light-responsive proton pumps are expressed on the plasma membranes of the neural cells.

In some embodiments, the light-responsive proton pump protein can be responsive to blue light and can be derived from Guillardia theta, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:31. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:31 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:31. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:31. The polynucleotides may be used for expression of the light-responsive protein in neural cells.

Further disclosure related to light-responsive proton pump proteins can be found in International Patent Application No. PCT/US2011/028893, the disclosure of which is hereby incorporated by reference in its entirety.

In some embodiments, the light-responsive proton pump protein can be responsive to green or yellow light and can be derived from *Halorubrum sodomense* or *Halorubrum* sp. TP009, wherein the proton pump protein can be capable of mediating a hyperpolarizing current in the cell when the cell is illuminated with green or yellow light. The light can have a wavelength between about 560 and about 570 nm or can have a wavelength of about 566 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:25 or SEQ ID NO:26. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:25 or SEQ ID NO:26 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:25 or SEQ ID NO:26. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:25 or SEQ ID NO:26. The polynucleotides may be used for expression of the light-responsive protein in neural cells.

Light-responsive Cation Channel Proteins

In some aspects of the methods provided herein, one or more light-responsive cation channels can be expressed on the plasma membranes of the neural cells.

In some aspects, the light-responsive cation channel protein can be derived from *Chlamydomonas reinhardtii*, wherein the cation channel protein can be capable of mediating a depolarizing current in the cell when the cell is illuminated with light. In another embodiment, the light-responsive cation channel protein can comprise an amino acid sequence at least about 90%, 91%, 92%, 93%, 94%, 95%, 96%, 97%, 98%, 99%, or 100% identical to the sequence shown in SEQ ID NO:1. The light used to activate the light-responsive cation channel protein derived from *Chlamydomonas reinhardtii* can have a wavelength between about 460 and about 495 nm or can have a wavelength of about 480 nm. Additionally, the light can have an intensity of at least about 100 Hz. In some embodiments, activation of the light-responsive cation channel derived from *Chlamydomonas reinhardtii* with light having an intensity of 100 Hz can cause depolarization-induced synaptic depletion of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to depolarize the plasma membrane of a neuronal cell in response to light.

In some embodiments, the light-responsive cation channel comprises a T159C substitution of the amino acid sequence set forth in SEQ ID NO:1. In some embodiments, the light-responsive cation channel comprises a L132C substitution of the amino acid sequence set forth in SEQ ID NO:1. In some embodiments, the light-responsive cation channel comprises an E123T substitution of the amino acid sequence set forth in SEQ ID NO:1. In some embodiments, the light-responsive cation channel comprises an E123A substitution of the amino acid sequence set forth in SEQ ID NO:1. In some embodiments, the light-responsive cation channel comprises a T159C substitution and an E123T substitution of the amino acid sequence set forth in SEQ ID NO:1. In some embodiments, the light-responsive cation channel comprises a T159C substitution and an E123A substitution of the amino acid sequence set forth in SEQ ID NO:1. In some embodiments, the light-responsive cation channel comprises a T159C substitution, an L132C substitution, and an E123T substitution of the amino acid sequence set forth in SEQ ID NO:1. In some embodiments, the light-responsive cation channel comprises a T159C substitution, an L132C substitution, and an E123A substitution of the amino acid sequence set forth in SEQ ID NO:1. In some embodiments, the light-responsive cation channel comprises an L132C substitution and an E123T substitution of the amino acid sequence set forth in SEQ ID NO:1. In some embodiments, the light-responsive cation channel comprises an L132C substitution and an E123A substitution of the amino acid sequence set forth in SEQ ID NO:1.

Further disclosure related to light-responsive cation channel proteins can be found in U.S. Patent Application Publication No. 2007/0054319 and International Patent Application Publication Nos. WO 2009/131837 and WO 2007/024391, the disclosures of each of which are hereby incorporated by reference in their entireties.

Step Function Opsins and Stabilized Step Function Opsins

In other embodiments, the light-responsive cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:1. In other embodiments, the SFO protein has a C128A mutation in SEQ ID NO:1. In other embodiments, the SFO protein has a C128S mutation in SEQ ID NO:1. In another embodiment, the SFO protein has a C128T mutation in SEQ ID NO:1. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:2, SEQ ID NO:3, or SEQ ID NO:4.

In some embodiments, the SFO protein can have a mutation at amino acid residue D156 of SEQ ID NO:1. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:5.

In other embodiments, the SSFO protein can have a mutation at both amino acid residues C128 and D156 of SEQ ID NO:1. In one embodiment, the SSFO protein has an C128S and a D156A mutation in SEQ ID NO:1. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:6. In another embodiment, the SSFO protein can comprise a C128T mutation in SEQ ID NO:1. In some embodiments, the SSFO protein comprises C128T and D156A mutations in SEQ ID NO:1.

In some embodiments the SFO or SSFO proteins provided herein can be capable of mediating a depolarizing current in the cell when the cell is illuminated with blue light. In other embodiments, the light can have a wavelength of about 445 nm. Additionally, the light can have an intensity of about 100 Hz. In some embodiments, activation of the SFO or SSFO protein with light having an intensity of 100 Hz can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970 and U.S. Provisional Patent Application Nos. 61/410,704 and 61/511,905, the disclosures of each of which are hereby incorporated by reference in their entireties.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:13 or SEQ ID NO:49.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, the light can have an intensity of about 100 Hz. In some embodiments, activation of the C1V1 chimeric protein with light having an intensity of 100 Hz can cause depolarization-induced synaptic depletion of the neurons expressing the C1V1 chimeric protein. In some embodiments, the disclosed C1V1 chimeric protein can have specific properties and characteristics for use in depolarizing the membrane of a neuronal cell in response to light.

C1V1 Chimeric Mutant Variants

In some aspects, the present disclosure provides polypeptides comprising substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:13 or SEQ ID NO:49. In some embodiments, the C1V1 protein can have a mutation at amino acid residue E162 of SEQ ID NO:13 or SEQ ID NO:49. In other embodiments, the C1V1 protein can have a mutation at both amino acid residues E162 and E122 of SEQ ID NO:13 or SEQ ID NO:49. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:14, SEQ ID NO:15, SEQ ID NO:16, SEQ ID NO:17, SEQ ID NO:18, or SEQ ID NO:19. In some embodiments, each of the disclosed mutant C1V1 chimeric proteins can have specific properties and characteristics for use in depolarizing the membrane of an animal cell in response to light.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E122 mutant chimeric protein with light having an intensity of 100 Hz can cause depolarization-induced synaptic depletion of the neurons expressing the C1V1-E122 mutant chimeric protein. In some embodiments, the disclosed C1V1-E122 mutant chimeric protein can have specific properties and characteristics for use in depolarizing the membrane of a neuronal cell in response to light.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E162 mutant chimeric protein with light having an intensity of 100 Hz can cause depolarization-induced synaptic depletion of the neurons expressing the C1V1-E162 mutant chimeric protein. In some embodiments, the disclosed C1V1-E162 mutant chimeric protein can have specific properties and characteristics for use in depolarizing the membrane of a neuronal cell in response to light.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, the light can have an intensity of about 100 Hz. In some embodiments, activation of the C1V1-E122/E162 mutant chimeric protein with light having an intensity of 100 Hz can cause depolarization-induced synaptic depletion of the neurons expressing the C1V1-E122/E162 mutant chimeric protein. In some embodiments, the disclosed C1V1-E122/E162 mutant chimeric protein can have specific properties and characteristics for use in depolarizing the membrane of a neuronal cell in response to light.

Further disclosure related to C1V1 chimeric cation channels as well as mutant variants of the same can be found in U.S. Provisional Patent Application Nos. 61/410,736, 61/410,744, and 61/511,912, the disclosures of each of which are hereby incorporated by reference in their entireties.

Champ

In some embodiments, the light-responsive protein is a chimeric protein comprising Arch-TS-p2A-ASIC 2a-TS-EYFP-ER-2 (Champ). Champ comprises an Arch domain and an Acid-sensing ion channel (ASIC)-2a domain. Light activation of Champ activates a proton pump (Arch domain) that activates the ASIC-2a proton-activated cation channel (ASIC-2a domain). A polynucleotide encoding Champ is shown in SEQ ID NO:50.

Polynucleotides

The disclosure also provides polynucleotides comprising a nucleotide sequence encoding a light-responsive protein described herein. In some embodiments, the polynucleotide comprises an expression cassette. In some embodiments, the polynucleotide is a vector comprising the above-described nucleic acid. In some embodiments, the nucleic acid encoding a light-responsive protein of the disclosure is operably linked to a promoter. Promoters are well known in the art. Any promoter that functions in the host cell can be used for expression of the light-responsive opsin proteins and/or any variant thereof of the present disclosure. In one embodiment, the promoter used to drive expression of the light-responsive opsin proteins can be a promoter that is specific to motor neurons. In other embodiments, the promoter is capable of driving expression of the light-responsive opsin proteins in neurons of both the sympathetic and/or the parasympathetic nervous systems. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. Examples of motor neuron-specific genes can be found, for example, in Kudo, et al., Human Mol. Genetics, 2010, 19(16): 3233-3253, the contents of which are hereby incorporated by reference in their entirety. In some embodiments, the promoter used to drive expression of the light-responsive protein can be the Thy1 promoter, which is capable of driving robust expression of transgenes in neurons of both the central and peripheral nervous systems (See, e.g., Llewellyn, et al., 2010, Nat. Med., 16(10):1161-1166). In other embodiments, the promoter used to drive expression of the light-responsive protein can be the EF1α promoter, a cytomegalovirus (CMV) promoter, the CAG promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the light-responsive opsin proteins in the peripheral neurons of mammals.

Also provided herein are vectors comprising a nucleotide sequence encoding a light-responsive protein or any variant thereof described herein. The vectors that can be administered according to the present invention also include vectors comprising a nucleotide sequence which encodes an RNA (e.g., an mRNA) that when transcribed from the polynucleotides of the vector will result in the accumulation of light-responsive opsin proteins on the plasma membranes of target animal cells. Vectors which may be used, include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p5-14, Hudder Arnold, London, UK (2006); and DE Bowles, J E Rabinowitz, R J Samulski "The Genus Dependovirus" (JR Kerr, S F Cotmore. M E Bloom, R M Linden, C R Parrish, Eds.) p15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element-irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method for illuminating, from within the intrathecal space of the spine of a patient, a nerve root pair that has been genetically modified to comprise light sensitive protein, comprising:
   a. surgically delivering an implantable optical applicator in a compressed state through a small surgical access created between calcified structures of the spine to the intrathecal space; and
   b. expanding the implantable optical applicator inside of the intrathecal space to an expanded state, the implantable optical applicator comprising a first lighting segment, a second lighting segment, and one or more biasing segments operatively coupled to one or more of the first and second lighting segments, wherein the first lighting segment is configured to illuminate a first nerve root of a selected nerve root pair while the second lighting segment is configured to illuminate a second nerve root from the selected nerve root pair, and wherein the one or more biasing segments are configured to engage a dura portion of the spine and place at least one of the first and second lighting segments in apposition to the first or second nerve root.

2. The method of claim 1, further comprising providing a first implantable light source immediately coupled to the first lighting segment of the implantable optical applicator, and a second implantable light source immediately coupled to the second lighting segment, wherein each of the light sources is operatively coupled to a power supply and a controller, such that the controller activates the first and second implantable light sources by controlling current thereto from the power supply.

3. The method of claim 2, further comprising operatively coupling the first and second light sources to the power supply and controller with a delivery segment configured to carry electrical current.

4. The method of claim 2, wherein the power supply is implantable.

5. The method of claim 4, further comprising housing the power supply and controller within a common implantable housing.

6. The method of claim 2, wherein the controller is implantable.

7. The method of claim 6, further comprising coupling the power supply to one or more implantable inductive coils configured to receive magnetic flux from a transcutaneous magnetic flux source configured to recharge the implantable power supply.

8. The method of claim 7, further comprising configuring a transcutaneous magnetic flux source to be positioned in a charging position near the skin adjacent the one or more implantable inductive coils.

9. The method of claim 8, further comprising coupling the transcutaneous magnetic flux source to a mounting device configured to retain the transcutaneous magnetic flux source in the charging position for a period of time while the patient is active.

10. The method of claim 9, wherein the mounting device is selected from the group consisting of: a vest, a sling, a strap, a shirt, and a pant.

11. The method of claim 2, wherein the light source comprises a light emitting diode.

12. The method of claim 1, further comprising operatively coupling each of the first and second lighting segments to an implantable light source.

13. The method of claim 12, further comprising intercoupling a delivery segment between the implantable light source and the implantable optical applicator, the delivery segment configured to propagate light from the implantable light source to the implantable optical applicator where it may be distributed to the nerve root pair through the first and second lighting segments.

14. The method of claim 12, wherein the delivery segment comprises a waveguide configured to propagate substantially all light that is passed through it via total internal reflection.

15. The method of claim 12, further comprising operatively coupling the implantable light source to a power supply and controller, such that the controller activates the light source by controlling current thereto from the power supply.

16. The method of claim 15, further comprising housing the implantable light source, power supply, and controller within a common implantable housing.

17. The method of claim 15, further comprising coupling the power supply to one or more implantable inductive coils configured to receive magnetic flux from a transcutaneous magnetic flux source configured to recharge the implantable power supply.

18. The method of claim 17, further comprising providing a transcutaneous magnetic flux source configured to be positioned in a charging position near the skin adjacent the one or more implantable inductive coils.

19. The method of claim 18, further comprising coupling the transcutaneous magnetic flux source to a mounting device configured to retain the transcutaneous magnetic flux source in the charging position for a period of time while the patient is active.

20. The method of claim 19, wherein the mounting device is selected from the group consisting of: a vest, a sling, a strap, a shirt, and a pant.

21. The method of claim 12, wherein the implantable light source comprises a light emitting diode.

22. The method of claim 1, wherein the tissue structure comprising the light sensitive protein has been genetically modified to encode an opsin protein.

23. The method of claim 22, wherein the opsin protein is an inhibitory opsin protein.

24. The method of claim 23, wherein the inhibitory opsin protein is selected from the group consisting of: NpHR, eNpHR 1.0, eNpHR 2.0, eNpHR 3.0, Mac, Mac 3.0, Arch, and ArchT.

25. The method of claim 22, wherein the opsin protein is a stimulatory opsin protein.

26. The method of claim 23, wherein the stimulatory opsin protein is selected from the group consisting of: ChR2, C1V1-T, C1V1-TT, CatCh, VChR1-SFO, and ChR2-SFO.

27. The method of claim 1, further comprising aligning, in the expanded state, the first lighting segment to be immediately adjacent the first nerve root of the selected nerve root pair, and aligning, in the expanded state, the second lighting segment to be immediately adjacent the second nerve root of the selected nerve root pair, to form a deployment geometric configuration.

28. The method of claim 27, wherein at least one of the one or more biasing segments is configured to retain the deployment geometric configuration when activated.

29. The method of claim 28, further comprising operatively coupling a pullwire to at least one of the one or more biasing segments, the pullwire configured to adjust the geometry of the intercoupled implantable optical applicator to facilitate reaching the deployment geometric configuration.

30. The method of claim 1, wherein the nerve root pair is a dorsal root pair.

31. The method of claim 1, wherein the nerve root pair is a ventral root pair.

* * * * *